United States Patent
Layton et al.

(10) Patent No.: US 9,586,968 B2
(45) Date of Patent: Mar. 7, 2017

(54) BICYCLOAMINE-SUBSTITUTED-N-BENZENESULFONAMIDE COMPOUNDS WITH SELECTIVE ACTIVITY IN VOLTAGE-GATED SODIUM CHANNELS

(71) Applicants: Merck Sharp & Dohme Corp., Rahway, NJ (US); Dansu Li, Warrington, PA (US); Mark E. Layton, West Point, PA (US); Anthony J. Roecker, West Point, PA (US); Melissa Egbertson, Ambler, PA (US); Kristen L. G. Jones, West Point, PA (US); Xiu Wang, Shanghai (CN); Xuanjia Peng, Shanghai (CN)

(72) Inventors: Mark E. Layton, West Point, PA (US); Anthony J. Roecker, West Point, PA (US); Melissa Egbertson, West Point, PA (US); Kristen L. G. Jones, West Point, PA (US); Dansu Li, Warrington, PA (US); Xiu Wang, Shanghai (CN); Xuanjia Peng, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/038,805

(22) PCT Filed: Nov. 24, 2014

(86) PCT No.: PCT/US2014/067001
§ 371 (c)(1),
(2) Date: May 24, 2016

(87) PCT Pub. No.: WO2015/080988
PCT Pub. Date: Jun. 4, 2015

(65) Prior Publication Data
US 2017/0002008 A1    Jan. 5, 2017

(30) Foreign Application Priority Data
Nov. 29, 2013 (WO) ................ PCT/CN2013/001476

(51) Int. Cl.
*C07D 487/04* (2006.01)
*A61K 31/407* (2006.01)
*C07D 471/04* (2006.01)
*A61K 31/4353* (2006.01)
*C07D 491/20* (2006.01)
*C07D 487/10* (2006.01)
*C07D 277/52* (2006.01)
*C07D 213/76* (2006.01)
*C07D 239/42* (2006.01)
*C07D 237/20* (2006.01)
*C07D 285/135* (2006.01)

(52) U.S. Cl.
CPC ......... *C07D 487/04* (2013.01); *C07D 213/76* (2013.01); *C07D 237/20* (2013.01); *C07D 239/42* (2013.01); *C07D 277/52* (2013.01); *C07D 285/135* (2013.01); *C07D 471/04* (2013.01); *C07D 487/10* (2013.01); *C07D 491/20* (2013.01)

(58) Field of Classification Search
None
See application file for complete search history.

(56) References Cited

U.S. PATENT DOCUMENTS

| 5,942,535 A | 8/1999 | Laufer et al. |
| 2002/0143033 A1 | 10/2002 | Gregory et al. |

FOREIGN PATENT DOCUMENTS

| WO | WO2005/013914 | 2/2005 |
| WO | WO2007/075895 | 7/2007 |
| WO | WO2009012242 | 1/2009 |
| WO | WO2010033350 | 3/2010 |

OTHER PUBLICATIONS

PubChem, Compound Summary for: CID 10610731. Retrieved from the Internet http://pubchem.ncbl.nlm.nih.gov/compund/10610731.
PubChem, Compound Summary for: CID 16573778. Retrieved from the Internet http://pubchem.ncbl.nlm.nih.gov/compund/16573778.
International Search Report—PCT/US2014-067002 dated Feb. 20, 2015.
International Search Report—PCT2013/001476 dated Sep. 11, 2014.

*Primary Examiner* — Michael Barker
(74) *Attorney, Agent, or Firm* — H. Eric Fischer; John C. Todaro

(57) ABSTRACT

Disclosed are compounds of Formula A-a, or a salt thereof: Where "B¹" and "R¹" through "R⁵" are as defined herein, which compounds have properties for blocking $Na_v$ 1.7 ion channels found in peripheral and sympathetic neurons. Also described are pharmaceutical formulations comprising the compounds of Formula A-a or their salts, and methods of treating neuropathic pain disorders using the same.

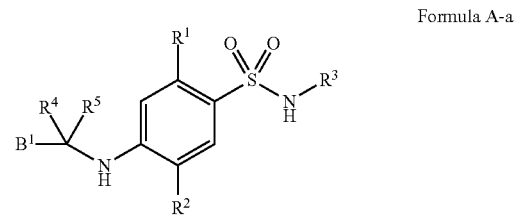

Formula A-a

19 Claims, No Drawings

BICYCLOAMINE-SUBSTITUTED-N-BENZENESULFONAMIDE COMPOUNDS WITH SELECTIVE ACTIVITY IN VOLTAGE-GATED SODIUM CHANNELS

CROSS-REFERENCE TO RELATED APPLICATIONS

This application is a U.S. National Phase application under 35 U.S.C. §371 of PCT Application No. PCT/US2014/067001, filed Nov. 24, 2014, which application in turn claims the priority of International Application Serial No. PCT/CN2013/001476 filed Nov. 29, 2013.

BACKGROUND

Voltage-gated sodium channels play a central role in initiating and propagating action potentials in electrically excitable cells, see for example Yu and Catterall, Genome Biology 4:207 (2003) and references therein. Voltage-gated sodium channels are multimeric complexes characterized by an Alpha-subunit which encompasses an ion-conducting aqueous pore, and is the site of the essential features of the channel, and at least one Beta-subunit that modifies the kinetics and voltage-dependence of the channel gating. These structures are ubiquitous in the central and peripheral nervous system and are believed to play a central role in initiation and propagation of electrical signals in the nervous system.

It has been shown in human patients as well as in animal models of neuropathic pain that damage to primary afferent sensory neurons can lead to neuroma formation and spontaneous activity, as well as evoked activity in response to normally innocuous stimuli. [Carter, G. T. and Galer, B. S., Advances in the Management of Neuropathic Pain, Physical Medicine and Rehabilitation Clinics of North America, 2001, 12(2): pp 447 to 459]. Injuries of the peripheral nervous system often result in neuropathic pain persisting long after an initial injury resolves. Examples of neuropathic pain include, for example, post herpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias. The ectopic activity of normally silent sensory neurons is thought to contribute to the generation and maintenance of neuropathic pain, which is generally assumed to be associated with an increase in sodium channel activity in the injured nerve. [Baker, M. D. and Wood, J. N., Involvement of Na Channels in Pain Pathways, TRENDS is Pharmacological Sciences, 2001, 22(1): pp27 to 31.

Nine different Alpha-subunits have been identified and characterized in mammalian voltage-gated sodium channels. These structures are designated $Na_v$ 1.X sodium channels (X=1 to 9) in accordance with currently accepted nomenclature practice, designating their ion selectivity (Na), the physiological regulator ('v', potential, i.e. voltage), and the gene subfamily encoding them (1.), with the number designator X (1 to 9) being assigned for the alpha subunit present in the structure (see Aoldin et al., Neuron, 28:365-368 (2000)). $Na_v$1.7 voltage-gated sodium ion channels (herein designated "Nav 1.7 channels" in some instances for convenience) are expressed primarily in sensory and sympathetic neurons, are believed to play a role in nociception, and in particular have a central role in inflammatory pain perception, (see Wood et al. J. Neurobiol. 61: pp55-71 (2004) and Nassar et al., Proc. Nat. Acad. Sci. 101(34): pp12706-12711 (2004)). Accordingly it is believed that identification and administration of agents which interact to block $Na_v$ 1.7 voltage-gated sodium ion channels represents a rational approach for providing treatment or therapy for nociception disorders stemming from dysfunction of $Na_v$1.7 voltage-gated sodium ion channels (see Clare et al., Drug Discovery Today, 5: pp506-520 (2000)).

Because voltage gated sodium ion channels are ubiquitous in the central and peripheral nervous system and conservation of structures in the various Alpha-subunits characterizing voltage-gated sodium ion channels implicates the potential for producing serious side effects when utilizing therapeutic agents that target blocking voltage-gated sodium ion channels, therapeutic agents suitable for use in addressing nociception disorders require specificity in their action, for example, in discriminating between action upon $Na_v$ 1.5 sodium ion channels, thought to be important in regulation of cardiac function and action upon $Na_v$ 1.7 sodium ion channels, thought to be central in inflammatory nociception and disorders arising from dysfunctional $Na_v$~1.7 sodium ion channels.

Published international application no. WO09/012242 (the '242 publication) describes compounds having the structure of Formula PA:

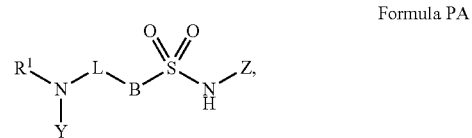

Formula PA wherein $R^1$ is a proton, alkyl or heteroalkyl, aryl, or heteroaryl group, Y is an aryl group or a 5 or 6 member-ring heteroaryl group, L is either not present or is a cyclic structure containing nitrogen or substituted with nitrogen, B is a cycloalkyl, heterocycloalkyl, aryl or heteroaryl moiety, and Z is a five or six-member ring heteroaryl moiety, and optionally R*, N, and Y form a cyclic structure which may be a heteroaryl moiety, for example, the compound of Formula PB:

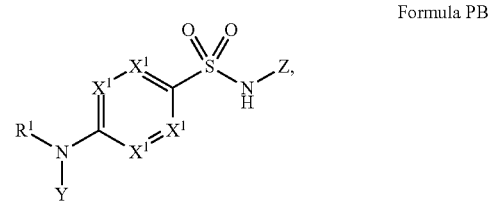

Formula PB wherein $R^1$, Y, and Z are as defined for the compound of Formula PA, and wherein each $X^1$ is independently N or unsaturated carbon optionally substituted with hydrogen, halogen, CN, OH, alkyl or substituted alkyl. These compounds are said to have activity as Nav 1.7 channel and Nav 1.3 channel blockers but are not shown to have selectivity as specific Nav 1.7 channel blockers.

Published international application WO 2013/025883 (the '883 publication) and WO2013/086229 (the '229 publication) describes compounds having the structure of Formula PC:

Formula PC

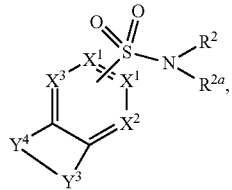

Wherein the aminosulfonyl moiety is bonded to one of $X^1$ and the other of $X^1$ is [=N-] or [=CR$^3$—]($R^3$ is a wide number of substituents including alkyl and halogen), one of $R^{2a}$ or $R^{2b}$ is an aryl or heteroaryl moiety and the other is —H or alkyl, and $Y^3$-$Y^4$ form a 5 or 6 member unsaturated ring which may contain one or more nitrogen atoms and may be substituted on one or more ring atoms.

Compounds having Na$_v$1.7 activity described in published international applications WO 2010/079443 (the '443 publication) and related WO2012/004706, WO2012/004714, WO2012/064984, WO2013/064983, and WO2013/064984 have the structure of Formula PD:

Formula PD

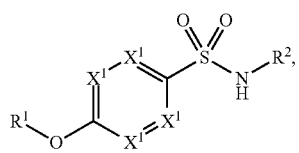

wherein $X^1$ is [=N-] or [=CR$^3$—], —$R^3$ is a wide number of substituents including halogen, $R^1$ is a cycloalkyl, aryl or heteroaryl moiety and $R^2$ is a heteroaryl moiety.

Examples of these compounds include compounds of Formula PE:

Formula PE

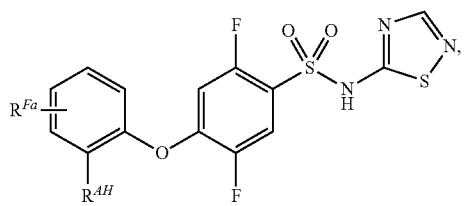

where $R^{AH}$ is an aryl or heteroaryl moiety and $R^{Fa}$ is one or more of a wide variety of substituents, for example the hetero-substituted aryl compounds of Formula PF:

Formula PF

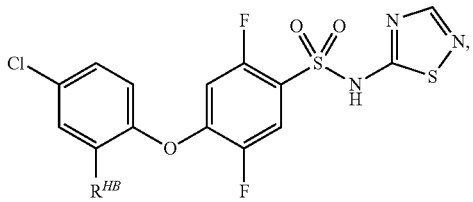

wherein $R^{HB}$ is a heterobicyclo moiety, and Formula PG:

Formula PG

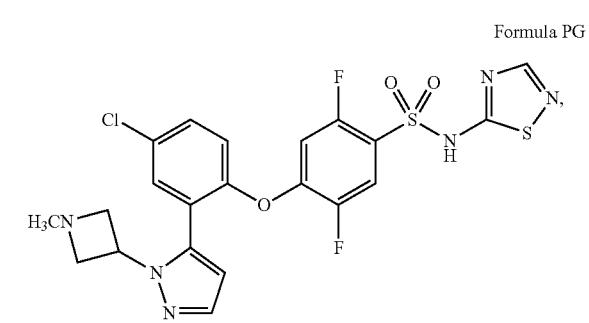

An additional example of these compounds are the heterocycloalkyl-substituted compounds of Formula PH:

Formula PH

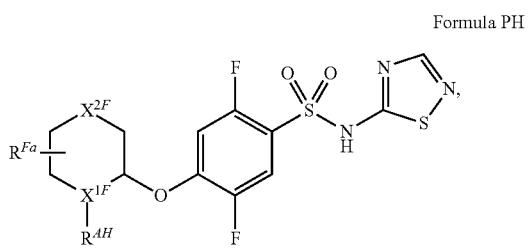

wherein at least one of $X^{1F}$ and $X^{2F}$ are a heteroatom and the other is either a substituted carbon or CH, $R^{AH}$ is an aryl or heteroaryl moiety and $R^{Fa}$ is one or more of a wide variety of substituents. These foregoing compounds are said to have affinity for Nav 1.7 sodium channels and modest or low affinity for Na$_v$1.5 sodium channels, but do not offer much structural diversity.

Recently, compounds described in published international applications WO 2013/025883 WO2013/086229, and WO2013/134518, having the structure of Formula PJ:

Formula PJ

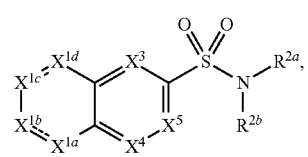

wherein one of $R^{2a}$ or $R^{2b}$ is an aryl or heteroaryl moiety and the other is —H or alkyl, $X^3$ to $X^5$ are =N— or =CR$^5$— (where $R^5$ is a wide range of compatible substituents), $X^{1a-1d}$ d are [=N—], —NR$^4$— (where $R^4$ is H, alkyl, or a wide variety of other substituents compatible with N), or [=CR$^3$—] ($R^3$ is a wide number of substituents, including, H, alkyl, aryl and heteroaryl) and wherein $X^{1c}$ may be absent, in which case $X^{1b}$ is CH. These compounds claim activity for Nav1.7 sodium ion channels and selectivity over Nav1.5 channels.

There remains a need for additional compounds having both high potency for blocking Na$_v$1.7 sodium ion channels and selective activity for Na$_v$ 1.7 sodium ion channels, while having also acceptable bioavailability properties, and which provide a variety of cores to facilitate rational development of therapeutic agents for use as selective Na$_v$ 1.7 sodium ion channel blockers.

SUMMARY OF THE INVENTION

In one aspect, the invention provides compounds having selective activity as $Na_v$ 1.7 sodium ion channel blockers which have the structure of Formula A-a, or a salt thereof:

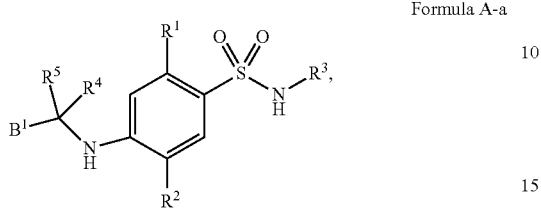

Formula A-a wherein:

$R^1$ and $R^2$ are independently: (a) hydrogen; (b) halogen, and when halogen are preferable —Cl or —F; (c) —CN; or (d) an alkyl moiety which is —$C_{1-10}$-linear-alkyl, —$C_{3-10}$-branched-alkyl, or —$C_{3-10}$-cycloalkyl, which alkyl moiety is optionally substituted with one or more halogen atoms, and when selected to be halogen-substituted, the halogen is preferably —F or —Cl;

$R^3$ is:

(i) a moiety of Formula S1 or S2:

Formula S1

Formula S2 wherein: one or two of $X^1$ to $X^3$ is —N= and the others are [=$CR^6$—], where "$R^6$" is:

A. —H;

B. an alkyl moiety which is —$C_{1-6}$-linear alkyl or —$C_{3-6}$-branched alkyl, which alkyl moiety is optionally substituted with one or more moieties which are independently for each occurrence: (a) halogen, preferably —F, and when halogen substitution is selected to provide a perfluorinated alkyl moiety, preferably the perfluorinated alkyl moiety provided is —$CF_3$; or (b) —$C_{3-6}$-cycloalkyl, which is optionally substituted;

C. $C_{1-6}$-linear alkyl-C(O)—O—, $C_{3-6}$-branched alkyl-C(O)—O— or $C_{3-6}$-cycloalkyl-C(O)—O—;

D. —$C_{3-6}$-cycloalkyl optionally substituted with —F or $C_{1-6}$-linear alkyl; or E. halogen, and when selected to be a halogen, "$R^6$" is preferably —Cl or —F; or (ii) a moiety of Formula S4:

Formula S4 wherein "$X^4$" and "$X^5$" are independently [=N-] or [=$CR^7$—], wherein "$R^7$" is independently for each occurrence —H or —F, and wherein no more than two "$R^7$" are selected to be "—F".

$R^4$ and $R^5$ are independently for each occurrence: (a) hydrogen; or (b) an alkyl moiety which is —$C_{1-6}$-linear-alkyl, —$C_{3-6}$-branched-alkyl, or —$C_{3-6}$-cycloalkyl, which alkyl moiety is optionally substituted with one or more moieties which are: (i) —F; (ii) perfluoro-$C_{1-4}$-linear-alkyl; (iii) $C_{3-6}$-cycloalkyl; (iv) —N($R^{S4a}$)$_2$, wherein "$R^{S4a}$" is independently for each occurrence, —H or lower-alkyl; or (v) an alkoxy moiety which is —$C_{1-6}$-linear-alkoxy, —$C_{3-6}$-branched-alkoxy or —$C_{3-6}$-cycloalkoxy; and $B^1$ is a moiety of the formula:

wherein, $A^1$ and $A^2$ are, independently, (—$CR^8R^9$—)$_n$, wherein:

"n" is independently for each occurrence 2, 3, 4 or 5; and $R^8$ and $R^9$ are independently for each occurrence:

(a) hydrogen;

(b) halogen, preferably —Cl or —F;

(c) an alkyl moiety which is —$C_{1-6}$-linear-alkyl, —$C_{3-6}$-branched-alkyl, or —$C_{3-6}$-cycloalkyl, which alkyl moiety is optionally substituted with one or more moieties which are, independently:

(i) halogen, preferably —Cl or —F;

(ii) —OH;

(iii) an alkoxy moiety which is —$C_{1-6}$-linear-alkoxy, —$C_{3-6}$-branched-alkoxy, or —$C_{3-6}$-cyclic-alkoxy;

(iv) —N($R^{44a}$)$_2$, wherein "$R^{44a}$" is independently for each occurrence, —H or an alkyl moiety which is $C_{1-6}$-linear-alkyl, $C_{3-6}$-branched-alkyl, or $C_{3-6}$-cycloalkyl;

(v) -heterocycloalkyl, where said heterocycloalkyl comprises from 2 to 6 carbon atoms and one or two nitrogen atoms in the ring;

(vi) —$C_{6-10}$-aryl which is optionally substituted on any ring carbon atom thereof with one or more moieties which are independently: halogen; an alkoxy moiety which is —$C_{1-6}$-linear-alkoxy, —$C_{3-6}$-branched-alkoxy, or —$C_{3-6}$-cyclic-alkoxy; or an alkyl moiety which is —$C_{1-6}$-linear-alkyl, $C_{3-6}$-branched-alkyl, or —$C_{3-6}$-cycloalkyl; or (vii) —$C_{6-10}$-heteroaryl, as defined herein, which is optionally substituted on any ring carbon atom thereof with one or more moieties which are independently: halogen; an alkoxy moiety which is —$C_{1-6}$-linear-alkoxy, —$C_{3-6}$-branched-alkoxy, or —$C_{3-6}$-cyclic-alkoxy; or an alkyl moiety which is —$C_{1-6}$-linear-alkyl, $C_{3-6}$-branched-alkyl, or $C_{3-6}$-cycloalkyl;

(d) an alkoxy moiety which is —$C_{1-6}$-linear-alkoxy, —$C_{3-6}$-branched-alkoxy, or —$C_{3-6}$-cyclic-alkoxy;

(e) —$N(R^{45a})_2$, wherein "$R^{45a}$" is independently for each occurrence: —H; or an alkyl moiety which is —$C_{1-6}$-linear-alkyl, $C_{3-6}$-branched-alkyl, or $C_{3-6}$-cycloalkyl;

(f) —$C_{2-6}$-heterocycloalkyl, where said heterocycloalkyl comprises from 2 to 6 carbon atoms and one or two nitrogen atoms in the ring;

(g) aryl, optionally substituted with one or more moieties which are, independently: (i) halogen; (ii) an alkoxy moiety which is —$C_{1-6}$-linear-alkoxy, —$C_{3-6}$-branched-alkoxy or —$C_{3-6}$-cyclic-alkoxy; or (iii) an alkyl moiety which is —$C_{1-6}$-linear-alkyl, $C_{3-6}$-branched-alkyl, or $C_{3-6}$-cycloalkyl;

(h) heteroaryl, as defined herein, optionally substituted with one more moieties which are, independently: (i) halogen; (ii) an alkoxy moiety which is —$C_{1-6}$-linear-alkoxy, —$C_{3-6}$-branched-alkoxy or —$C_{3-6}$-cyclic-alkoxy; or (iii) an alkyl moiety which is —$C_{1-6}$-linear-alkyl, $C_{3-6}$-branched-alkyl, or $C_{3-6}$-cycloalkyl; or "$R^8$" and "$R^9$" on one carbon together form:
(a) a dioxalane moiety, as defined herein;
(b) an arylspirocycloalkyl moiety having a $C_{3-6}$-cycloalkyl portion that, together with the substrate carbon to which it is bonded forms a spirocycloalkyl structure wherein two carbons of the spirocycloalkyl ring portion is fused to an aryl moiety;
(c) a heteroarylspirocycloalkyl moiety having a $C_{3-6}$-cycloalkyl portion that, together with the substrate carbon to which it is bonded forms a spirocycloalkyl structure wherein two carbon atoms of the cycloalkyl ring portion of the moiety are fused to a heteroaryl moiety; or
(d) —$C_{3-6}$-spirocycloalkyl moiety.

In some embodiments, in a compound of Formula A-a, or a salt thereof, it is preferred for the moiety of Formula $B^1$ to be a moiety of Formula $B^{1a}$:

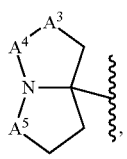

Formula $B^{1a}$ wherein:
"$A^3$" is —$(CR^{10}R^{11})_p$, wherein:
"p" is 1 or 2; and
"$R^{10}$" and "$R^{11}$" are independently for each occurrence: (a) hydrogen; (b) halogen, preferably —Cl or —F; (c) an alkyl moiety which is —$C_{1-6}$-linear-alkyl, —$C_{3-6}$-branched-alkyl, or —$C_{3-6}$-cycloalkyl, which moiety is optionally substituted with one or more substituents which are independently: (i) halogen; (ii) aryl, which is optionally substituted with linear-, -branched, or -cyclic alkoxy; or (iii) —OH; (d) aryl; (e) heteroaryl; (f) —OH; (g) —$N(R^{3a})_2$ wherein "$R^{3a}$" is independently for each occurrence: (i) —H; or (ii) an alkyl moiety which is —$C_{1-6}$-linear-alkyl, —$C_{3-6}$-branched-alkyl, or —$C_{3-6}$-cycloalkyl; or "$R^{10}$" and "$R^{11}$" together form: (i) a dioxalane moiety, as defined herein; or (ii) a $C_{3-6}$-spirocycloalkyl moiety;

"$A^4$" is —$(CR^{12}R^{13})$, wherein $R^{12}$ and $R^{13}$ are independently: (a) hydrogen; (b) an alkyl moiety which is —$C_{1-6}$-linear-alkyl, —$C_{3-6}$-branched-alkyl, or —$C_{3-6}$-cycloalkyl, any of which are optionally substituted with one or more —OH, or partially or fully substituted with halogen; or (c) aryl, which is optionally substituted on any ring carbon atom available with an alkoxy-moiety of up to four carbon atoms; and "$A^5$" is —$(CR^{14}R^{15})_m$, wherein: "m" is 1 or 2, and $R^{14}$ and $R^{15}$ are independently for each occurrence: (a) hydrogen; or (b) an alkyl moiety which is —$C_{1-6}$-linear-alkyl, —$C_{3-6}$-branched-alkyl, or —$C_{3-6}$-cycloalkyl, which alkyl moiety is optionally substituted with one or more substituents which are, independently, —OH or halogen.

In some embodiments wherein the compound of Formula A-a has a moiety of Formula $B^1$ which has the structure of Formula $B^{1a}$, preferably $R^4$ and $R^5$ therein are, independently for each occurrence: (a) hydrogen; or (b) a lower alkyl which is optionally substituted on one or more carbon atoms thereof with one or more moieties which are: (i) perfluoro-$C_{1-4}$-alkyl; (ii) $C_{3-6}$-cycloalkyl; (iii) —$N(R^{B4a})_2$, wherein "$R^{B4a}$" is independently for each occurrence: (i) —H; (ii) -aryl; or (iii) an alkyl moiety which is —$C_{1-6}$-linear-alkyl, —$C_{3-6}$-branched-alkyl, or —$C_{3-6}$-cycloalkyl, which alkyl moiety is optionally substituted.

In some embodiments, in a compound of Formula A-a, or a salt thereof, it is preferred for the moiety $R^3$ to be a moiety of the Formula $R^{3a}$:

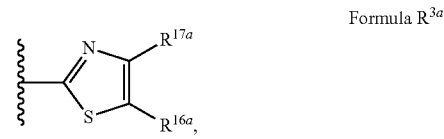

Formula $R^{3a}$ wherein: "$R^{16a}$" and "$R^{17a}$" are independently: (a) —H; (b) a lower alkyl moiety, preferably a branched-, or linear-alkyl moiety comprising up to 6 carbon atoms, which is optionally substituted with one or more halogen moieties, preferably —Cl or —F, and when halogen substitution is selected to provide a perhalogenated alkyl moiety, preferably the perhalogenated alkyl moiety is —$CF_3$; (c) ester of the formula $C_{1-6}$-linear-, $C_{3-6}$-branched- or $C_{3-6}$-cyclic-alkyl-C(O)—O—; (d) —$C_{3-5}$-cycloalkyl optionally substituted with: (i) —F; or (ii) lower alkyl, preferably branched- or linear-alkyl of up to 6 carbon atoms; (e) —CN; (f) heteroaryl; (g) aryl; or (h) halogen, preferably —F.

In some embodiments, in a compound of Formula A-a, or a salt thereof, it is preferred for the moiety $R^3$ to be a moiety of the Formula $R^{3b}$:

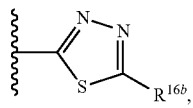

Formula $R^{3b}$ wherein: —$R^{16b}$ is:
- (a) —H;
- (b) a cyclic-, branched-, or linear-alkyl moiety comprising up to 6 carbon atoms which is optionally substituted with one or more moieties which are, independently for each occurrence:
  - (i) lower alkyl, optionally substituted with one or more halogen substituents, preferably —F, and when halogen substitution is selected to provide a perfluorinated alkyl moiety, preferably the perfluorinated alkyl moiety is —$CF_3$;
  - (ii) a heteroaryl substituent; or
  - (iii) a —$C_{3-5}$-cycloalkyl moiety which is optionally substituted with —F or lower alkyl.
- (c) heteroaryl.

In some embodiments, in a compound of Formula A-a, or a salt thereof, it is preferred for the moiety $R^3$ to be a moiety of the Formula $R^{3c}$:

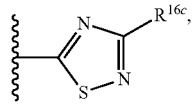

Formula $R^{3c}$ wherein: —$R^{16c}$ is: (a) —H; (b) a cyclic-, branched-, or linear-alkyl moiety comprising up to 6 carbon atoms which is optionally substituted with one or more moieties which are, independently for each occurrence: (a) halogen, preferably —Cl or —F, and when halogen substitution is selected to provide a perfluorinated alkyl, preferably the perfluorinated alkyl is —$CF_3$; (b) ester of the formula $C_{1-6}$-linear-, $C_{3-6}$-branched- or $C_{3-6}$-cyclic-alkyl-C(O)—O—; or (c) —$C_{3-5}$-cycloalkyl optionally substituted with —F or lower alkyl.

In some embodiments, in a compound of Formula A-a, or a salt thereof, it is preferred for the moiety $R^3$ to be a moiety of the Formula $R^{3d}$:

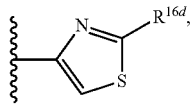

Formula $R^{3d}$ wherein: —$R^{16d}$ is:
- (i) —H;
- (ii) a cyclic- or branched-, or linear-alkyl moiety comprising up to 6 carbon atoms which is optionally substituted with one or more substituents which are independently for each occurrence:
  - (a) halogen;
  - (b) an ester of the formula: (1) $C_{1-6}$-linear-; (2) $C_{3-6}$-branched-; or (3) $C_{3-6}$-cyclic-alkyl-C(O)—O—; or
  - (c) —$C_{3-5}$-cycloalkyl optionally substituted with, independently for each occurrence: (1) —F; or (2) lower alkyl.
- (a) —H; (b) lower alkyl which is optionally substituted.

In some embodiments, in a compound of Formula A-a, or a salt thereof, it is preferred for the moiety $R^3$ to be a heteroaryl moiety of the Formula $R^{3e}$:

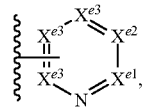

Formula $R^{3e}$ wherein:
one of "$X^{e1}$" or "$X^{e2}$" is [=$CR^{e4}$—], and the other is independently [=N—] or [=$CR^{e4}$—], wherein, "$R^{e4}$" is, independently for each occurrence: (a) —H; (b) halogen, preferably —F or —Cl; or (c) $C_{1-6}$-linear alkyl or —$C_{3-6}$-branched alkyl; and
"$X^{e3}$" is [=$CR^{e5}$—], wherein, one of "$R^{e5}$" is a bond to the substrate and the other two are, independently for each occurrence: (i) —H; (ii) lower alkyl, preferably $C_{1-6}$-linear alkyl, or —$C_{3-6}$-branched alkyl.

In some embodiments, preferably the moiety $R^3$ is a heteroaryl moiety of the Formula $R^{3ea}$:

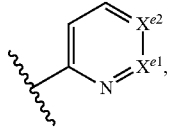

Formula $R^{3ea}$ wherein: one of "$X^{e1}$" or "$X^{e2}$" is [=$CR^{e4}$—], and the other is independently [=N—] or [=$CR^{e4}$—], wherein "$R^{e4}$" is: (a) —H; (b) halogen, preferably —F or —Cl; or (c) lower alkyl, preferably $C_{1-6}$-linear alkyl, or —$C_{3-6}$-branched alkyl.

In one aspect the invention provides a pharmaceutical composition comprising at least one compound of Formula A-a and at least one pharmaceutically acceptable excipient adapted for administration to a patient via any pharmaceutically acceptable route, including dosage forms for oral, intravenous, subcutaneous, transcutaneous, intramuscular, intradermal, transmucosal, or intramucosal routes of administration.

In one aspect this invention provides also a pharmaceutical composition comprising a pharmaceutical carrier, an effective amount of at least one compound of Formula A-a, or a salt thereof, an effective amount of at least one other pharmaceutically active ingredient which is: (i) an opiate agonist or antagonist; (ii) a calcium channel antagonist; (iii) an NMDA receptor agonist or antagonist; (iv) a COX-2 selective inhibitor; or (v) an NSAID (non-steroidal anti-inflammatory drug), and a pharmaceutically acceptable carrier.

In one aspect the invention provides also a method of treatment, management, alleviation or amelioration of conditions or disease states which can be treated, managed, alleviated or ameliorated by specific blocking of Nav 1.7 channel activity, the method comprising administering to a patient in need thereof a composition comprising at least one compound of Formula A-a, or a salt thereof, in an amount providing a serum level of at least one said compound sufficient to effect said treatment, management, alleviation or amelioration of said conditions or disease states. Preferably the condition or disease state to be treated, managed, alleviated or ameliorated is a chronic pain disorder.

DETAILED DESCRIPTION OF THE INVENTION

As mentioned above, the invention provides compounds believed to have selective activity as $Na_v$ 1.7 sodium ion channel blockers which have the structure of Formula A-a, or a salt thereof:

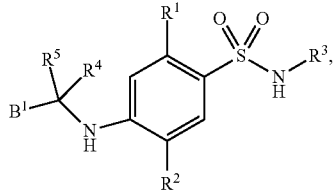

Formula A-a wherein "$R^1$", "$R^2$", "$R^3$", "$R^4$", "$R^5$", and "$B^1$" are defined herein above.

As used herein, unless otherwise specified, the term "$Na_v$ 1.7 (equivalently, Nav 1.7) blocker" means a compound of the invention exhibiting a potency ($IC_{50}$) of less than about 2 M when assayed in accordance with PatchXpress® assays described herein. Preferred compounds exhibit at least 10-fold selectivity for $Na_v$ 1.7 sodium channels over $Na_v$ 1.5 sodium channels, more preferably at least 100-fold selectivity for $Na_v$ 1.7 sodium channels over $Na_v$ 1.5 sodium channels when functional potency for each channel are compared using the PatchXpress® assay systems described herein.

Compounds of the invention and formulations comprising compounds of the invention are believed to be useful in providing treatment, management, alleviation or amelioration of conditions or disease states which can be treated, managed, alleviated or ameliorated by specific blocking of Nav 1.7 channel activity. Examples of disease states which can be desirably affected using such therapy include, but are not limited to, blocking neuropathic pain, for example, postherpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias.

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in IIIus-I and IIIus-II. Accordingly, the methyl group of IIIus-I is emerging from the page of the paper and the ethyl group in IIIus-III is descending into the page, where the cyclohexene ring resides within the plane of the paper. It is assumed that the hydrogen on the same carbon as the methyl group of IIIus-I descends into the page and the hydrogen on the same carbon as the ethyl group of IIIus-II emerges from the page. The convention is the same where both a hashed and solid rectangle are appended to the same carbon as in IIIus-III, the Methyl group is emerging from the plane of the paper and the ethyl group is descending into the plane of the paper with the cyclohexene ring in the plane of the paper.

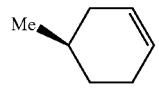

Illus-1

Illus-2

Illus-3

As is conventional, unless otherwise noted in accompanying text, ordinary "stick" bonds or "wavy" bonds indicate that all possible stereochemistry is represented, including, pure compounds, mixtures of isomers, and racemic mixtures.

As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

"at least one" used in reference to substituents on a compound or moiety appended to the core structure of a compound means that one substituent of the group of substituents specified is present, and more than one substituent may be bonded to any of the chemically accessible bonding points of the core.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating neuropathic pain with one or more of the compounds described herein "effective amount" (or "therapeutically effective amount") means, for example, providing the amount of at least one compound of Formula A that results in a therapeutic response in a patient afflicted with a neuropathic pain condition ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula A to a compound of Formula A, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

"solvate" means a physical association of a compound of this invention with one or more solvent molecules; this physical association involves varying degrees of ionic and covalent bonding, including hydrogen bonding; in certain instances the solvate will be capable of isolation, for example when one or more solvent molecules are incorporated in the crystal lattice of the crystalline solid; "solvate" encompasses both solution-phase and isolatable solvates; non-limiting examples of suitable solvates include ethanolates, methanolates, and the like; "hydrate" is a solvate wherein the solvent molecule is $H_2O$.

The term "substituted" means that one or more of the enumerated substituents (or, where a list of substituents are not specifically enumerated, the default substituents specified in this "Definitions" section for the particular type of substrate which contains variable substituents) can occupy one or more of the bonding positions on the substrate typically occupied by "—H", provided that such substitution does not exceed the normal valency rules for the atom in the bonding configuration presented in the substrate, and that the substitution ultimate provides a stable compound, for example, but not limited to: such substitution does not provide compounds with mutually reactive substituents located geminal or vicinal to each other; and wherein the substitution provides a compound sufficiently robust to survive isolation to a useful degree of purity from a reaction mixture.

Where optional substitution of a moiety is described (e.g. "optionally substituted") the term means that if substituents are present, one or more of the enumerated (or default substituents for the specified substrate) can be present on the substrate in a bonding position normally occupied by a hydrogen atom, in accordance with the definition of "substituted" presented herein.

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, the chemical term "acyl", defined below, is equivalently described herein by the term itself, or by typographical representations "R'—(C=O)—" or "R'—C(O)—", or by the structural representation:

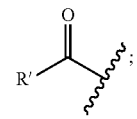

"acyl" means an R'—C(O)—, where R' is linear, branched or cycloalkyl; linear, branched or cyclic alkenyl; or linear, branched or cyclic alkynyl moiety, which moieties are optionally substituted; wherein the acyl substituent is bonded through the carbonyl carbon to the substrate of which it is a substituent, or —NH—$SO_2$—R', where —R' is as previously defined; non-limiting examples of suitable acyl groups include formyl, acetyl, propanoyl, 2-methylpropanoyl, butanoyl and cyclohexanoyl;

"alkenyl" means an aliphatic hydrocarbon moiety which is not aromatic but includes in its structure at least one constituent of the structure —(R'C=CR'$_2$) or —(R'C=CR')—, where R' is a defined substituent, for example —H or -alkyl; the alkenyl moiety can be incorporated into a linear hydrocarbon chain, or incorporated into a cyclic hydrocarbon chain (termed "cycloalkenyl"), which hydrocarbon chain can comprise further, linear, branched, or cyclic substituents depending from the carbon atoms of the chain, preferably the chain comprises about 2 to about 15 carbon atoms; more preferably from about 2 to about 12 carbon atoms; and more preferably chains comprise from about 2 to about 6 carbon atoms;

the term "substituted alkenyl", unless specified otherwise by a recitation of specific substituents defining the term, means that the alkenyl group is substituted by one or more substituents which are independently for each occurrence: $C_{1-10}$ alkyl, $C_{3-10}$ cycloalkyl, and $C_{1-10}$ alkoxy;

"alkoxy" means a moiety of the structure: alkyl-O— (i.e., the bond to the substrate moiety is through the oxygen), wherein the alkyl portion of the moiety is as defined below for alkyl; non-limiting examples of suitable alkoxy groups include methoxy, ethoxy, n-propoxy, isopropoxy, n-butoxy and heptoxy;

"alkoxycarbonyl" means a moiety of the structure alkyl-O—C(O)—, equivalently represented as [alkyl-O—(C=O)—] and also as R—O(C=O)—, where "R" is a defined alkyl moiety, i.e., the bond to the parent moiety is through the carbonyl carbon; non-limiting examples of suitable alkoxycarbonyl groups include methoxycarbonyl and ethoxycarbonyl;

"alkoxy-aryl" means a moiety of the structure alkyl-O-aryl-, where the substituent is bonded to a substrate through the aryl portion of the moiety and the terms "alkyl" and "aryl" have the meaning presented herein;

"alkoxy-aryl" means a moiety of the structure alkyl-O-aryl-, where the substituent is bonded to a substrate through the aryl portion of the moiety and the terms "alkyl" and "aryl" have the meaning presented herein;

"alkyl" (including the alkyl portions of other moieties, such as trifluoromethyl-alkyl- and alkoxy-) means an aliphatic hydrocarbon moiety comprising up to about 20 carbon atoms (for example, a designation of "$C_{1\text{-}20}$-alkyl" indicates an aliphatic hydrocarbon moiety of from 1 to 20 carbon atoms). In some embodiments, alkyls preferably comprise up to about 10 carbon atoms, unless the term is modified by an indication that a shorter chain is contemplated, for example, an alkyl moiety of from 1 up to 8 carbon atoms is designated herein "$C_{1\text{-}8}$-alkyl". The term "alkyl" is further defined by "Linear", "Branched" or "Cyclic. Where the term "alkyl" is indicated with two hyphens (i.e., "-alkyl-" it indicates that the alkyl moiety is bonded in a manner that the alkyl moiety connects the substituents on either side of it, for example, "-alkyl-OH" indicates an alkyl moiety connecting a hydroxyl moiety to a substrate.

The term "linear alkyl" includes alkyl moieties which comprise a hydrocarbon chain with no aliphatic hydrocarbon "branches" appended to it, although other substituents may replace a C—H bond on the hydrocarbon chain. Examples of linear alkyl include, but are not limited to, methyl-, ethyl-, n-propyl-, n-butyl-, n-pentyl- or n-hexyl-.

The term "branched alkyl" is a moiety comprising a main hydrocarbon chain of up to the maximum specified number of carbon atoms with a lower-alkyl chain appended to one or more of the carbon atoms comprising, but not terminating, the main hydrocarbon chain. A branched alkyl moiety therefore comprises at least 3 carbon atoms in the main chain. Examples of branched alkyl moieties include, but are not limited to, t-butyl-, neopentyl-, or 2-methyl-4-ethyl-hexyl- The term "cyclo-alkyl" or "cyclic akyl" is a moiety comprising a main hydrocarbon chain forming a cyclic aliphatic moiety, which comprises at least 3 carbon atoms (the minimum number necessary to provide a cyclic moiety) up to the maximum number of specified carbon atoms. Examples of cycloalkyl moieties include, but are not limited to, cyclopropyl, cyclobutyl, cyclopentyl or cyclohexyl.

For any of the foregoing linear-, branched-, or cyclic-alkyl moieties, one or more of the carbon atoms in the cyclic structure can have one or more of the C—H bonds associated therewith substituted with a substituent selected from the list of substituents called out in the definition of the moiety or, where no such list is provided, the list provided herein in the definition of "substituted" or "optionally substituted alkyl".

When the term "alkyl" is modified by "substituted" or "optionally substituted" it means that one or more C—H bond in the alkyl group is substituted by a C-substituent bond, wherein the substituents are selected from a list of specified having substituents in accordance with the relevant definitions appearing below; where use of the terms "substituted" or "optionally substituted" modify "alkyl" and substituent moieties are not specifically enumerated, the substituents bonded to the alkyl substrate are independently for each occurrence (in accordance with definitions appearing herein): $C_{1\text{-}20}$ alkyl; halogen; -alkoxy; —OH; —CN; alkylthio-; amino, —NH(alkyl), —NH(cycloalkyl), —N(alkyl)$_2$, —(C═O)—OH; —C(O)O-alkyl; —S(alkyl); or —S(O$_2$)-alkyl; or -aryl; cycloalkyl moieties may alternatively, or in addition, be substituted with one or more, "ring-system substituents" as that term is defined herein.

Examples of suitable alkyl groups include, but are not limited to, methyl, ethyl, n-propyl, isopropyl, n-butyl, t-butyl, n-pentyl, heptyl, nonyl, decyl, fluoromethyl, trifluoromethyl and cyclopropylmethyl;

"lower alkyl" means a linear, branched, or cycloalkyl moiety comprising up to about 6 carbon atoms; non-limiting examples of suitable lower alkyl groups include methyl, ethyl, n-propyl, isopropyl, cyclopropyl, n-butyl, t-butyl, cyclobutyl, n-pentyl, isopentyl, neopentyl, cyclopentyl, n-hexyl, cyclohexyl and the like;

"lower alkoxy" means [R—O-] where "R" is a linear, branched, or cycloalkyl moiety comprising up to about 6 carbon atoms; examples of suitable lower alkoxy groups include, but are not limited to, methoxy, ethoxy, n-propoxy, isopropoxy, cyclopropoxy, n-butoxy, t-butoxy, cyclobutoxy, n-pentoxy, isopentoxy, neopentoxy, cyclopentoxy, methoxycyclopentane, and the like "alkylaryl-" (or alkaryl) means an alkyl-aryl- group (i.e., the bond to the parent moiety is through the aryl group) wherein the alkyl group is unsubstituted or substituted as defined above, and the aryl group is unsubstituted or substituted as defined below; preferred alkylaryl moieties comprise a lower alkyl group; non-limiting examples of suitable alkylaryl groups include o-tolyl, p-tolyl and xylyl;

in general, as exemplified by the term "alkyl-aryl" defined above, a substituent which is the called out by the combination of terms used to define two other substituent fragments indicates that the substituent called out by the last term used is bonded to the substrate whilst the preceding term called out is bonded in turn to the substituent fragment it precedes, proceeding right to left to understand the order in which the various fragments are bonded to the substrate;

"alkylsulfinyl" means an alkyl-S(O)— moiety (i.e., the moiety is bonded to a substrate through the sulfur atom of the sulfinyl moiety); "alkylthio" means an alkyl-S— group (i.e., the moiety is bonded to a substrate through the sulfur atom of the moiety); "alkylsulfonyl" means an alkyl-S(O$_2$)— group (i.e., the moiety is bonded to a substrate through the sulfur atom of the sulfonyl moiety), suitable alkyl groups can be unsubstituted or substituted as previously defined; preferred groups are those in which the alkyl group is lower alkyl;

"alkynyl" means an aliphatic hydrocarbon group (chain) comprising at least one moiety of the structure:

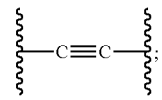

or the structure:

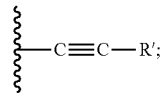

herein R' is a defined substituent, the alkynyl moiety can be incorporated into a linear or branched hydrocarbon chain, or incorporated into a cyclic hydrocarbon chain (non-aromatic, termed "cycloalkynyl",); preferably hydrocarbon chains of an alkynyl moiety comprises about 2 to about 15 carbon atoms; more preferably alkynyl groups comprise about 2 to about 12 carbon atoms in the chain; and more preferably about 2 to about 4 carbon atoms in the chain;

"amino" means an —NR$_2$ group wherein R is selected independently for each occurrence from —H or alkyl, alkylamino means —NR'$_2$, wherein one R' is -alkyl and the other is —H or -alkyl selected independently for each occurrence, non-limiting examples of alkylamino moieties are —NH—CH$_3$ (methylamino-) and —N(CH$_3$)$_2$ (dimethylamino);

"aryl" (sometimes abbreviated "ar") means an aromatic monocyclic or multicyclic ring system comprising about 6 to about 14 carbon atoms (denoted herein also as "C$_{6-14}$-aryl"), preferably about 6 to about 10 carbon atoms ("C$_{6-10}$-aryl"); the aryl group can be optionally substituted with one or more independently selected "ring system substituents" (defined below). Non-limiting examples of suitable aryl groups include phenyl

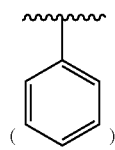 [SMILES: *c1ccccc1]

and naphthyl

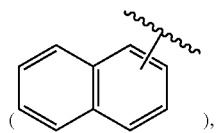

wherein bonding can be through any of the carbons in the aromatic ring, and wherein any ring carbon atoms not participating in a bond to the substrate may have bonded to it a substituent other than —H, independently selected in each instance from the list of "ring-system substituents" defined herein, or as defined in each instance where the term is used in conjunction with an enumerated list of substituents;

"arylalkyl-" means and aryl-C$_{1-6}$-alkyl group (i.e., the moiety is bonded to the substrate through a lower alkyl group) wherein the aryl group is as defined above;

"arylcycloalkyl" means a moiety having an aryl-portion fused to two carbon atoms of a cycloalkyl portion, wherein either portion may be optionally substituted with one or more ring-system substituents, and wherein the aryl portion and the cycloalkyl portion comprises up to 10 carbon atoms in the ring, and in some embodiments the cycloalkyl portion preferably comprises 6 carbon atoms. Examples of arylcycloalkyl moieties include, but are not limited to, tetrahydroanthracene, tetrahydronaphthalene, dihydroindene, and the like. Unless specified otherwise, bonding of an arylcycloalkyl moiety to a substrate may be through any aryl or cycloalkyl ring carbon atom. When the term is used with "spiro", e.g. "arylspirocycloalkyl" it means that the alkyl portion of the moiety contains one carbon in common with a substrate to which it is attached forming a spirocylo structure, for example, the structure:

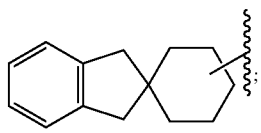

wherein the structure is bonded to a substrate through the cycloalkyl portion with which the arylcycloalkyl moiety forms a spirocyloalkyl structure;

"aryloxy" means an aryl-O— group (i.e., the moiety is bonded to a substrate through the ether oxygen) wherein the aryl group is as defined above; non-limiting examples of suitable aryloxy groups include phenoxy and naphthoxy;

"aryloxycarbonyl" means an aryl-O—C(O)— group (i.e., the bond to a substrate is through the carbonyl carbon) wherein the aryl group is unsubstituted or substituted as previously defined; non-limiting examples of suitable aryloxycarbonyl groups include phenoxycarbonyl and naphthoxycarbonyl;

the term the terms "sulfinyl" means (—SO—), "sulfonyl" means (—S(O$_2$)—), and the term "thio" means (—S—), and in combination with any other substituent terms, mean the same thing, thus, for example: "arylsulfinyl" means an aryl-S(O)— group; "arylsulfonyl" means an aryl-S(O$_2$)— group; and "arylthio" means an aryl-S— group (i.e., the bond of the first-named substituent is to the substrate through the sulfur atom in each case) wherein aryl is unsubstituted or substituted as previously defined;

a "carboxylic acid" moiety means a substituent having the formula "—C(O)—OH", wherein the moiety is bonded to a substrate is through the carbonyl carbon;

"cycloalkyl" defined above with the "alkyl" definition, means a non-aromatic mono- or multicyclic ring system comprising about 3 to about 20 carbon atoms which may optionally be substituted as defined herein; the term includes multicyclic cycloalkyls, for example, 1-decalin, norbornyl, adamantyl and the like;

A "dioxalane moiety" is a substituent of the structure:

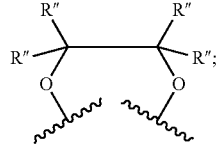

wherein R" is independently for each occurrence: —H; or linear, branched, or cycloalkyl which is optionally substituted with aryl or —OH, and when R" is selected to be an alkyl, it is preferably a lower alkyl;

"halogen" means fluorine, chlorine, bromine, or iodine; preferred halogens, unless specified otherwise where the term is used, are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is methyl, the term perfluoroalkyl means —CF$_3$;

"heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; the "heteroaryl" can be optionally substituted at chemically available ring atoms by one or more independently selected "ring system substituents" (defined below); the prefix aza, azo, oxa, oxo, thia or thio before the heteroaryl root name means that at least a nitrogen, oxygen or sulfur atom, respectively, is present as a ring atom, and in some embodiments 2 or more heteroatoms are present in a ring, for example, a pyrazole or a thiazole moiety; a nitrogen atom of a heteroaryl can be optionally oxidized to the corresponding N-oxide; non-limiting examples of heteroaryl moieties include: pyridyl-,

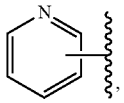

thiopenyl-,

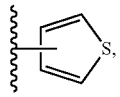

furanyl-,

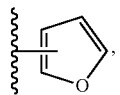

pyrazinyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine, and, for example, heteroaryl moieties of the following structure:

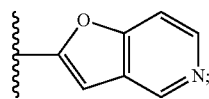 [SMILES: *c1cc2cnccc2o1]

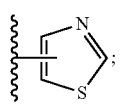

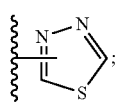

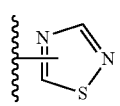

and the like (unless otherwise noted, bonded to the substrate through any available ring atom that results in a stable bonding arrangement);

"heteroarylcycloalkyl" means a moiety having a heteroaryl-portion fused to two carbon atoms of a cycloalkyl portion, wherein ring carbon atoms in either portion may be optionally substituted with one or more ring-system substituents, and wherein the heteroaryl portion comprises up to 8 carbon atoms and up to three hetero atoms which are independently nitrogen, oxygen or sulfur, and the cycloalkyl portion comprises up to 10 carbon atoms. In some embodiments it is preferred for the cycloalkyl portion to comprise up to 6 carbon atoms. Examples of arylcycloalkyl moieties include, but are not limited to, tetrahydroquinoxaline, tetrahydroquinoline, dihydrocyclopentapyridine, and the like. Unless specified otherwise, bonding of an arylcycloalkyl moiety to a substrate may be through any heteroaryl or cycloalkyl ring atom. When the term is used with "spiro", e.g. "heteroarylspirocycloalkyl" it means that the alkyl portion of the moiety contains one carbon in common with a substrate to which it is attached forming a spirocyloalkyl structure, for example, the structure:

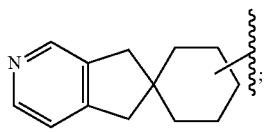

wherein the structure is bonded to a substrate through the cycloalkyl portion with which the heteroarylcycloalkyl moiety forms the spirocyloalkyl structure.

"heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen (e.g. piperidyl- or pyrrolidinyl), oxygen (e.g. furanyl and tetrahydropyranyl) or sulfur (e.g. tetrahydrothiopheneyl and tetrahydrothiopyranyl); and wherein the heteroatoms can be alone or in combination provided that the moiety does not contain adjacent oxygen and/or sulfur atoms present in the ring system; preferred heterocyclyl moieties contain about 5 to about 6 ring atoms; the prefix aza, oxa or thia before the heterocyclyl root name means that at least one nitrogen, oxygen or sulfur atom, respectively, is present as a ring atom; the heterocyclyl can be optionally substituted by one or more independently selected "ring system substituents" (defined below); the nitrogen or sulfur atom of the heterocyclyl can be optionally oxidized to the corresponding N-oxide, S-oxide or S,S-dioxide (SO$_2$); non-limiting examples of suitable monocyclic heterocyclyl rings include piperidyl, pyrrolidinyl, piperazinyl, morpholinyl-

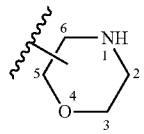

(where unless otherwise noted the moiety is bonded to the substrate through any of ring carbon atoms C2, C3, C5, or C6), thiomorpholinyl, thiazolidinyl, 1,3-dioxolanyl, 1,4-dioxanyl, tetrahydrofuranyl, tetrahydrothiophenyl, tetrahydrothiopyranyl, and the like; and polycyclicheterocyclyl compounds, for example, moieties of the structure:

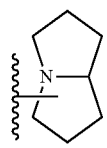

and

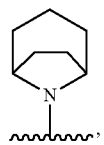

and the like.

"ring-system substituent" means a substituent attached to an aromatic or non-aromatic ring system that, for example, replaces a bonding position normally occupied by a hydrogen atom on the ring system; unless modified by exclusions or additions, the term "ring-system substituent" means one or more moieties independently selected from: alkyl, aryl, heteroaryl, aralkyl, alkylaryl, aralkenyl, heteroaralkyl, alkylheteroaryl, heteroaralkenyl, hydroxy (also termed "hydroxyl" when standing alone as a substituent moiety), hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N-$, $R^{60}R^{65}N$-alkyl-, $R^{60}R^{65}NC(O)-$ and $R^{60}R^{65}NSO_2-$, wherein $R^{60}$ and $R^{65}$ are each independently: hydrogen, alkyl, aryl, and aralkyl (as defined herein);

"tetrahydropyranyl" moiety means a 6-member cyclic ether of the formula:

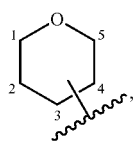

where, the bond line having an open end in the center of the structure and terminated at the other end with a wavy line indicates that the substituent is bonded to the substrate to which it is attached through any of carbon atoms 1 to 5, and wherein any of the bonding positions on carbons 1 to 5 normally occupied by a hydrogen atom, that is, the bonding positions on carbon atoms 1 to 5 which are not occupied by the bond to the substrate can optionally be occupied by specified or optional substituents;

"piperidinyl" means:

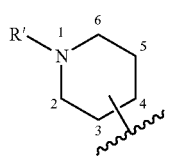

or

where, the open bond line terminated on one end with a wavy line indicates the ring atom through which the moiety is bonded to the substrate (i.e., any of carbon atoms 2 to 6 (left-hand structure) or the ring nitrogen atom (right-hand structure), and wherein any of the bonding positions on the nitrogen atom or on carbon atoms 2 to 6 not participating in a bond to the substrate and normally occupied by a hydrogen atom can be bonded to a specified or optional substituent, and wherein R', if present, is either —H or another specified substituent;

"pyridinyl" means:

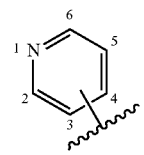

where, the bond-terminated-with-wavy-line indicates that the pyridinyl moiety is bonded to the substrate at any of carbon atoms 2 to 6, and wherein any of the bonding positions on carbons 2 to 6 normally occupied by a hydrogen atom, that is, any position on carbon 2 to 6 which is not the bond to the substrate, can optionally be occupied by a specified substituent;

"quinoline" means:

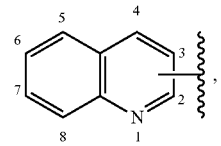

where, the bond-terminated-with-wavy-line indicates that the moiety is bonded to the substrate through any of carbon atoms 2 to 8, and wherein any of the bonding positions on carbon atoms 2 to 8 normally occupied by a hydrogen atom, that is, any bonding positions on carbon atoms 2 to 8 which are not bonded to the substrate, can optionally be occupied by one of a list of enumerated substituents;

"hydroxyl moiety" and "hydroxy" means an HO— group, "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

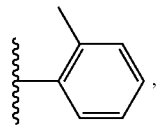

indicates that the methylphenyl moiety is bonded to a substrate through a carbon atom ortho to the methyl substituent, while a bond representation terminated with a wavy line and drawn into a structure without any particular indication of a atom to which it is bonded indicates that the moiety may be bonded to a substrate via any of the atoms in the moiety which are available for bonding as described in the examples above.

Unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

The term "pharmaceutical composition" as used herein encompasses both the bulk composition and individual dosage units comprised of more than one (e.g., two) pharmaceutically active agents such as, for example, a compound of the present invention and an additional agent as described herein, along with any pharmaceutically inactive excipients. As will be appreciated by the ordinarily skilled artisan, excipients are any constituent which adapts the composition to a particular route of administration or aids the processing of a composition into a dosage form without itself exerting an active pharmaceutical effect. The bulk composition and each individual dosage unit can contain fixed amounts of the afore-said "more than one pharmaceutically active agents". The bulk composition is material that has not yet been formed into individual dosage units.

This invention also includes the compounds of this invention in isolated and purified form obtained by routine techniques. Polymorphic forms of the compounds of Formula A, and of the salts, solvates and prodrugs of the compounds of Formula A, are intended to be included in the present invention. Certain compounds of the invention may exist in different isomeric (e.g., enantiomers, diastereoisomers, atropisomers) forms. The invention contemplates all such isomers both in pure form and in admixture, including racemic mixtures.

In the same manner, tautomeric forms of the compounds presented hereis are included by structurally representing any of the tautomers. Accordingly, where compounds of the invention, their salts, and solvates and prodrugs thereof, may exist in different tautomeric forms or in equilibrium among such forms, all such forms of the compound are embraced and included within the scope of the invention. Examples of such tautomers include, but are not limited to, ketone/enol tautomeric forms, imine-enamine tautomeric forms, and for example heteroaromatic forms such as the following moieties:

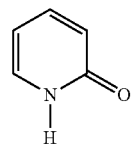

and

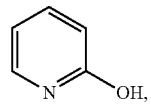

In particular, compounds of the invention are presented herein having a portion of their structure represented by the structural drawing:

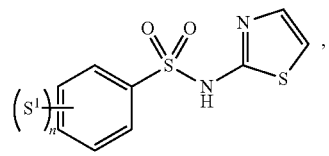

where $(S^1)_n$ is one to five substituents on the aryl ring, the structural drawing representation is intended to include the tautomer:

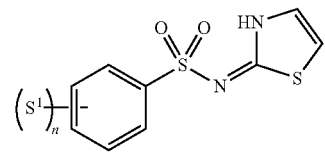

within the scope of the structures represented thereby.

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

As the term is employed herein, salts of the inventive compounds, whether acidic salts formed with inorganic and/or organic acids, basic salts formed with inorganic and/or organic bases salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, are included in the scope of the inventive compounds described herein. The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

A functional group in a compound termed "protected" means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in organic Synthesis (1991), Wiley, New York.

When a variable (e.g., aryl, heterocycl, R3, etc.) appears more than once in any moiety or in any compound of the invention, the selection of moieties defining that variable for each occurrence is independent of its definition at every other occurrence unless specified otherwise in the variable definition.

As used herein, the term "composition" is intended to encompass a product comprising the specified ingredients in the specified amounts, and any product which results, directly or indirectly, from combination of the specified ingredients in the specified amounts.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. It will be appreciated that other isotopes may be incorporated by know means also.

Certain isotopically-labeled compounds of the invention (e.g., those labeled with $^3H$ and $^{14}C$) are recognized as being particularly useful in compound and/or substrate tissue distribution assays. Tritiated (i.e., $^3H$) and carbon-14 (i.e., $^{14}C$) isotopes are particularly preferred for their ease of preparation and detection. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

As mentioned above, in one aspect the invention provides pharmaceutical formulations (pharmaceutical compositions) suitable for use in selectively blocking Nav 1.7 sodium channels found in sensory and sympathetic neurons, comprising at least one compound of Formula A-a, or a salt thereof:

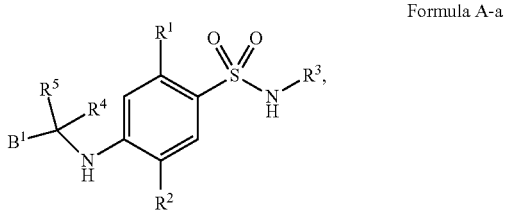

Formula A-a wherein "$R^1$", "$R^2$", "$R^3$", "$R^4$", "$R^5$", and "$B^1$" are defined herein above.

In some embodiments the formulation preferably comprises a compound of Formula A-a, as defined herein, and at least one pharmaceutically acceptable carrier (described below). It will be appreciated that pharmaceutically formulations of the invention may comprise more than one compound of Formula A-a, for example, the combination of two or three compounds of Formula A-a, each present by adding to the formulation the desired amount of the compound in a pharmaceutically acceptably pure form. It will be appreciated that compositions of the invention may comprise, in addition to one or more of the compounds of Formula A-a, one or more additional compounds which also have pharmacological activity, for example, as described herein below.

While formulations of the invention may be employed in bulk form, it will be appreciated that for most applications the inventive formulations will be incorporated into a dosage form suitable for administration to a patient, each dosage form comprising an amount of the selected formulation which contains an effective amount of said one or more compounds of Formula A. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for intramuscular administration (IM), for example, an injectable solution or suspension, and which may be adapted to form a depot having extended release properties; (iii) a dosage form adapted for intravenous administration (IV), for example, a solution or suspension, for example, as an IV solution or a concentrate to be injected into a saline IV bag; (iv) a dosage form adapted for administration through tissues of the oral cavity, for example, a rapidly dissolving tablet, a lozenge, a solution, a gel, a sachets or a needle array suitable for providing intramucosal administration; (v) a dosage form adapted for administration via the mucosa of the nasal or upper respiratory cavity, for example a solution, suspension or emulsion formulation for dispersion in the nose or airway; (vi) a dosage form adapted for transdermal administration, for example, a patch, cream or gel; (vii) a dosage form adapted for intradermal administration, for example, a microneedle array; and (viii) a dosage form adapted for delivery via rectal or vaginal mucosa, for example, a suppository.

For preparing pharmaceutical compositions containing compounds of the invention, generally the compounds of the invention will be combined with one or more pharmaceutically acceptable excipients. These excipients impart to the composition properties which make it easier to handle or process, for example, lubricants or pressing aids in powdered medicaments intended to be tableted, or adapt the formulation to a desired route of administration, for example, excipients which provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier". Typically formulations may comprise up to about 95 percent active ingredient, although formulations with greater amounts may be prepared.

Pharmaceutical compositions can be solid, semi-solid or liquid. Solid form preparations can be adapted to a variety of modes of administration, examples of which include, but are not limited to, powders, dispersible granules, mini-tablets, beads, which can be used, for example, for tableting, encapsulation, or direct administration. Liquid form preparations include, but are not limited to, solutions, suspensions and emulsions which for example, but not exclusively, can be employed in the preparation of formulations intended for parenteral injection, for intranasal administration, or for administration to some other mucosal membrane. Formulations prepared for administration to various mucosal membranes may also include additional components adapting them for such administration, for example, viscosity modifiers.

Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

The compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, 20$^{th}$ Edition, (2000), Lippincott Williams & Wilkins, Baltimore, Md.

Preferably, the pharmaceutical preparation is in a unit dosage form. In such form, the preparations subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

In another embodiment the present invention provides for treatment, management, prevention, alleviation or amelioration of conditions or disease states which can be treated, managed, prevented, alleviated or ameliorated by specific blocking of Nav 1.7 channel activity, for example, blocking neuropathic pain, for example, post herpetic neuralgia, trigeminal neuralgia, diabetic neuropathy, chronic lower back pain, phantom limb pain, chronic pelvic pain, vulvodynia, complex regional pain syndrome and related neuralgias, pain associated with cancer and chemotherapy, pain associate with HIV, and HIV treatment-induced neuropathy, nerve injury, root avulsions, painful traumatic mononeuropathy, painful polyneuropathy, erythromyelalgia, paroxysmal extreme pain disorder, small fiber neuropathy, burning mouth syndrome, central pain syndromes (potentially caused by virtually any lesion at any level of the nervous system), postsurgical pain syndromes (e.g., post mastectomy syndrome, post thoracotomy syndrome, stump pain)), bone and joint pain (osteoarthritis), repetitive motion pain, dental pain, myofascial pain (muscular injury, fibromyalgia), perioperative pain (general surgery, gynecological), chronic pain, dysmennorhea, pain associated with angina, inflammatory pain of varied origins (e.g. osteoarthritis, rheumatoid arthritis, rheumatic disease, teno-synovitis and gout), shoulder tendonitis or bursitis, gouty arthritis, and aolymyalgia rheumatica, primary hyperalgesia, secondary hyperalgesia, primary allodynia, secondary allodynia, or other pain caused by central sensitization, complex regional pain syndrome, chronic arthritic pain and related neuralgias acute pain, migraine, migraine headache, headache pain, cluster headache, non-vascular headache, traumatic nerve injury, nerve compression or entrapment, and neuroma pain.

In accordance with the present invention, treatment, alleviation, amelioration, or management of a disease state amenable to treatment by blocking $Na_v1.7$ channel activity, for example, one or more of the conditions or disease states mentioned above, comprises administering to a patient in need thereof an effective amount of one or more compounds of Formula A-a, as defined herein, or a pharmaceutically acceptable salt thereof.

In some embodiments it is preferred for the compound to be administered in the form of a pharmaceutical composition comprising the compound of Formula A-a, or a salt thereof, and at least one pharmaceutically acceptable carrier (described below). It will be appreciated that pharmaceutically formulations of the invention may comprise more than one compound of Formula A-a or a salt thereof, for example, the combination of two or three compounds of Formula A-a, each present by adding to the formulation the desired amount of the compound or a salt thereof which has been isolated in a pharmaceutically acceptably pure form.

As mentioned above, administration of a compound of Formula A-a in accordance with the present invention is preferably accomplished by incorporating the compound into a pharmaceutical formulation incorporated into a dosage form, for example, one of the above-described dosage forms comprising an effective amount of at least one compound of Formula A-a (e.g., 1, 2 or 3, or 1 or 2, or 1, and usually 1 compound of Formula A-a), or a pharmaceutically acceptable salt thereof. Methods for determining safe and effective administration of compounds which are pharmaceutically active, for example, a compound of Formula A-a, are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56th Edition, 2002 (published by Medical Economics company, Inc. Montvale, N.J. 07645-1742), or the Physician's Desk Reference, 57th Edition, 2003 (published by Thompson PDR, Montvale, N.J. 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the instant invention can be administered at a total daily dosage of up to 1,000 mg, which can be administered in one daily dose or can be divided into two to four doses per day.

In general, in what ever form administered, the dosage form administered will contain an amount of at least one compound of Formula A-a, or a salt thereof, which will provide a therapeutically effective serum level of the compound in some form for a period of at least 2 hours, preferably at least four hours, and preferably longer. In general, as is known in the art, dosages of a pharmaceutical composition providing a therapeutically effective serum level of a compound of the invention can be spaced in time to provide serum level meeting or exceeding the minimum therapeutically effective serum level on a continuous basis throughout the period during which treatment is administered. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active compositions as may be additionally needed in the course of providing treatment. Such additional therapeutic agents can include, for example, i) opiate agonists or antagonists, ii) calcium channel antagonists, iii) NMDA receptor agonists or antagonists, iv) COX-2 selective inhibitors, and v) non-steroidal anti-inflammatory drugs ("NSAID").

Those skilled in the art will appreciate that treatment protocols utilizing at least one compound of Formula A-a can be varied according to the needs of the patient. Thus, compounds of the invention used in the methods of the invention can be administered in variations of the protocols described above. For example, compounds of the invention can be administered discontinuously rather than continuously during the treatment cycle.

As mentioned above, in some embodiments it is preferred for compounds of the invention to have the structure of Formula A-a, or a salt thereof:

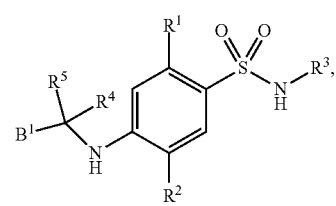

Formula A-a wherein "$R^1$", "$R^2$", "$R^3$", "$R^4$", "$R^5$", and "$B^1$" are defined herein above.

In some embodiments of the compound of Formula A-a, preferably the moiety of Formula $B^1$ has the structure of Formula $B^{1a}$:

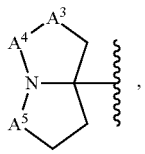

Formula $B^{1a}$ wherein "$A^3$", "$A^4$", and "$A^5$" are defined herein above.

In some embodiments, in a compound of Formula A-a, wherein the moiety of Formula $B^1$ has the structure of Formula $B^{1a}$, it is preferred for "$A^3$", "$A^4$" and "$A^5$" in the moiety of Formula $B^{1a}$ to each be [—$CH_2$—], and for "$R^1$", "$R^2$", "$R^4$", and "$R^5$" to be defined, respectively as "$R^{1a1}$", "$R^{2a1}$", "$R^{4a1}$", and "$R^{5a1}$", thereby providing a structure of Formula A-a1:

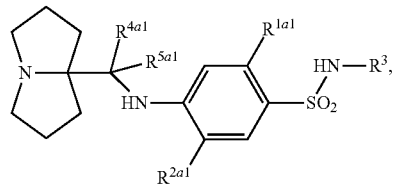

Formula A-a1 wherein:
$R^3$ is as defined herein above;
"$R^{4a1}$" and "$R^{5a1}$" are independently —H or $C_{1-6}$-alkyl, in some embodiments, preferably —H or —$CH_3$; and
"$R^1$" and "$R^2$" are independently: (i) —H; (ii) halogen, and when selected to be halogen are preferably —F, —Cl, or —Br; (iii) —CN; or (iv) $C_{1-4}$-linear-alkyl or $C_{3-4}$-branched, cyclic-alkyl, and when selected to be alkyl are preferably methyl or ethyl, optionally substituted with —F, and when selected to be fluorine-substituted alkyl are preferably-$CF_3$. In some embodiments of compounds of Formula A-a1, preferably "$R^{1a1}$" is independently: —H; —F; —Cl; —Br; —CN; or $CH_3$; and preferably "$R^{2a1}$" is independently: —H; —F; —Cl; —Br; —CN; —$CF_3$, —$CH_3$; or —$CH_2CH_3$.

In some embodiments, in a compound of Formula A-a, wherein the moiety of Formula $B^1$ has the structure of Formula $B^{1a}$, it is preferred for "$A^3$" in the moiety of Formula $B^{1a}$ to be [—$CR^{10a2}R^{11a2}$—], for "$A^4$" and "$A^5$" in the moiety of Formula $B^{1a}$ each to be [—$CH_2$—], and for "$R^1$", "$R^2$", "$R^4$", and "$R^5$" to be defined, respectively as "$R^{1a2}$", "$R^{2a2}$", "$R^{4a2}$", and "$R^{5a2}$", thereby providing a structure of Formula A-a2:

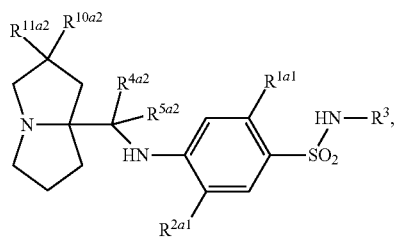

Formula A-a2 wherein:
[—$R^3$] is as defined above;
[—$R^{10a2}$] and [—$R^{11a2}$] are independently for each occurrence:
(a) hydrogen;
(b) halogen, preferably —Cl or —F;
(c) is —$C_{1-6}$-linear-alkyl, —$C_{3-6}$-branched-alkyl, or —$C_{3-6}$-cycloalkyl, which alkyl moiety is optionally substituted with: (i) halogen; (ii) an aryl moiety which is optionally substituted with $C_{1-4}$-alkoxy-; or (iii) —OH, wherein, when selected to be alkyl, it is preferably —$CH_3$ or —$CH_2$—$CH_3$, when selected to be an alkyl moiety substituted with an alkoxyl-substituted aryl it is
preferably a moiety of the formula:

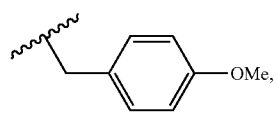 [SMILES: *Cc1ccc(OC)cc1]

and when selected to be an alkyl substituted with halogen it is preferably —$CF_3$; or
(d) an aryl moiety optionally substituted with a lower-alkoxy, and when selected to be an alkoxy-substituted aryl, preferably it is a moiety of the formula;

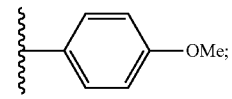 [SMILES: *c1ccc(OC)cc1]

or
"$R^{10a2}$" and "$R^{11a2}$" together form: (a) a dioxalane moiety or (b) a $C_{3-6}$-spirocycloalkyl moiety, and when "$R^{10a2}$" and "$R^{11a2}$" are selected to form a dioxalane moiety, and when selected to be a dioxalane moiety, preferably the moiety is:

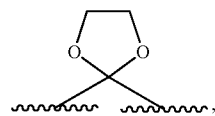 [SMILES: *C1(*)OCCO1]

and when "$R^{10a2}$" and "$R^{11a2}$" are selected to form a spirocycloalkyl moiety, preferably the moiety is:

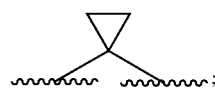 [SMILES: *C1(*)CC1]

"$R^{4a2}$" and "$R^{5a2}$" are independently —H or lower-alkyl; and "$R^{1a2}$" is independently —H or —F; and "$R^{2a2}$" is independently: (i) —H; (ii) —Cl; (iii) —CN; or (iv) $C_{1-4}$-linear-alkyl or $C_{3-4}$-branched, cyclic-alkyl, and when selected to be alkyl, preferably the moiety is methyl or ethyl, optionally substituted with —F, and when selected to be fluorine-substituted alkyl the moiety is preferably —$CF_3$. In some embodiments, preferably, "$R^{2a2}$" is preferably: —H; —Cl; —CN; —$CF_3$; —$CH_3$; or —$CH_2$—$CH_3$.

In some embodiments, in a compound of Formula A-a, having a moiety of Formula $B^{1a}$, it is preferred for "$A^4$" in the moiety of Formula $B^{1a}$ to be [—$CR^{12a3}R^{13a3}$—], and for "$A^3$" and "$A^5$" in the moiety of Formula $B^{1a}$ each to be [—$CH_2$—], and for "$R^1$", "$R^2$", "$R^4$", and "$R^5$" to be defined, respectively as "$R^{1a3}$", "$R^{2a3}$", "$R^{4a3}$", and "$R^{5a3}$", thereby providing a structure of Formula A-a3:

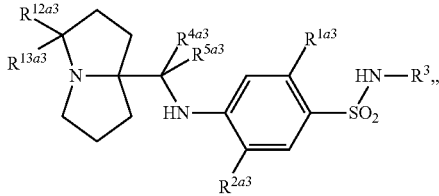

Formula A-a3 wherein:
[—$R^3$] is as defined above;
[—$R^{12a3}$] and [—$R^{13a3}$] are independently for each occurrence:
(a) hydrogen;
(b) is —$C_{1-6}$-linear-alkyl, —$C_{3-6}$-branched-alkyl, or —$C_{3-6}$-cycloalkyl, optionally substituted with one or more substituents which are: (i) halogen, preferably —F; or (ii) —OH, and when selected to be unsubstituted alkyl, it is preferably —$CH_3$, and when selected to be a halogen-substituted alkyl, it is preferably —$CF_3$, and when selected to be a hydroxyl-substituted alkyl, it is preferably —$CH_2$—OH;
"$R^{4a3}$" and "$R^{5a3}$" are independently: (i) —H; or (ii) —$C_{1-6}$-linear-alkyl, —$C_{3-6}$-branched-alkyl, or —$C_{3-6}$-cycloalkyl, and in some embodiments, preferably both "$R^{4a3}$" and "$R^{5a3}$" are —H; and
"$R^{1a3}$" and "$R^{2a3}$" are independently: (i) —H; (ii) halogen, and when selected to be halogen are preferably —F, —Cl, or —Br; (iii) —CN; or (iv) $C_{1-4}$-alkyl, and when selected to be alkyl are preferably methyl or ethyl, optionally substituted with —F, and when selected to be fluorine-substituted alkyl are preferably —$CF_3$.

In some embodiments of a compound of Formula A-a3, preferably, "$R^{1a3}$" is independently: —H or —F, and "$R^{2a3}$" is independently: —Cl or —$CF_3$.

In some embodiments, in a compound of Formula A-a, having a moiety of Formula $B^{1a}$, it is preferred for "$A^3$" in the moiety of Formula $B^{1a}$ to be [(—$CH_2$—)$_{1-2}$], "$A^4$" in the moiety of Formula $B^{1a}$ to be (—$CH_2$—) and "$A^5$" in the moiety of Formula $B^{1a}$ each to be [—$CH_2CH_2$—], and for "$R^1$", "$R^2$", "$R^4$", and "$R^5$" to be defined, respectively as "$R^{1a4}$", "$R^{2a4}$", "$R^{4a4}$", and "$R^{5a4}$", thereby providing a structure of Formula A-a4:

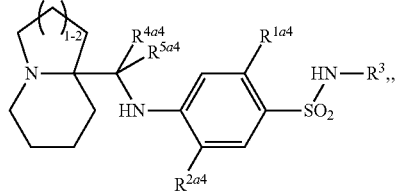

Formula A-a4 wherein:
[—$R^3$] is as defined above;
"$R^{4a4}$" and "$R^{5a4}$" are independently: (i) —H; or (ii) —$C_{1-6}$-linear-alkyl, —$C_{3-6}$-branched-alkyl, or —$C_{3-6}$-cycloalkyl; and "$R^{1a4}$" and "$R^{2a4}$" are independently: (i) —H; (ii) halogen, preferably —F or —Cl; (iii) —CN; or (iv) cyclic-, branched- or linear-alkyl comprising up to 4 carbon atoms, and when selected to be alkyl are preferably methyl or ethyl, optionally substituted with —F, and when selected to be fluorine-substituted alkyl is preferably —$CF_3$.

In some embodiments of compounds of Formula A-a4, preferably "$R^{1a4}$" is —F and "$R^{2a4}$" is —Cl.

In some embodiments where the compound is of Formula A-a1, Formula A-a2, Formula A-a3, or Formula A-a4, preferably the moiety of Formula $R^3$ has the structure of Formula $R^{3az}$:

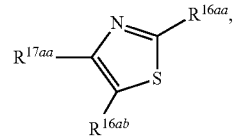

Formula $R^{3az}$ wherein, one of —$R^{16aa}$, —$R^{16ab}$ or —$R^{17aa}$ are bonded to the sulfonamide nitrogen of the compound, and the others are independently:
(a) —H;
(b) —$C_{1-6}$-linear-alkyl or $C_{3-6}$-branched-alkyl, which alkyl moiety is optionally substituted with one or more, independently: (i) —F, and when selected to be a perfluorinated alkyl, preferably the perfluorinated alkyl is —$CF_3$; or (ii) —$C_{3-5}$-cycloalkyl; or
(c) $C_{1-6}$-alkyl-O—C(O)—; or
(d) —$C_{3-5}$-cycloalkyl optionally substituted with —F or lower-alkyl In some embodiments where the compound is of Formula A-a1, Formula A-a2, Formula A-a3, or Formula A-a4, preferably the moiety of Formula $R^3$ has the structure of Formula $R^{3a}$:

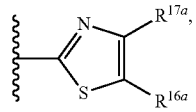

Formula $R^{3a}$ wherein: —$R^{16a}$ and —$R^{17a}$ are independently:
(a) —H;
(b) —$C_{1-6}$-linear-alkyl or $C_{3-6}$-branched-alkyl, which alkyl moiety is optionally substituted with one or more, independently: (i) —F, and when selected to be a perfluorinated alkyl, preferably the perfluorinated alkyl is —$CF_3$; or (ii) —$C_{3-5}$-cycloalkyl;
(c) $C_{1-6}$-alkyl-O—C(O)—;
(d) —$C_{3-5}$-cycloalkyl optionally substituted with —F or lower-alkyl; or
(e) halogen, and when selected to be a halogen, $R^6$ is preferably —Cl or —F.

In some embodiments preferably —$R^{16a}$ is —H, —Cl, —$CH_3$, —F, —Br or —(O)C—O—$CH_2$—$CH_3$ and —$R^{17a}$ is —H, —Cl, or —$CH_3$.

In some embodiments where the compound is of Formula A-a1, preferably the moiety of Formula $R^3$ has the structure of Formula $R^{3b}$:

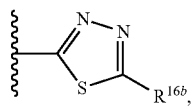

Formula R$^{3b}$ wherein: —R$^{16b}$ is: (a) —H; (b) a halogen; (c) cyclic-, branched-, or linear-alkyl moiety comprising up to 6 carbon atoms which is optionally substituted with one or more substituents which are, independently: (i) —F, and when a fluorinated alkyl is selected is preferably —CF$_3$; (ii) C$_{1-6}$-linear-alkyl-O—C(O)—; (iii) —C$_{3-6}$-branched-alkyl-O—C(O)—; or (iv) C$_{3-6}$-branched-alkyl-O—C(O)—. In some embodiments having the moiety R$^{3b}$, preferably R$^{16b}$ is —H, —CH$_3$, or lower alkyl.

In some embodiments where the compound is of Formula A-a1, preferably the moiety of Formula R$^3$ has the structure of Formula R$^{3c}$:

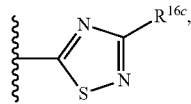

Formula R$^{3c}$ wherein: —R$^{16c}$ is: (a) —H; (b) cyclic-, branched-, or linear-alkyl moiety comprising up to 6 carbon atoms which is optionally substituted with one or more substituents which are, independently: (a) —F, and when a fluorinated alkyl is selected is preferably —CF$_3$; (b) C$_{1-6}$-linear-alkyl-O—C(O)—; (c) C$_{3-6}$-branched-alkyl-O—C(O)—; or (d) C$_{3-6}$-branched-alkyl-O—C(O)—. In some embodiments having the moiety "R$^{3c}$", preferably "R$^{16c}$" is —H or lower alkyl.

In some embodiments where the compound is of Formula A-a1, or a salt thereof, preferably the moiety of Formula R$^3$ has the structure of Formula R$^{3d}$:

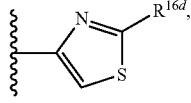

Formula R$^{3d}$ wherein: —R$^{16d}$ is: (a) —H; (b) —C$_{1-6}$-linear-alkyl or C$_{3-6}$-branched-alkyl which is optionally substituted. In some embodiments, preferably R$^{16d}$ is —H.

In some embodiments where the compound is of Formula A-a1, preferably the moiety of Formula R$^3$ has the structure of Formula R$^{3e}$:

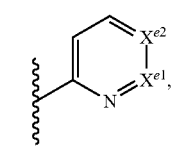

Formula R$^{3e}$ wherein, one of "X$^{e1}$" and "X$^{e2}$" is [—CR$^{e4}$=], and the other is independently [—N=] or [—CR$^{e4}$=], wherein "R$^{e4}$" is, independently: (a) —H; or (b) halogen, and when halogen is preferably, independently, —F or —Cl.

In some embodiments where a moiety of Formula R$^3$ in a compound of Formula A-a1, has the structure of the moiety of Formula R$^{3e}$, preferably the moiety of R$^{3e}$ is:

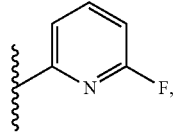 [SMILES: *c1cccc(F)n1]

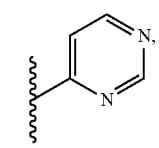 [SMILES: *c1ccncn1]

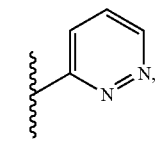 [SMILES: *c1cccnn1]

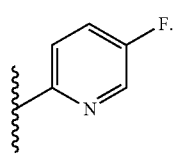 [SMILES: *c1ccc(F)cn1]

EXAMPLES

Examples of the preparation of compounds of the invention are shown next. In each of the Examples, the identity of the compounds prepared were confirmed by a variety of techniques. In all cases the compounds were analyzed by LC/MS.

LC/MS determinations used either an Agilent YMC J'Sphere H-80 (3×50 mm) 5 μm column using mobile phase containing A: 0.1% Trifluoroacetic acid in water and B: acetonitrile with a gradient from 95:5 (A:B) to 0:100 (A:B) over 3.6 min and 0:100 (A:B) for 0.4 min at a flow rate of 1.4 mL/min, UV detection at 254 and 220 nm and Agilent 1100 quadrupole mass spectrometer or an Agilent TC-C18 (2.1×50 mm) 5 μm column using mobile phase containing A: 0.0375% Trifluoroacetic acid in water and B: 0.01875% Trifluoroacetic acid in acetonitrile with a gradient from 90:10 (A:B) for 0.4 min to 90:10 to 0:100 (A:B) over 3 min and 10:90 (A:B) for 0.6 min at a flow rate of 0.8 mL/min, UV detection at 254 and 220 nm and Agilent 6110 quadrupole mass spectrometer.

For some compounds, the identity of the compound was verified by proton NMR and high-resolution MS. Proton NMR was were acquired using a Varian Unity-Inova 400 MHz NMR spectrometer equipped with a either a Varian 400 ATB PFG 5 mm, Nalorac DBG 400-5 or a Nalorac IDG 400-5 probe in accordance with standard analytical techniques, unless specified otherwise, and results of spectral analysis are reported".

High resolving power accurate mass measurements were acquired by use of a Bruker Daltonics 7T Fourier transform ion cyclotron resonance (FTICR) mass spectrometer. Samples were dissolved in acetonitrile:water:acetic acid (50:50:0.1% v/v), and ionized by use of electrospray ionization (ESI) yielding [M+H]+ and/or [M+Na]+. External calibration was accomplished with oligomers of polypropylene glycol (PPG, average molecular weight 1000 Da).

Compounds were tested on human Nav1.7 and Nav1.5 channels stably expressed in HEK 293 cells. Activity toward Nav 1.7 and Nav 1.5 channels was assessed using the following assay methodology.

Sodium Current Measurements on the PatchXpress 7000®:

To measure inactivated state block of sodium channels, test compounds were characterized in an automated PatchXpress® assay (Molecular Devices) using a double-pulse protocol on human Nav1.7 and Nav1.5 channels stably expressed in HEK 293 cells. Cells were held at a potential 20 mV negative to V0.5 inact. An 8000 ms pre-pulse 7 mV positive to V0.5 inact was given followed by a hyperpolarizing 2 ms pulse to −120 mV and a 20 ms test pulse to −20 mV. Protocol was applied to cells in the absence, presence of compound and after washout. The temperature of PatchXpress instruments was maintained at 22° C. The following recording solutions were used. Internal solution (mM): 30 CsCl, 5 HEPES, 10 EGTA, 120 CsF, 5 NaF, 2 $MgCl_2$. External solution (mM): 120 NMDG, 40 NaCl, 1 KCl, 0.5 MgCl2, 5 HEPES, 2.7 CaCl2.

For all electrophysiology experiments, offline analysis was used to correct for current rundown and to determine percent inhibition as a function of drug concentration. $IC_{50}$ values were determined by fitting to the Hill equation.

In the examples that follow certain of the exemplified compounds are prepared as pure enantiomers, or prepared from enantiopure precursors, or are isolated using chiral separation methods after synthesis, for example, chiral chromatography. After isolation of chiral compounds the absolute stereochemistry of the isolated compound was not determined in every example. Accordingly, where pure isomers have been prepared but the absolute configuration has not been verified, the enantiomer isolated in pure form is specified by the label which lists the particular enantiomer in the alternative, e.g., compound "18-9 R or S" and, where there is more than one chiral center the pair is identified in the alternative, e.g. compound "15-9 S,R or R,S (Trans)". In the latter example, "Trans" indicates the relationship of substituents bonded to the different sterocenters relative to a plane in which both stereocenters lie.

Labelling compounds described herein in this manner indicates that stereopure product was isolated and, where two example compounds have been identified as enantiomers, each enantiomer was prepared in isolated form even though the absolute stereochemical configuration was not in every instance determined. Similar designation is entered into the IUPAC names identifying each of the pure isomers isolated in a particular example although the absolute configuration is not in every case determined.

In the examples that follow certain of the exemplified compounds are prepared as pure enantiomers, or prepared from enantiopure precursors, or are isolated using chiral separation methods after synthesis, for example, chiral chromatography. After isolation of chiral compounds the absolute stereochemistry of the isolated compound was not determined in every example. Accordingly, where pure isomers have been prepared but the absolute configuration has not been verified, the enantiomer isolated in pure form is specified by the following convention.

Unless indicated otherwise in the text, where present, isomers of example compounds were not separated. Unless indicated otherwise in the text, where isomers were separated into pure fractions, for example, by super critical fluid chromatography, absolute stereochemistry of separated isomers was not determined.

Where a reaction scheme appearing in an example employs a compound having one or more stereocenters, the stereocenters are indicated with an asterisk, as shown below in illustration compound Def-1.

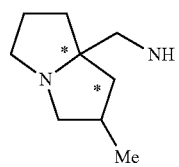

Def-1

Accordingly, Def-1 consists of the following pairs of isomers: (i) Trans-isomers ((2R,7aS)-2-methylhexahydro-1H-pyrrolizin-7a-yl)methanamine (Compound ABC-1) and ((2S,7aR)-2-methylhexahydro-1H-pyrrolizin-7a-yl)methanamine (Compound ABC-2); and (ii) Cis-isomers ((2R,7aR)-2-methylhexahydro-1H-pyrrolizin-7a-yl)methanamine (Compound ABC-3) and ((2S,7aS)-2-methylhexahydro-1H-pyrrolizin-7a-yl)methanamine (Compound ABC-4).

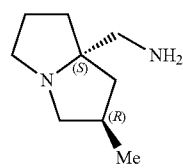

ABC-1

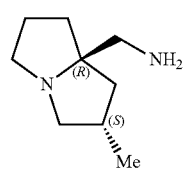

ABC-2

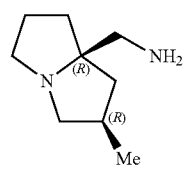

ABC-3

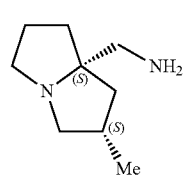

ABC-4

When the compound is prepared and separated into pure enantiomers, albeit without determining the absolute configuration of each enantiomer of the compound, the product will be identified in the title using both enantiomer names, e.g., where ABC-1 and ABC-2 are prepared and separated into pure enantiomers, the title will read "preparation of ((2R,7aS)-2-methylhexahydro-1H-pyrrolizin-7a-yl)methanamine and ((2S,7aR)-2-methylhexahydro-1H-pyrrolizin-7a-yl)methanamine, Compound ABC-enantiomer A (trans) and ABC-enantiomer B (trans), the designation "trans" or "cis"

included in parenthesis with the compound identifier when it is not otherwise unambiguous which pair of enantiomers is being designated when multiple stereocenters are present in the compound. As will be appreciated, identification of each product in the experimental preparation as "ABC-enantiomer A" or "ABC-enantiomer B" is not an association of the enantiomer prepared and isolated with any stereospecific name, only that both said enantiomers were prepared and isolated without the absolute configuration of either compound thus prepared being unambiguously determined.

Where isomeric compounds are prepared in a racemic mixture, asterisks will be inserted into the structural representation to indicate the stereocenters, but the title will reference the preparation of both enantiomers, e.g., where ABC-3 and ABC-4 are prepared as a racemate, the title will read "preparation of ((2R,7aR and 2S7aS)-2-methylhexahydro-1H-pyrrolizin-7a-yl)methanamine".

Throughout the Examples section, the following abbreviations are used to indicate various reagents, substituents and solvents: AcOH=acetic acid; Boc$_2$O=di-tert-butyl carbonate; Bn=Benzyl; DABCO=1,4-diazabicyclo[2.2.2]octane; DAST=diethylaminosulfur trifluoride; DCM=dichloromethane; DEAD=diethylazodicarboxylate; DIPEA=diisopropylamine; 2,4-DMB (2, 4-dimethoxybenzyl-); DMF=dimethylformamide; DMSO=dimethylsulfoxide; DPPA=diphenylphosphoryl azide; dppf=1,1'-bis(diphenylphosphino)ferrocene; EtOAc=ethyl acetate; EtOH=ethanol; HATU=2-(7-Aza-1H-benzotriazole-1-yl)-1,1,3,3-tetramethyluronium hexafluorophosphate; HMPA=hexamethylphosphoramide; HPLC=high-performance liquid chromatography; LDA=lithium diisopropylamide; LiHMDS=lithium bis(trimethylsilyl)amide; MeOH=methanol; MOMCl=methyl chloromethyl ether; MsCl=methanesulfonyl chloride; OTBS=tert-butyldimethylsilyl ether; Pd/C=palladium on carbon; Pd$_2$(dba)$_3$=tris(dibenzylideneacetone)dipalladium (0); PE=petroleum ether; PMBCl=para-methoxybenzyl chloride; Prep-TLC=preparative thin layer chromatography; Py=pyridine; Selectfluor=1-(chloromethyl)-4-fluoro-1,4-diazoniabicyclo[2.2.2]octane ditetrafluoroborate; SFC=Supercritical Fluid Chromatography; TBSCl=tert-butyldimethylsilyl chloride; THF=Tetrahydrofuran; TFA=trifluoroacetic acid; TsOH=para-toluenesulfonic acid; Xantphos=4,5-Bis(diphenylphosphino)-9,9-dimethylxanthene.

EXAMPLES

Generally, compounds of the invention may be prepared in accordance with Scheme A:

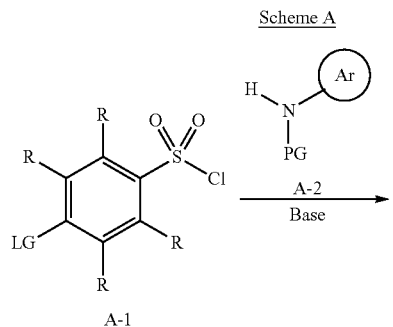

Scheme A

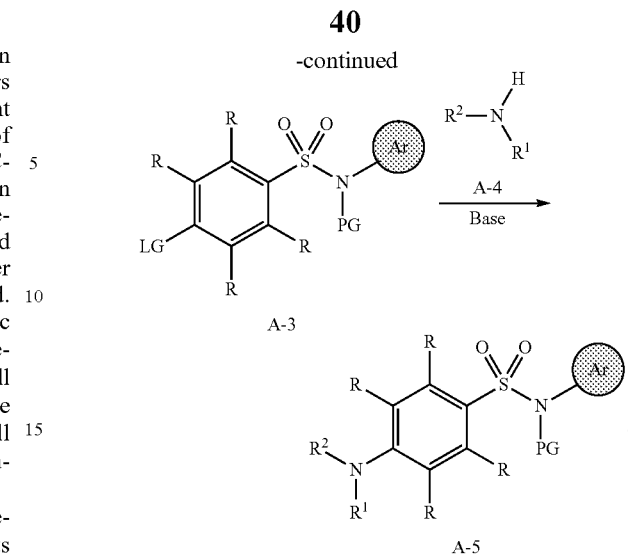

Scheme A illustrates acylation of A-2 with the appropriately functionalized sulfonyl chloride reagent A-1. As illustrated above, A-2 is either a protected heterocyclic amine (wherein PG is a protecting group, for example, but not limited to, Boc, DMB, PMB, or MOM, as defined above) or an unprotected heterocyclic amine (wherein PG is H). With reference to Scheme A, A-1 is a sulfonyl chloride reagent which has the desired substituents (R) and a leaving group (LG) wherein LG can be, for example, but is not limited to, F, Cl, or Br. In the reaction shown, acylation affords intermediate compounds of type A-3 which can undergo nucleophilic aromatic substitution reactions with amine reagents (A-4) to afford final compounds of type A-5. Amine reagents of type A-4 are commercially available, for example, [1-(tetrahydro-1H-pyrrolizin-7a(5H)-yl)methanamine] or can be synthesized as demonstrated in Schemes 4 to 18, as generalized in Scheme B.

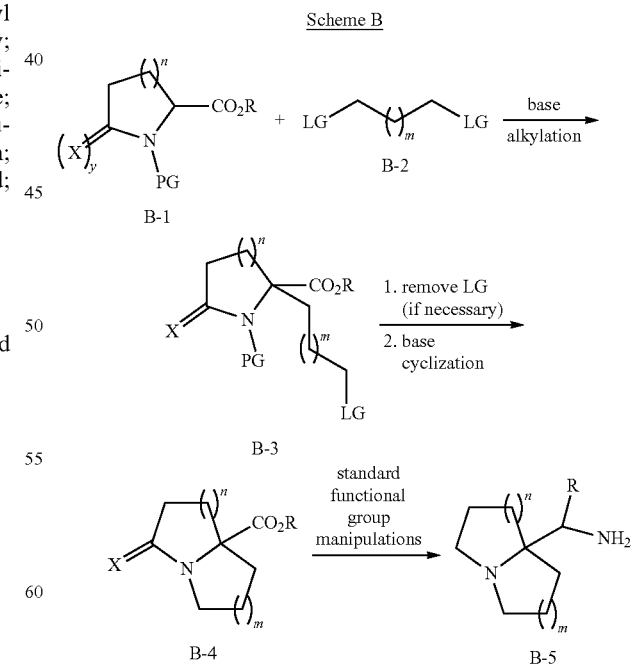

In general, amines suitable for use as reagent compounds used in the preparation of compounds of the invention can be prepared by alkylation of B-1 by reagents of the formula B-2, to provide intermediate B-3. In Scheme B, B-1 represents: (i) a pyrrolidine (n=1, y=0) or piperidine (n=2, y=0); or (ii) a pyrrolidinone (n=1, y=1, X=O) or piperidinone (n=2, y=1, X=O), which is either protected (PG is a protecting group, which can be, but is not limited to, Boc, Cbz, Bn, as defined herein, above) or unprotected (PG=H). Intermediates of type B-3 can undergo alkylation-mediated cyclizations, after PG removal (when PG is a protecting group), to afford bicyclic amines B-4. Standard functional group manipulations, for example, but not limited to, alkylation, amide carbonyl removal, and conversion of ester to methylamine functionality can afford amines of type B-5. These amines can then be used in the chemistry described in Scheme A. Leading references for synthesis of similar ring systems are: 1) *Tetrahedron* 2007, 63, 4712-4724, 2) *Bioorg. Med. Chem. Lett.* 2008, 18, 3737-3740, C) *J. Am. Chem. Soc.* 1998, 120, 10660-10668.

Example 1

Preparation of 5-chloro-2-fluoro-4-[(tetrahydro-1H-pyrrolizin-7a(5H)-yl methyl)amino]-N-(1,2,4-thiadiazol-5-yl)benzenesulfonamide (1-3)

Scheme 1

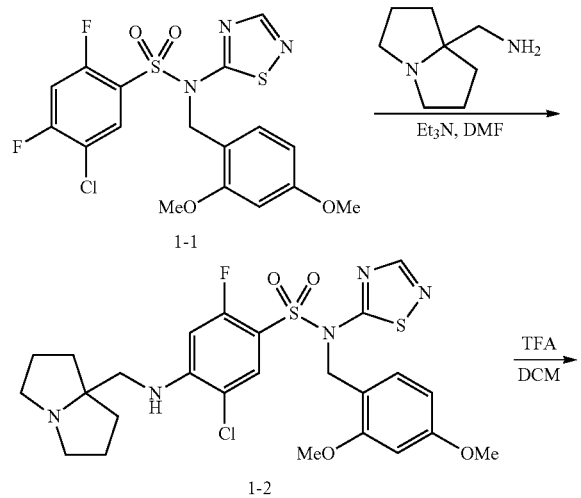

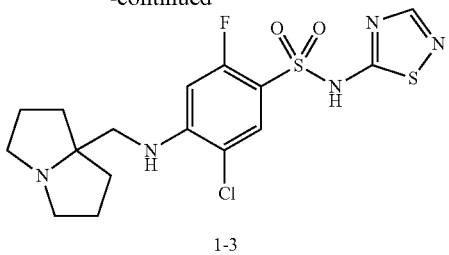

Preparation of 5-chloro-N-(2,4-dimethoxybenzyl)-2-fluoro-4-(((hexahydro-1H-pyrrolizin-7a-yl)methyl)amino)-N-(1,2,4-thiadiazol-5-yl)benzenesulfonamide (1-2)

A mixture of 1-(tetrahydro-1H-pyrrolizin-7a(5H)-yl)methanamine (38 mg, 0.216 mmol), 1-1 (100 mg, 0.216 mmol), Et₃N (109 mg, 1.1 mmol) and DMF (2 mL) was stirred at room temperature overnight. The mixture was poured into water and extracted with EtOAc. The combined organic layers were washed with brine, dried over Na₂SO₄, filtered and the filtrate was concentrated to obtain crude 1-2 which was used in next step directly. MS m/z (M+H): 582.3.

Preparation of 5-chloro-2-fluoro-4-[(tetrahydro-1H-pyrrolizin-7a(5H)-ylmethyl)amino]-N-(1,2,4-thiadiazol-5-yl)benzenesulfonamide (1-3)

To a mixture of 1-2 (70 mg, 0.12 mmol) in DCM (1 mL) was added TFA (0.3 mL). The mixture was stirred at room temperature under N₂ for 2 h. The mixture was concentrated. The crude product was purified by prep-HPLC to give 1-3. ¹H NMR (400 MHz DMSO-d₆) δ 10.26 (s, 1H), 8.39 (s, 1H), 7.59 (d, J=6.8 Hz, 1H), 7.11 (d, J=13.2 Hz, 1H), 6.48 (s, 1H), 3.67 (d, J=6.4 Hz, 2H), 3.42 (d, J=4.8 Hz, 2H), 3.15 (s, 2H), 1.97~2.00 (m, 2H), 1.81~1.88 (m, 6H). HRMS m/z (M+H) 432.0722 found, 432.0731 required.

TABLE 1

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Expl | Structure | Name | Data |
|---|---|---|---|
| 1-4 | 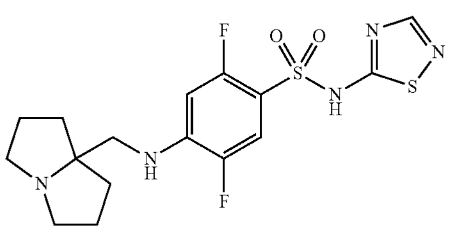 [SMILES: O=S(=O)(Nc1ncns1)c1cc(F)c(NCC23CCCN2CCC3)cc1F] | 2,5-difluoro-4-[(tetrahydro-1H-pyrrolizin-7a(5H)-ylmethyl)amino]-N-(1,2,4-thiadiazol-5-yl)benzenesulfonamide | ¹H NMR (400 MHz DMSO-d₆) δ 11.37 (s, 1H), 8.47 (s, 1H), 7.37 (dd, J = 10.8, 6.4 Hz, 1H), 7.04~7.09 (m, 2H), 3.64 (d, J = 6.4 Hz, 2H), 3.34~3.38 (m, 2H), 3.05~3.08 (m, 2H), 1.78~1.98 (m, 8H). HRMS m/z (M + H) 416.1021 found, 416.1201 required |

TABLE 1-continued

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Expl | Structure | Name | Data |
|---|---|---|---|
| 1-5 | 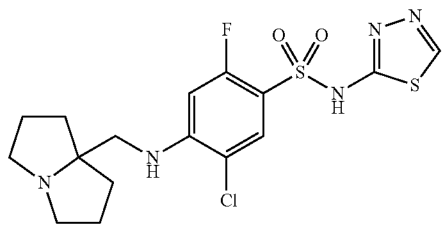 [SMILES: O=S(=O)(Nc1nncs1)c1cc(Cl)c(NCC23CCCN2CCC3)cc1F] | 5-chloro-2-fluoro-4-[(tetrahydro-1H-pyrrolizin-7a(5H)-ylmethyl)amino]-N-(1,3,4-thiadiazol-2-yl)benzenesulfonamide | $^1$H NMR (400 MHz CD$_3$OD) δ 8.53 (s, 1H), 7.74 (d, J = 7.2 Hz, 1H), 6.90 (d, J = 12.8 Hz, 1H), 3.69 (s, 2H), 3.56~3.60 (m, 2H), 3.23~3.28 (m, 2H), 2.00~2.18 (m, 8H). HRMS m/z (M + H) 432.0709 found, 432.0731 required. |
| 1-6 | 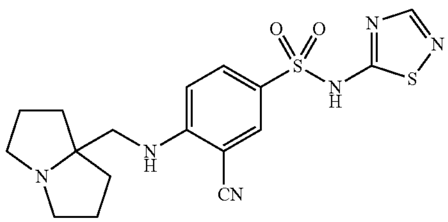 [SMILES: N#Cc1cc(S(=O)(=O)Nc2ncns2)ccc1NCC12CCCN1CCC2] | 3-cyano-4-[(tetrahydro-1H-pyrrolizin-7a(5H)-ylmethyl)amino]-N-(1,2,4-thiadiazol-5-yl)benzenesulfonamide | $^1$H NMR (400 MHz CD$_3$OD) δ 8.17 (s, 1H), 7.93 (d, J = 2.0 Hz, 1H), 7.86 (dd, J = 9.2, 2.0 Hz, 1H), 7.12 (d, J = 9.2 Hz, 1H), 3.73 (s, 2H), 3.56~3.62 (m, 2H), 3.22~3.25 (m, 2H), 2.00~2.19 (m, 8H). HRMS m/z (M + H) 405.1167 found, 405.1167 required. |
| 1-7 | 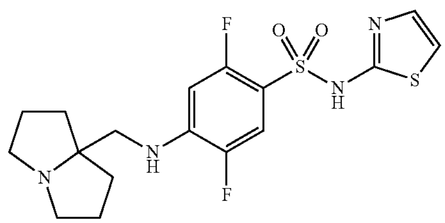 [SMILES: O=S(=O)(Nc1nccs1)c1cc(F)c(NCC23CCCN2CCC3)cc1F] | 5-chloro-2-fluoro-4-[(tetrahydro-1H-pyrrolizin-7a(5H)-ylmethyl)amino]-N-(1,3-thiazol-2-yl)benzenesulfonamide | 1H NMR (400 MHz CD$_3$OD) δ 7.76 (d, J = 7.2 Hz, 1H), 7.12 (d, J = 4.8 Hz, 1H), 6.90 (d, J = 12.4 Hz, 1H), 6.74 (d, J = 4.8 Hz, 1H), 3.68 (s, 2H), 3.55~3.61 (m, 2H), 3.22~3.28 (m, 2H), 2.00~2.18 (m, 8H). HRMS m/z (M + H) 431.0769 found, 431.0778 required. |
| 1-8 | 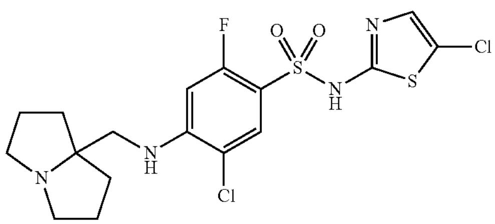 [SMILES: O=S(=O)(Nc1ncc(Cl)s1)c1cc(Cl)c(NCC23CCCN2CCC3)cc1F] | 5-chloro-N-(5-chloro-1,3-thiazol-2-yl)-2-fluoro-4-[(tetrahydro-1H-pyrrolizin-7a(5H)-ylmethyl)amino]benzene-sulfonamide | $^1$H NMR (400 MHz CD$_3$OD) δ 7.71 (d, J = 7.2 Hz, 1H), 7.19 (s, 1H), 7.90 (d, J = 12.8 Hz, 1H), 3.75 (s, 2H), 3.57~3.58 (m, 2H), 3.21~3.23 (m, 2H), 2.02~2.15 (m, 8H). HRMS m/z (M + H) 465.0382 found, 465.0389 required. |
| 1-9 | 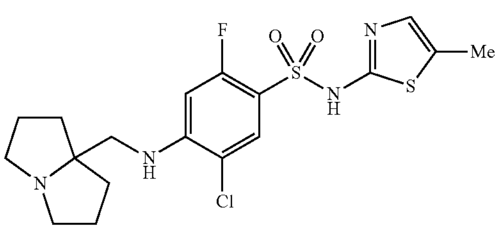 [SMILES: Cc1cnc(NS(=O)(=O)c2cc(Cl)c(NCC34CCCN3CCC4)cc2F)s1] | 5-chloro-2-fluoro-N-(5-methyl-1,3-thiazol-2-yl)-4-[(tetrahydro-1H-pyrrolizin-7a(5H)-ylmethyl)amino]benzene-sulfonamide | $^1$H NMR (400 MHz CD$_3$OD) δ 7.72 (d, J = 7.2 Hz, 1H), 6.89 (d, J = 12.4 Hz, 1H), 6.83 (s, 1H), 3.75 (s, 2H), 3.59 (brs, 2H), 3.23 (brs, 2H), 2.24 (s, 3H), 2.05~2.12 (m, 8H). HRMS m/z (M + H) 445.0925 found, 445.0935 required. |
| 1-10 | 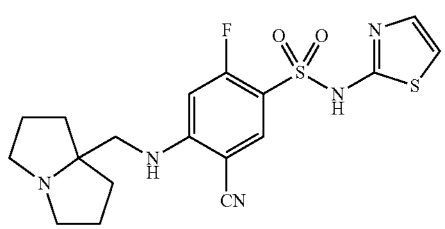 [SMILES: N#Cc1cc(S(=O)(=O)Nc2nccs2)c(F)cc1NCC12CCCN1CCC2] | 5-cyano-2-fluoro-4-[(tetrahydro-1H-pyrrolizin-7a(5H)-ylmethyl)amino]-N-(1,3-thiazol-2-yl)benzenesulfonamide | $^1$H NMR (400 MHz CD$_3$OD) δ 7.98 (d, J = 7.6 Hz, 1H), 7.12 (d, J = 4.8 Hz, 1H), 7.95 (d, J = 12.8 Hz, 1H), 6.74 (d, J = 4.4 Hz, 1H), 3.70 (s, 2H), 3.56~3.62 (m, 2H), 3.22~3.26 (m, 2H), 2.00~2.18 (m, 8H). HRMS m/z (M + H) 422.1127 found, 422.1120 required. |

TABLE 1-continued

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Expl | Structure | Name | Data |
|---|---|---|---|
| 1-11 | 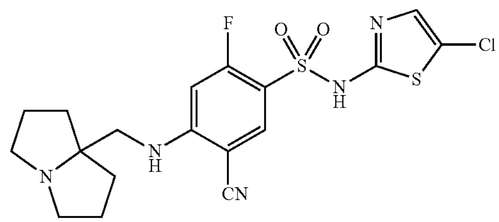 [SMILES: N#Cc1cc(S(=O)(=O)Nc2ncc(Cl)s2)c(F)cc1NCC12CCCN1CCC2] | N-(5-chloro-1,3-thiazol-2-yl)-5-cyano-2-fluoro-4-[(tetrahydro-1H-pyrrolizin-7a(5H)-ylmethyl)amino]benzenesulfonamide | $^1$H NMR (400 MHz CD$_3$OD) δ 7.97 (d, J = 7.6 Hz, 1H), 7.19 (s, 1H), 6.97 (d, J = 12.8 Hz, 1H), 3.71 (s, 2H), 3.57~3.63 (m, 2H), 3.22~3.26 (m, 2H), 2.00~2.18 (m, 8H). HRMS m/z (M + H) 456.0714 found, 456.0731 required. |
| 1-12 | 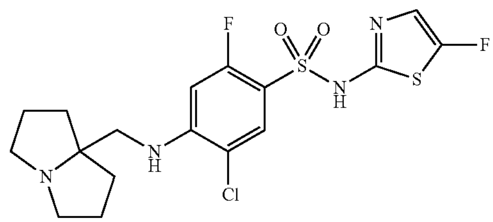 [SMILES: O=S(=O)(Nc1ncc(F)s1)c1cc(Cl)c(NCC23CCCN2CCC3)cc1F] | 5-chloro-2-fluoro-N-(5-fluorothiazol-2-yl)-4-(((hexahydro-1H-pyrrolizin-7a-yl)methyl)amino)benzenesulfonamide | $^1$H NMR (400 MHz, CD$_3$OD) δ 7.76 (d, J = 6.8 Hz, 1H), 7.02 (s, 1H), 6.94 (d, J = 12.4 Hz, 1H), 3.74 (s, 2H), 3.60 (dd, J = 11.2, 6.0 Hz, 2H), 3.29 (s, 2H), 2.06~2.17 (m, 8H). HRMS m/z (M + H) 449.0695 found, 449.0679 required. |
| 1-13 | 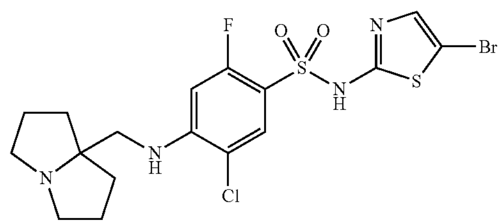 [SMILES: O=S(=O)(Nc1ncc(Br)s1)c1cc(Cl)c(NCC23CCCN2CCC3)cc1F] | N-(5-bromothiazol-2-yl)-5-chloro-2-fluoro-4-(((hexahydro-1H-pyrrolizin-7a-yl)methyl)amino)benzenesulfonamide | $^1$H NMR (400 MHz, CD$_3$OD) δ 7.71 (d, J = 7.2 Hz, 1H), 7.24 (s, 1H), 6.90 (d, J = 12.4 Hz, 1H), 3.72 (s, 2H), 3.56-3.58 (m, 2H), 3.20-3.23 (m, 2H), 2.01-2.16 (m, 8H). HRMS m/z (M + H) 508.9848 found, 508.9878 required. |
| 1-14 | 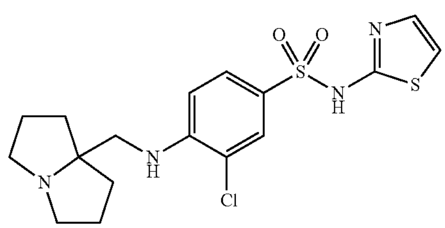 [SMILES: O=S(=O)(Nc1nccs1)c1ccc(NCC23CCCN2CCC3)c(Cl)c1] | 3-chloro-4-(((hexahydro-1H-pyrrolizin-7a-yl)methyl)amino)-N-(thiazol-2-yl)benzenesulfonamide | $^1$H NMR (400 MHz, CD$_3$OD) δ 7.77 (s, 1H), 7.70 (d, J = 8.4 Hz, 1H), 7.13 (d, J = 4.4 Hz, 1H), 7.06 (d, J = 8.8 Hz, 1H), 6.74 (d, J = 4.8 Hz, 1H), 3.77 (s, 2H), 3.60 (dd, J = 11.2, 5.6 Hz, 2H), 3.26 (t, J = 5.2 Hz, 2H), 2.17 (d, J = 6.8 Hz, 4H), 2.08 (d, J = 8.0 Hz, 4H). HRMS m/z (M + H) 413.0860 found, 413.0867 required. |
| 1-15 | 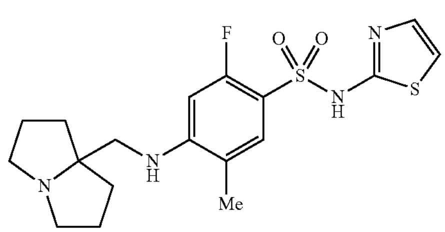 | 2-fluoro-4-(((hexahydro-1H-pyrrolizin-7a-yl)methyl)amino)-5-methyl-N-(thiazol-2-yl)benzenesulfonamide | $^1$H NMR (400 MHz, CD$_3$OD) δ 7.54 (d, J = 8.0 Hz, 1H), 7.12 (d, J = 4.4 Hz, 1H), 6.72 (t, J = 4.8 Hz, 1H), 6.69 (d, J = 13.2 Hz, 1H), 3.70 (s, 2H), 3.57-3.62 (m, 2H), 3.21-3.25 (m, 2H), 3.23 (s, 3H), 2.14-2.19 (m, 4H), 2.06 (s,4H). HRMS m/z (M + H) 411.1323 found, 411.1319 required. |
| 1-16 | 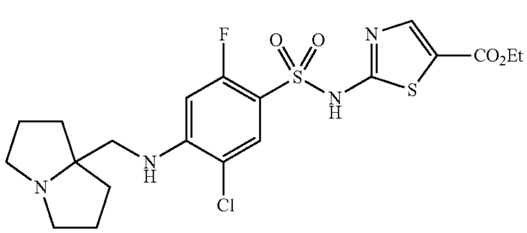 [SMILES: CCOC(=O)c1cnc(NS(=O)(=O)c2cc(Cl)c(NCC34CCCN3CCC4)cc2F)s1] | ethyl 2-(5-chloro-2-fluoro-4-(((hexahydro-1H-pyrrolizin-7a-yl)methyl)amino)phenyl sulfonamido)thiazole-5-carboxylate | $^1$H NMR (400 MHz, CD$_3$OD) δ 7.86 (s, 1H), 7.75 (d, J = 7.2 Hz, 1H), 6.90 (d, J = 13.2 Hz, 1H), 4.31 (q, J = 7.2 Hz, 2H), 3.70 (s, 2H), 3.56~3.70 (m, 2H), 3.22~3.28 (m, 2H), 2.12~2.16 (m, 4H), 2.03~2.09 (m, 4H), 1.33 (t, J = 7.2 Hz, 3H). HRMS m/z (M + H) 503.0996 found, 503.0984 required. |

TABLE 1-continued

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Expl | Structure | Name | Data |
|---|---|---|---|
| 1-17 | 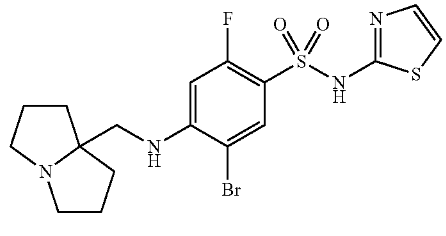 [SMILES: O=S(=O)(Nc1nccs1)c1cc(Br)c(NCC23CCCN2CCC3)cc1F] | 5-bromo-2-fluoro-4-(((hexahydro-1H-pyrrolizin-7a-yl)methyl)amino)-N-(thiazol-2-yl)benzenesulfonamide | $^1$H NMR (400 MHz, CD$_3$OD) δ 7.90 (d, J = 7.4 Hz, 1H), 7.10 (d, J = 4.7 Hz, 1H), 6.85 (d, J = 12.5 Hz, 1H), 6.73 (d, J = 4.7 Hz, 1H), 3.67 (s, 2H), 3.54-3.60 (m, 2H), 3.17-3.27 (m, 2H), 2.13~2.17 (m, 4H), 2.03~2.08 (m, 4H). HRMS m/z (M + H) 475.0279 found, 475.0268 required. |
| 1-18 | 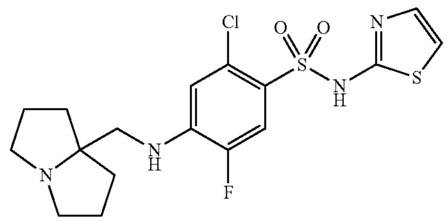 | 2-chloro-5-fluoro-4-(((hexahydro-1H-pyrrolizin-7a-yl)methyl)amino)-N-(thiazol-2-yl)benzenesulfonamide | $^1$H NMR (400 MHz, CD$_3$OD) δ 7.70 (d, J = 11.6 Hz, 1H), 7.09 (t, J = 4.8 Hz, 2H), 6.72 (d, J = 4.8 Hz, 1H), 3.59~3.64 (m, 4H), 3.21~3.30 (m, 2H), 2.13~2.20 (m, 4H), 2.00~2.10 (m, 4H). HRMS m/z (M + H) 431.0773 found, 431.0773 required. |
| 1-19 | 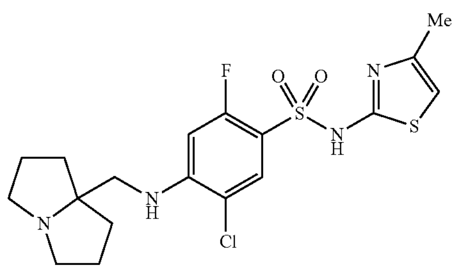 [SMILES: Cc1csc(NS(=O)(=O)c2cc(Cl)c(NCC34CCCN3CCC4)cc2F)n1] | 5-chloro-2-fluoro-4-(((hexahydro-1H-pyrrolizin-7a-yl)methyl)amino)-N-(4-methylthiazol-2-yl)benzenesulfonamide | $^1$H NMR (400 MHz, CD$_3$OD) δ 7.71 (d, J = 6.8 Hz, 1H), 6.87 (d, J = 12.8 Hz, 1H), 6.27 (s, 1H), 3.72 (s, 2H), 3.55-3.58 (m, 2H), 3.20-3.22 (m, 2H), 2.00-2.15 (m, 8H). HRMS m/z (M + H) 445.0943 found, 445.0930 required. |
| 1-20 | 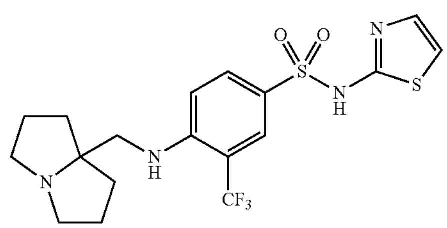 [SMILES: O=S(=O)(Nc1nccs1)c1ccc(NCC23CCCN2CCC3)c(C(F)(F)F)c1] | 4-(((hexahydro-1H-pyrrolizin-7a-yl)methyl)amino)-N-(thiazol-2-yl)-3-(trifluoromethyl)benzenesulfonamide | $^1$H NMR (400 MHz, CD$_3$OD) δ 7.95 (s, 1H), 7.92 (d, J = 8.8 Hz, 1H), 7.19 (d, J = 8.8 Hz, 1H), 7.09 (d, J = 4.8 Hz, 1H), 6.72 (d, J = 4.4 Hz, 1H), 3.75 (s, 2H), 3.52~3.57 (m, 2H), 3.30 (dd, J = 3.2, 1.6 Hz, 2H), 2.02~2.14 (m, 8H). HRMS m/z (M + H) 447.1141 found, 447.1131 required. |
| 1-21 | 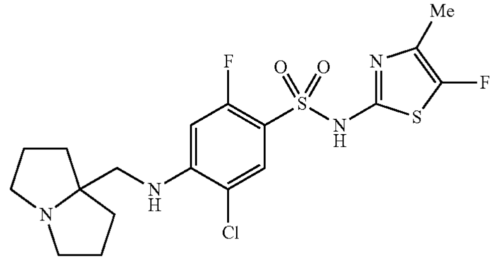 [SMILES: Cc1nc(NS(=O)(=O)c2cc(Cl)c(NCC34CCCN3CCC4)cc2F)sc1F] | 5-chloro-2-fluoro-N-(5-fluoro-4-methylthiazol-2-yl)-4-(((hexahydro-1H-pyrrolizin-7a-yl)methyl)amino)benzenesulfonamide | $^1$H NMR (400 MHz, CD$_3$OD) δ 7.71 (d, J = 7.2 Hz, 1H), 6.88 (d, J = 12.8 Hz, 1H), 3.69 (s, 2H), 3.55-3.61 (m, 2H), 3.22-3.25 (m, 2H), 2.01-2.13 (m, 11H). HRMS m/z (M + H) 463.0849 found, 463.0835 required. |

Example 2

3-cyano-4-[(tetrahydro-1H-pyrrolizin-7a(5H)-ylmethyl)amino]-N-(1,3-thiazol-2-yl)benzenesulfonamide (2-2)

Scheme 2

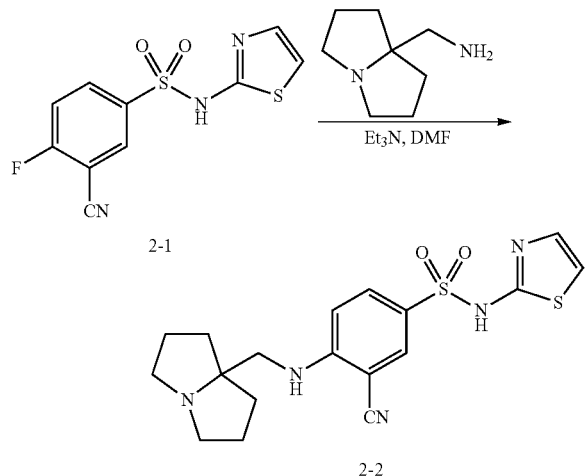

2-1

2-2

Preparation of 3-cyano-4-[(tetrahydro-1H-pyrrolizin-7a(5H)-ylmethyl)amino]-N-(1,3-thiazol-2-yl)benzenesulfonamide (2-2)

A mixture of 1-(tetrahydro-1H-pyrrolizin-7a(5H)-yl) methanamine (137 mg, 0.77 mmol), 2-1 (200 mg, 0.70 mmol), $Et_3N$ (357 mg, 3.53 mmol) and DMF (2 mL) was stirred at 40° C. under $N_2$ overnight. The mixture was concentrated. The crude product was purified by prep-HPLC to give 2-2. $^1$H NMR (400 MHz $CD_3OD$) δ 7.95 (d, J=2 Hz, 1H), 7.90 (dd, J=9.2, 2.4 Hz, 1H), 7.09~7.13 (m, 2H), 6.72 (d, J=4.8 Hz, 1H), 3.73 (s, 2H), 3.57~3.63 (m, 2H), 3.23~3.29 (m, 2H), 2.00~2.17 (m, 8H). HRMS m/z (M+H) 404.1228 found, 404.1215 required.

TABLE 2

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Expl | Structure | Name | Data |
|---|---|---|---|
| 2-3 | 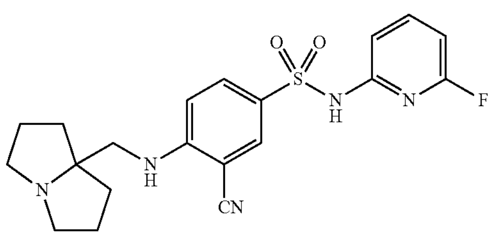 [SMILES: N#Cc1cc(S(=O)(=O)Nc2cccc(F)n2)ccc1NCC12CCCN1CCC2] | 3-cyano-N-(6-fluoropyridin-2-yl)-4-[(tetrahydro-1H-pyrrolizin-7a(5H)-ylmethyl)amino]benzenesulfonamide | $^1$H NMR (400 MHz $CD_3OD$) δ 8.09 (d, J = 2.0 Hz, 1H), 8.99 (d, J = 9.2 Hz, 1H), 7.74 (dd, J = 16.4, 8.4 Hz, 1H), 7.12 (d, J = 9.2 Hz, 1H), 6.91 (d, J = 8.0 Hz, 1H), 6.58 (dd, J = 8.0, 2.0 Hz, 1H), 3.71 (s, 2H), 3.55~3.61 (m, 2H), 3.21~3.25 (m, 2H), 1.99~2.17 (m, 8H). HRMS m/z (M + H) 416.1546 found, 416.1556 required. |
| 2-4 | 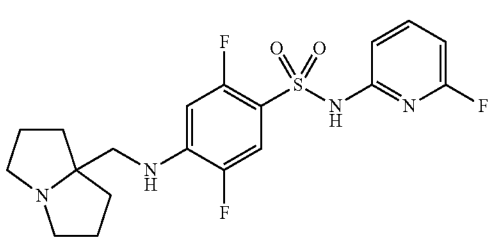 [SMILES: O=S(=O)(Nc1cccc(F)n1)c1cc(F)c(NCC23CCCN2CCC3)cc1F] | 2,5-difluoro-N-(6-fluoropyridin-2-yl)-4-[(tetrahydro-1H-pyrrolizin-7a(5H)-ylmethyl)amino]benzenesulfonamide | $^1$H NMR (400 MHz $CD_3OD$) δ 7.73 (dd, J = 16.4, 8.0 Hz, 1H), 7.59 (dd, J = 10.8, 6.4 Hz, 1H), 6.90 (dd, J = 8.0, 1.2 Hz, 1H), 6.83 (dd, J = 12.0, 6.8 Hz, 1H), 6.57 (dd, J = 8.0, 2.0 Hz, 1H), 3.54~3.58 (m, 4H), 3.19~3.24 (m, 2H), 2.07~2.18 (m, 4H), 1.97~2.04 (m, 4H). HRMS m/z (M + H) 427.1416 found, 427.1415 required. |

Example 3

5-chloro-2-fluoro-N-(pyrimidin-4-yl)-4-[(tetrahydro-1H-pyrrolizin-7a(5H)-ylmethyl)amino]benzenesulfonamide (3-3)

Scheme 3

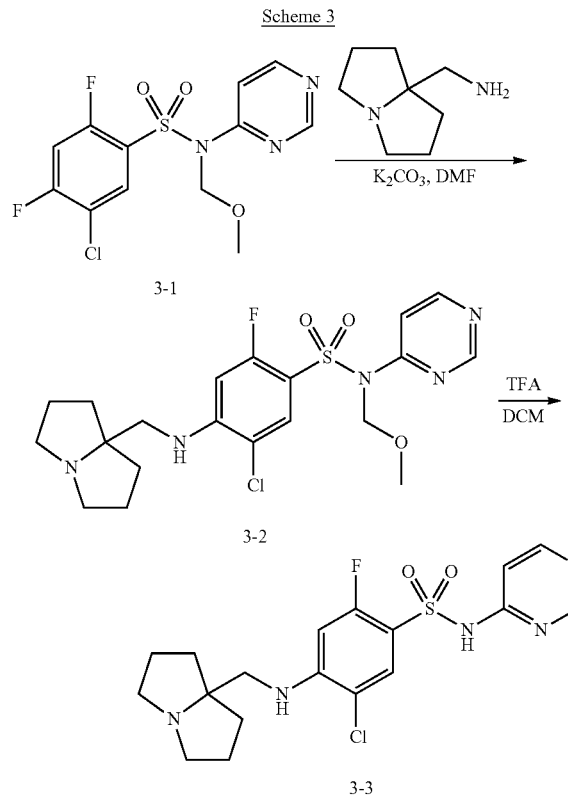

Preparation of 5-chloro-2-fluoro-4-(((hexahydro-1H-pyrrolizin-7a-yl)methyl)amino)-N-(methoxymethyl)-N-(pyrimidin-4-yl)benzenesulfonamide (3-2)

A mixture of 1-(tetrahydro-1H-pyrrolizin-7a(5H)-yl)methanamine (35 mg, 0.2 mmol), 3-1 (65 mg, 0.2 mmol), $K_2CO_3$ (82 mg, 0.59 mmol) and DMF (2 mL) was stirred at room temperature under $N_2$ overnight. The mixture was poured into water and extracted with EtOAc. The combined organic layers were washed with brine, dried over $Na_2SO_4$, filtered and the filtrate was concentrated. The crude 3-2 was used in next step directly. MS m/z (M+H) 470.1.

Preparation of 5-chloro-2-fluoro-N-(pyrimidin-4-yl)-4-[(tetrahydro-1H-pyrrolizin-7a (5H)-ylmethyl)amino]benzenesulfonamide (3-3)

To a mixture of 3-2 (50 mg, 0.1 mmol) in DCM (1 mL) was added TFA (0.3 mL). The mixture was stirred at 40° C. under $N_2$ for 4 h. The mixture was concentrated. The crude product was purified by prep-HPLC to give 3-3. $^1$H NMR (400 MHz $CD_3OD$) δ 8.64 (s, 1H), 8.34 (d, J=6.4 Hz, 1H), 7.89 (d, J=7.2 Hz, 1H), 7.09 (d, J=6.4 Hz, 1H), 6.88 (d, J=12.8 Hz, 1H), 3.69 (s, 2H), 3.56~3.59 (m, 2H), 3.20~3.23 (m, 2H), 1.99~2.15 (m, 8H). HRMS m/z (M+H) 426.1179 found, 426.1167 required.

TABLE 3

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Example | Structure | Name | Data |
|---|---|---|---|
| 3-4 | 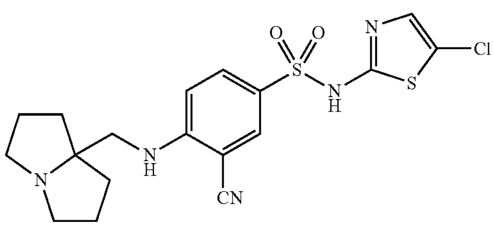 [SMILES: N#Cc1cc(S(=O)(=O)Nc2ncc(Cl)s2)ccc1NCC12CCCN1CCC2] | N-(5-chloro-1,3-thiazol-2-yl)-3-cyano-4-[(tetrahydro-1H-pyrrolizin-7a(5H)-ylmethyl)amino]benzenesulfonamide | $^1$H NMR (400 MHz $CD_3OD$) δ 7.94 (d, J = 2.4 Hz, 1H), 7.87 (dd, J = 8.8, 2.0 Hz, 1H), 7.17 (s, 1H), 7.13 (d, J = 9.2 Hz, 1H), 3.74 (s, 2H), 3.57~3.63 (m, 2H), 3.23~3.27 (m, 2H), 2.12~2.19 (m, 4H), 2.01~2.10 (m, 4H). HRMS m/z (M + H) 438.0801 found, 438.0825 required. |
| 3-5 | 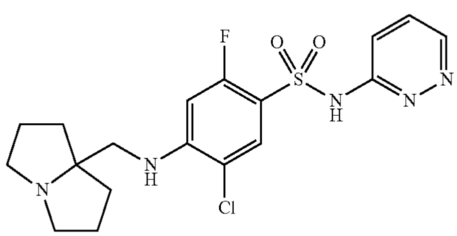 [SMILES: O=S(=O)(Nc1cccnn1)c1cc(Cl)c(NCC23CCCN2CCC3)cc1F] | 5-chloro-2-fluoro-N-(pyridazin-3-yl)-4-[(tetrahydro-1H-pyrrolizin-7a(5H)-ylmethyl)amino]benzenesulfonamide | $^1$H NMR (400 MHz $CD_3OD$) δ 8.28 (d, J = 3.2 Hz, 1H), 7.90 (d, J = 9.6 Hz, 1H), 7.82 (d, J = 7.2 Hz, 1H), 7.60 (dd, J = 9.6, 4.4 Hz, 1H), 6.87 (d, J = 12.8 Hz, 1H), 3.68 (s, 2H), 3.54~3.60 (m, 2H), 3.20~3.26 (m, 2H), 2.00~2.16 (m, 8H). HRMS m/z (M + H) 426.1140 found, 426.1167 required. |

TABLE 3-continued

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Example | Structure | Name | Data |
|---|---|---|---|
| 3-6 | 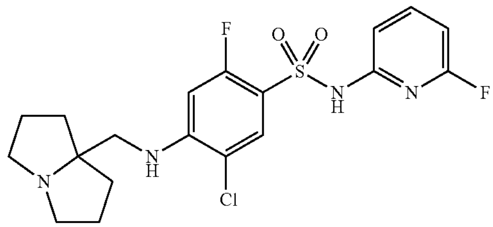 [SMILES: O=S(=O)(Nc1cccc(F)n1)c1cc(Cl)c(NCC23CCCN2CCC3)cc1F] | 5-chloro-2-fluoro-N-(6-fluoropyridin-2-yl)-4-[(tetrahydro-1H-pyrrolizin-7a(5H)-ylmethyl)amino]benzenesulfonamide | $^1$H NMR (400 MHz CD$_3$OD) δ 7.86 (d, J = 7.2 Hz, 1H), 7.73 (q, J = 8.0 Hz, 1H), 6.85~6.91 (m, 2H), 6.57 (d, J = 7.2 Hz, 1H), 3.67 (s, 2H), 3.55~3.56 (m, 2H), 3.21~3.23 (m, 2H), 2.00~2.14 (m,8H). HRMS m/z (M + H) 443.1100 found, 443.1120 required. |
| 3-7 | 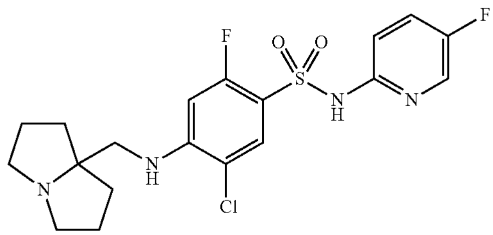 [SMILES: O=S(=O)(Nc1ccc(F)cn1)c1cc(Cl)c(NCC23CCCN2CCC3)cc1F] | 5-chloro-2-fluoro-N-(5-fluoropyridin-2-yl)-4-[(tetrahydro-1H-pyrrolizin-7a(5H)-ylmethyl)amino]benzenesulfonamide | $^1$H NMR (400 MHz DMSO-d$_6$) δ 11.58 (s, 1H), 11.16 (s, 1H), 8.13 (d, J = 2.8 Hz, 1H), 7.63~7.65 (m, 2H), 7.02~7.07 (m, 2H), 3.68 (d, J = 4.4 Hz, 2H), 3.31 (s, 2H), 3.03~3.06 (m, 2H), 1.92~1.95 (m, 2H), 1.74~1.87 (m, 6H). HRMS m/z (M + H) 443.1105 found, 443.1120 required. |

Example 4

3-cyano-4-{[((2S,7aR and 2R,7aS)-2-methyltetrahydro-1H-pyrrolizin-7a(5H)-yl)methyl]amino}-N-(1,3-thiazol-2-yl)benzenesulfonamide (4-8)

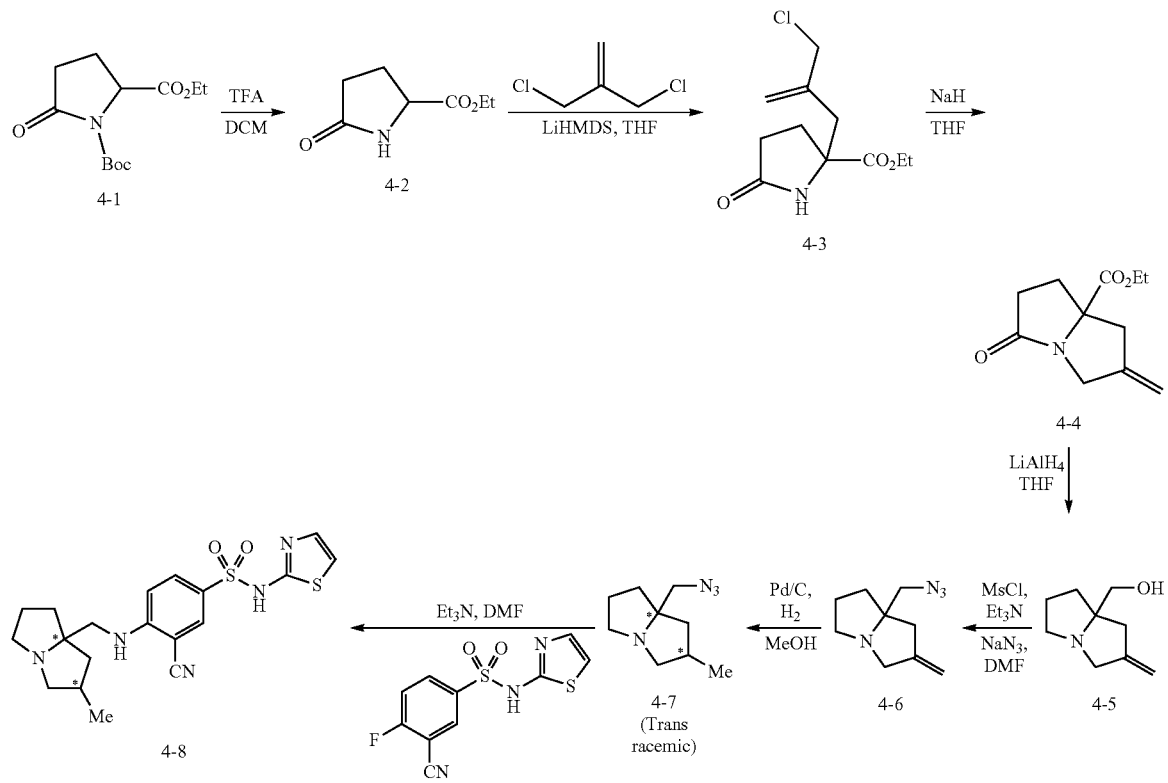

Scheme 4

Preparation of ethyl 5-oxopyrrolidine-2-carboxylate (4-2)

A mixture of 4-1 (24 g, 93 mmol, TFA (20 mL) in DCM (40 mL) was stirred at room temperature under $N_2$ overnight. The mixture was concentrated in vacuo to give a residue which was diluted with a solution of saturated $NaHCO_3$, extracted with EtOAc. The organic layer was washed with brine, dried over $Na_2SO_4$ and filtered. The filtrate was concentrated in vacuo to give the final product. $^1$H NMR δ (ppm) ($CDCl_3$): 6.31 (s, 1H), 4.13~4.19 (m, 3H), 2.12~2.46 (m, 4H), 1.25~1.28 (m, 3H).

Preparation of ethyl 2-(2-(chloromethyl)allyl)-5-oxopyrrolidine-2-carboxylate (4-3)

To a solution of 4-2 (8.0 g, 51 mmol) and 3-chloro-2-(chloromethyl) prop-1-ene (25.4 g, 204 mmol) in dry THF (50 mL) was added LiHMDS (107 mL, 107 mmol) at −40° C. under $N_2$. Then the mixture was stirred at room temperature for 2 h. After the reaction completed, $NH_4Cl$ was added into the mixture until the pH was adjusted to 7. The mixture was extracted with EtOAc. The organic layer was washed with brine, dried over $Na_2SO_4$. The product was purified by column chromatography (PE:EtOAc=1:1). $^1$H NMR δ (ppm) ($CDCl_3$): 6.46 (s, 1H), 5.29 (s, 1H), 5.03 (s, 1H), 4.16~4.21 (m, 2H), 3.97 (s, 2H), 2.88~2.92 (m, 1H), 2.34~2.52 (m, 4H), 2.10~2.17 (m, 1H), 1.25~1.28 (m, 3H).

Preparation of ethyl 2-methylene-5-oxohexahydro-1H-pyrrolizine-7a-carboxylate (4-4)

To a mixture of NaH (980 mg, 24.5 mmol) in dry THF (400 mL) was added the solution of 4-3 (5.0 g, 20 mmol) in THF at 0° C. under $N_2$. Then the mixture was refluxed overnight. After the reaction completed, water was added into the mixture carefully. The mixture was extracted with EtOAc. The organic layer was washed with brine, dried over $Na_2SO_4$. The product was purified by column chromatography (PE:EtOAc=1:1). $^1$H NMR δ (ppm) ($CDCl_3$): 5.20 (s, 1H), 4.98 (s, 1H), 4.12~4.25 (m, 3H), 3.65~3.69 (m, 1H), 2.98~3.02 (m, 1H), 2.68~2.78 (m, 1H), 2.53~2.59 (m, 1H), 2.36~2.45 (m, 2H), 2.04~2.12 (m, 1H), 1.20~1.25 (m, 3H).

Preparation of (2-methylenehexahydro-1H-pyrrolizin-7a-yl)methanol (4-5)

To a solution of $LiAlH_4$ (545 mg, 14 mmol) in THF (20 mL) was added the solution of 4-4 (600 mg, 2.9 mmol) in THF at 0° C. under $N_2$. Then the mixture was refluxed for 4 h. After the reaction completed, water (0.3 mL) was added into the mixture which was stirred for 10 min. $MgSO_4$ was added and the mixture was stirred for another 30 min. The solid was removed by filtration and the filtrate was concentrated by vacuo to give a product. The crude product was used in the next step directly. $^1$H NMR δ (ppm) ($CDCl_3$): 4.85~4.88 (m, 2H), 3.56~3.60 (m, 1H), 3.21~3.27 (m, 3H), 3.00~3.06 (m, 1H), 2.59~2.65 (m, 1H), 2.27~2.43 (m, 2H), 1.71~1.90 (m, 4H).

Preparation of 7a-(azidomethyl)-2-methylenehexahydro-1H-pyrrolizine (4-6)

To a solution of 4-5 (2.0 g, 13 mmol), $Et_3N$ (3.9 g, 39 mmol) in $CH_2Cl_2$ was added MsCl (1.8 g, 15.7 mmol) dropwise at 0° C. under $N_2$. Then the mixture was stirred at room temperature under $N_2$ for 1 h. After the reaction completed, the mixture was diluted with water and extracted with $CH_2Cl_2$. The organic layer was washed with brine, dried over $Na_2SO_4$, filtered and concentrated. The crude product was used in next step without further purification To the solution of the above crude product in DMF was added $NaN_3$ (5.1 g, 70 mmol), then the mixture was stirred at 80° C. under $N_2$ overnight. After the reaction completed, the mixture was diluted with EtOAc and the solid was removed by filtration, the filtrate was washed with water. The organic layer was washed with brine, dried over $Na_2SO_4$. The product was purified by column chromatography (PE:EtOAc=5:1). $^1$H NMR δ (ppm) ($CDCl_3$): 4.78~4.89 (m, 2H), 3.60~3.64 (m, 1H), 3.05~3.60 (m, 4H), 2.54~2.60 (m, 1H), 2.25~2.48 (m, 2H), 1.80~1.89 (m, 4H).

Preparation of ((2R,7aS and 2S,7aR)-2-methylhexahydro-1H-pyrrolizin-7a-yl)methanamine (4-7)

To a solution of 4-6 (200 mg, 1.1 mmol) in $CH_3OH$ was added Pd/C (50 mg, wt %: 10%). Then the mixture was stirred at room temperature under $H_2$ for 2 h. After completion of the reaction, Pd/C was removed by filtration and the filtrate was concentrated in vacuo to give the crude product, (4-7) which was used in the next step directly.

Preparation of 3-cyano-4-{[((2R,7aS and 2S,7aR)-2-methyltetrahydro-1H-pyrrolizin-7a(5Hyl)methyl]amino}-N-(1,3-thiazol-2-yl)benzenesulfonamide (4-8)

A mixture of 4-7 (100 mg, 0.65 mmol), 2-1 (184 mg, 0.65 mmol), $Et_3N$ (262 mg, 2.6 mmol) in DMF was stirred for 3 h at room temperature under $N_2$. After the reaction completed, the mixture was concentrated in vacuo to give the crude product, 4-8, which comprises a racemic mixture of 3-cyano-4-{[((2R,7aS)-2-methyltetrahydro-1H-pyrrolizin-7a(5Hyl)methyl]amino}-N-(1,3-thiazol-2-yl)benzenesulfonamide and 3-cyano-4-{[((2S,7aR)-2-methyltetrahydro-1H-pyrrolizin-7a(5Hyl)methyl]amino}-N-(1,3-thiazol-2-yl) benzenesulfonamide, as crude product which was purified by prep-HPLC. $^1$H NMR δ (ppm) ($CD_3OD$): 7.88~7.96 (m, 2H), 7.10~7.13 (m, 2H), 7.6.73 (d, J=8.0 Hz, 1H), 3.72~3.83 (m, 3H), 3.35~3.37 (m, 2H), 2.65~2.77 (m, 1H), 2.35~2.49 (m, 2H), 2.00~2.26 (m, 4H), 1.61~1.69 (m, 1H), 1.08~1.15 (m, 3H). HRMS $C_{19}H_{23}N_5O_2S_2$ [M+H] calc 418.1371, obs 418.1381.

TABLE 4

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Expl | Structure | Name | Data |
|---|---|---|---|
| 4-9 | 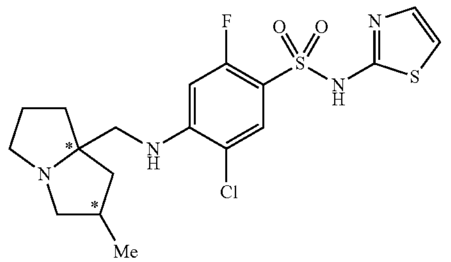 | 5-chloro-2-fluoro-4-{[((2S,7aR and 2R,7aS)-2-methyl-tetrahydro-1H-pyrrolizin-7a(5H)-yl)methyl]amino}-N-(1,3-thiazol-2-yl)-benzenesulfonamide | $^1$HNMR (400 MHz, CD$_3$OD) δ 7.75 (d, J = 8.0 Hz, 1H), 7.10 (d, J = 8.0 Hz, 1H), 6.85-6.89 (m, 1H), 6.73 (d, J = 8.0 Hz, 1H), 3.68-3.84 (m, 3H), 3.32-3.41 (m, 3H), 2.62-2.75 (m, 1H), 1.93-2.46 (m, 5H), 1.59-1.65 (m, 1H), 1.07-1.10 (m, 3H). MS m/z (M + H): 446.1 |
| 4-10 | 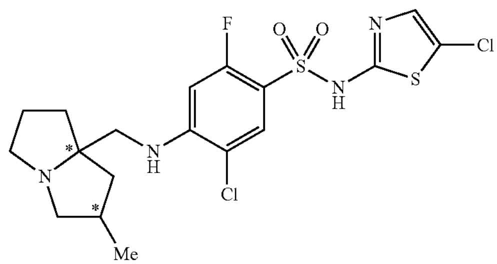 [SMILES: CC1CN2CCCC2(CNc2cc(F)c(S(=O)(=O)Nc3ncc(Cl)s3)cc2Cl)C1] | 5-chloro-N-(5-chlorothiazol-2-yl)-2-fluoro-4-((((2S,7aR and 2R,7aS)-2-methylhexahydro-1H-pyrrolizin-7a-yl)methyl)-amino)benzene-sulfonamide | $^1$HNMR (400 MHz, CD$_3$OD) δ 7.70 (d, J = 8.0 Hz, 1H), 7.18 (s, 1H), 6.82-6.90 (m, 1H), 3.68-3.82 (m, 3H), 3.32 (s, 3H), 2.66-2.72 (m, 1H), 1.91-2.42 (m, 5H), 1.58-1.64 (m, 1H), 1.07-1.08 (m, 3H). MS m/z (M + H): 481.0 |
| 4-11 | 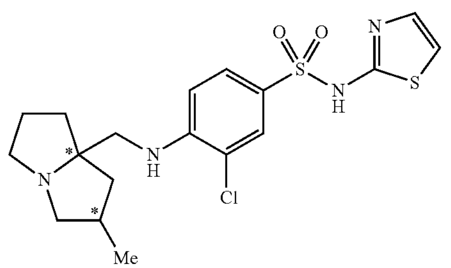 [SMILES: CC1CN2CCCC2(CNc2ccc(S(=O)(=O)Nc3nccs3)cc2Cl)C1] | 3-chloro-4-((((2S/7aR and 2R,7aS)-2-methylhexahydro-1H-pyrrolizin-7a-yl)methyl)amino)-N-(thiazol-2-yl)benzenesulfonamide | $^1$H NMR (400 MHz, CD$_3$OD) δ 7.75 (s, 1H), 7.67 (d, J = 2.0 Hz, 8.8 Hz, 1H), 7.09 (d, J = 4.8 Hz, 1H), 7.02 (d, J = 4.4 Hz, 1H), 6.71 (d, J = 4.4 Hz, 1H), 3.80-3.84 (m, 1H), 3.71 (s, 2H) 3.30-3.34 (m, 2H), 2.70-2.75 (m, 1H), 2.34-2.48 (m, 2H), 2.25-2.27 (m, 1H), 2.17-2.24 (m, 3H), 2.10-2.12 (m, 1H), 1.96-2.11 (m, 3H). HRMS m/z (M + H) 427.1028 found, 427.1024 required. |

Example 5

3-cyano-4-{[(1S)-1-(tetrahydro-1H-pyrrolizin-7a(5H)-yl)ethyl]amino}-N-(1,3-thiazol-2-yl)benzene-sulfonamide and 3-cyano-4-{[(1R)-1-(tetrahydro-1H-pyrrolizin-7a(5H)-yl)ethyl]amino}-N-(1,3-thiazol-2-yl)benzenesulfonamide (5-6 isomer A and 5-7 isomer B)

Scheme 5

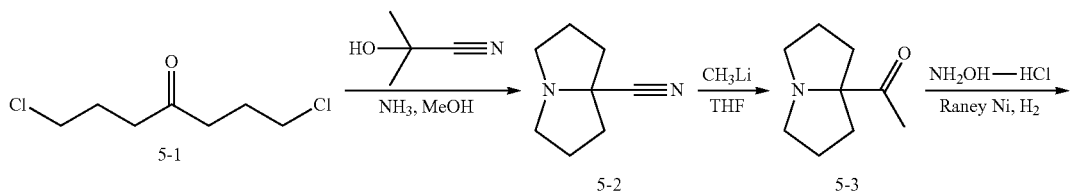

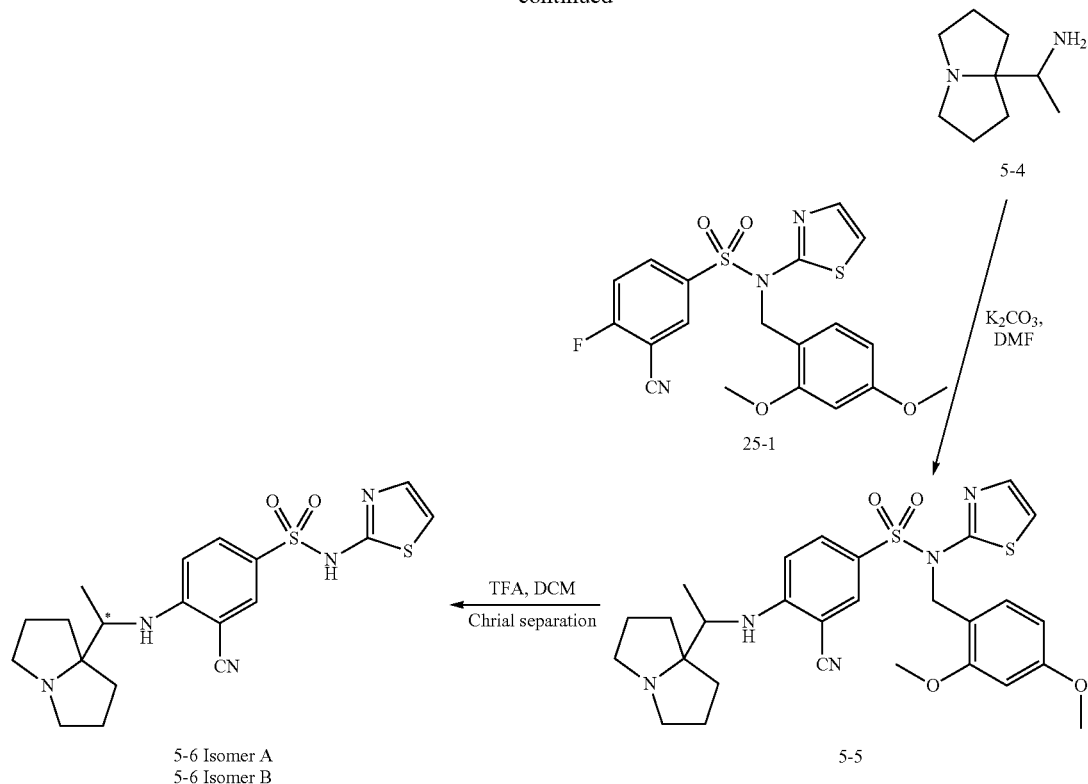

5-6 Isomer A
5-6 Isomer B

Preparation of hexahydro-1H-pyrrolizine-7a-carbonitrile (5-2)

A mixture of 5-1 (20 g, 109.2 mmol) and 2-hydroxy-2-methylpropanenitrile (105 g, 1.1 mmol), in NH$_3$/MeOH (1000 mL) was stirred at room temperature for 24 h. The mixture was concentrated. The residue was purified by column chromatography on silica gel (PE:EtOAc=10:1) to give the product of 5-2 as a yellow oil. $^1$H NMR δ (ppm) (CDCl$_3$): 3.15~3.21 (m, 2H), 2.52~2.58 (m, 2H), 2.28~2.34 (m, 2H), 1.88~2.03 (m, 4H), 1.75~1.85 (m, 2H).

Preparation of 1-(hexahydro-1H-pyrrolizin-7a-yl)ethanone (5-3)

MeLi (59 mL, 59 mmol) was added into a mixture of 5-2 (2 g, 14.68 mmol) in THF (20 mL) at −78° C. under N$_2$. The mixture was stirred at −78° C. for 2 h. Then the reaction was quenched with NH$_4$Cl and extracted with EtOAc. The organic layer was washed with brine, dried over MgSO$_4$. MgSO$_4$ was removed by filtration and the filtrate was concentrated. The product was purified by column chromatography (PE:EtOAc=2:1) as a yellow oil. $^1$H NMR δ (ppm) (CDCl$_3$): 3.03~3.09 (m, 2H), 2.60~2.67 (m, 2H), 2.16 (s, 3H), 2.09~2.15 (m, 2H), 1.66~1.76 (m, 4H), 1.51~1.64 (m, 2H).

Preparation of 1-(hexahydro-1H-pyrrolizin-7a-yl)ethanamine (5-4)

NH$_2$OH.HCl (408 mg, 5.87 mmol) was added into a mixture of 5-3 (300 mg, 1.96 mmol) and NaOAc (482 mg, 5.87 mmol) in EtOH (10 mL). The mixture was refluxed for 2 h under N$_2$ then was concentrated. The residue was dissolved in DCM/MeOH (10:1), filtered and concentrated. The crude product was used in next step directly. To a solution of the crude product (300 mg, 1.78 mmol) in EtOH (10 mL) was added Raney Ni (100 mg). The mixture was stirred under H$_2$ (30 psi) for 10 h at room temperature. The reaction mixture was filtered and the filtrate was concentrated. The crude racemic product was used in next step without further purification.

Preparation of 3-cyano-N-(2,4-dimethoxybenzyl)-4-(1-(hexahydro-1H-pyrrolizin-7a-yl) ethylamino)-N-(thiazol-2-yl)benzenesulfonamide (5-5)

A mixture of racemic 5-4 (300 mg, crude), 25-1 (200 mg, 0.46 mmol) and K$_2$CO$_3$ (537 mg, 3.89 mmol) in DMF (3 mL) was stirred at 40° C. under N$_2$ overnight. The mixture was filtered and concentrated. The crude racemic product was purified by prep-TLC (DCM: MeOH=10:1) to give the product of (5-5). $^1$H NMR (400 MHz CD$_3$OD) (400 MHz CDCl$_3$) δ 7.83 (d, J=6.8 Hz, 1H), 7.41 (d, J=3.6 Hz, 1H), 7.27 (d, J=3.6 Hz, 1H), 7.14 (d, J=10.0 Hz, 1H), 7.07 (d, J=8.4 Hz, 1H), 6.37~6.42 (m, 3H), 4.98 (s, 2H), 4.09~4.12 (m, 1H), 3.75 (s, 3H), 3.69 (s, 3H), 3.50~3.73 (m, 2H), 3.21~3.30 (m, 2H), 2.00~2.29 (m, 8H), 1.36 (d, J=6.8 Hz, 3H).

Preparation of 3-cyano-4-{[(1 S)-1-(tetrahydro-1H-pyrrolizin-7a(5H)-yl)ethyl]amino}-N-(1,3-thiazol-2-yl)benzenesulfonamide and 3-cyano-4-{[(1R)-1-(tetrahydro-1H-pyrrolizin-7a(5H)-yl)ethyl]amino}-N-(1,3-thiazol-2-yl)benzenesulfonamide ((5-6 Isomer A and Isomer B)

To a racemic mixture of 5-5 previously prepared (100 mg, 0.18 mmol) in DCM (5 mL) was added TFA (2 mL). The mixture was stirred at room temperature for 2 h. The reaction mixture was concentrated. The residue was purified by prep-HPLC to give a racemate which was separated by SFC thus providing 5-6 Isomer A (faster eluting) and 5-6 Isomer B (slower eluting), (Chiralpak AS-H 150* 4.6 mm I.D., 3 micron; Mobil Phase: isopropanol (0.05% in DEA)/CO$_2$ from 5% to 40%'F; pw Rate" 4 mL/min; RT=6.072 min. (5-6 Isomer A), RT=6.643 min. (5-7 Isomer B).

$^1$HNMR δ (ppm) (CD$_3$OD): 7.95 (d, J=2.0 Hz, 1H), 7.90 (dd, J=2.0, 9.2 Hz, 1H), 7.09~7.12 (m, 2H), 6.72 (d, J=4.4 Hz, 1H), 4.02~4.07 (m, 1H), 3.49~3.62 (m, 2H), 3.33~3.34 (m, 1H), 3.17~3.32 (m, 1H), 2.48~2.55 (m, 1H), 2.11~2.27 (m, 4H), 2.02~2.09 (m, 3H), 1.30 (d, J=7.2 Hz, 3H). HRMS C$_{19}$H$_{23}$N$_2$O$_2$S$_2$[M+H] calc 418.1371, obs 418.1339.

$^1$HNMR δ (ppm) (CD$_3$OD): 7.97 (d, J=2.0 Hz, 1H), 7.90 (dd, J=2.0, 8.8 Hz, 1H), 7.09~7.12 (m, 2H), 6.72 (d, J=4.8 Hz, 1H), 4.01~4.06 (m, 1H), 3.49~3.62 (m, 2H), 3.33~3.34 (m, 1H), 3.17~3.32 (m, 1H), 2.48~2.55 (m, 1H), 2.11~2.27 (m, 4H), 2.01~2.09 (m, 3H), 1.30 (d, J=7.2 Hz, 3H). HRMS C$_{19}$H$_{23}$N$_2$O$_2$S$_2$[M+H] calc 418.1371, obs 418.1386.

TABLE 5

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Example | Structure | Name | HRMS m/z (M + H) |
|---|---|---|---|
| 5-8 Isomer A<br><br>Enantiomer of 5-8 Isomer B | (structure) | 5-chloro-2-fluoro-4-{[(R or S)1-(tetrahydro-1H-pyrrolizin-7a(5H)-yl)ethyl]amino}-N-(1,3-thiazol-2-yl)benzenesulfonamide | $^1$HNMR δ (ppm) (CD$_3$OD): 7.77 (d, J = 6.8 Hz, 1H), 7.13 (d, J = 4.8 Hz, 1H), 6.91 (d, J = 12.8 Hz, 1H), 6.75 (d, J = 4.8 Hz, 1H), 3.99~4.00 (m, 1H), 3.48~3.61 (m, 2H), 3.29~3.34 (m, 1H), 3.19~3.25 (m, 1H), 2.48~2.55 (m, 1H), 2.15~2.29 (m, 4H), 2.00~2.12 (m, 3H), 1.30 (d, J = 7.2 Hz, 3H). MS (M + H)$^+$: 445.1 |
| 5-8 Isomer B<br><br>Enantiomer of 5-8 Isomer A | (structure) | 5-chloro-2-fluoro-4-{[(1S or R)-1-(tetrahydro-1H-pyrrolizin-7a(5H)-yl)ethyl]amino}-N-(1,3-thiazol-2-yl)benzenesulfonamide | $^1$HNMR δ (ppm) (CD$_3$OD): 7.74 (d, J = 7.2 Hz, 1H), 7.11 (d, J = 4.8 Hz, 1H), 6.88 (d, J = 12.8 Hz, 1H), 6.72 (d, J = 4.8 Hz, 1H), 3.96~4.00 (m, 1H), 3.47~3.58 (m, 2H), 3.28~3.32 (m, 1H), 3.16~3.26 (m, 1H), 2.45~2.52 (m, 1H), 2.13~2.26 (m, 4H), 2.04~2.12 (m, 3H), 1.30 (d, J = 7.2 Hz, 3H). HRMS m/z (M + H) 445.1 |

Example 6

(R and S)-3-cyano-4-{[(2,2-difluorotetrahydro-1H-pyrrolizin-7a(5H)-yl)methyl]amino}-N-(1,3-thiazol-2-yl)benzenesulfonamide (6-6)

Scheme 6

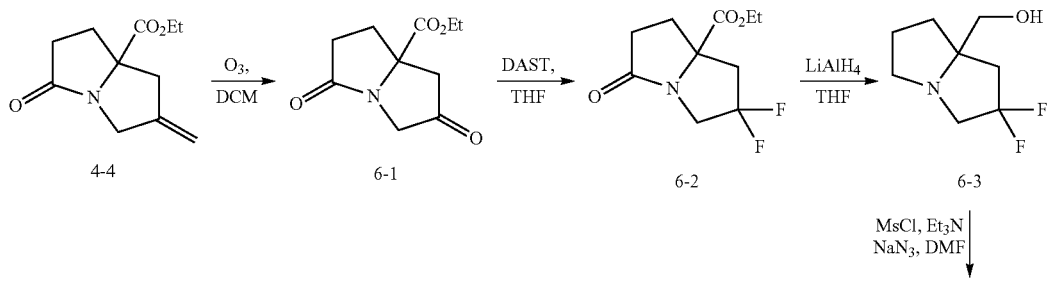

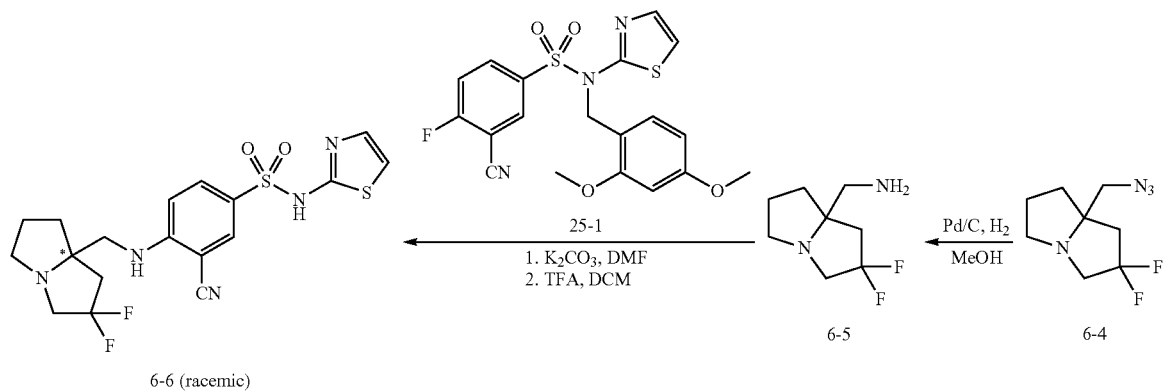

Preparation of ethyl 2,5-dioxohexahydro-1H-pyrrolizine-7a-carboxylate (6-1)

To a solution of 4-4 (400 mg, 1.8 mmol) in $CH_2Cl_2$ was bubbled with $O_3$ until the mixture was turned to blue. After the reaction completion, $CH_3SCH_3$ was added to the mixture and the mixture was stirred at room temperature overnight. The mixture was washed with NaCl. The organic layer was washed with brine, dried over $Na_2SO_4$. The product was purified by column chromatography (PE:EtOAc=1:1). $^1H$ NMR δ (ppm) ($CDCl_3$): 4.19~4.24 (m, 2H), 4.08~4.13 (m, 1H), 3.52~3.57 (m, 1H), 2.94~3.01 (m, 2H), 2.76~2.85 (m, 1H), 2.41~2.48 (m, 2H), 2.12~2.20 (m, 1H), 1.24~1.29 (m, 3H).

Preparation of ethyl 2,2-difluoro-5-oxohexahydro-1H-pyrrolizine-7a-carboxylate (6-2)

To a solution of 6-1 (160 mg, 0.76 mmol) in $CH_2Cl_2$ (10 mL) was added DAST (305 mg, 1.9 mmol) at 0° C. Then the mixture was stirred at room temperature overnight under $N_2$. The reaction was quenched with MeOH. Then water was added and the mixture was extracted with EtOAc. The organic layer was washed with brine, dried over $Na_2SO_4$. The product was purified by column chromatography (PE:EtOAc=5:1). $^1H$ NMR δ (ppm) ($CDCl_3$): 4.21~4.26 (m, 2H), 4.09~4.14 (m, 1H), 3.39~3.49 (m, 1H), 2.92~3.01 (m, 1H), 2.67~277 (m, 1H), 2.58~263 (m, 1H), 2.23~2.44 (m, 2H), 2.11~2.20 (m, 1H), 1.24~1.29 (m, 3H).

Preparation of (2,2-difluorohexahydro-1H-pyrrolizin-7a-yl)methanol (6-3)

To a solution of $LiAlH_4$ (50 mg, 1.28 mmol) in THF (3 mL) was added the solution of 6-2 (100 mg, 0.43 mmol) in THF at 0° C. under $N_2$. Then the mixture was refluxed for 4 h. After the reaction completed, water (0.3 mL) was added into the mixture which was stirred for 10 min. $MgSO_4$ was added and the mixture was stirred for another 30 min. The solid was removed by filtration and the filtrate was removed by vacuo. The product was used in the next step directly.

Preparation of (2,2-difluorohexahydro-1H-pyrrolizin-7a-yl)methanol (6-4)

To a solution of 6-3 (300 mg, 1.7 mmol), $Et_3N$ (515 mg, 5.1 mmol) in $CH_2Cl_2$ was added MsCl (292 mg, 2.5 mmol) at 0° C. dropwise under $N_2$. Then the mixture was stirred at room temperature under $N_2$ for 1 h. After the reaction completed, the mixture was diluted with water and extracted with $CH_2Cl_2$. The organic layer was washed with brine, dried over $Na_2SO_4$, filtered and concentrated. The crude product was used in next step without further purification To the solution of the above crude product in DMF was added $NaN_3$ (884 mg, 13.6 mmol), then the mixture was stirred at 80° C. overnight under $N_2$. After the reaction completed, the mixture was diluted with EtOAc and the solid was removed by filtration. The filtrate was washed with water. The organic layer was washed with brine, dried over $Na_2SO_4$. The product was purified by column chromatography (PE:EtOAc=5:1).

Preparation of (2,2-difluorohexahydro-1H-pyrrolizin-7a-yl)methanamine (6-)

To a solution of 6-4 (250 mg, 1.23 mmol) in $CH_3OH$ was added Pd/C (50 mg, wt %: 10%). Then the mixture was stirred at room temperature under $H_2$ for 2 h. After completion of the reaction, Pd/C was removed by filtration and the filtrate was concentrated by vacuo to give the crude product which was used in next step directly.

Preparation of (R and S)-3-cyano-4-{[(2,2-difluorotetrahydro-1H-pyrrolizin-7a(5H)-yl)methyl]amino}-N-(1,3-thiazol-2-yl)benzenesulfonamide (6-6)

A mixture of 6-5 (130 mg, 0.74 mmol), 25-1 (280 mg, 0.74 mmol) and $K_2CO_3$ (266 mg, 2.2 mmol) in DMF was stirred for 3 h at room temperature under $N_2$. After the reaction completed, the mixture was concentrated by vacuo to give the crude product. The product was purified by prep-TLC (PE:EtOAc=1:1). A mixture of above product (42 mg, 0.05 mmol), TFA (1 mL) in DCM (4 mL) was stirred at room temperature overnight. After the reaction completed, the mixture was concentrated by vacuo to give the crude product which was purified by prep-HPLC to give the title product as a racemate. $^1H$ NMR δ (ppm) ($CD_3OD$): 7.89~7.99 (m, 2H), 7.10~7.14 (m, 2H), 6.73 (s, 1H), 3.66~3.99 (m, 3H), 3.41~3.45 (m, 3H), 2.90~3.02 (m, 1H), 2.57~2.78 (m, 2H), 2.16~2.33 (m, 1H), 1.88~2.00 (m, 2H). HRMS $C_{18}H_{19}F_2N_5O_2S_2$ [M and H] calc 440.1026, obs 440.1012.

TABLE 6

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Example | Structure | Name | HRMS m/z (M + H) |
|---|---|---|---|
| 6-7 | 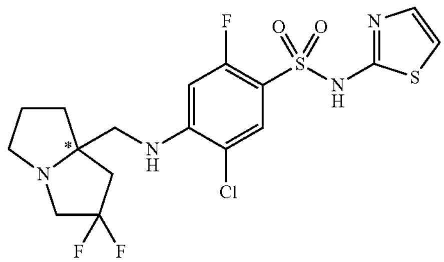 [SMILES: O=S(=O)(Nc1nccs1)c1cc(Cl)c(NCC23CCCN2CC(F)(F)C3)cc1F] | (R and S)-5-chloro-4-{[(2,2-difluorotetrahydro-1H-pyrrolizin-7a(5H)-yl)methyl]amino}-2-fluoro-N-(1,3-thiazol-2-yl)benzenesulfonamide | $^1$H NMR δ (ppm) (CD$_3$OD): 7.74 (d, J = 8.0 Hz, 1H), 7.10 (d, J = 8.0 Hz, 1H), 6.85 (d, J = 8.0 Hz, 1H), 6.71 (d, J = 8.0 Hz, 1H), 4.03~4.12 (m, 1H), 3.59~3.89 (m, 4H), 3.35~3.42 (m, 1H), 2.67~2.74 (m, 2H), 2.07~2.32 (m, 4H). HRMS m/z (M + H) 467.0578 found, 467.0590 required. |
| 6-8 | 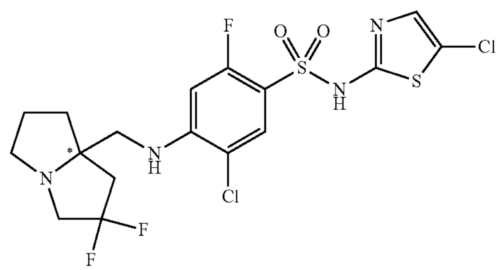 [SMILES: O=S(=O)(Nc1ncc(Cl)s1)c1cc(Cl)c(NCC23CCCN2CC(F)(F)C3)cc1F] | (R and S)-5-chloro-N-(5-chloro-1,3-thiazol-2-yl)-4-{[(2,2-difluorotetrahydro-1H-pyrrolizin-7a(5H)-yl)methyl]amino}-2-fluorobenzenesulfonamide | $^1$H NMR δ (ppm) (CD$_3$OD): 7.73 (d, J = 8.0 Hz, 1H), 7.17 (s, 1H), 6.87 (d, J = 12.0 Hz, 1H), 3.99~4.08 (m, 1H), 3.57~3.82 (m, 4H), 3.33~3.39 (m, 1H), 2.65~2.72 (m, 2H), 2.06~2.09 (m, 4H). HRMS m/z (M + H) 501.0202 found, 501.0200 required. |

Example 7

5-chloro-2-fluoro-4-[(tetrahydro-1H-pyrrolizin-7a(5H)-ylmethyl)amino]-N-(1,3-thiazol-4-yl)benzenesulfonamide (7-3)

Scheme 7

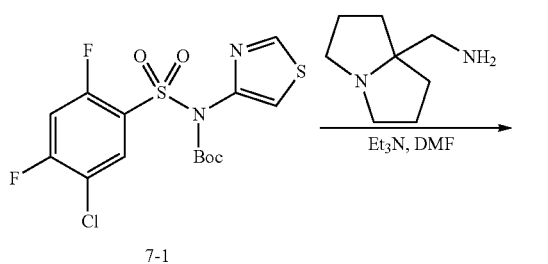

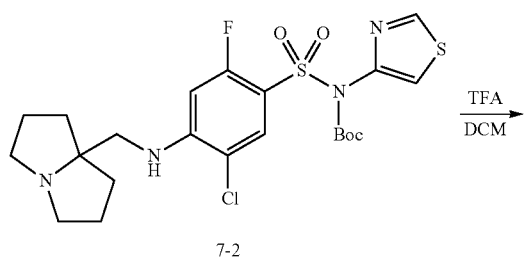

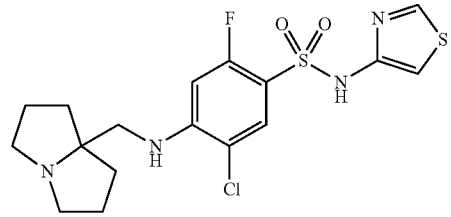

Preparation of tert-butyl (5-chloro-2-fluoro-4-(((hexahydro-1H-pyrrolizin-7a-yl)methyl)amino)phenyl)sulfonyl(thiazol-4-yl)carbamate (7-2)

A mixture of 1-(tetrahydro-1H-pyrrolizin-7a(5H)-yl)methanamine (70 mg, 0.4 mmol), 7-1 (165 mg, 0.4 mmol) and Et$_3$N (202 mg, 2 mmol) and DMF (2 mL) was stirred at room temperature under N$_2$ overnight. The mixture was poured into water and extracted with EtOAc. The combined organic layers were washed with brine, dried over Na$_2$SO$_4$, filtered and the filtrate was concentrated. The crude 7-2 was used in next step directly. MS m/z (M+H): 531.1.

Preparation of 5-chloro-2-fluoro-4-[(tetrahydro-1H-pyrrolizin-7a(5H)-ylmethyl)amino]-N-(1,3-thiazol-4-yl)benzenesulfonamide (7-3)

To a mixture of 7-2 previously prepared (123 mg, 0.23 mmol) in DCM (2 mL) was added TFA (0.5 mL). The mixture was stirred at room temperature under N$_2$ overnight. The mixture was concentrated. The crude product was purified by prep-HPLC to give the product of 7-3. $^1$H NMR (400 MHz CD$_3$OD) δ 8.85 (s, 1H), 7.68 (d, J=6.8 Hz, 1H), 7.04 (s, 1H), 6.89 (d, J=12.8 Hz, 1H), 3.73 (s, 2H), 3.56~3.55 (m, 2H), 3.21~3.20 (m, 2H), 2.03~2.14 (m, 8H). HRMS m/z (M+H) 431.0757 found, 431.0778 required.
Example 8
(S)-5-chloro-4-(((2,2-dimethylhexahydro-1H-pyrrolizin-7a-yl)methyl)amino)-2-fluoro-N-(thiazol-2-yl)benzenesulfonamide and (R)-5-chloro-4-(((2,2-dimethylhexahydro-1H-pyrrolizin-7a-yl)methyl)amino)-2-fluoro-N-(thiazol-2-yl)benzenesulfonamide (8-17 Isomer A and Isomer B)
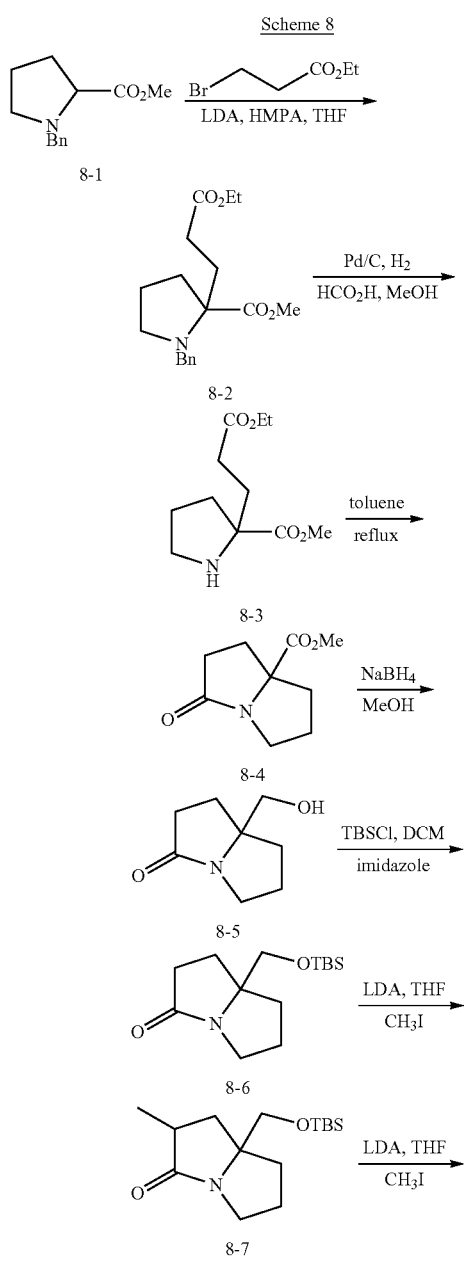
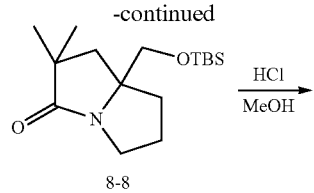
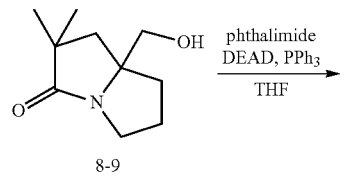
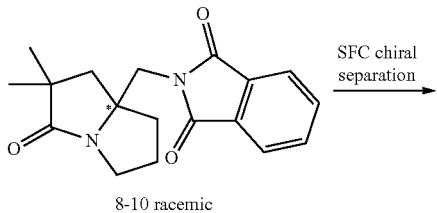
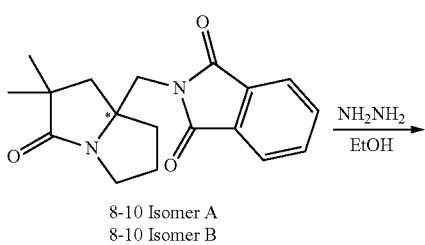
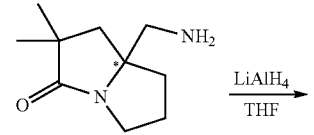

Preparation of methyl 1-benzyl-2-(3-ethoxy-3-oxo-propyl)pyrrolidine-2-carboxylate (8-2)

To a solution of 8-1 (20 g, 91 mmol) in THF (80 mL) cooled to −78° C. was added dropwise a solution of LDA (50 mL, 100 mmol) in THF. The reaction mixture was allowed to warm up to −65° C. (1 h), cooled again to −78° C. and a mixture of ethyl 3-bromopropionate (49 g, 0.27 mol) and HMPA (104 g, 0.58 mol) in THF (50 mL) was added. The solution was allowed to warm to room temperature and then stirred for 16 h. Then the reaction was quenched with saturated aqueous $NH_4Cl$ and was extracted with EtOAc. The combined organic layer was dried over $Na_2SO_4$, filtered and concentrated under reduced pressure. The crude product was purified by flash chromatography (PE:EtOAc=100:0 to 4:1) to afford 8-2 as a yellow oil.

$^1$H NMR (400 MHz, $CD_3OD$) δ 7.33-7.18 (m, 5H), 4.13 (q, J=7.0 Hz, 2H), 3.94 (d, J=13.7 Hz, 1H), 3.74 (s, 3H), 3.30 (d, J=13.7 Hz, 1H), 2.91 (t, J=7.0 Hz, 1H), 2.61-2.45 (m, 2H), 2.44-2.33 (m, 1H), 2.32-2.14 (m, 2H), 2.12-2.01 (m, 1H), 1.90-1.67 (m, 3H), 1.26 (t, J=7.0 Hz, 3H).

Preparation of methyl 2-(3-ethoxy-3-oxopropyl)pyrrolidine-2-carboxylate (8-3)

A mixture of 8-2 (5 g, 15.7 mmol), few drops of $HCO_2H$ and Pd/C (0.5 g, 10% wt.) in MeOH (40 mL) was stirred under $H_2$ (50 psi) at room temperature for 10 h. Then the reaction mixture was filtered through Celite and the filtrate was concentrated to afford 8-3 as a colorless oil, which was used in the next step directly.

Preparation of methyl 3-oxohexahydro-1H-pyrrolizine-7a-carboxylate (8-4)

A solution of 8-3 (3.3 g, 14.4 mmol) in toluene (30 mL) was refluxed for 16 h. Then the reaction mixture was concentrated. The crude product was purified by flash chromatography to afford 8-4 as a colorless oil.

$^1$H NMR (400 MHz, $CDCl_3$) δ 3.71 (s, 3H), 3.66-3.56 (m, 1H), 3.16-3.05 (m, 1H), 2.82-2.68 (m, 1H), 2.56-2.45 (m, 1H), 2.44-2.31 (m, 2H), 2.11-1.93 (m, 3H), 1.69-1.57 (m, 1H).

Preparation of methyl 7a-(hydroxymethyl)tetrahydro-1H-pyrrolizin-3(2H)-one (8-5)

To a mixture of 8-4 (20 g, 108.6 mmol) in MeOH (200 mL) was added $NaBH_4$ (16.0 g, 434.7 mmol) at 0° C. The mixture was stirred at room temperature for 30 mins. The mixture was concentrated and the residue was purified by column chromatography on silica gel (DCM: MeOH=10:1) to give (8-5) as yellow oil.

$^1$H NMR (400 MHz, $CD_3OD$) δ 3.57~3.63 (m, 1H), 3.42~3.51 (m, 2H), 2.99~3.05 (m, 1H), 2.79~2.88 (m, 1H), 2.24~2.37 (m, 2H), 2.04~2.12 (m, 2H), 1.85~1.95 (m, 2H), 1.54~1.61 (m, 1H).

Preparation of 7a-((tert-butyldimethylsilyloxy)methyl)tetrahydro-1H-pyrrolizin-3(2H)-one (8-6)

A solution of 8-5 (12.8 g, 82.05 mmol) was added dropwise into a solution of TBSCl (18.46 g, 123.07 mmol) and imidazole (16.73 g, 246.15 mmol) in DCM (300 mL) at 0° C. under $N_2$. The mixture was stirred at room temperature for 5 h. The mixture was concentrated and the residue was purified by column chromatography on silica gel (DCM: MeOH=3:1) providing 8-6.

$^1$H NMR (400 MHz, $CD_3OD$) δ 3.62~3.68 (m, 1H), 3.43 (s, 2H), 2.92~2.99 (m, 1H), 2.72~2.81 (m, 1H), 2.29~2.35 (m, 1H), 2.15~2.21 (m, 1H), 1.72~2.02 (m, 4H), 1.44~1.51 (m, 1H), 0.84 (s, 9H), 0.00 (s, 6H).

Preparation of 7a-((tert-butyldimethylsilyloxy)methyl)-2-methyltetrahydro-1H-pyrrolizin-3(2H)-one (8-7)

A solution of compound 8-6 (5.0 g, 18.58 mmol) was dissolved in dry THF (50 mL) and the solution was cooled to −78° C., prior to addition of 2M LDA (12 mL, 24.12 mmol). The mixture was stirred under $N_2$ for 0.5 h. $CH_3I$ (3.43 g, 24.12 mmol) was added dropwise via a syringe and the reaction mixture was stirred for 3 h. The solvent was quenched with saturated aqueous $NH_4Cl$. The resulting solution was extracted with EtOAc for three times and dried over magnesium sulfate, filtered and evaporated to afford the crude compound, then the crude product was purified by silica gel chromatography eluted with PE:EA=10:1 to give the compound 8-7.

$^1$H NMR (400 MHz, $CD_3OD$) δ 3.63~3.65 (m, 1H), 3.43 (s, 2H), 2.87~2.97 (m, 2H), 2.39~2.44 (m, 1H), 1.91~1.98 (m, 3H), 1.33~1.43 (m, 2H), 1.10 (d, J=6.8 Hz, 3H), 0.84 (s, 9H), 0.00 (s, 6H).

Preparation of 7a-((tert-butyldimethylsilyloxy)methyl)-2,2-dimethyltetrahydro-1H-pyrrolizin-3(2H)-one (8-8)

A solution of compound 8-7 (3.0 g, 10.6 mmol) was dissolved in dry THF (50 mL) and the solution was cooled to −78° C., prior to addition of a 2M LDA (10.6 mL, 21.2 mmol). After stirring under nitrogen atmosphere for 0.5 h, $CH_3I$ (2.25 g, 15.9 mmol) was added dropwise via a syringe and the reaction mixture was stirred for 3 h. The solvent was quenched with saturated aqueous $NH_4Cl$. The resulting solution was extracted with EtOAc for three times and dried over magnesium sulfate, filtered and evaporated to afford the crude compound, then the crude product was purified by silica gel chromatography eluted with PE:EA=10:1 to give the compound 8-8.

$^1$H NMR (400 MHz $CD_3OD$) δ 3.66~3.69 (m, 1H), 3.40~3.47 (m, 2H), 2.96~2.99 (m, 1H), 1.95~2.05 (m, 5H), 1.67~1.70 (m, 1H), 1.20 (s, 3H), 1.11 (s, 3H), 0.84 (s, 9H), 0.00 (s, 6H).

Preparation of methyl 7a-(hydroxymethyl)-2,2-dimethyltetrahydro-1H-pyrrolizin-3(2H)-one (8-9)

A solution of 8-8 (19.0 g, 63.8 mmol) in MeOH—HCl (50 mL) was stirred under $N_2$ at room temperature for 1 h. The mixture was concentrated, the residue was purified by silica gel chromatography eluted with PE:EA=2:1 to give the compound 8-9.

¹H NMR (400 MHz, CD₃OD) δ 3.76~3.79 (m, 1H), 3.52 (d, J=11.2 Hz, 1H), 3.42 (d, J=11.8 Hz, 1H), 3.40~3.43 (m, 1H), 2.22 (d, J=13.6 Hz, 1H), 1.99~2.03 (m, 3H), 1.97 (d, J=10.8 Hz, 1H), 1.78~1.81 (m, 1H), 1.45 (s, 3H), 1.11 (s, 3H).

Preparation of racemic (R and S)-2-((2,2-dimethyl-3-oxohexahydro-1H-pyrrolizin-7a-yl)methyl)isoindoline-1,3-dione (8-10) and of pure enantiomers (R)-2-((2,2-dimethyl-3-oxohexahydro-1H-pyrrolizin-7a-yl)methyl)isoindoline-1,3-dione and (S or R)-2-((2,2-dimethyl-3-oxohexahydro-1H-pyrrolizin-7a-yl)methyl)isoindoline-1,3-dione (8-10 Isomer A and Isomer B)

To a solution of compound 8-9 (17 g, 92.8 mmol), phthalimide (27.3 g, 185.7 mmol) and PPh₃ (48.6 g, 185.7 mmol) in THF (400 mL) was added DEAD (32.3 g, 185.7 mmol) at 0° C. The reaction mixture was allowed to ambient temperature and stirred at room temperature overnight. The reaction mixture was concentrated in vacuum to give crude product. The crude product was purified by silica gel chromatography eluted with PE:EA=5:1 to give the compound (8-10) which is a racemic mixture of (R)-2-((2,2-dimethyl-3-oxohexahydro-1H-pyrrolizin-7a-yl)methyl)isoindoline-1,3-dione and (S)-2-((2,2-dimethyl-3-oxohexahydro-1H-pyrrolizin-7a-yl)methyl)isoindoline-1,3-dione. The racemic product (8-10) was separated into pure isomers by chiral column (Column: IC 250×4.6 mm I.D., 5 um; Mobile phase: ethanol (0.05% DEA) in CO₂ from 5% to 40%; Flow rate: 2.5 mL/min; Wavelength: 220 nm; Run time: 12 min, Retention time: (8-10 Isomer A (faster eluting)): 6.05 min; and (8-10 Isomer B (slower eluting)): 9.09 min) providing the products shown.

¹H NMR (400 MHz, CD₃OD) δ 7.83~7.85 (m, 2H), 7.71~7.73 (m, 2H), 3.69~3.76 (m, 3H), 3.24~3.30 (m, 1H), 2.47 (d, J=13.6 Hz, 1H), 2.25~2.27 (m, 1H), 2.05~2.10 (m, 2H), 1.78 (d, J=13.6 Hz, 1H), 1.32~1.38 (m, 1H), 1.18 (s, 3H), 1.12 (s, 3H). MS m/z (M+H): 313.1

Preparation of (R)-7a-(aminomethyl)-2,2-dimethyl-tetrahydro-1H-pyrrolizin-3(2H)-one and (S)-7a-(aminomethyl)-2,2-dimethyltetrahydro-1H-pyrrolizin-3(2H)-one (8-13 Isomer A and Isomer B)

To a solution of compound (8-10 Isomer A) (19.0 g, 60.83 mmol) in EtOH (150 mL) was added NH₂NH₂·H₂O (40 mL). The resulting solution was stirred and heated at 78° C. for 4 h. The mixture was filtered and the filtrate was concentrated in vacuum to give crude product (8-13 Isomer A), which was used in next step without further purification.

Compound (8-13 Isomer B) was prepared from compound (8-10 Isomer B) using the same procedure that was used to prepare compound (8-13 Isomer A) from compound (8-10 Isomer B).

Preparation of (R)-7a-(aminomethyl)-2,2-dimethyl-tetrahydro-1H-pyrrolizin-3(2H)-one and (R)-7a-(aminomethyl)-2,2-dimethyltetrahydro-1H-pyrrolizin-3(2H)-one (8-15 Isomer A and Isomer B)

To a mixture of (8-13 Isomer A) (6.0 g, 32.9 mmol) in THF (50 mL) was added BH₃.Me₂S (32 mL, 329 mmol) at 0° C. The mixture was stirred at room temperature for 8 h. Then MeOH (100 mL) was added into the mixture to quench the reaction and concentrated. Then the residue was stirred in HCl-MeOH (100 mL) at 70° C. for 3 h. The resulting mixture was concentrated to give desired compound (8-15 Isomer A), which was used in the next step without further purification.

Compound (8-15 Isomer B) was prepared from (8-13 Isomer B) using the same procedure that was used to prepare compound (8-15 Isomer A) from compound (8-13 Isomer A).

Preparation of methyl (R)-5-chloro-4-((2,2-dimethylhexahydro-1H-pyrrolizin-7a-yl)methylamino)-2-fluoro-N-(thiazol-2-yl)benzenesulfonamide and (S)-5-chloro-4-((2,2-dimethylhexahydro-1H-pyrrolizin-7a-yl)methylamino)-2-fluoro-N-(thiazol-2-yl)benzenesulfonamide (8-17 Isomer A and 8-17 Isomer B)

A mixture of 20-3 (100 mg, 0.59 mmol), (8-15 Isomer A) previously prepared (274 mg, 0.59 mmol), K₂CO₃ (246 mg, 1.78 mmol) in DMF was stirred for 3 h at room temperature under N₂. After the reaction completed, the mixture was concentrated by vacuo to give the crude product. The crude product was purified by prep-TLC (PE:EtOAc=1:1) to give the coupled product. ¹H NMR (400 MHz, CD₃OD) δ 7.71 (d, J=7.2 Hz, 1H), 7.36 (d, J=3.6 Hz, 1H), 7.19 (d, J=8.8 Hz, 1H), 6.94 (d, J=3.6 Hz, 1H), 6.35 (d, J=2.4 Hz, 2H), 6.25 (d, J=12.4 Hz, 1H), 5.17 (s, 2H), 4.16~4.25 (m, 1H), 3.74 (s, 3H), 3.73 (s, 3H), 3.51~3.69 (m, 3H), 3.10~3.12 (m, 1H), 2.64 (d, J=11.2 Hz, 1H), 2.01~2.09 (m, 4H), 1.90~1.99 (m, 2H), 1.22 (s, 3H), 1.21 (s, 3H).

A mixture of the coupled product, prepared in the previous step (260 mg, 0.43 mmol), and TFA (2 mL) in DCM (10 mL) was stirred at room temperature overnight. After the reaction completed, the mixture was concentrated by vacuo to give the crude product which was purified by prep-HPLC to yield (8-17 Isomer A). ¹H NMR (400 MHz, CD₃OD) δ 7.35 (d, J=7.2 Hz, 1H), 7.11 (d, J=4.4 Hz, 1H), 6.85 (d, J=12.4 Hz, 1H), 6.73 (d, J=4.4 Hz, 1H), 3.73 (s, 2H), 3.38~3.48 (m, 3H), 3.05 (d, J=12.0 Hz, 1H), 1.99~2.31 (m, 6H), 1.23 (s, 3H), 1.21 (s, 3H). HRMS m/z (M+H) 459.1095 found, 459.1086 required.

Compound (8-17 Isomer B) was prepared from (8-15 Isomer B) using the same procedure that was used to prepare compound (8-17 Isomer A) from compound (8-15 Isomer A).

¹H NMR (400 MHz, CD₃OD) δ 7.36 (d, J=7.2 Hz, 1H), 7.13 (d, J=4.4 Hz, 1H), 6.84 (d, J=12.4 Hz, 1H), 6.73 (d, J=4.0 Hz, 1H), 3.75~3.76 (m, 2H), 3.35~3.48 (m, 3H), 3.31 (d, J=12.4 Hz, 1H), 2.21~2.24 (m, 1H), 1.98~2.15 (m, 5H), 1.23 (s, 3H), 1.21 (s, 3H). HRMS m/z (M+H) 459.1100 found, 459.1086 required.

TABLE 8

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Example | Structure | Name | Data |
|---|---|---|---|
| 8-19 Isomer A | Enantiomer of 8-19 Isomer B | (R or S) 5-chloro-N-(5-chlorothiazol-2-yl)-4-(((2,2-dimethylhexahydro-1H-pyrrolizin-7a-yl)methyl)amino)-2-fluorobenzenesulfonamide | $^1$HNMR (400 MHz CD$_3$OD) δ 7.73 (d, J = 7.2 Hz, 1H), 7.17 (s, 1H), 6.86 (d, J = 12.8 Hz, 1H), 3.73 (s, 2H), 3.48 (d, J = 12.0 Hz, 1H), 3.39 (d, J = 5.6 Hz, 1H), 3.05 (d, J = 12.0 Hz, 1H), 2.21~2.28 (m, 1H), 2.07~2.16 (m, 4H), 2.00 (d, J = 14 Hz, 1H), 1.22 (s, 3H), 1.20 (s, 3H). HRMS m/z (M + H) 493.0710 found, 493.0696 required. |
| 8-19 Isomer B | Enantiomer of 8-19 Isomer A | (S or R) 5-chloro-N-(5-chlorothiazol-2-yl)-4-(((2,2-dimethylhexahydro-1H-pyrrolizin-7a-yl)methyl)amino)-2-fluorobenzenesulfonamide | $^1$HNMR (400 MHz CD$_3$OD) δ 7.73 (d, J = 7.2 Hz, 1H), 7.17 (s, 1H), 6.86 (d, J = 12.8 Hz, 1H), 3.73 (s, 2H), 3.48 (d, J = 12.0 Hz, 1H), 3.39 (d, J = 5.6 Hz, 1H), 3.05 (d, J = 12.0 Hz, 1H), 2.21~2.28 (m, 1H), 2.07~2.16 (m, 4H), 2.00 (d, J = 14 Hz, 1H), 1.22 (s, 3H), 1.20 (s, 3H). HRMS m/z (M + H) 493.0711 found, 493.0696 required. |
| 8-21 Isomer A | Enantiomer of 8-21 Isomer B | (R or S) 5-chloro-4-(((2,2-dimethylhexahydro-1H-pyrrolizin-7a-yl)methyl)amino)-2-fluoro-N-(5-fluorothiazol-2-yl)benzenesulfonamide | $^1$HNMR (400 MHz CD$_3$OD) δ 7.72 (d, J = 6.8 Hz, 1H), 6.98 (s, 1H), 6.87 (d, J = 12.8 Hz, 1H), 3.74 (s, 2H), 3.38~3.48 (m, 3H), 3.05 (d, J = 11.6 Hz, 1H), 2.25 (d, J = 6.4 Hz, 1H), 2.08~2.16 (m, 4H), 2.01 (d, J = 14 Hz, 1H), 1.22 (s, 6H). HRMS m/z (M + H) 477.0996 found, 477.0992 required. |
| 8-21 Isomer B | Enantiomer of 8-21 Isomer A | (S or R) 5-chloro-4-(((2,2-dimethylhexahydro-1H-pyrrolizin-7a-yl)methyl)-amino)-2-fluoro-N-(5-fluorothiazol-2-yl)-benzenesulfonamide | $^1$HNMR (400 MHz CD$_3$OD) δ 7.75~7.70 (m, 1H), 6.98 (s, 1H), 6.91~6.84 (m, 1H), 3.78~3.70 (m, 2H), 3.50~3.36 (m, 3H), 3.10~3.03 (m, 1H), 2.30~2.22 (m, 1H), 2.18~1.98 (m, 5H), 1.23 (s, 6H). HRMS m/z (M + H) 477.0995 found, 477.0992 required. |
| 8-23 Isomer A | Enantiomer of 8-23 Isomer B | (R or S) 4-(((2,2-dimethylhexahydro-1H-pyrrolizin-7a-yl)methyl)-amino)-N-(thiazol-2-yl)-3-(trifluoromethyl)benzene-sulfonamide | $^1$HNMR (400 MHz CD$_3$OD) δ 7.94 (s, 1H), 7.91 (d, J = 9.0 Hz, 1H), 7.18 (d, J = 7.2 Hz, 1H), 7.10 (d, J = 7.1 Hz, 1H), 6.73 (d, J = 6.7 Hz, 1H), 3.86 (s, 2H), 3.53~3.46 (m, 1H), 3.42~3.33 (m, 2H), 3.07 (s, 1H), 2.29~2.20 (m, 1H), 2.19~2.01 (m, 5H), 1.24 (d, J = 11.0 Hz, 6H). HRMS m/z (M + H) 475.1451 found, 475.1444 required. |

TABLE 8-continued

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Example | Structure | Name | Data |
|---|---|---|---|
| 8-23 Isomer B | Enantiomer of 8-23 Isomer A | (S or R) 4-(((2,2-dimethylhexahydro-1H-pyrrolizin-7a-yl)methyl)amino)-N-(thiazol-2-yl)-3-(trifluoromethyl)-benzenesulfonamide | $^1$HNMR (400 MHz CD$_3$OD) δ 7.96 (s, 2H), 7.20~7.14 (m, 1H), 7.12~7.07(m, 1H), 6.75~6.69 (m, 1H), 3.91~3.85 (m, 1H), 3.82~3.75 (m, 1H), 3.52~3.46 (m, 1H), 3.42~3.35 (m, 2H), 3.11~3.03 (m, 1H), 2.31~2.23 (m, 1H), 2.19~2.01(m, 5H), 1.24 (s, 6H). HRMS m/z (M + H) 475.1453 found, 475.1444 required. |
| 8-25 | 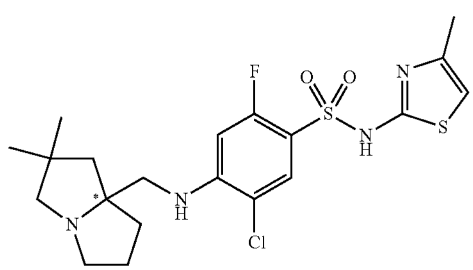 [SMILES: Cc1csc(NS(=O)(=O)c2cc(Cl)c(NCC34CCCN3CC(C)(C)C4)cc2F)n1] | (R and S)-5-chloro-4-(((2,2-dimethylhexahydro-1H-pyrrolizin-7a-yl)methyl)amino)-2-fluoro-N-(4-methylthiazol-2-yl)benzenesulfonamide | $^1$HNMR (400 MHz CD$_3$OD) δ 7.74 (d, J = 6.8 Hz, 1H), 6.86 (d, J = 12.8 Hz, 1H), 6.27 (s, 1H), 3.72 (s, 2H), 3.39~3.41 (m, 3H), 3.07 (d, J = 12 Hz, 1H), 2.26 (d, J = 6.8 Hz, 1H), 2.13 (d, J = 14.8 Hz, 7H), 2.01 (d, J = 14 Hz, 1H), 1.22 (s, 6H). HRMS m/z (M + H) 473.1252 found, 473.1243 required. |

Example 9

5-chloro-2-fluoro-4-((((2R,7aS)-2-fluorohexahydro-1H-pyrrolizin-7a-yl)methyl)amino)-N-(thiazol-2-yl)benzenesulfonamide and 5-chloro-2-fluoro-4-((((2S,7aR)-2-fluorohexahydro-1H-pyrrolizin-7a-yl)methyl)amino)-N-(thiazol-2-yl)benzenesulfonamide (9-8 Isomer A and Isomer B)

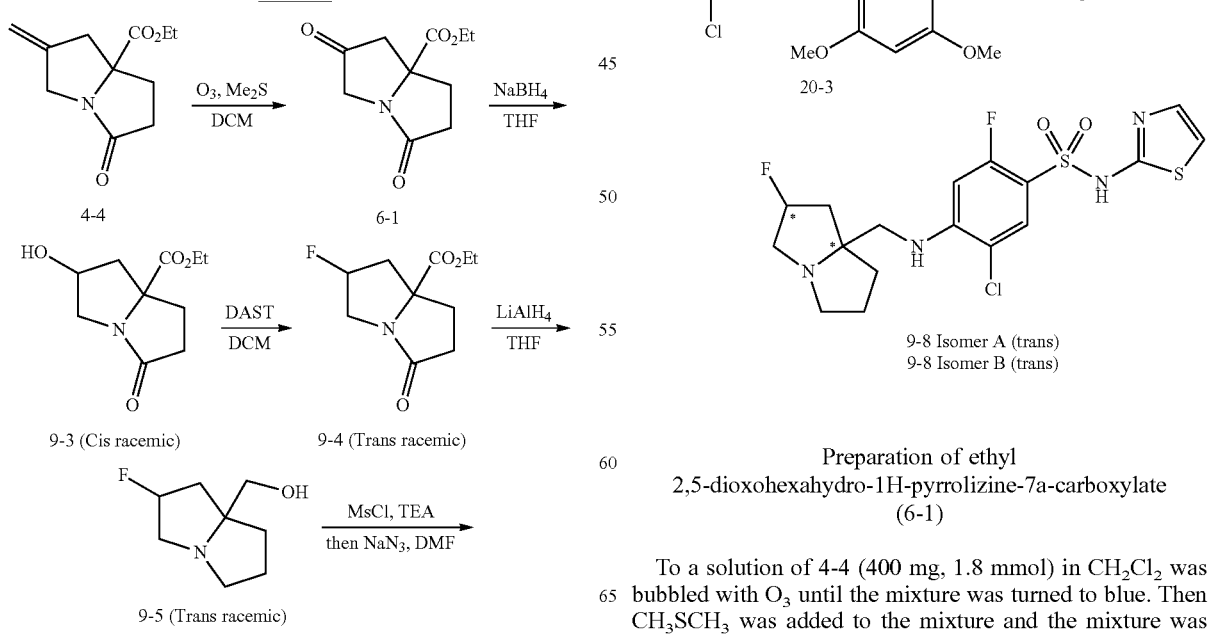

Preparation of ethyl 2,5-dioxohexahydro-1H-pyrrolizine-7a-carboxylate (6-1)

To a solution of 4-4 (400 mg, 1.8 mmol) in CH$_2$Cl$_2$ was bubbled with O$_3$ until the mixture was turned to blue. Then CH$_3$SCH$_3$ was added to the mixture and the mixture was stirred at room temperature overnight. The mixture was washed with NaCl. The organic layer was washed with water, brine, dried over Na₂SO₄. The product, 6-1, was purified by column chromatography (PE:EtOAc=1:1).

¹H NMR (400 MHz, CDCl₃) δ 4.19~4.24 (m, 2H), 4.08~4.13 (m, 1H), 3.52~3.57 (m, 1H), 2.94~3.01 (m, 2H), 2.76~2.85 (m, 1H), 2.41~2.48 (m, 2H), 2.12~2.20 (m, 1H), 1.24~1.29 (m, 3H).

Preparation of racemic ((2R,7aR) and (2S,7aS))-ethyl 2-hydroxy-5-oxohexahydro-1H-pyrrolizine-7a-carboxylate (9-3 (Cis))

To a solution of 6-1, prepared in the previous step (6.0 g, 28.4 mmol), in MeOH (60 mL) was added NaBH₄ (281 mg, 7.1 mmol) at 0° C. under N₂. Then the mixture was stirred at 0° C. for 5 min. The mixture was concentrated by vacuo to give the crude product. The product, 9-3 (Cis), which is a racemic mixture of (2R,7aR)-ethyl 2-hydroxy-5-oxohexahydro-1H-pyrrolizine-7a-carboxylate and (2S,7aS)-ethyl 2-hydroxy-5-oxohexahydro-1H-pyrrolizine-7a-carboxylate, was purified by column chromatography on silic gel (PE: EtOAc=1:1).

¹H NMR (400 MHz, CDCl₃) δ 4.51~4.58 (m, 1H), 4.13~4.21 (m, 2H), 3.81~3.87 (m, 1H), 3.03~3.40 (m, 2H), 2.62~2.80 (m, 1H), 1.76~2.57 (m, 4H), 1.21~1.26 (m, 3H).

Preparation of racemic ((2S,7aR) and (2R,7aS))-ethyl2-fluoro-5-oxohexahydro-1H-pyrrolizine-7a-carboxylate (9-4 (Trans))

To a solution of 9-3 (Cis), previously prepared (4.0 g, 18.7 mmol), in CH₂Cl₂ (10 mL) was added DAST (3.33 g, 21 mmol) at −78° C. under N₂. Then the mixture was stirred at room temperature overnight under N₂. The reaction was quenched with MeOH. Then water was added and the mixture was extracted with EtOAc. The organic layer was washed with water, brine, dried over Na₂SO₄. The product, 9-4 (Trans), which is a racemic mixture of (2S,7aR)-ethyl2-fluoro-5-oxohexahydro-1H-pyrrolizine-7a-carboxylate and (2R,7aS)-ethyl2-fluoro-5-oxohexahydro-1H-pyrrolizine-7a-carboxylate, was purified by column chromatography (PE: EtOAc=1:1).

¹H NMR (400 MHz, CDCl₃) δ 5.21~5.34 (m, 1H), 4.14~4.24 (m, 2H), 3.75~3.77 (m, 1H), 3.08~3.21 (m, 1H), 2.56~2.82 (m, 3H), 2.06~2.46 (m, 3H), 1.25~1.29 (m, 3H).

Preparation of racemic ((2S,7aR) and (2R,7aS))-(2-fluorohexahydro-1H-pyrrolizin-7a-yl)methanol (9-5 (Trans)

To a solution of LiAlH₄ (1.6 g, 42 mmol) in THF (40 ml) was added the solution of 9-4 (Trans), previously prepared (3.0 g, 14 mmol), in THF at 0° C. under N₂. Then the mixture was stirred at refluxing for 4 h. Water (0.3 mL) was added to the mixture which was stirred for 10 min. MgSO₄ was added and the mixture was stirred for 30 min. The solid was removed by filtration and the solvent was removed by vacuo. The product, 9-5 (Trans), which is a racemic mixture of (2R,7aS)-(2-fluorohexahydro-1H-pyrrolizin-7a-yl) methanol and (2S,7aR)-(2-fluorohexahydro-1H-pyrrolizin-7a-yl)methanol was used in the next step directly.

¹H NMR (400 MHz, CDCl₃) δ 5.21~5.34 (m, 1H), 4.14~4.24 (m, 2H), 3.75~3.77 (m, 1H), 3.08~3.21 (m, 1H), 2.56~2.82 (m, 3H), 2.06~2.46 (m, 3H), 1.25~1.29 (m, 3H).

Preparation of racemic ((2S,7aR) and (2R,7aS))-7a-(azidomethyl)-2-fluorohexahydro-1H-pyrrolizine (9-6 (Trans))

To a solution of 9-5 (Trans), previously prepared (2.7 g, 17 mmol), Et₃N (5.1 g, 51 mmol) in CH₂Cl₂ was added MsCl (2.5 g, 22 mmol) at 0° C. dropwise under N₂. Then the mixture was stirred at room temperature under N₂ for 1 h. The mixture was diluted with water and extracted with CH₂Cl₂. The organic layer was washed with water, brine, dried over Na₂SO₄, filtered and concentrated. The crude product was used in next step without further purification. To the solution of the above crude product in DMF was added NaN₃ (5.5 g, 85 mmol), then the mixture was stirred at 80° C. overnight under N₂. The mixture was diluted with EtOAc and the solid was removed by filtering, the filtrate was washed with water. The organic layer was washed with water, brine, dried over Na₂SO₄. The product, 9-6 (Trans), which is a mixture of (2S,7aR)-7a-(azidomethyl)-2-fluorohexahydro-1H-pyrrolizine and (2R,7aS))-7a-(azidomethyl)-2-fluorohexahydro-1H-pyrrolizine, was purified by column chromatography (PE:EtOAc=1:1).

¹H NMR (400 MHz CDCl₃) δ 4.60~4.76 (m, 1H), 3.01~3.30 (m, 1H), 2.63~2.96 (m, 3H), 1.75~2.49 (m, 7H), 1.49~1.57 (m, 1H).

Preparation of racemic ((2S,7aR) and (2R,7aS))-(2-fluorohexahydro-1H-pyrrolizin-7a-yl)methanamine (9-7 (Trans))

To a solution of 9-6 (Trans), prepared in the previous step (500 mg, 2.7 mmol), in CH₃OH was added Pd/C (50 mg, wt %: 10%). Then the mixture was stirred at room temperature under H₂ for 2 h. Pd/C was removed by filtering and the filtrate was concentrated in vacuo to give the crude product, 9-7 (Trans), which is a mixture of (2S,7aR)-(2-fluorohexahydro-1H-pyrrolizin-7a-yl)methanamine and (2R,7aS))-(2-fluorohexahydro-1H-pyrrolizin-7a-yl)methanamine, was used in the next step directly.

¹H NMR (400 MHz CDCl₃) δ 4.57~4.71 (m, 1H), 3.08~3.43 (m, 2H), 2.83~2.92 (m, 2H), 2.32~2.63 (m, 2H), 1.33~2.10 (m, 6H).

Preparation of 5-chloro-2-fluoro-4-(((2R,7aS)-2-fluorohexahydro-1H-pyrrolizin-7a-yl)methylamino)-N-(thiazol-2-yl)benzenesulfonamide and 5-chloro-2-fluoro-4-(((2S,7aR)-2-fluorohexahydro-1H-pyrrolizin-7a-yl)methylamino)-N-(thiazol-2-yl)benzenesulfonamide ((9-8 Isomer A (Trans) and Isomer B (Trans))

A mixture of 9-7 (Trans), prepared in the previous step (80 mg, 0.5 mmol), 20-3 (233 mg, 0.5 mmol) and K₂CO₃ (281 mg, 2 mmol) in DMF was stirred for 3 h at room temperature under N₂. Then the mixture was concentrated in vacuo to give the crude coupled product. The coupled product was purified by prep-TLC (PE:EtOAc=1:1).

A mixture of coupled product prepared in the previous step (43 mg, 0.07 mmol) and TFA (0.5 mL) in DCM (4 mL) was stirred at room temperature overnight. The mixture was concentrated by vacuo to give the crude product which was purified by prep-HPLC to give a racemic product. The racemic product was separated by chiral column (Column: Chiralpak AD-H 250×4.6 mm I.D., 5 um; Mobile phase: 40% methanol (0.05% DEA) in CO₂; Flow rate: 2.35 mL/min; Wavelength: 220 nm; Run time: 12 min; Retention time: (9-8 Isomer A (Trans) faster eluting): 9.6 min; (9-8 Isomer B (Trans) slower eluting): 10.9 min). These compounds were characterized by NMR to give, respectively, the following results:

¹H NMR (400 MHz, CD₃OD) δ 7.74 (d, J=8.0 Hz, 1H), 7.10 (d, J=8.0 Hz, 1H), 6.87 (d, J=8.0 Hz, 1H), 6.72 (d, J=8.0 Hz, 1H), 5.36~5.49 (m, 1H), 3.67~3.89 (m, 5H), 3.36~3.42 (m, 1H), 2.05~2.57 (m, 6H). HRMS m/z (M+H) 449.0681 found, 449.0679 required.

¹H NMR (400 MHz, CD₃OD) δ 7.75 (d, J=8.0 Hz, 1H), 7.11 (d, J=8.0 Hz, 1H), 6.88 (d, J=8.0 Hz, 1H), 6.73 (d, J=8.0 Hz, 1H), 5.38~5.51 (m, 1H), 3.68~3.92 (m, 5H), 3.38~3.44 (m, 1H), 2.07~2.59 (m, 6H). HRMS m/z (M+H) 449.0689 found, 449.0679 required.

TABLE 9

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Example | Structure | Name | Data |
|---|---|---|---|
| 9-10 Isomer A (trans) | Enantiomer of 9-10 Isomer B | 5-chloro-2-fluoro-4-((((2R,7aS or 2S,7aR)-2-fluoro-hexahydro-1H-pyrrolizin-7a-yl)methyl)amino)-N-(5-fluorothiazol-2-yl)-benzenesulfonamide | ¹HNMR (400 MHz CD₃OD) δ 7.76 (d, J = 7.8 Hz, 1H), 7.06~6.98 (m, 1H), 6.94 (dd, J = 6.9, 7.0 Hz, 1H), 5.30~5.16 (m, 1H), 3.99~3.79 (m, 2H), 3.71 (d, J = 10.2 Hz, 1H), 3.50 (brs, 3H), 2.76~2.59 (m, 2H), 2.48~2.29 (m, 2H), 2.07~1.90 (m, 2H). HRMS m/z (M + H) 467.0594 found, 467.0585 required. |
| 9-10 Isomer B (trans) | Enantiomer of 9-10 Isomer A | 5-chloro-2-fluoro-4-((((2S,7aR or 2R,7aS)-2-fluoro-hexahydro-1H-pyrrolizin-7a-yl)methyl)amino)-N-(5-fluorothiazol-2-yl)-benzenesulfonamide | ¹HNMR (400 MHz CD₃OD) δ 7.76 (d, J = 7.8 Hz, 1H), 7.06~6.98 (m, 1H), 6.94 (dd, J = 6.9, 7.0 Hz, 1H), 5.30~5.16 (m, 1H), 3.99~3.79 (m, 2H), 3.71 (d, J = 10.2 Hz, 1H), 3.50 (brs, 3H), 2.76~2.59 (m, 2H), 2.48~2.29 (m, 2H), 2.07~1.90 (m, 2H). HRMS m/z (M + H) 467.0591 found, 467.0585 required. |
| 9-12 Isomer A (trans) | Enantiomer of 9-12 Isomer B | 4-((((2R,7aS or 2S,7aR)-2-fluoro-hexahydro-1H-pyrrolizin-7a-yl)-methyl)amino)-N-(5-fluorothiazol-2-yl)-3-(trifluoromethyl)-benzenesulfonamide | ¹HNMR (400 MHz CD₃OD) δ 7.89~7.93 (m, 2H), 7.21 (d, J = 8.0 Hz, 1H), 6.98 (s, 1H), 5.39~5.52(m, 1H), 3.64~3.88 (m, 5H), 3.30~3.42 (m, 1H), 2.07~2.59(m, 6H). HRMS m/z (M + H) 483.0953 found, 483.0942 required. |
| 9-12 Isomer B (trans) | Enantiomer of 9-12 Isomer A | 4-((((2S,7aR or 2R,7aS)-2-fluoro-hexahydro-1H-pyrrolizin-7a-yl)methyl)amino)-N-(5-fluorothiazol-2-yl)-3-(trifluoromethyl)-benzenesulfonamide | ¹HNMR (400 MHz CD₃OD) δ 7.90~7.93 (m, 2H), 7.21 (d, J = 8.0 Hz, 1H), 6.98 (s, 1H), 5.39~5.53(m, 1H), 3.64~3.89 (m, 5H), 3.30~3.42 (m, 1H), 2.07~2.60 (m, 6H). HRMS m/z (M + H) 483.0953 found, 483.0942 required. |
| 9-14 Isomer A (trans) | Enantiomer of 9-14 Isomer B | 3-chloro-4-((((2R,7aS or 2S,7aR)-2-fluoro-hexahydro-1H-pyrrolizin-7a-yl)-methyl)amino)-N-(5-fluorothiazol-2-yl)-benzenesulfonamide | ¹HNMR (400 MHz CD₃OD) δ 7.65~7.74 (m, 2H), 6.97~7.06 (m, 2H), 5.39~5.52 (m, 1H), 3.68~3.88 (m, 5H), 3.39~3.42 (m, 1H), 2.08~2.60 (m, 6H). HRMS m/z (M + H) 449.0683 found, 449.0679 required. |

TABLE 9-continued

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Example | Structure | Name | Data |
|---|---|---|---|
| 9-14 Isomer B (trans) | Enantiomer of 9-14 Isomer A | 3-chloro-4-((((2S,7aR or 2R,7aS)-2-fluoro-hexahydro-1H-pyrrolizin-7a-yl)methyl)amino)-N-(5-fluorothiazol-2-yl)-benzenesulfonamide | $^1$HNMR (400 MHz CD$_3$OD) δ 7.66~7.74(m, 2H), 6.97~7.06 (m, 2H), 5.39~5.52 (m, 1H), 3.68~3.89 (m, 5H), 3.40~3.44 (m, 1H), 2.08~2.60 (m, 6H). HRMS m/z (M + H) 449.0688 found, 449.0679 required. |

Example 10

(R)-5-chloro-2-fluoro-4-(((hexahydrospiro[[1,3]di-oxolane-2,2'-pyrrolizin]-7a'-yl)methyl)amino)-N-(thiazol-2-yl)benzenesulfonamide and (S)-5-chloro-2-fluoro-4-(((hexahydrospiro[[1,3]dioxolane-2,2'-pyrrolizin]-7a'-yl)methyl)amino)-N-(thiazol-2-yl)benzenesulfonamide (10-7 Isomer A and Isomer B)

Scheme 10

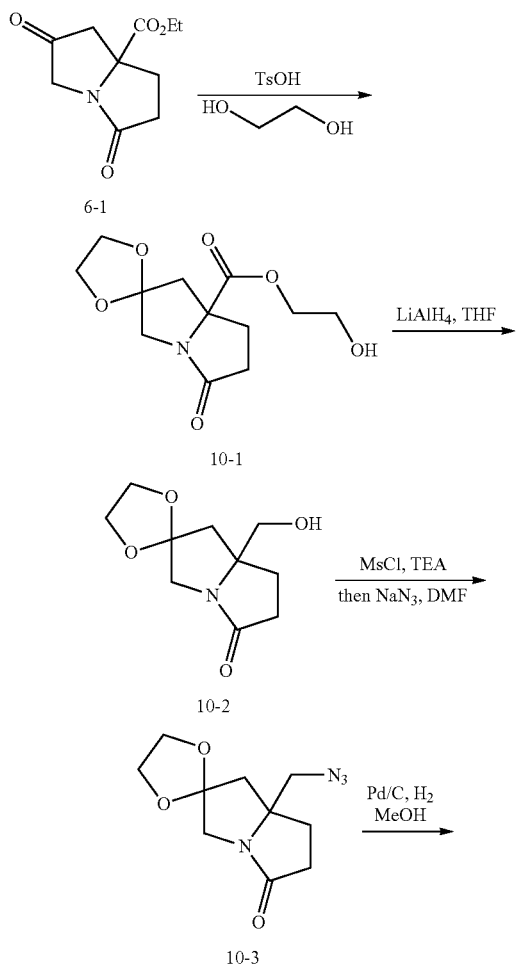

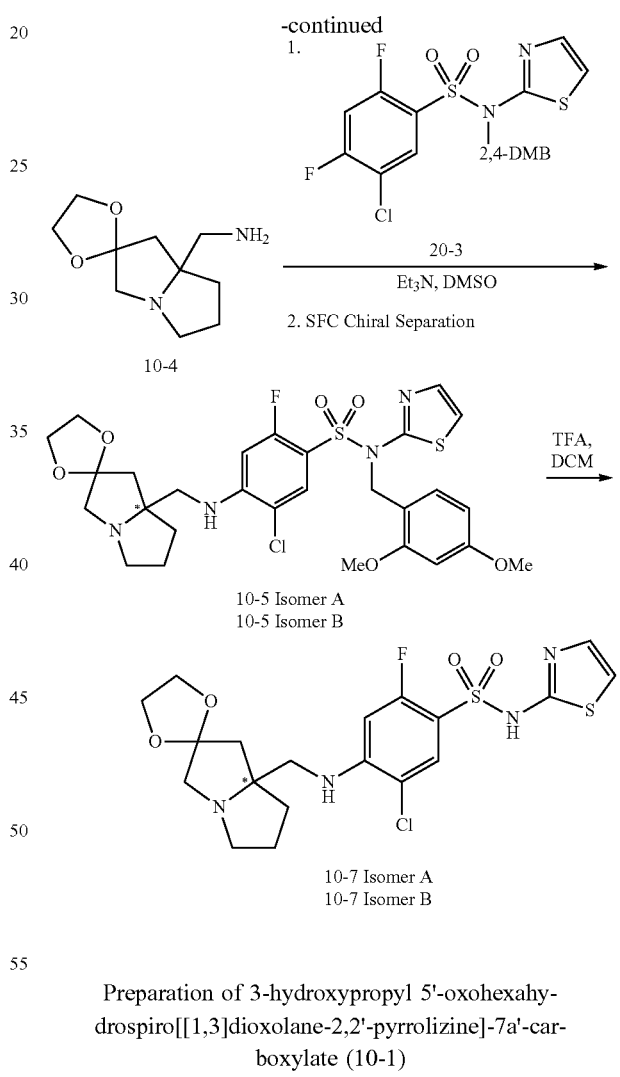

Preparation of 3-hydroxypropyl 5'-oxohexahydrospiro[[1,3]dioxolane-2,2'-pyrrolizine]-7a'-carboxylate (10-1)

To a mixture of 6-1 (10.0 g, 47.35 mmol) and HO(CH$_2$)$_2$OH (52.90 g, 85.2 mmol) in toluene (100 mL) was added TsOH (1.17 g, 6.15 mmol). The mixture was stirred for 12 h at 120° C. Then the reaction mixture was filtered and concentrated. The residue was treated with 40 mL of water and diluted with 100 mL of ethyl acetate. The layers were separated and the aqueous layer was back-extracted with EtOAc (3×50 mL). The combined organic layers were dried over sodium sulfate, filtered and concentrated. Purification by normal phase chromatography (0-50% EtOAc in PE) yielded 10-1 as an oil.

Preparation of (hexahydrospiro[[1,3]dioxolane-2,2'-pyrrolizine]-7a'-yl)methanol (10-2)

To a solution of LiAlH$_4$ (2.18 g, 57.5 mmol) in THF (50 mL) was added 10-1 (5.2 g, 19.7 mmol) at 0° C. under N$_2$. The mixture was stirred at 50° C. for 2 h. Then the reaction mixture was quenched by addition of 0.8 mL of H$_2$O, followed by 15% aqueous NaOH. After being stirred at room temperature for 0.5 h, the solid was removed by filtration. The filtrate was concentrated. The residue was purified by column chromatography on silica gel (DCM: MeOH=20:1) to give the product of 10-2 as an oil.

Preparation of 7a'-(azidomethyl)hexahydrospiro[[1,3]dioxolane-2,2'-pyrrolizine] (10-3)

To a solution of 10-2 (3.5 g, 17.58 mmol) in DCM (15 mL) was added Et$_3$N (5.30 g, 52.76 mmol). The reaction mixture was cooled to 0° C. MsCl (3 g, 26.37 mmol) was added dropwise to the reaction mixture at this temperature. Then the mixture was stirred for 2 h and concentrated in vacuum to give crude product, which was used in next step without further purification. The crude product was dissolved in dry DMF (50 mL) and NaN$_3$ (5.71 g, 87.90 mmol) was added. The reaction mixture was stirred at 70~80° C. overnight. Water (20 mL) was added into the mixture and the aqueous phase was extracted with DCM: MeOH (10:1, 100 mL×5). The combined organic layers were washed with brine (30×5 mL), dried over Na$_2$SO$_4$, filtered and the filtrate was concentrated in vacuum to give crude product, which was purified by column chromatography on silica gel (PE: EtOAc=3:1) to give the product compound 10-3.

$^1$HNMR (400 MHz CDCl$_3$) δ 3.83~4.04 (m, 4H), 3.25 (dd, J=26.4 Hz, J=12.0 Hz, 2H), 3.11~3.14 (m, 1H), 2.94~3.10 (m, 1H), 2.69~2.37 (m, 3H), 1.75~2.19 (m, 5H).

Preparation of (hexahydrospiro[[1,3]dioxolane-2,2'-pyrrolizine]-7a'-yl)methanamine (10-4)

To a solution of 10-3 (1.6 g, 10.7 mmol) in MeOH (100 mL) was added Pd/C (0.5 g) under nitrogen. The mixture was stirred at room temperature for 4 h and then filtered, concentrated to give 10-4, which was used in the next step without further purification.

Preparation of (R)-5-chloro-N-(2,4-dimethoxybenzyl)-2-fluoro-4-((hexahydrospiro[[1,3]dioxolane-22'-pyrrolizine]-7a'-yl)methylamino)-N-(thiazol-2-yl)benzenesulfonamide and (S)-5-chloro-N-(2,4-dimethoxybenzyl)-2-fluoro-4-((hexahydrospiro[[1,3]dioxolane-2,2'-pyrrolizine]-7a'-yl)methylamino)-N-(thiazol-2-yl)benzenesulfonamide (10-5 Isomer A and 10-5 Isomer B)

To a solution of 10-4 (200 mg, 1.01 mmol) and 20-3 (460 mg, 1.01 mmol) in DMF (3 mL) was added Et$_3$N (306 mg, 3.03 mmol). The reaction mixture was stirred at 50° C. overnight. The mixture was concentrated in vacuum to give crude product, which was purified by prep-TLC (DCM: MeOH=20:1) to give the coupled product as a racemic mixture. This racemic product was separated into the pure enantiomers using SFC (Column: Chiralpak AD-3 50×4.6 mm I.D., 3 um; Mobile phase: 40% methanol (0.05% DEA) in CO$_2$; Flow rate: 4 mL/min; Wavelength: 220 nm; Run time: 12 min; Retention time: (10-5 Isomer A (faster eluting)): 1.337 min; (10-5 Isomer B (slower eluting)): 2.025 min), which were characterized by proton NMR to give the following results:

$^1$HNMR (400 MHz, CDCl$_3$) δ 7.53 (d, J=4.8 Hz, 1H), 7.51 (s 1H), 7.36 (s, 1H), 7.17 (d, J=3.6 Hz, 1H), 6.60 (d, J=8.8 Hz, 1H), 6.32~6.37 (m, 2H), 5.70 (s, 2H) 3.86~3.92 (m, 4H), 3.70 (s, 6H), 3.04~3.17 (m, 4H), 2.82 (d, J=10.4 Hz, 2H), 1.76~2.00 (m, 8H).

Preparation of (R)-5-chloro-2-fluoro-4-((hexahydrospiro[[1,3]dioxolane-2,2'-pyrrolizine]-7a'-yl)methylamino)-N-(thiazol-2-yl)benzenesulfonamide and (S)-5-chloro-2-fluoro-4-((hexahydrospiro[[1,3]dioxolane-2,2'-pyrrolizine]-7a'-yl)methylamino)-N-(thiazol-2-yl)benzenesulfonamide (10-7 isomer A and Isomer B)

To a solution of (10-5 Isomer A) (80 mg, 0.16 mmol) in DCM (3 mL) was added TFA (1.0 mL), the resulting solution was stirred at room temperature for 2 h. The mixture was concentrated in vacuum to give crude product, which was purified by prep-HPLC to give 10-7 Isomer A, which was characterized by proton NMR: $^1$HNMR (400 MHz, CD$_3$OD) δ 7.73 (d, J=7.2 Hz, 1H), 7.11 (d, J=4.4 Hz, 1H), 6.76 (s, 1H), 6.73 (s, 1H), 3.96~3.99 (m, 4H), 3.50 (d, J=16.4 Hz, 2H), 3.15 (d J=16.4 Hz, 2H), 3.10 (m, 2H), 2.22 (d, J=12.0 Hz, 2H), 1.99~2.05 (m, 4H). HRMS m/z (M+H) 489.0836 found, 489.0828 required.

Compound (10-7 Isomer B) was prepared from (10-5 Isomer B) using the same procedure that was used to prepare compound (10-7 Isomer A) from compound (10-5 Isomer A).

Compound 10-7 Isomer B is the enantiomer of compound 10-7 Isomer A and was characterized by proton NMR: $^1$HNMR (400 MHz, CD$_3$OD) δ 7.72 (d, J=7.2 Hz, 1H), 7.10 (d, J=4.4 Hz, 1H), 6.73 (s, 1H), 6.70 (s, 1H), 3.95~3.98 (m, 4H), 3.43~3.33 (m, 4H), 3.08 (s, 2H), 2.13~2.26 (m, 2H), 1.96~2.11 (m, 4H). HRMS m/z (M+H) 489.0839 found, 489.0828 required.

TABLE 10

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Example | Structure | Name | Data |
|---|---|---|---|
| 10-9 Isomer A | Enantiomer of 10-9 Isomer B | (S or R)-5-chloro-N-(5-chlorothiazol-2-yl)-2-fluoro-4-(((hexahydrospiro[[1,3]dioxolane-2,2'-pyrrolizin]-7a'-yl)-methyl)amino)-benzenesulfonamide | $^1$HNMR (400 MHz CD$_3$OD) δ 7.76 (d, J = 6.8 Hz, 1H), 7.19 (s, 1H), 6.87 (d, J = 12.8 Hz, 1H), 4.04~4.11 (m, 4H), 3.74 (s, 2H), 3.66 (d, J = 12.4 Hz, 1H), 3.43~3.44 (m, 1H), 3.31~3.39 (m, 2H), 2.34~2.40 (m, 3H), 2.15~2.20 (m, 3H). HRMS m/z (M + H) 523.0450 found, 523.0438 required. |
| 10-9 Isomer B | Enantiomer of 10-9 Isomer A | (R or S)-5-chloro-N-(5-chloro-thiazol-2-yl)-2-fluoro-4-(((hexahydrospiro[[1,3]-dioxolane-2,2'-pyrrolizin]-7a'-yl)-methyl)amino)-benzenesulfonamide | $^1$HNMR (400 MHz CD$_3$OD) δ 7.76 (d, J = 6.8 Hz, 1H), 7.19 (s, 1H), 6.87 (d, J = 12.8 Hz, 1H), 4.04~4.11 (m, 4H), 3.74 (s, 2H), 3.66 (d, J = 12.4 Hz, 1H), 3.43~3.44 (m, 1H), 3.31~3.39 (m, 2H), 2.34~2.40 (m, 3H), 2.15~2.20 (m, 3H). HRMS m/z (M + H) 523.0448 found, 523.0438 required. |

Example 11

5-chloro-2-fluoro-4-((((3S,7aS)-3-methylhexahydro-1H-pyrrolizin-7a-yl)methyl)amino)-N-(thiazol-2-yl)benzenesulfonamide and 5-chloro-2-fluoro-4-((((3R,7aR)-3-methylhexahydro-1H-pyrrolizin-7a-yl)methyl)amino)-N-(thiazol-2-yl)benzenesulfonamide (11-8 Isomer A and 11-8 Isomer B)

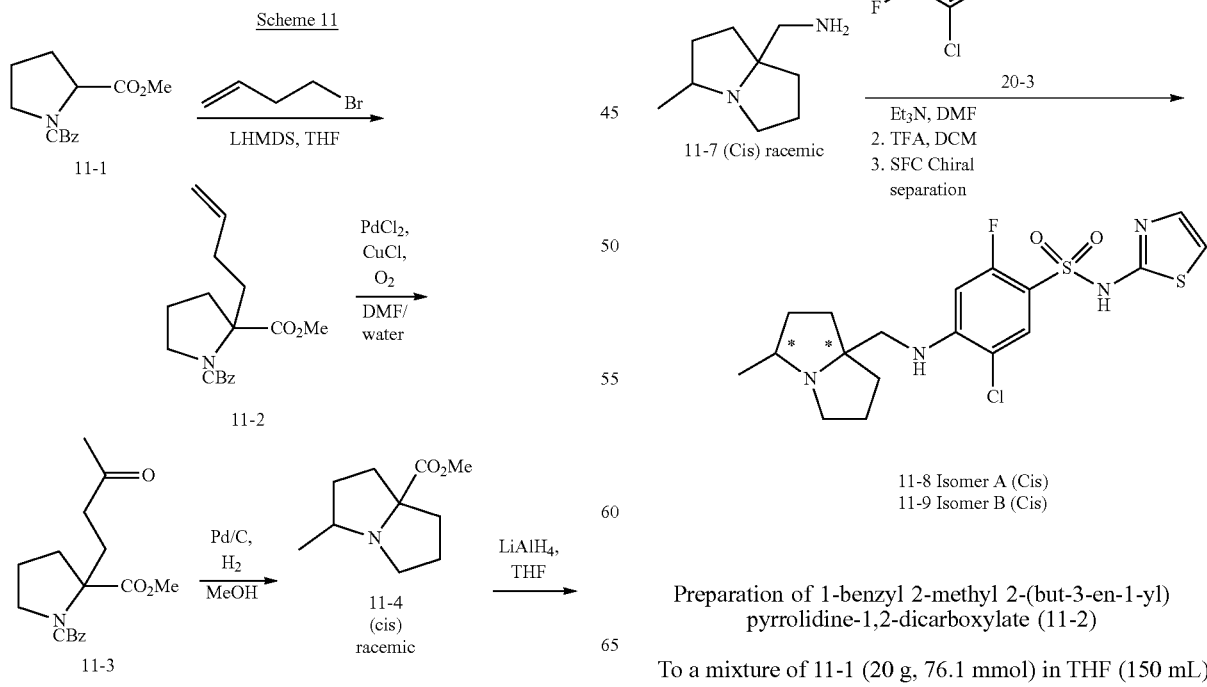

Preparation of 1-benzyl 2-methyl 2-(but-3-en-1-yl) pyrrolidine-1,2-dicarboxylate (11-2)

To a mixture of 11-1 (20 g, 76.1 mmol) in THF (150 mL) cooled to −78° C. was added dropwise a solution of LiH- MDS (91.26 mL, 91.26 mmol) in THF. The mixture was stirred at −78° C. for 1 h. 4-Bromo-1-butene (20.53 g, 152.1 mmol) was added into the mixture dropwise at −78° C. The mixture was stirred at room temperature overnight. Then the mixture was quenched with saturated NH$_4$Cl solution and extracted with EtOAc. The combined organic phases were dried with Na$_2$SO$_4$ and concentrated. The residue was purified by column chromatography on silica gel (PE:EtOAc=5:1) to give 11-2.

Preparation of 1-benzyl 2-methyl 2-(3-oxobutyl) pyrrolidine-1,2-dicarboxylate (11-3)

A mixture of 11-2 (3 g, 9.43 mmol), PdCl$_2$ (671 mg, 3.77 mmol), CuCl (4.67 g, 47.17 mmol) in 100 mL of DMF and 10 mL of water was stirred at room temperature under O$_2$ overnight. The mixture was filtered and the filtrate was poured into water, extracted with EtOAc. The combined organic layers were washed with brine, filtered and concentrated. The residue was purified by column chromatography on silica gel (PE:EA=2:1) to give 11-3.

Preparation of methyl ((3S,7aS) and (3R,7aR))-3-methylhexahydro-1H-pyrrolizine-7a-carboxylate (11-4 (Cis) racemic)

A mixture of 11-3 (10 g, 34 mmol) and Pd/C (1 g) in MeOH (100 mL) and AcOH (1 mL) was stirred at 25° C. for 8 h under H$_2$. Then the reaction solution was filtered, concentrated and the residue was purified by column chromatography on silica gel (PE:EtOAc=1:1) to give (11-4 (Cis) racemic), a mixture of (3S,7aS)-3-methylhexahydro-1H-pyrrolizine-7a-carboxylate and (3R,7aR)-3-methylhexahydro-1H-pyrrolizine-7a-carboxylate.

$^1$H NMR (400 MHz, CDCl$_3$) δ 3.68 (s, 3H), 3.98~4.05 (m, 1H), 2.68~2.76 (m, 2H), 2.32~2.44 (m, 1H), 2.12~2.24 (m, 1H), 1.54~1.97 (m, 6H), 1.10 (d, J=6.4 Hz, 3H).

Preparation of ((3S,7aR) and (3R,7aS))-(3-methylhexahydro-1H-pyrrolizin-7a-yl)methanol (11-5 (Cis) racemic)

To a mixture of LiAlH$_4$ (1.2 g, 32.74 mmol) in THF (100 mL) was added 11-4 (Cis) racemic (5 g, 27.29 mmol) in 20 mL THF at 0° C. The mixture was stirred at 25° C. for 2 h. Then the reaction solution was quenched with water, dried with Mg$_2$SO$_4$ and filtered. The combined organic phases were concentrated. The residue was purified by column chromatography on silica gel (DCM: MeOH=20:1) to give 11-5 (Cis), which is a mixture of (3S,7aR)-(3-methylhexahydro-1H-pyrrolizin-7a-yl)methanol and (3R,7aS)-(3-methylhexahydro-1H-pyrrolizin-7a-yl)methanol.

$^1$H NMR (400 MHz CDCl$_3$) δ 3.67~3.55 (m, 2H), 3.37~3.29 (m, 1H), 3.07~2.90 (m, 2H), 2.24~2.17 (m, 1H), 2.00~1.89 (m, 5H), 1.75~1.66 (m, 2H), 1.39 (d, J=6.8 Hz, 3H).

Preparation of ((3S,7aS) and (3R,7aR)-7a-(azidomethyl)-3-methylhexahydro-1H-pyrrolizine ((11-6 Cis) racemic)

A mixture of 11-5 (Cis) (1.5 g, 9.66 mmol), MsCl (2.2 g, 19.33 mmol) and TEA (2.9 g, 28.99 mmol) in 20 mL of DCM was stirred at room temperature for 3 h. The mixture was concentrated. The residue and NaN$_3$ (2.5 g, 38.57 mmol) in 30 mL of DMF was stirred overnight at 70° C. The mixture was filtered and washed with EtOAc. The solvent was quenched with water, extracted with EtOAc, dried with Mg$_2$SO$_4$ and filtered. The combined organic phases were concentrated, purified by column chromatography (PE:EtOAc=1:1) to afford 11-6 (Cis racemic), a mixture of (3S, 7aS)-7a-(azidomethyl)-3-methylhexahydro-1H-pyrrolizine and (3R,7aR)-7a-(azidomethyl)-3-methylhexahydro-1H-pyrrolizine.

$^1$H NMR (400 MHz, CDCl$_3$) δ 3.23~3.02 (m, 2H), 2.96~2.82 (m, 1H), 2.75~2.54 (m, 2H), 1.93~1.65 (m, 5H), 1.60 (d, J=7.0 Hz, 1H), 1.55~1.44 (m, 2H), 1.10 (d, J=6.4 Hz, 3H).

Preparation of ((3S,7aS and 3R,7aR)-3-methylhexahydro-1H-pyrrolizin-7a-yl)methanamine (11-7 (Cis) racemic)

A mixture of 11-6 (Cis), prepared above (400 mg, 2.22 mmol), and Pd/C (50 mg) in MeOH (10 mL) was stirred at 25° C. overnight under H$_2$. Then the reaction solution was filtered, concentrated and the residue was purified by column chromatography (DCM/MeOH=10:1) to afford 11-7 (Cis), a mixture of ((3S,7aS)-3-methylhexahydro-1H-pyrrolizin-7a-yl)methanamine and ((3R,7aR)-3-methylhexahydro-1H-pyrrolizin-7a-yl)methanamine.

$^1$H NMR (400 MHz, CDCl$_3$) δ 2.88~2.58 (m, 4H), 2.51~2.47 (m, 1H), 1.85~1.74 (m, 4H), 1.60~1.40 (m, 4H), 1.08 (d, J=6.4 Hz, 3H).

Preparation of 5-chloro-2-fluoro-4-((((3S,7aS)-3-methylhexahydro-1H-pyrrolizin-7a-yl)methyl)amino)-N-(thiazol-2-yl)benzenesulfonamide and 5-chloro-2-fluoro-4-((((3R,7aR)-3-methylhexahydro-1H-pyrrolizin-7a-yl)methyl)amino)-N-(thiazol-2-yl)benzenesulfonamide (11-8 Isomer A and 11-8 Isomer B)

A mixture of 11-7 (Cis), previously prepared (50 mg, 0.32 mmol), 20-3 (149 mg, 0.32 mmol) and K$_2$CO$_3$ (89 mg, 0.64 mmol) in DMF (5 mL) was stirred at room temperature overnight. Then the mixture was concentrated. The crude compound was purified by prep-TLC (DCM/MeOH=20:1) to give a coupled product.

The coupled product obtained in the last step (90 mg, 0.15 mmol) was dissolved in CH$_2$Cl$_2$/TFA (5 mL/4:1) and stirred at room temperature for 1 h. The mixture was concentrated and the residue was purified by prep-HPLC to give a racemic product, which was resolved by SFC to obtain pure amounts of the separated Cis enantiomers (Column: IC 250×4.6 mm I.D., 5 um; Mobile phase: 60% ethanol (0.05% DEA) in CO$_2$, Flow rate: 2.0 mL/min; Wavelength: 280 nm; Run time: 15 min; Retention time: (11-8 Isomer A (faster eluting)): 6.71 min; and (11-8 Isomer B (slower eluting)): 7.62 min).

$^1$H NMR (400 MHz, CD$_3$OD) δ 7.74 (d, J=7.2 Hz, 1H), 7.09 (d, J=4.8 Hz, 1H), 6.88 (d, J=12.8 Hz, 1H), 6.71 (d, J=4.4 Hz, 1H), 3.82~3.64 (m, 2H), 3.56~3.46 (m, 1H), 3.44~3.35 (m, 2H), 2.29~1.96 (m, 7H), 1.86~1.72 (m, 1H), 1.48 (d, J=6.4 Hz, 3H). HRMS m/z (M+H) 445.0940 found, 445.0930 required (11-8 Isomer A); HRMS m/z (M+H) 445.0941 found, 445.0930 required (11-8 Isomer B).

TABLE 11

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Example | Structure | Name | Data |
| --- | --- | --- | --- |
| 11-10 Isomer A | Enantiomer of 11-10 Isomer B | 4-((((3S,7aS or 3R,7aR)-3-methyl-hexahydro-1H-pyrrolizin-7a-yl)methyl)-amino)-N-(thiazol-2-yl)-3-(trifluoromethyl)-benzenesulfonamide | $^1$H NMR (400 MHz, CD$_3$OD) δ 7.90-7.95 (m, 2H), 7.20 (d, J = 8.8 Hz, 1H), 7.10 (d, J = 0.4 Hz, 1H), 6.72 (d, J = 4.8 Hz, 1H), 3.78-3.85 (m, 2H), 3.49-3.51 (m, 1H), 3.36-3.40 (m, 2H), 2.18-2.25 (m, 4H), 1.99-2.04 (m, 3H), 1.79 (m, 1H), 1.47 (d, J = 6.4 Hz, 3H). HRMS m/z (M + H) 461.1289 found, 461.1287 required. |
| 11-10 Isomer B | Enantiomer of 11-10 Isomer A | 4-((((3R,7aR or 3S,7aS)-3-methylhexahydro-1H-pyrrolizin-7a-yl)methyl)-amino)-N-(thiazol-2-yl)-3-(trifluoromethyl)-benzenesulfonamide | $^1$H NMR (400 MHz, CD$_3$OD) δ 7.90-7.95 (m, 2H), 7.20 (d, J = 8.8 Hz, 1H), 7.10 (d, J = 0.4 Hz, 1H), 6.72 (d, J = 4.8 Hz, 1H), 3.78-3.85 (m, 2H), 3.49-3.51 (m, 1H), 3.36-3.40 (m, 2H), 2.18-2.25 (m, 4H), 1.99-2.04 (m, 3H), 1.79 (m, 1H), 1.47 (d, J = 6.4 Hz, 3H). HRMS m/z (M + H) 461.1291 found, 461.1287 required. |
| 11-12 Isomer A | Enantiomer of 11-12 Isomer B | 3-chloro-N-(5-fluorothiazol-2-yl)-4-((((3S,7aS or 3R,7aR)-3-methylhexahydro-1H-pyrrolizin-7a-yl)methyl)amino)benzene-sulfonamide | $^1$H NMR (400 MHz, CD$_3$OD) δ 7.73 (d, J = 1.6 Hz, 1H), 7.65 (d, J = 8.0 Hz, 1H), 7.05 (d, J = 8.4 Hz, 1H), 6.97 (s, 1H), 3.80-3.65 (m, 2H), 3.57-3.46 (m, 1H), 3.44-3.36 (m, 2H), 2.32-2.09 (m, 4H), 2.07-1.95 (m, 3H), 1.86-1.72 (m, 1H), 1.49 (d, J = 6.8 Hz, 3H). HRMS m/z (M + H) 445.0938 found, 445.0930 required. |
| 11-12 Isomer B | Enantiomer of 11-12 Isomer A | 3-chloro-N-(5-fluorothiazol-2-yl)-4-((((3R,7aR or 3S,7aS)-3-methylhexahydro-1H-pyrrolizin-7a-yl)methyl)-amino)benzene-sulfonamide | $^1$H NMR (400 MHz, CD$_3$OD) δ 7.73 (d, J = 1.6 Hz, 1H), 7.65 (d, J = 8.0 Hz, 1H), 7.04 (d, J = 8.4 Hz, 1H), 6.96 (s, 1H), 3.81-3.65 (m, 2H), 3.56-3.46 (m, 1H), 3.42-3.36 (m, 2H), 2.31-2.09 (m, 4H), 2.07-1.93 (m, 3H), 1.84-1.73 (m, 1H), 1.48 (d, J = 6.8 Hz, 3H). HRMS m/z (M + H) 445.0940 found, 445.0930 required. |

Example 12

2-bromo-5-chloro-4-(((hexahydro-1H-pyrrolizin-7a-yl)methyl)amino)-N-(thiazol-2-yl)benzenesulfonamide (12-5), 5-chloro-2-cyano-4-(((hexahydro-1H-pyrrolizin-7a-yl)methyl)amino)-N-(thiazol-2-yl)benzenesulfonamide (12-6), and 5-chloro-4-(((hexahydro-1H-pyrrolizin-7a-yl)methyl)amino)-2-methyl-N-(thiazol-2-yl)benzenesulfonamide (12-7)

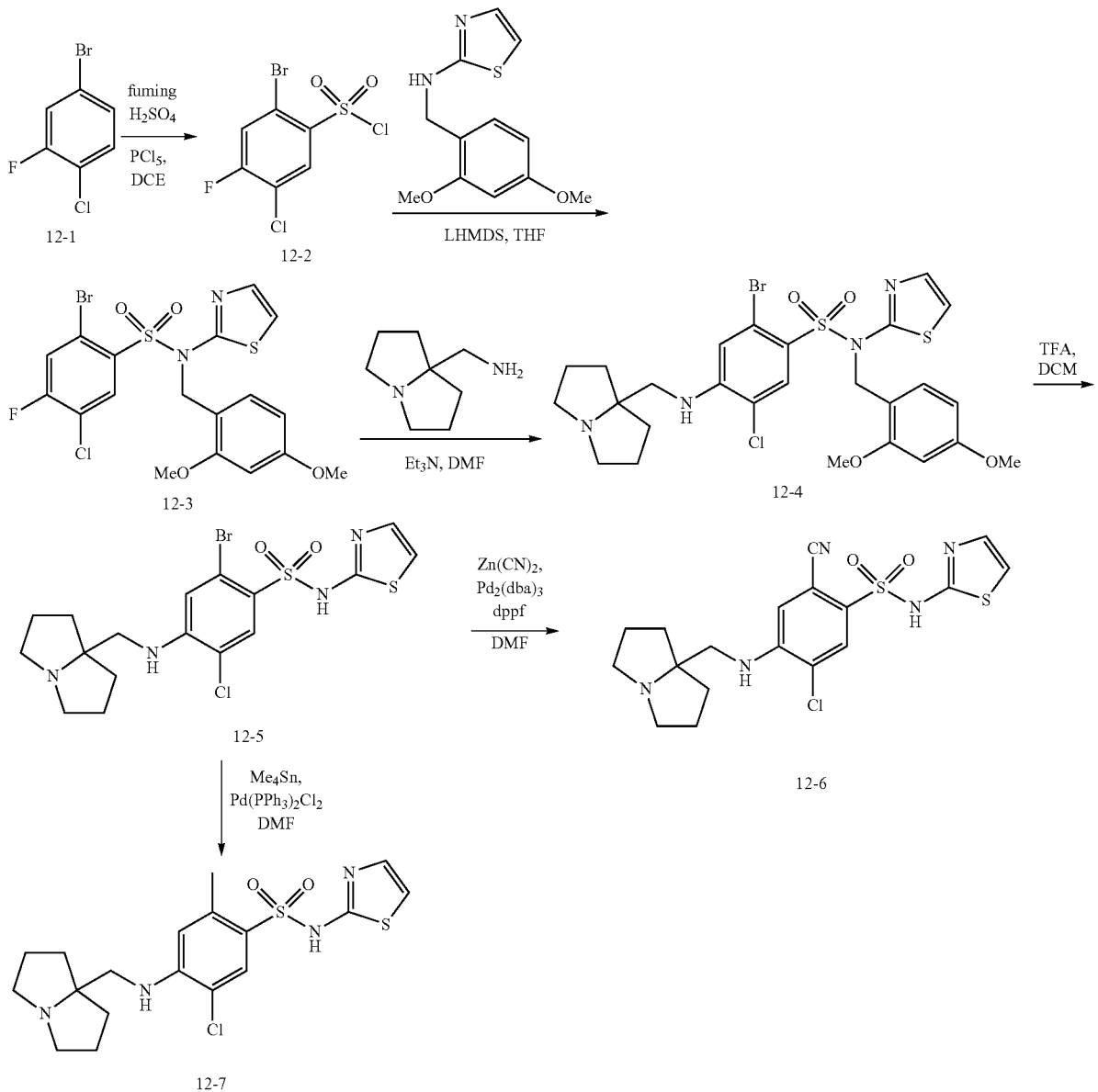

Scheme 12 vacuum. The precipitate was filtered off and the filtrate was diluted with DCE (100 mL). To the solution PCl$_5$ (16 g, 83.33 mmol) was added which was stirred at 110° C. under nitrogen overnight. The mixture was cooled to room temperature and carefully poured into ice. The resulting solution was stirred at room temperature for 30 mins, followed by addition of EtOAc. The organic layer was isolated and concentrated in vacuum. The residue was purified by column chromatography on silica gel (PE:EA=10:1) to give 12-2. $^1$H NMR (400 MHz, CDCl$_3$) δ 8.26 (d, J=7.2 Hz, 1H), 7.65 (d, J=8.0 Hz, 1H).

Preparation of 2-bromo-5-chloro-4-fluorobenzene-1-sulfonyl chloride (12-2)

A mixture of 12-1 (10 g, 48.54 mmol) in fuming sulfuric acid (50 mL) was stirred and heated at 110° C. overnight. The mixture was cooled to room temperature and carefully poured into ice. The resulting solution was stirred at room temperature for 30 mins, followed by addition of EtOAc. The aqueous layer was isolated and concentrated under

Preparation of 2-bromo-5-chloro-N-(2,4-dimethoxybenzyl)-4-fluoro-N-(thiazol-2-yl)benzenesulfonamide (12-3)

Under an atmosphere of nitrogen, 20-2 (3 g, 9.24 mmol) was dissolved in THF (30 mL) and cooled to −78° C.

LiHMDS (14 mL, 13.86 mmol, 1M in THF) was added dropwise, keeping the temperature below −60° C. After 30 mins, the cooling bath was removed and the reaction warmed to room temperature, stirred for a further 1 h then cooled back to −78° C. 12-2 (3.65 g, 14.61 mmol) in THF (10 mL) was added dropwise keeping the temperature below −60° C. and the reaction mixture was warmed to room temperature for 1 h. Saturated aqueous ammonium chloride solution (20 mL) was added followed by water to dissolve the solid which had precipitated out. The aqueous layer was extracted with ethyl acetate and the organic extracts dried over Na$_2$SO$_4$, filtered and concentrated. The residue was purified by column chromatography on silica gel (PE:EtOAc=5:1) to give 12-3.

$^1$H NMR (400 MHz, CDCl$_3$) δ 8.19 (d, J=7.6 Hz, 1H), 7.43 (d, J=8.0 Hz, 1H), 7.38 (d, J=3.6 Hz, 1H), 7.20 (s, 1H), 6.95 (d, J=2.8 Hz, 1H), 6.32-6.37 (m, 2H), 5.24 (s, 2H), 3.74 (s, 3H), 3.72 (s, 3H). MS m/z (M+H): 521

Preparation of 2-bromo-5-chloro-N-(2,4-dimethoxybenzyl)-4-(((hexahydro-1H-pyrrolizin-7a-yl)methyl)amino)-N-(thiazol-2-yl)benzenesulfonamide (12-4)

A mixture of 12-3 (500 mg, 0.96 mmol), amine (204 mg, 1.15 mmol), Et$_3$N (485 mg, 4.8 mmol) and DMF (10 mL) was stirred at room temperature under N$_2$ overnight. The mixture was poured into water and extracted with EtOAc. The combined organic layers were washed with brine, dried over Na$_2$SO$_4$, filtered and the filtrate was concentrated. The crude product was purified by column chromatography on silica gel (DCM: MeOH=20:1) to give the product of 12-4.

Preparation of 2-bromo-5-chloro-4-(((hexahydro-1H-pyrrolizin-7a-yl)methyl)amino)-N-(thiazol-2-yl)benzenesulfonamide (12-5)

To a mixture of 12-4 (80 mg, 0.124 mmol) in DCM (3 mL) was added TFA (0.6 ml), and the resulting solution was stirred at room temperature for 1 h. The mixture was concentrated in vacuo. The residue was dissolved in DMF (5.0 ml), filtered and purified by prep-HPLC to give 12-5.

$^1$H NMR (400 MHz, CD$_3$OD) δ 7.91 (s, 1H), 7.19 (s, 1H), 7.02 (d, J=4.0 Hz, 1H), 6.64 (d, J=4.0 Hz, 1H), 3.62 (s, 2H), 3.50 (brs, 2H), 3.16 (brs, 2H), 1.96-2.05 (m, 8H). HRMS m/z (M+H) 490.9991 found, 490.9972 required.

Preparation of 5-chloro-2-cyano-4-(((hexahydro-1H-pyrrolizin-7a-yl)methyl)amino)-N-(thiazol-2-yl)benzenesulfonamide (12-6)

To a solution of 12-5 (50 mg, 0.1 mmol) in 1.5 mL of DMF was added Zn(CN)$_2$ (15 mg, 0.12 mmol), Pd(PPh$_3$)$_4$ (12 mg, 0.01 mmol) under N$_2$. The mixture was stirred under microwave at 165° C. for 30 min. The mixture was cooled to room temperature, filtered and purified by prep-HPLC to give 12-6 as a white solid.

$^1$H NMR (CD$_3$OD, 400 MHz) δ 7.97 (s, 1H), 7.47 (s, 1H), 7.12 (d, J=4.8 Hz, 1H), 6.75 (d, J=4.8 Hz, 1H), 3.75 (s, 2H), 3.61-3.57 (m, 2H), 3.26-3.23 (m, 2H), 2.16-2.04 (m, 8H). HRMS m/z (M+H) 438.0825 found, 438.0820 required.

Preparation of 5-chloro-4-(((hexahydro-1H-pyrrolizin-7a-yl)methyl)amino)-2-methyl-N-(thiazol-2-yl)benzenesulfonamide (12-7)

To a solution of 12-5 (50 mg, 0.1 mmol) in 1.5 mL of DMF were added LiCl (29 mg, 0.7 mmol), Pd(PPh$_3$)$_2$Cl$_2$ (7 mg, 0.01 mmol) and Me$_4$Sn (52 mg, 0.3 mmol). The mixture was stirred at 110° C. for 3 h. The mixture was filtered and purified by prep-HPLC to give 12-7 as a white solid.

$^1$H NMR (CD$_3$OD, 400 MHz) δ 7.84 (s, 1H), 7.07 (d, J=4.8 Hz, 1H), 6.86 (s, 1H), 6.67 (d, J=4.8 Hz, 1H), 3.68 (s, 2H), 3.58-3.54 (m, 2H), 3.25-3.22 (m, 2H), 2.56 (s, 3H), 2.15-2.11 (m, 4H), 2.06-2.02 (m, 4H). HRMS m/z (M+H) 427.1030 found, 427.1024 required.

Example 13

(S)-5-chloro-2-fluoro-4-(((hexahydrospiro[cyclopropane-1,2'-pyrrolizin]-7a'-yl)-methyl)amino)-N-(thiazol-2-yl)benzenesulfonamide and (S)-5-chloro-2-fluoro-4-(((hexahydrospiro[cyclopropane-1,2'-pyrrolizin]-7a'-yl)-methyl)amino)-N-(thiazol-2-yl)benzenesulfonamide (compound 13-10 Isomer A and 13-10 isomer B)

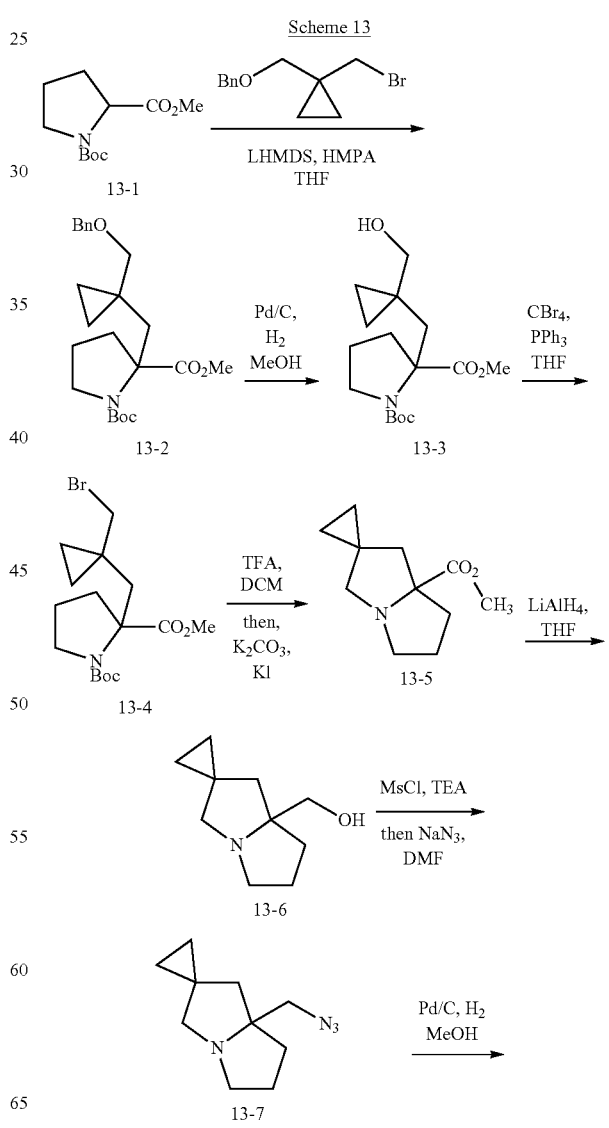

Scheme 13

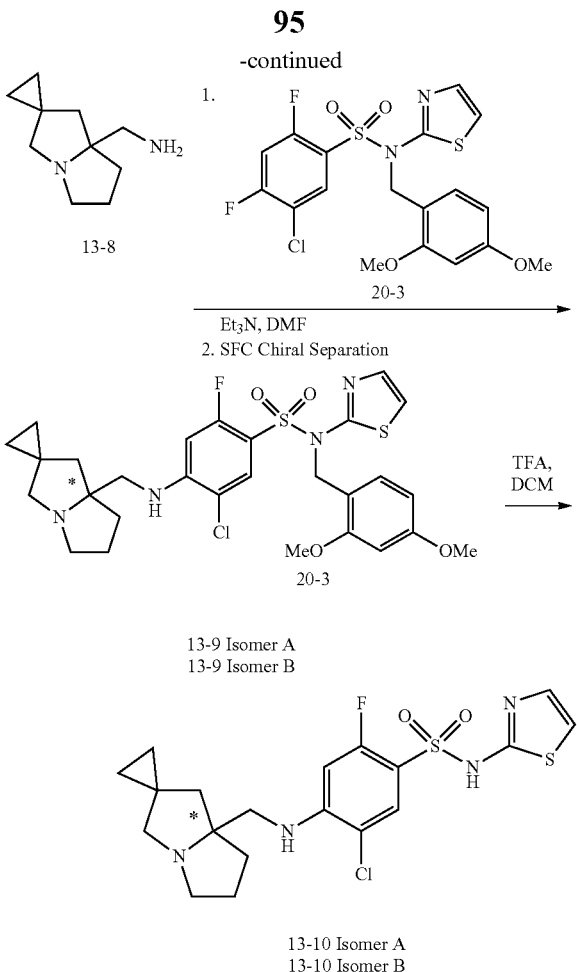

13-8

20-3

1. Et₃N, DMF
2. SFC Chiral Separation 13-9 Isomer A
13-9 Isomer B

TFA, DCM 20-3

13-10 Isomer A
13-10 Isomer B

Preparation of 1-tert-butyl 2-methyl 2-((1-(benzyloxymethyl) cyclopropyl)methyl) pyrrolidine-1,2-dicarboxylate (13-2)

To a mixture of LiHMDS (2.8 ml, 2.8 mmol) in dry THF was added 13-1 (522 mg, 2.28 mmol) dropwise at −78° C. under N₂. Then the mixture was stirred for 1 h. Then (((1-(bromomethyl)cyclopropyl)methoxy)methyl)benzene (814 mg, 2.96 mmol) and HMPA (2 g, 8.6 mmol) was added into the above mixture and the mixture was stirred at room temperature overnight. Then water was added. The mixture was extracted with EtOAc. The organic layer was washed with water, brine, dried over Na₂SO₄. The product was purified by column chromatography (PE:EA=1:1).

¹HNMR (400 MHz, CD₃OD) δ 7.19~7.27 (m, 5H), 4.28~4.51 (m, 2H), 3.6~3.66 (m, 4H), 3.01~3.26 (m, 3H), 1.81~2.50 (m, 6H), 1.18~1.38 (m, 9H), 0.40~0.68 (m, 4H).

Preparation of 1-tert-butyl 2-methyl 2-((1-(hydroxymethyl)cyclopropyl)methyl) pyrrolidine-1,2-dicarboxylate (13-3)

To a solution of 13-2 (500 mg, 1.24 mmol) in CH₃OH was added Pd/C (50 mg, wt %: 10%). Then the mixture was stirred at room temperature under H₂ for 2 h. After completion of the reaction, Pd/C was removed by filtering and the filtrate was concentrated by vacuo to give the crude product used in the next step directly.

¹HNMR (400 MHz, CD₃OD) δ 3.01~3.54 (m, 5H), 2.50~2.85 (m, 2H), 2.02~2.86 (m, 2H), 1.51~1.69 (m, 4H), 1.05~1.3 (m, 9H), 0.42~0.53 (m, 4H).

Preparation of 1-tert-butyl 2-methyl 2-((1-(bromomethyl)cyclopropyl)methyl)pyrrolidine-1,2-dicarboxylate (13-4)

A mixture of 13-3 (2 g, 6.4 mmol), CBr₄ (3.2 g, 9.6 mmol) and PPh₃ (2.5 g, 9.4 mmol) in DCM (30 mL) was stirred at room temperature overnight. The mixture was concentrated by vacuo to give the crude product which was purified by column chromatography to give the final product.

¹HNMR (400 MHz, CDCl₃) δ 3.48~3.71 (m, 5H), 2.78~3.07 (m, 2H), 1.89~2.06 (m, 5H), 1.60~1.74 (m, 1H), 1.43~1.44 (m, 9H), 0.55~0.74 (m, 4H).

Preparation of methylhexahydrospiro[cyclopropane-1,2'-pyrrolizine]-7a'-carboxylate (13-5)

To a solution of 13-4 (450 mg, 1.2 mmol) in CH₂Cl₂ (6 mL) was added TFA (3 mL) at 0° C. Then the mixture was stirred at room temperature under N₂. After the reaction completed, the mixture was concentrated by vacuo to give the crude product used in the next step directly.

A mixture of the above crude product and K₂CO₃ (662 mg, 4.8 mmol) in DMF (10 mL) was stirred at room temperature overnight. Then water was added. The mixture was extracted with EtOAc. The organic layer was washed with water, brine, dried over Na₂SO₄. The product was purified by column chromatography (PE:EA=1:1).

¹HNMR (400 MHz, CDCl₃) δ 3.67 (s, 3H), 2.63~3.15 (m, 4H), 1.98~2.19 (m, 2H), 1.75~1.81 (m, 4H), 0.43~0.50 (m, 4H). MS m/z (M+H): 196.1

Preparation of (hexahydrospiro[cyclopropane-1,2'-pyrrolizine]-7a'-yl)methanole (13-6)

To a solution of LiAlH₄ (90 mg, 2.3 mmol) in THF (4 mL) was added the solution of 13-5 (300 mg, 1.54 mmol) in THF at 0° C. under N₂. Then the mixture was stirred at refluxing for 4 h. Then water (0.1 mL) was added to the mixture which was stirred for 10 min. MgSO₄ was added and the mixture was stirred for 30 min. The solid was removed by filtration and the solvent was removed by vacuo. The product was used in the next step directly.

Preparation of 7a'-(azidomethyl)hexahydrospiro[cyclopropane-1,2'-pyrrolizine] (13-7)

To a solution of 13-6 (230 mg, 1.4 mmol), Et₃N (417 mg, 4.13 mmol) in CH₂Cl₂ was added MsCl (236 mg, 2.1 mmol) at 0° C. dropwise under N₂. Then the mixture was stirred at room temperature under N₂ for 1 h. The mixture was diluted with water and extracted with CH₂Cl₂. The organic layer was washed with water, brine, dried over Na₂SO₄, filtered and concentrated. The crude product was used in next step without further purification To the solution of the above crude product in DMF was added NaN₃ (447 mg, 6.9 mmol), then the mixture was stirred at 80° C. overnight under N2. Then the mixture was diluted with EtOAc and the solid was removed by filtering, the filtrate was washed with water. The organic layer was washed with water, brine, dried over Na₂SO₄. The product was purified by column chromatography (PE:EtOAc=5:1).

¹HNMR (400 MHz, CDCl₃) δ 2.86~3.01 (m, 1H), 2.46~59 (m, 3H), 1.76~1.85 (m, 1H), 1.22~1.66 (m, 7H), 0.42~0.53 (m, 4H).

Preparation of 1-tert-butyl 2-methyl 2-((1-(hydroxymethyl)cyclopropyl)methyl) pyrrolidine-1,2-dicarboxylate (13-8)

To a solution of 13-7 (170 mg, 0.9 mmol) in CH₃OH was added Pd/C (50 mg, wt %: 10%). Then the mixture was stirred at room temperature under H₂ for 2 h. Pd/C was removed by filtering and the filtrate was concentrated by vacuo to give the crude product used in the next step directly.

Preparation of (S)-5-chloro-N-(2,4-dimethoxybenzyl)-2-fluoro-4-((hexahydrospiro [cyclopropane-1,2'-pyrrolizine]-7a'-yl)methylamino)-N-(thiazol-2-yl)benzenesulfonamide and (R)-5-chloro-N-(2,4-dimethoxybenzyl)-2-fluoro-4-((hexahydrospiro [cyclopropane-1,2'-pyrrolizine]-7a'-yl)methylamino)-N-(thiazol-2-yl)benzenesulfonamide, (13-9 Isomer A and 13-9 Isomer B)

A mixture of 13-8 (100 mg, 0.6 mmol), 20-3 (277 mg, 0.6 mmol) and Et₃N (243 mg, 2.4 mmol) in DMF was stirred for 3 h at room temperature under N₂. Then the mixture was concentrated by vacuo to give a crude racemic product. The product was purified by prep-TLC (PE:EtOAc=1:1). The racemic product was separated by chiral column (Column: Chiralpak AD-3 150×4.6 mm I.D., 3 um; Mobile phase: ethanol (0.05% DEA) in CO₂ from 5% to 40%; Flow rate: 2.5 mL/min; Wavelength: 220 nm; Run time: 12 min; Retention time: (13-9 Isomer A (faster eluting)): 5.126 min; (13-9 Isomer B (slower eluting)): 8.066 min). MS m/z (M+H): 607.1

Preparation of (S)-5-chloro-2-fluoro-4-((hexahydrospiro[cyclopropane-1,2'-pyrrolizine]-7a'-yl)methylamino)-N-(thiazol-2-yl)benzenesulfonamide and (R)-5-chloro-2-fluoro-4-((hexahydrospiro[cyclopropane-1,2'-pyrrolizine]-7a'-yl)methylamino)-N-(thiazol-2-yl)benzenesulfonamide (compound 13-10 Isomer A and 13-10 Isomer B)

A mixture of 13-9 Isomer A (80 mg, 0.13 mmol), TFA (0.5 mL) in DCM (4 mL) was stirred at room temperature overnight. After the reaction completed, the mixture was concentrated by vacuo to give the crude product which was purified by prep-HPLC to give the final product, which was characterized by NMR.
¹HNMR (400 MHz, CD₃OD) δ 7.75 (d, J=8.0 Hz, 1H), 7.12 (d, J=8.0 Hz, 1H), 6.92 (d, J=8.0 Hz, 1H), 6.72 (d, J=8.0 Hz, 1H), 3.30~3.77 (m, 5H), 2.87~2.90 (m, 1H), 2.37~2.46 (m, 2H), 1.85~2.08 (m, 4H), 0.93~0.99 (m, 2H), 0.68~0.72 (m, 2H). HRMS m/z (M+H) 457.0936 found, 457.0930 required.

Compound 13-10 Isomer B was prepared from 13-9 Isomer B using the same procedure that was used to prepare compound 13-10 Isomer A from compound 13-9 Isomer A.

Compound 13-10 Isomer B, the enantiomer of 13-10 Isomer A, was characterized by proton NMR.
¹HNMR (400 MHz, CD₃OD) δ 7.76 (d, J=8.0 Hz, 1H), 7.12 (d, J=8.0 Hz, 1H), 6.92 (d, J=8.0 Hz, 1H), 6.73 (d, J=8.0 Hz, 1H), 3.45~3.77 (m, 5H), 2.87~2.90 (m, 1H), 2.37~2.46 (m, 2H), 1.85~2.07 (m, 4H), 0.93~0.99 (m, 2H), 0.68~0.72 (m, 2H). HRMS m/z (M+H) 457.0937 found, 457.0930 required.

TABLE 13

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Exp | Structure | Name | Data |
| --- | --- | --- | --- |
| 13-12 Isomer A<br>Enantiomer of 13-12 Isomer B | (structure image) | (S or R)-N-(5-fluorothiazol-2-yl)-4-(((hexahydrospiro-[cyclopropane-1,2'-pyrrolizin]-7a'-yl)methyl)-amino)-3-(trifluoromethyl)-benzenesulfonamide | ¹HNMR (400 MHz CD₃OD) δ 7.88~7.92 (m, 2H), 7.18 (d, J = 8.0 Hz, 1H), 6.97 (s, 1H), 3.85 (s, 2H), 3.21~3.54 (m, 4H), 2.04~2.30 (m, 6H), 0.81~0.84 (m, 2H), 0.67~0.74 (m, 2H). HRMS m/z (M + H) 491.1219 found, 491.1193 required. |
| 13-12 Isomer B<br>Enantiomer of 13-12 Isomer A | (structure image) | (R or S)-N-(5-fluorothiazol-2-yl)-4-(((hexahydrospiro-[cyclopropane-1,2'-pyrrolizin]-7a'-yl)methyl)-amino)-3-(trifluoromethyl)-benzenesulfonamide | ¹HNMR (400 MHz CD₃OD) δ 7.88~7.93 (m, 2H), 7.18 (d, J = 8.0 Hz, 1H), 6.97 (s, 1H), 3.86 (s, 2H), 3.21~3.54 (m, 4H), 2.04~2.28 (m, 6H), 0.81~0.84 (m, 2H), 0.70~0.74 (m, 2H). HRMS m/z (M + H) 491.1213 found, 491.1193 required. |

Example 14

5-chloro-2-fluoro-4-((((3S,7aS and 3R, 7aR)-3-(fluoromethyl)hexahydro-1H-pyrrolizin-7a-yl)methyl)amino)-N-(thiazol-2-yl)benzenesulfonamide (14-10 racemic (Trans)); 5-chloro-2-fluoro-4-((((3R, 7aR)-3-(hydroxymethyl)hexahydro-1H-pyrrolizin-7a-yl)methyl)amino)-N-(thiazol-2-yl)benzenesulfonamide and 5-chloro-2-fluoro-4-((((3S,7aS)-3-(hydroxymethyl)hexahydro-1H-pyrrolizin-7a-yl)methyl)amino)-N-(thiazol-2-yl)benzenesulfonamide (14-11 Isomer A and 14-11 Isomer B)

Preparation of 1-benzyl 2-methyl 2-(2-(oxiran-2-yl)ethyl)pyrrolidine-1,2-dicarboxylate (14-1)

A mixture of 11-2 (10.0 g, 31.5 mmol), mCPBA (13.5 g, 78.8 mmol) in 200 mL of DCM was stirred at room temperature for 8 h. The mixture was quenched with NaHSO$_3$, extracted with DCM, dried with Mg$_2$SO$_4$ and filtered. The combined organic phases were concentrated, purified by column chromatography (PE:EtOAc=10:1) to afford 14-1.

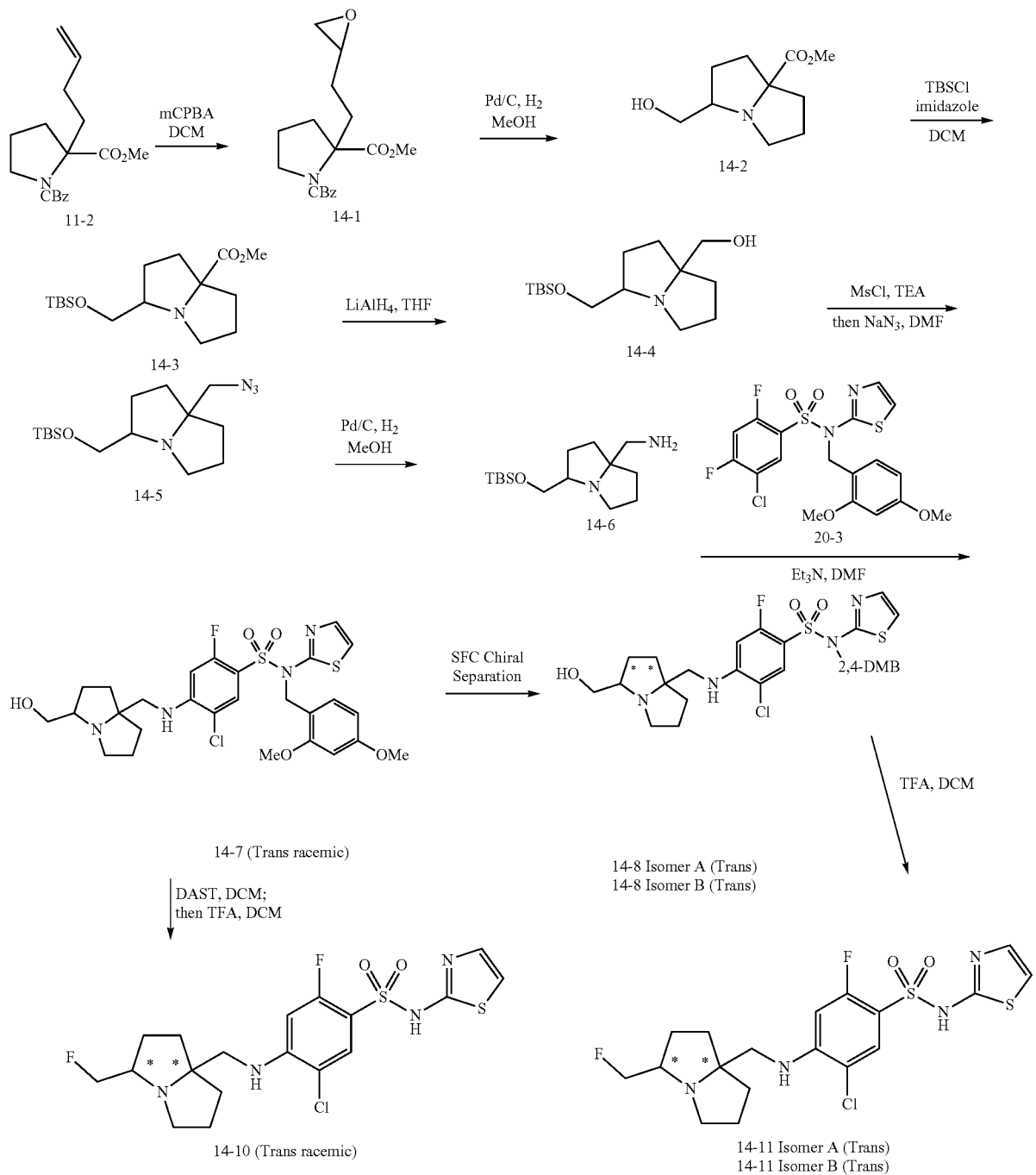

Scheme 14

¹H NMR (CDCl₃, 400 MHz) δ 7.24~7.32 (m, 5H), 5.05~5.12 (m, 2H), 3.67 (s, 3H), 3.42~3.48 (m, 2H), 2.69~2.71 (m, 2H), 2.07~2.47 (m, 2H), 1.82~2.05 (m, 5H), 1.42~1.59 (m, 2H).

Preparation of methyl 3-(hydroxymethyl)hexahydro-1H-pyrrolizine-7a-carboxylate (14-2)

To a solution of 14-1 (6 g, 18 mmol) in MeOH (150 mL) was added Pd—C (10%, 600 mg) under N₂. The suspension was degassed under vacuum and purged with H₂ (15 psi) several times. The mixture was stirred at room temperature for 4 h. The mixture was filtered and concentrated. The residue was used in the next step without purification. MS m/z (M+H): 200.1

Preparation of methyl 3-(((tert-butyldimethylsilyl)oxy)methyl)hexahydro-1H-pyrrolizine-7a-carboxylate (14-3)

To a solution of 14-2 (2.0 g, 10.0 mmol) in DCM (100 mL) was added imidazole (2.1 g, 30.0 mmol) and TBSCl (2.3 g, 15.0 mmol) and the mixture was stirred at room temperature for 4 h. The mixture was diluted with water and extracted with DCM. The combined organic layers were concentrated. The residue was purified by column chromatography on silica gel (PE: EtOAc=8:1) to give 14-3.
¹H NMR (CDCl₃, 400 MHz) δ 3.81~3.85 (m, 1H), 3.69~3.74 (m, 1H), 3.65 (s, 3H), 3.20~3.25 (m, 1H), 2.87~2.89 (m, 1H), 2.76~2.78 (m, 1H), 2.37~2.41 (m, 1H), 2.12~2.15 (m, 1H), 1.59~1.78 (m, 6H), 0.84 (s, 9H), 0.02 (s, 6H). MS m/z (M+H): 314.2

Preparation of (3-(((tert-butyldimethylsilyl)oxy)methyl)hexahydro-1H-pyrrolizin-7a-yl)methanol (14-4)

To a mixture of LiAlH₄ (133 mg, 3.51 mmol) in 15 mL of THF was added 14-3 (1.0 g, 3.19 mmol) in 10 mL THF at 0° C. The mixture was stirred at room temperature for 2 h. Then the reaction solution was quenched with water, dried over MgSO4, filtered and concentrated. Purification by normal phase chromatography (0-30% EtOAc in Petroleum ether) yielded 14-4 as an oil.
¹H NMR (CDCl₃, 400 MHz) δ 3.79~3.82 (m, 1H), 3.62~3.66 (m, 1H), 3.19~3.22 (m, 2H), 3.03~3.04 (m, 1H), 2.75~2.77 (m, 1H), 2.66~2.68 (m, 1H), 1.86~1.89 (m, 1H), 1.50~1.69 (m, 7H), 0.84 (s, 9H), 0.02 (s, 6H).

Preparation of 7a-(azidomethyl)-3-(((tert-butyldimethylsilyl)oxy)methyl)hexahydro-1H-pyrrolizine (14-5)

A solution of MsCl (0.4 g, 3.5 mmol) in DCM (10 mL) was added dropwise into a solution of Et₃N (0.6 g, 6.3 mmol) and 14-4 (0.6 g, 2.1 mmol) in DCM (10 mL) at 0° C. under N₂. The mixture was stirred at room temperature for 2 h. The mixture was concentrated and the residue was used in the next step without purification.
The residue was dissolved in DMF (10 mL), and then NaN₃ (0.5 g, 6.8 mmol) was added in one portion. The mixture was stirred at 70° C. for 6 h, then cooled to room temperature and filtered. Then H₂O (100 mL) was added into the mixture which was extracted with EtOAc (100 mL×3). The combined organic phases were dried over Na₂SO₄, filtered and concentrated. The residue was purified by column chromatography on silica gel (PE:EtOAc=10:1) to give 14-5.
¹H NMR (CDCl₃, 400 MHz) δ 3.80~3.84 (m, 1H), 3.62~3.66 (m, 1H), 3.04~3.16 (m, 3H), 2.77~2.78 (m, 1H), 2.68~2.70 (m, 1H), 1.76~1.86 (m, 1H), 1.60~1.73 (m, 6H), 1.40~1.44 (m, 1H), 0.84 (s, 9H), 0.02 (s, 6H).

Preparation of (3-(((tert-butyldimethylsilyl)oxy)methyl)hexahydro-1H-pyrrolizin-7a-yl)methanamine (14-6)

To a solution of 14-5 (0.3 g, 1 mmol) in MeOH (10 mL) was added Pd—C (10%, 30 mg) under N₂. The suspension was degassed under vacuum and purged with H₂ (15 psi) several times. The mixture was stirred at room temperature for 6 h. The mixture was filtered and concentrated, the residue was used in the next step without purification.
¹H NMR (CDCl₃, 400 MHz) δ 3.83~3.87 (m, 1H), 3.62~3.66 (m, 1H), 3.01~3.03 (m, 1H), 2.72~2.75 (m, 1H), 2.63~2.64 (m, 1H), 2.45~2.52 (m, 2H), 1.86~1.89 (m, 1H), 1.55~1.69 (m, 6H), 1.40~1.42 (m, 1H), 0.84 (s, 9H), 0.02 (s, 6H).

Preparation of 5-chloro-N-(2,4-dimethoxybenzyl)-2-fluoro-4-((((3S,7aS and 3R,7aR)-3-(hydroxymethyl)hexahydro-1H-pyrrolizin-7a-yl)methyl)amino)-N-(thiazol-2-yl)benzenesulfonamide (14-7 (Trans) racemic)

To a mixture of 14-6 (150 mg, 0.5 mmol) in DMF (5 mL) was added 20-3 (243 mg, 0.5 mmol) and TEA (267 mg, 2.6 mmol). The mixture was stirred at 25° C. for 6 h and concentrated. The residue was purified by prep-TLC. The product was (1.5 g, 2.1 mmol) in THF (10 mL), was added to a solution of TBAF (2.5 mmol, 1M in THF) at 0° C. and the mixture was stirred at 25° C. for 5 h. The mixture was concentrated and the residue was purified by column chromatography on silica gel (PE:EtOAc=1:1, DCM:MeOH=10:1) to give 14-7 (Trans) racemic product.

Preparation of: 5-chloro-N-(2,4-dimethoxybenzyl)-2-fluoro-4-((((3S,7aS)-3-(hydroxymethyl)hexahydro-1H-pyrrolizin-7a-yl)methyl)amino)-N-(thiazol-2-yl)benzenesulfonamide and 5-chloro-N-(2,4-dimethoxybenzyl)-2-fluoro-4-((((3R,7aR)-3-(hydroxymethyl)hexahydro-1H-pyrrolizin-7a-yl)methyl)amino)-N-(thiazol-2-yl)benzenesulfonamide (14-8 Isomer A and 14-8 Isomer B)

A solution of 14-7 (Trans) racemic) prepared in the previous step, was resolved by SFC (Column: Chiralpak AD-H 250×4.6 mm I.D., 5 um; Mobile phase: methanol (0.05% DEA) in CO₂ from 5% to 40%; Flow rate: 2.35 mL/min; Wavelength: 220 nm; Run time: 15 min; providing the title isomers at: Retention time: 14-8 Isomer A (faster eluting): 10.160 min; 14-8 Isomer B (slower eluting): 11.116 min). These enantiomers were characterized by proton NMR.
¹H NMR (CDCl₃, 400 MHz) δ 7.65 (d, J=7.0 Hz, 1H), 7.31 (d, J=3.5 Hz, 1H), 7.14 (d, J=8.6 Hz, 1H), 6.89 (d, J=3.5 Hz, 1H), 6.32~6.27 (m, 2H), 6.23 (d, J=12.1 Hz, 1H), 5.13 (s, 2H), 3.82~3.74 (m, 2H), 3.68 (s, 6H), 3.42~3.33 (m, 1H), 3.24~3.10 (m, 3H), 2.84~2.74 (m, 1H), 1.93~1.59 (m, 8H). MS m/z (M+H): 611.1

Preparation of 5-chloro-2-fluoro-4-((((3S,7aS and 3R,7aR)-3-(fluoromethyl)hexahydro-1H-pyrrolizin-7a-yl)methyl)amino)-N-(thiazol-2-yl)benzenesulfonamide (14-10 (Trans) racemic)

To a mixture of 14-7 (Trans) prepared in the previous step (20 mg, 0.32 mmol) in DCM (5 mL) was added DAST (0.2 mL) at −78° C. under N₂. The mixture was stirred at −78° C. for 2 h. The residue was purified by prep-TLC. To the product (30 mg, 49 umol) in DCM (1 mL) was added TFA (0.2 mL). The mixture was stirred at 26° C. for 1 h. The residue was purified by prep-HPLC to give 14-10 (trans), which is a racemic mixture of 5-chloro-2-fluoro-4-((((3S,7aS)-3-(fluoromethyl)hexahydro-1H-pyrrolizin-7a-yl)methyl)amino)-N-(thiazol-2-yl)benzenesulfonamide and 5-chloro-2-fluoro-4-((((3R,7aR)-3-(fluoromethyl)hexahydro-1H-pyrrolizin-7a-yl)methyl)amino)-N-(thiazol-2-yl)benzenesulfonamide.

¹H NMR (400 MHz, CD₃OD) δ 7.76 (d, J=7.0 Hz, 1H), 7.10 (d, J=4.3 Hz, 1H), 6.91 (d, J=12.5 Hz, 1H), 6.73 (d, J=4.7 Hz, 1H), 4.81~4.75 (m, 1H), 4.72~4.62 (m, 1H), 4.07~3.95 (m, 1H), 3.75~3.63 (m, 2H), 3.62~3.54 (m, 1H), 3.44~3.35 (m, 1H), 2.33~1.87 (m, 8H). HRMS m/z (M+H) 463.0843 found, 463.0835 required.

Preparation of: 5-chloro-2-fluoro-4-((((3S,7aS)-3-(hydroxymethyl)hexahydro-1H-pyrrolizin-7a-yl)methyl)amino)-N-(thiazol-2-yl)benzenesulfonamide and 5-chloro-2-fluoro-4-((((3R,7aR)-3-(hydroxymethyl)hexahydro-1H-pyrrolizin-7a-yl)methyl)amino)-N-(thiazol-2-yl)benzenesulfonamide (14-11 Isomer A and 14-11 Isomer B)

A mixture of 14-8 Isomer A (Trans) prepared in the previous step, (80 mg, 0.11 mmol), and TFA (0.5 mL) in DCM (4 mL) was stirred at room temperature overnight. After the reaction completed, the mixture was concentrated in vacuo to give the crude product which was purified by prep-HPLC to give 14-11 Isomer A (Trans).

The compound 14-11 Isomer A (Trans) was characterized by proton NMR: ¹H NMR (400 MHz, CD₃OD) δ 7.74 (d, J=7.2 Hz, 1H), 7.10 (d, J=4.8 Hz, 1H), 6.89 (d, J=8.8 Hz, 1H), 6.72 (d, J=4.4 Hz, 1H), 3.86~3.89 (m, 1H), 3.72~3.75 (m, 4H), 3.65~3.68 (m, 1H), 3.56~3.61 (m, 1H), 1.90~2.23 (m, 8H). HRMS m/z (M+H) 461.0885 found, 461.0879 required.

Compound 14-11 Isomer B was prepared from compound 14-8 Isomer B using the same procedure employed to prepare compound 14-11 Isomer A from of 14-8 Isomer A.

The compound 14-11 Isomer B, which is the enantiomer of 14-11 Isomer A, was characterized by proton NMR: ¹H NMR (400 MHz, CD₃OD) δ 7.74 (d, J=7.2 Hz, 1H), 7.10 (d, J=4.8 Hz, 1H), 6.89 (d, J=8.8 Hz, 1H), 6.72 (d, J=4.4 Hz, 1H), 3.86~3.89 (m, 1H), 3.72~3.75 (m, 4H), 3.65~3.68 (m, 1H), 3.56~3.61 (m, 1H), 1.90~2.23 (m, 8H). HRMS m/z (M+H) 461.0884 found, 461.0879 required.

Example 15

5-chloro-2-fluoro-4-((((2R,7aS)-2-(4-methoxybenzyl)hexahydro-1H-pyrrolizin-7a-yl)methyl)amino)-N-(thiazol-2-yl)benzenesulfonamide and 5-chloro-2-fluoro-4-((((2S,7aR)-2-(4-methoxybenzyl)hexahydro-1H-pyrrolizin-7a-yl)methyl)amino)-N-(thiazol-2-yl)benzenesulfonamide ((15-10 Isomer A and 15-10 Isomer B)

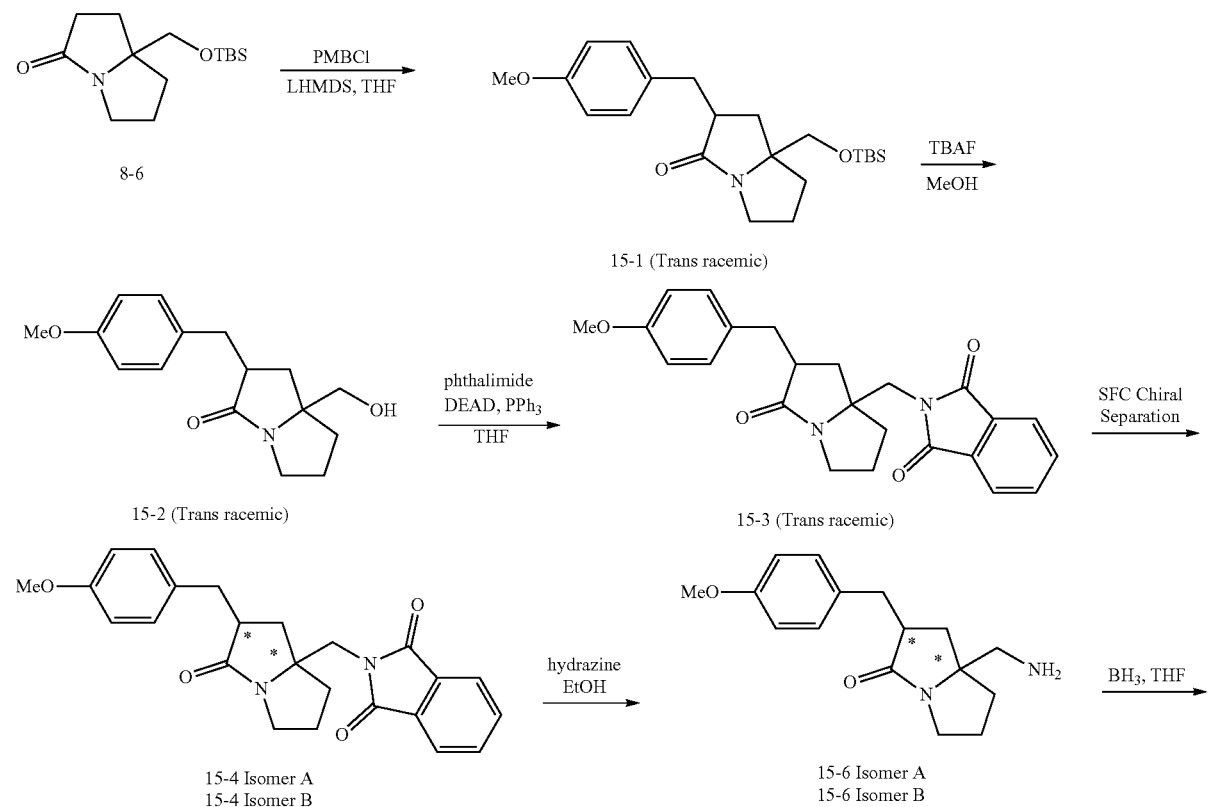

Scheme 15

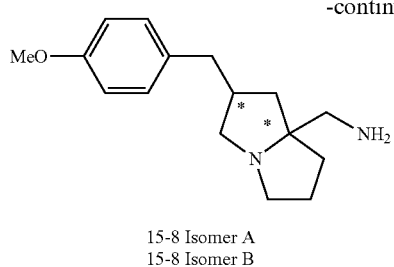
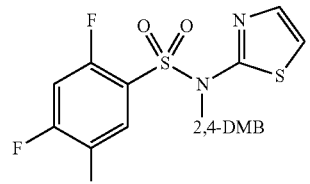

15-8 Isomer A
15-8 Isomer B 20-3

Et₃N, DMF;
then TFA, DCM

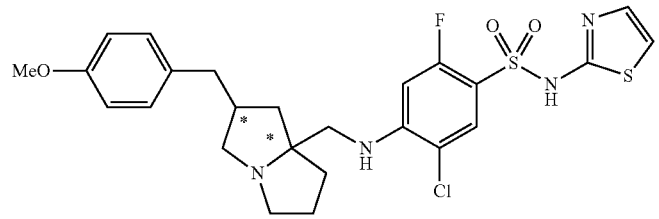

15-10 Isomer A
15-10 Isomer B

Preparation of racemic (2R,7aS and 2S,7aR)-7a-((tert-butyldimethylsilyloxy)methyl)-2-(4-methoxybenzyl) tetrahydro-1H-pyrrolizin-3(2H)-one (15-1 (Trans))

To a mixture of LiHMDS (2.2 ml, 2.2 mmol) in dry THF was added 8-6 (0.5 g, 1.9 mmol) dropwise at −78° C. under N₂. Then the mixture was stirred for 1 h. Then PMBCl (0.43 g, 2.8 mmol) was added into the above mixture and the mixture was stirred at room temperature overnight. Then water was added. The mixture was extracted with EtOAc. The organic layer was washed with water, brine, dried over Na₂SO₄. The product was purified by column chromatography (PE:EA=1:1).

¹H NMR (400 MHz, CDCl₃) δ 7.08 (d, J=8.0 Hz, 2H), 6.81 (d, J=8.0 Hz, 2H), 3.78~3.81 (m, 5H), 3.42~3.48 (m, 2H), 3.01~3.22 (m, 3H), 2.43~2.51 (m, 2H), 2.18~2.22 (m, 1H), 1.88~2.02 (m, 3H), 0.85 (s, 9H), 0.06 (m, 6H). MS m/z (M+H): 390.2

Preparation of (2R,7aS and 2S,7aR)-7a-(hydroxymethyl)-2-(4-methoxybenzyl)tetrahydro-1H-pyrrolizin-3(2H)-one (15-2 (Trans) racemic)

To a solution of 15-1 Trans racemic, prepared above (500 mg, 1.3 mmol), in THF (4 mL) was added the solution of TBAF (503 mg, 1.9 mmol) in THF at 0° C. Then the mixture was stirred at room temperature for 4 h. THF was removed in vacuo. The product was purified by column chromatography on silic gel.

¹H NMR (400 MHz, CDCl₃) δ 7.08 (d, J=8.0 Hz, 2H), 6.81 (d, J=8.0 Hz, 2H), 3.40~3.77 (m, 5H), 3.12~3.19 (m, 3H), 2.30~2.54 (m, 2H), 1.54~2.29 (m, 4H), 0.88~1.37 (m, 2H). MS m/z (M+H): 276.1

Preparation of racemic 2-(((2R,7aS and 2S,7aR)-2-(4-methoxybenzyl)-3-oxohexahydro-1H-pyrrolizin-7a-yl)methyl)isoindoline-1,3-dione (15-3 (Trans)); and chiral separation into trans isomers 2-(((2R,7aS)-2-(4-methoxybenzyl)-3-oxohexahydro-1H-pyrrolizin-7a-yl)methyl)isoindoline-1,3-dione and 2-(((2S,7aR)-2-(4-methoxybenzyl)-3-oxohexahydro-1H-pyrrolizin-7a-yl)methyl)isoindoline-1,3-dione (compounds 15-4 Isomer A and 15-4 Isomer B)

To a solution of 15-2 (Trans), previously prepared (300 mg, 1.1 mmol), PPh₃ (576 mg, 2.2 mmol) and phthalimide (323 mg, 2.2 mmol) in THF, was added DEAD (382 mg, 2.2 mmol) at 0° C. dropwise under N₂, and the mixture was stirred at room temperature under N₂ for 2 h. The mixture was diluted with water and extracted with EtOAc. The organic layer thus obtained was washed with water, brine, dried over Na₂SO₄, filtered, concentrated, and purified by column chromatography (PE:EtOAc=5:1) to provide 15-3, a racemic mixture of 2-(((2R,7aS)-2-(4-methoxybenzyl)-3-oxohexahydro-1H-pyrrolizin-7a-yl)methyl)isoindoline-1,3-dione and 2-(((2S,7a R)-2-(4-methoxybenzyl)-3-oxohexahydro-1H-pyrrolizin-7a-yl)methyl)isoindoline-1,3-dione ((15-3 (Trans)). The enantiomers present in the 15-3 (Trans) racemic product were obtained in pure form using chiral chromatography (Column: Chiralpak AD-3 150×4.6 mm I.D., 3 um; Mobile phase: 40% of methanol (0.05% DEA) in CO₂; Flow rate: 2.5 mL/min; Wavelength: 220 nm; Run time: 12 min; Retention time: 15-4 Isomer A (faster eluting): 3.51 min; 15-4 Isomer B (slower eluting): 7.82 min).

¹H NMR (400 MHz, CD₃OD) δ 7.83~7.85 (m, 2H), 7.72~7.75 (m, 2H), 7.04 (d, J=8.0 Hz, 2H), 6.80 (d, J=8.0 Hz, 2H), 3.78 (s, 3H), 3.72 (s, 2H), 3.62~3.64 (m, 1H), 3.04~3.25 (m, 3H), 2.53~2.59 (m, 2H), 2.02~2.08 (m, 3H), 1.25~1.56 (m, 2H). MS m/z (M+H): 405.2

Preparation of (2R,7aS)-7a-(aminomethyl)-2-(4-methoxybenzyl)tetrahydro-1H-pyrrolizin-3(2H)-one and (2S,7aR)-7a-(aminomethyl)-2-(4-methoxybenzyl)tetrahydro-1H-pyrrolizin-3(2H)-one (compounds 15-6 Isomer A and 15-6 Isomer B)

To a solution of 15-4 Isomer A prepared in the previous step (700 mg, 1.7 mmol), in EtOH was added N$_2$H$_4$.H$_2$O (1 mL). The mixture was stirred and refluxed for 2 h and thereafter EtOH was removed in vacuo. The residue was dissolved in CH$_2$Cl$_2$/MeOH (50:1) and filtered. The filtrate was concentrated in vacuo to afford the title product which was purified by column chromatography on silic gel.

$^1$H NMR (400 MHz, CD$_3$OD) δ 7.09 (d, J=8.0 Hz, 2H), 6.81 (d, J=8.0 Hz, 2H), 3.71~3.78 (m, 4H), 3.15~3.47 (m, 3H), 2.52~2.68 (m, 3H), 2.22~2.24 (m, 1H), 1.86~1.98 (m, 3H), 1.29~1.56 (m, 2H). MS m/z (M+H): 275.2

Compound 15-6 Isomer B was prepared from 15-4 Isomer B using the same procedure that was used to prepare compound 15-6 Isomer A from compound 15-4 Isomer A.

$^1$H NMR (400 MHz, CD$_3$OD) δ 7.09 (d, J=8.0 Hz, 2H), 6.81 (d, J=8.0 Hz, 2H), 3.71~3.78 (m, 4H), 3.15~3.47 (m, 3H), 2.52~2.68 (m, 3H), 2.22~2.24 (m, 1H), 1.86~1.98 (m, 3H), 1.29~1.56 (m, 2H). MS m/z (M+H): 275.2

Preparation of ((2R,7aS)-2-(4-methoxybenzyl)hexahydro-1H-pyrrolizin-7a-yl)-methanamine and ((2S,7aR)-2-(4-methoxybenzyl)hexahydro-1H-pyrrolizin-7a-yl)-methanamine (compounds 15-8 Isomer A and 15-8 Isomer B)

To a solution of 15-6 Isomer A, previously prepared (500 mg, 1.8 mmol), in THF (6 mL) was added BH$_3$.MeSMe (2.5 mL) in THF at 0° C. under N$_2$. Then the mixture was stirred at room temperature overnight. MeOH (0.3 mL) was added into the mixture which was stirred for 10 min. The mixture was concentrated in vacuo to give a residue. The residue was dissolved in HCl/MeOH, stirred and refluxed for 2 h and concentrated in vacuo to give the crude title product used in the next step directly.

Compound 15-8 Isomer B was prepared from 15-6 Isomer B using the same procedure that was used to prepare compound 15-8 Isomer A from compound 15-6 Isomer A.

Preparation of 5-chloro-2-fluoro-4-(((2R,7aS)-2-(4-methoxybenzyl)hexahydro-1H-pyrrolizin-7a-yl)methylamino)-N-(thiazol-2-yl)benzenesulfonamide and 5-chloro-2-fluoro-4-(((2S,7aR)-2-(4-methoxybenzyl)hexahydro-1H-pyrrolizin-7a-yl)methylamino)-N-(thiazol-2-yl)benzenesulfonamide (15-10 Isomer A and 15-10 Isomer B)

A mixture of 15-8 Isomer A, prepared in the previous step (100 mg, 0.3 mmol), 20-3 (138 mg, 0.3 mmol), DIPEA (152 mg, 1.5 mmol) in DMSO was stirred for 3 h at 70° C. under N$_2$. Then the mixture was concentrated in vacuo to give the crude protected form of 15-10 Isomer A, which was purified by prep-TLC (PE:EtOAc=1:1).

A mixture of above protected product (80 mg, 0.11 mmol), TFA (0.5 mL) in DCM (4 mL) was stirred at room temperature overnight. Then the mixture was concentrated in vacuo to give crude 15-10 Isomer A which was purified by prep-HPLC to give the final product, which was characterized by proton NMR.

$^1$H NMR (400 MHz, CD$_3$OD) δ 7.76 (d, J=7.6 Hz, 1H), 7.12 (d, J=4.8 Hz, 1H), 6.99 (d, J=8.8 Hz, 2H), 6.78~6.80 (m, 3H), 6.73 (d, J=4.4 Hz, 1H), 3.78 (s, 3H), 3.64~3.76 (m, 3H), 3.33~3.36 (m, 2H), 2.73~2.86 (m, 1H), 2.73~2.75 (m, 1H), 2.57~2.60 (m, 2H), 2.18~2.22 (m, 2H), 2.04~2.08 (m, 2H), 1.93~2.03 (m, 1H), 1.66~1.69 (m, 1H). HRMS m/z (M+H) 551.1361 found, 551.1348 required.

Compound 15-10 Isomer B was prepared from 15-8 Isomer B using the same procedure that was used to prepare compound 15-10 Isomer A from compound 15-8 Isomer A. Compound 15-10 Isomer B is the enantiomer of compound 15-10 Isomer A. It was characterized by proton NMR:

$^1$H NMR (400 MHz, CD$_3$OD) δ 7.76 (d, J=7.6 Hz, 1H), 7.12 (d, J=4.8 Hz, 1H), 6.99 (d, J=8.8 Hz, 2H), 6.78~6.80 (m, 3H), 6.73 (d, J=4.4 Hz, 1H), 3.78 (s, 3H), 3.64~3.76 (m, 3H), 3.33~3.36 (m, 2H), 2.73~2.86 (m, 1H), 2.73~2.75 (m, 1H), 2.57~2.60 (m, 2H), 2.18~2.22 (m, 2H), 2.04~2.08 (m, 2H), 1.93~2.03 (m, 1H), 1.66~1.69 (m, 1H). HRMS m/z (M+H) 551.1368 found, 551.1348 required.

TABLE 15

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Example | Structure | Name | Data |
|---|---|---|---|
| 15-12 Isomer A | Enantiomer of 15-12 Isomer B | 5-chloro-2-fluoro-N-(5-fluorothiazol-2-yl)-4-(((((2R,7aS or 2S,7aR)-2-(4-methoxybenzyl)hexahydro-1H-pyrrolizin-7a-yl)-methyl)amino)benzenesulfonamide | $^1$HNMR (400 MHz CD$_3$OD) δ 7.75 (d, J = 8.0 Hz, 1H), 6.99(d, J = 8.0 Hz, 1H), 6.79~6.86 (m, 4H), 3.65~3.75 (m, 6H), 3.31~3.37 (m, 2H), 2.58~2.87 (m, 4H), 1.67~2.23 (m, 6H). HRMS m/z (M + H) 569.1273 found, 569.1254 required. |

TABLE 15-continued

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Example | Structure | Name | Data |
|---|---|---|---|
| 15-12 Isomer B | Enantiomer of 15-12 Isomer A | 5-chloro-2-fluoro-N-(5-fluorothiazol-2-yl)-4-((((2S,7aR or 2R,7aS)-2-(4-methoxybenzyl)hexahydro-1H-pyrrolizin-7a-yl)methyl)amino)benzene-sulfonamide | $^1$HNMR (400 MHz CD$_3$OD) δ 7.75 (d, J = 8.0 Hz, 1H), 6.99 (d, J = 8.0 Hz, 1H), 6.79~6.86 (m, 6H), 3.62~3.75 (m, 2H), 2.58~2.87 (m,4H), 1.67~2.23 (m, 6H). HRMS m/z (M + H) 569.1274 found, 569.1254 required. |

Example 16

5-chloro-2-fluoro-4-((((2R,7aS)-2-(4-methoxyphenyl)hexahydro-1H-pyrrolizin-7a-yl)methyl)amino)-N-(thiazol-2-yl)benzenesulfonamide and 5-chloro-2-fluoro-4-((((2S,7aR)-2-(4-methoxyphenyl)hexahydro-1H-pyrrolizin-7a-yl)methyl)amino)-N-(thiazol-2-yl)benzenesulfonamide (compounds 16-12 Isomer A and 16-12 Isomer B)

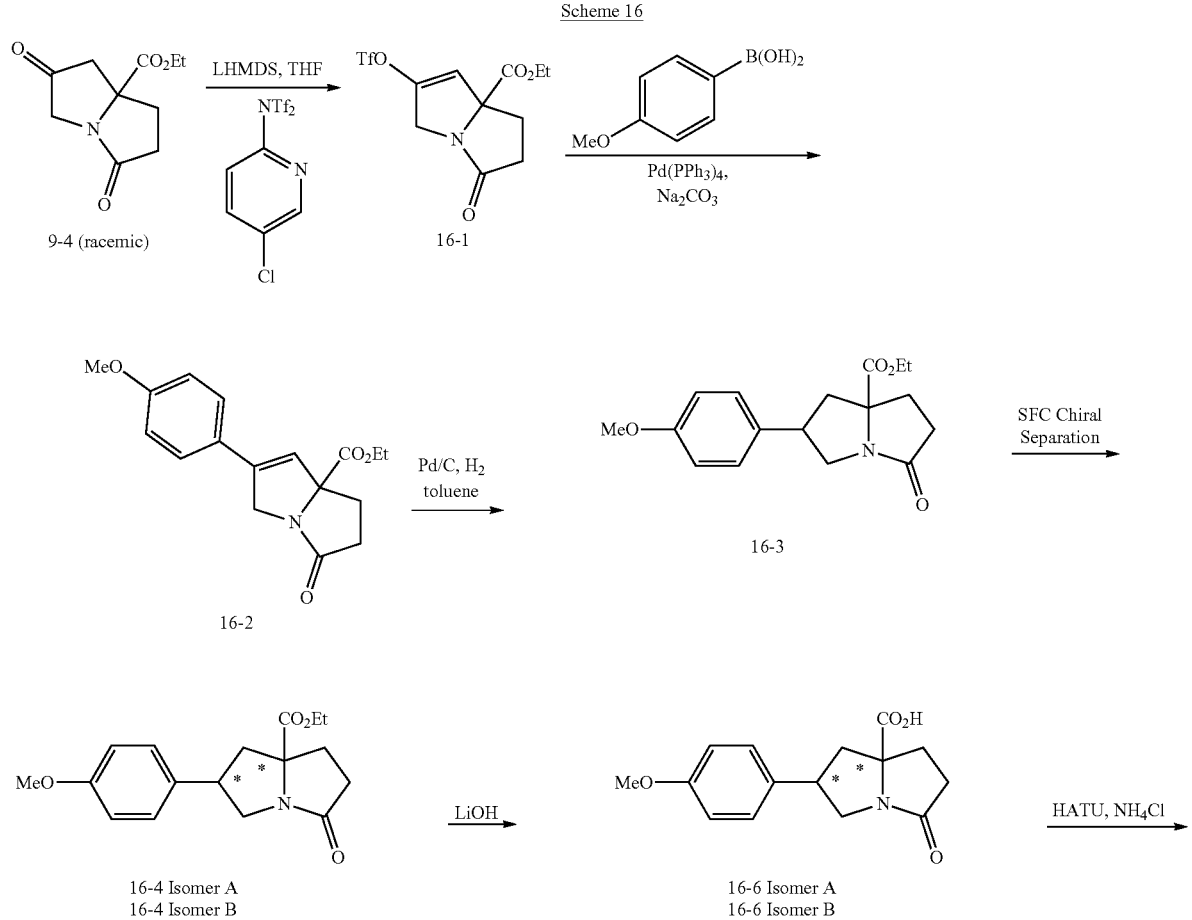

Scheme 16

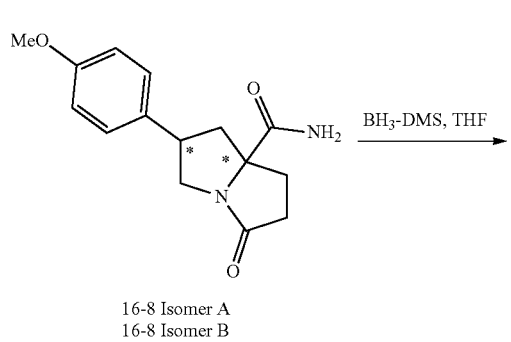

16-8 Isomer A
16-8 Isomer B

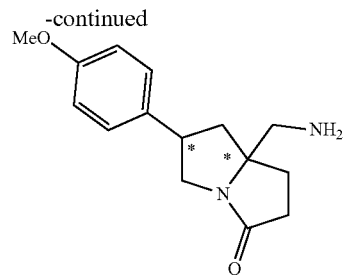

16-10 Isomer A
16-10 Isomer B

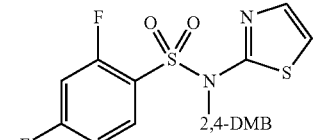

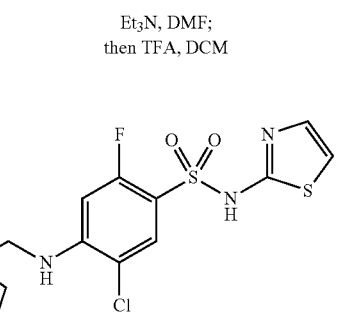

16-12 Isomer A
16-12 Isomer B

Preparation of ethyl 3-oxo-6-(trifluoromethylsulfonyloxy)-2,3,5,7a-tetrahydro-1H-pyrrolizine-7a-carboxylate (16-1)

A solution of LiHMDS (5.68 mL, 5.68 mmol,) was added into a solution of 9-4 (1.0 g, 4.73 mmol) in THF (10 mL) at −78° C. Then N-(5-chloropyridin-2-yl)-1,1,1-trifluoro-N-((trifluoromethyl)sulfonyl)methanesulfonamide (2.23 g, 5.68 mmol) in THF (10 mL) was added. The solution was allowed to warm to −20° C. and then stirred for 12 h. Then the reaction was quenched with saturated aqueous NH₄Cl and was extracted with EtOAc (2×50 mL). The combined organic layer was dried over Na₂SO₄, filtered and concentrated under reduced pressure. The crude product was purified by column chromatography on silica gel (PE:EA=3:1) as a yellow oil. MS m/z (M+H): 344

Preparation of ethyl 6-(4-methoxyphenyl)-3-oxo-2,3,5,7a-tetrahydro-1H-pyrrolizine-7a-carboxylate (16-2)

A mixture of 16-1 (200 mg, 0.58 mmol), (4-methoxyphenyl)boronic acid (106 mg, 0.7 mmol), Na₂CO₃ (144 mg, 1.36 mmol) and Pd(PPh₃)₄ (16 mg, 0.014 mmol) in 5 mL of dioxane and 0.7 mL H₂O was stirred at 100° C. under N₂ for 3 h. The reaction mixture was poured into water and extracted with EtOAc. The combined organic phases were dried with Na₂SO₄ and concentrated. The residue was purified by prep-TLC (PE:EA=1:1) to give 16-2. MS m/z (M+H): 302.1

Preparation of racemic (2R,7aS and 2S,7aR)-ethyl 2-(4-methoxyphenyl)-5-oxohexahydro-1H-pyrrolizine-7a-carboxylate (compound 16-3 (Cis)); and chiral separation to provide (2S,7aR)-ethyl 2-(4-methoxyphenyl)-5-oxohexahydro-1H-pyrrolizine-7a-carboxylate and (2R,7aS)-ethyl 2-(4-methoxyphenyl)-5-oxohexahydro-1H-pyrrolizine-7a-carboxylate (compounds 16-4 Isomer A and 16-4 Isomer B)

To a solution of 16-2 (120 mg, 0.4 mmol) in CH₃OH was added Pd/C (10 mg, wt %: 10%). Then the mixture was stirred at room temperature under H₂ for 6 h. Then Pd/C was removed by filtering and the filtrate was concentrated by vacuo to give the crude product 16-3 favoring the cis isomer.

Pure enantiomers were isolated from this mixed product. Separation was achieved using a chiral column (Column: Chiralpak AD-3 150×4.6 mm I.D., 3 um; Mobile phase: methanol (0.05% DEA) in CO₂ from 5% to 40%; Flow rate: 2.5 mL/min; Wavelength: 220 nm; Run time: 15 min; affording the following enantiomers: Retention time: 16-4 Isomer A (faster eluting); 4.95 min.; and Retention time: 16-4 Isomer B (slower eluting): 5.56 min.

$^1$H NMR (CDCl₃, 400 MHz) δ 7.12 (d, J=8.4 Hz, 2H), 6.83 (d, J=8.4 Hz, 2H), 4.18~4.24 (m, 3H), 3.76 (s, 3H), 3.20~3.23 (m, 1H), 2.97~3.07 (m, 1H), 2.71~2.79 (m, 2H), 2.35~2.40 (m, 3H), 1.98~2.00 (m, 1H), 1.28 (t, J=6.8 Hz, 3H). MS m/z (M+H): 303.1

Preparation of (2R,7aS)-2-(4-methoxyphenyl)-5-oxohexahydro-1H-pyrrolizine-7a-carboxylic acid and (2S,7aR)-2-(4-methoxyphenyl)-5-oxohexahydro-1H-pyrrolizine-7a-carboxylic acid (compounds 16-6 Isomer A and 16-6 Isomer B)

To a mixture of 16-4 Isomer A (150 mg, 0.49 mmol) in dioxane (5 mL) and H₂O (1 mL) was added LiOH.H₂O (104 mg, 2.47 mmol). The mixture was stirred at room temperature for 12 h. 1N HCl was added to adjust pH=2.0. The reaction solution was concentrated and extracted with EtOAc. The combined organic phases were dried with Na₂SO₄ and concentrated to give 16-6 Isomer A.

¹H NMR (CDCl₃, 400 MHz) δ 7.09 (d, J=8.4 Hz, 2H), 6.79 (d, J=8.4 Hz, 2H), 4.17~4.22 (m, 1H), 3.72 (s, 3H), 3.17~3.20 (m, 1H), 2.99~3.03 (m, 1H), 2.73~2.77 (m, 2H), 2.33~2.41 (m, 3H), 1.97~2.00 (m, 1H). MS m/z (M+H): 376.1

The compound, 16-6 Isomer B was prepared from 16-4 Isomer B using the same procedure that was used to prepare 16-6 Isomer A from 16-4 Isomer A.

Preparation of (2R,7aS)-2-(4-methoxyphenyl)-5-oxohexahydro-1H-pyrrolizine-7a-carboxamide and (2S,7aR)-2-(4-methoxyphenyl)-5-oxohexahydro-1H-pyrrolizine-7a-carboxamide (compounds 16-8 Isomer A and 16-8 Isomer B)

A mixture of 16-6 Isomer A prepared in the previous step, (130 mg, 0.47 mmol), and TEA (191 mg, 1.89 mmol) were dissolved in 5 mL of DMF. This solution was treated with HATU (358 mg, 0.94 mmol), followed by NH₄Cl (76 mg, 1.42 mmol). The reaction was stirred overnight at room temperature. The reaction mixture was diluted with water and was extracted with EtOAc three times. The combined organic layers were washed with HCl, brine, dried over sodium sulfate, filtered and concentrated in vacuo. Purification by prep-TLC (DCM: MeOH=20:1) yielded 16-8 Isomer A as a white solid. MS m/z (M+H): 375.1

¹H NMR (CDCl₃, 400 MHz) δ 7.10 (d, J=8.4 Hz, 2H), 6.84 (d, J=8.4 Hz, 2H), 4.28~4.33 (m, 1H), 3.77 (s, 3H), 3.14~3.17 (m, 1H), 2.83~2.89 (m, 1H), 2.73~2.76 (m, 2H), 2.50~2.53 (m, 1H), 2.34~2.41 (m, 2H), 2.07~2.10 (m, 1H).

The compound, 16-8 Isomer B, which is the enantiomer of 16-8 Isomer A, was prepared from 16-6 Isomer B using this same procedure.

Preparation of (6R,7aS)-7a-(aminomethyl)-6-(4-methoxyphenyl)tetrahydro-1H-pyrrolizin-3(2H)-one and (6S,7aR)-7a-(aminomethyl)-6-(4-methoxyphenyl)tetrahydro-1H-pyrrolizin-3(2H)-one (compounds 16-10 Isomer A and 16-10 Isomer B)

To a mixture of 16-8 Isomer A (0.12 g, 0.44 mmol) in THF (5 mL) was added BH₃.Me₂S (1 mL) at 0° C. The mixture was stirred at room temperature for 8 h. Then MeOH (10 mL) was added into the mixture to quench the reaction and concentrated. Then the residue was stirred in HCl-MeOH (5 mL) at 70° C. for 3 h. The resulting mixture was concentrated to give desired compound 16-10 Isomer A, which was used in the next step without purification.

The compound, 16-10 Isomer B, which is the enantiomer of 16-10 Isomer A, was prepared from 16-8 Isomer B using this same procedure.

Preparation of 5-chloro-2-fluoro-4-(((2R,7aS)-2-(4-methoxyphenyl)hexahydro-1H-pyrrolizin-7a-yl) methylamino)-N-(thiazol-2-yl)benzenesulfonamide and 5-chloro-2-fluoro-4-(((2S,7aR)-2-(4-methoxyphenyl)hexahydro-1H-pyrrolizin-7a-yl)methyl-amino)-N-(thiazol-2-yl)benzenesulfonamide (compounds 16-12 Isomer A and 16-12 Isomer B)

A mixture of 16-10 Isomer A, the enantiomer isolated in the previous step, (108 mg, 0.44 mmol), 20-3 (202 mg, 0.44 mmol) and Et₃N (221 mg, 2.19 mmol) in DMF (5 mL) was stirred for 12 h at room temperature under N₂. Then the mixture was concentrated by vacuo to give the crude coupled product. The coupled product was purified by prep-TLC (DCM: MeOH=20:1).

A mixture of coupled product produced in the previous step, (150 mg, 0.22 mmol), and TFA (1 mL) in DCM (5 mL) was stirred at room temperature for 2 h. Then the mixture was concentrated by vacuo to give the crude product, which was purified by prep-HPLC to provide the title compound, enantiomer 16-12 Isomer A, which is either 5-chloro-2-fluoro-4-(((2R,7aS)-2-(4-methoxyphenyl)hexahydro-1H-pyrrolizin-7a-yl)methylamino)-N-(thiazol-2-yl)benzenesulfonamide or 5-chloro-2-fluoro-4-(((2S,7aR)-2-(4-methoxyphenyl)hexahydro-1H-pyrrolizin-7a-yl) methylamino)-N-(thiazol-2-yl)benzenesulfonamide.

¹H NMR (400 MHz, CD₃OD) δ 7.77 (d, J=6.8 Hz, 1H), 7.15 (d, J=8.4 Hz, 2H), 7.10 (d, J=4.8 Hz, 1H), 6.90 (d, J=12.8 Hz, 1H), 6.86 (d, J=8.4 Hz, 2H), 6.72 (d, J=4.4 Hz, 1H), 3.78~3.85 (m, 4H), 3.74 (s, 3H), 3.57~3.64 (m, 1H), 3.28~3.44 (m, 2H), 2.37~2.44 (m, 1H), 2.25~2.32 (m, 1H), 2.01~2.22 (m, 4H). HRMS m/z (M+H) 537.1215 found, 5237.1192 required.

The compound, 16-12 Isomer B, which is the enantiomer of 16-12 Isomer A, was prepared from 16-10 Isomer B using the same procedure that was used to prepare 16-12 Isomer A from 16-10 Isomer A.

¹H NMR (400 MHz, CD₃OD) δ 7.77 (d, J=6.8 Hz, 1H), 7.15 (d, J=8.4 Hz, 2H), 7.10 (d, J=4.8 Hz, 1H), 6.94 (d, J=12.8 Hz, 1H), 6.86 (d, J=8.4 Hz, 2H), 6.73 (d, J=4.4 Hz, 1H), 3.76~3.95 (m, 4H), 3.74 (s, 3H), 3.57~3.64 (m, 1H), 3.31~3.46 (m, 2H), 2.37~2.44 (m, 1H), 2.25~2.32 (m, 1H), 2.01~2.23 (m, 4H). HRMS m/z (M+H) 537.1164 found, 5237.1192 required.

Example 17

Preparation of: (S or R) 5-chloro-2-fluoro-4-(((octahydroindolizin-8a-yl)methyl)amino)-N-(thiazol-2-yl) benzenesulfonamide (17-7 Isomer A) and (R or S) 5-chloro-2-fluoro-4-(((octahydroindolizin-8a-yl) methyl)amino)-N-(thiazol-2-yl)benzenesulfonamide (17-7 Isomer B)

Scheme 17

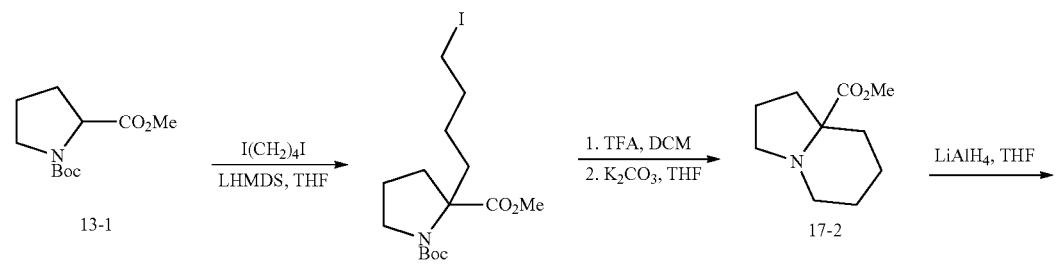

17-1

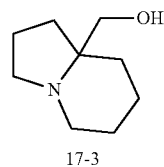 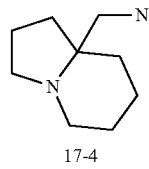 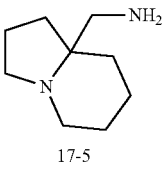

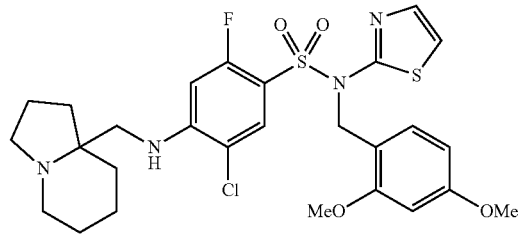 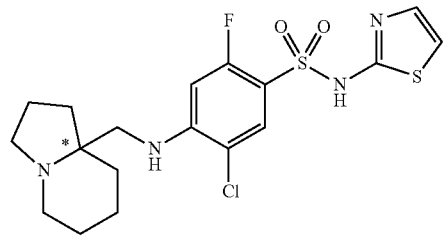

17-6

17-7 Isomer A
17-7 Isomer B

Preparation of 1-tert-butyl 2-methyl 2-(4-iodobutyl) pyrrolidine-1,2-dicarboxylate (17-1)

To a solution of 13-1 (1.0 g, 4.36 mmol) in dry THF (10 mL) was added LiHMDS (4.8 mL, 4.8 mmol) at −78° C. under N$_2$. Then the mixture was stirred at room temperature for 2 h. After the reaction completed, NH$_4$Cl was added into the mixture until the pH was adjusted to 7. The mixture was extracted with EtOAc. The organic layer was washed with water, brine, dried over Na$_2$SO$_4$. The product 17-1 was purified by column chromatography (PE:EtOAc=10:1).
$^1$H NMR (400 MHz, CDCl$_3$) δ 3.66~3.70 (m, 4H), 3.35~3.40 (m, 1H), 3.15~3.19 (m, 2H), 1.99~2.24 (m, 3H), 1.78~1.99 (m, 5H), 1.39~1.45 (m, 11H).

Preparation of methyl octahydroindolizine-8a-carboxylate (17-2)

A mixture of 17-1 (2.95 g, 7.17 mmol), TFA (4 mL) in DCM (20 mL) was stirred at room temperature for 2 h. Then the mixture was concentrated by vacuo to give the crude product used in the next step directly.
To a mixture of K$_2$CO$_3$ (630 mg, 15.76 mmol) in dry THF (20 mL) was added the solution of above product (2.49 g, 7.16 mmol) in THF at 0° C. under N$_2$. Then the mixture was stirred and refluxed overnight. Then water was added to the mixture carefully. The mixture was extracted with EtOAc. The organic layer was washed with water, brine, dried over Na$_2$SO$_4$. The product 17-2 was purified by column chromatography (PE:EtOAc=10:1). MS m/z (M+H): 184.1
$^1$H NMR (400 MHz, CDCl$_3$) δ 3.69 (s, 3H), 3.00~3.05 (m, 2H), 2.92~2.99 (m, 1H), 2.87~2.98 (m, 1H), 2.06 (d, J=12.0 Hz, 1H), 2.01~2.04 (m, 1H), 1.64~1.84 (m, 5H), 1.54~1.58 (m, 1H), 1.30~1.44 (m, 1H), 1.19~1.26 (m, 1H).

Preparation of (octahydroindolizin-8a-yl)methanol (17-3)

To a solution of LiAlH$_4$ (104 mg, 2.73 mmol) in THF (5 mL) was added the solution of 17-2 (500 mg, 2.73 mmol) in THF at 0° C. under N$_2$. Then the mixture was stirred at refluxing for 4 h. Then water (0.3 mL) was added into the mixture which was stirred for 10 min. MgSO$_4$ was added and the mixture was stirred for 30 min. The solid was removed by filtration and the solvent was removed by vacuo. The product 17-3 was used in the next step directly.
$^1$H NMR (400 MHz, CDCl$_3$) δ 3.56 (d, J=9.6 Hz, 1H), 3.06 (d, J=10.0 Hz, 1H), 2.95~3.02 (m, 1H), 2.85~2.91 (m, 1H), 2.68~2.71 (m, 2H), 1.81~1.85 (m, 1H), 1.65~1.79 (m, 2H), 1.39~1.64 (m, 5H), 1.12~1.22 (m, 2H). MS m/z (M+H): 156.1

Preparation of 8a-(azidomethyl)octahydroindolizine (17-4)

To a solution of 17-3 (300 mg, 1.93 mmol), Et$_3$N (587 mg, 5.8 mmol) in CH$_2$Cl$_2$ was added MsCl (332 mg, 2.9 mmol) at 0° C. dropwise under N$_2$. Then the mixture was stirred at room temperature under N$_2$ for 1 h. The mixture was diluted with water and extracted with CH$_2$Cl$_2$. The organic layer was washed with water, brine, dried over Na$_2$SO$_4$, filtered and concentrated. The crude product was used in next step without further purification
To the solution of the above crude product in DMF was added NaN$_3$ (627 mg, 9.64 mmol), then the mixture was stirred at 80° C. overnight under N$_2$. The mixture was diluted with EtOAc and the solid was removed by filtering, the filtrate was washed with water. The organic layer was washed with water, brine, dried over Na$_2$SO$_4$. The product 17-4 was purified by column chromatography (PE: EtOAc=5:1).

Preparation of (octahydroindolizin-8a-yl)methanamine (17-5)

To a solution of 17-4 (300 mg, 1.80 mmol) in CH$_3$OH was added Pd/C (50 mg, wt %: 10%). Then the mixture was stirred at room temperature under H$_2$ for 2 h. Pd/C was removed by filtering and the filtrate was concentrated by vacuo to give the crude product used in the next step directly.
$^1$H NMR (400 MHz, CD$_3$OD) δ 2.63~3.17 (m, 5H), 2.44~2.59 (m, 1H), 1.26~1.93 (m, 10H).

Preparation of racemic 5-chloro-N-(2,4-dimethoxybenzyl)-2-fluoro-4-((octahydroindolizin-8a-yl)methylamino)-N-(thiazol-2-yl)benzenesulfonamide (17-6)

A mixture of 17-5 prepared in the previous step, (100 mg, 0.65 mmol), 20-3 (299 mg, 0.65 mmol) and $K_2CO_3$ (269 mg, 1.94 mmol) in DMF was stirred for 3 h at room temperature under $N_2$. After the reaction completed, the mixture was concentrated by vacuo to give the crude product, which was purified by prep-TLC (DCM: MeOH=20:1) to afford 17-6, a racemic mixture of (S)-5-chloro-N-(2,4-dimethoxybenzyl)-2-fluoro-4-((octahydroindolizin-8a-yl)methylamino)-N-(thiazol-2-yl)benzenesulfonamide and (R)-5-chloro-N-(2,4-dimethoxybenzyl)-2-fluoro-4-((octahydroindolizin-8a-yl)methylamino)-N-(thiazol-2-yl)benzenesulfonamide. MS m/z (M+H): 595.1

Preparation of (S)-5-chloro-2-fluoro-4-((octahydroindolizin-8a-yl)methylamino)-N-(thiazol-2-yl)benzenesulfonamide and (R)-5-chloro-2-fluoro-4-((octahydroindolizin-8a-yl)methylamino)-N-(thiazol-2-yl)benzenesulfonamide (compounds 17-7 Isomer A and 17-7 Isomer B)

A mixture of racemic 17-6 prepared in the previous step, (100 mg, 0.17 mmol), TFA (0.5 mL) in DCM (4 mL) was stirred at room temperature overnight. After the reaction completed, the mixture was concentrated by vacuo to give the crude product which was purified by prep-HPLC to provide the corresponding deprotected compound as a racemic mixture of the "S" and "R" enantiomers. This product was separated using SFC/chiral chromatography (Column: Chiralpak AD-H 250×4.6 mm I.D., 5 um; Mobile phase: ethanol (0.05% DEA) in $CO_2$ from 5% to 40%; Flow rate: 2.35 mL/min; Wavelength: 220 nm; Run time: 15 min; to provide: Retention time: 17-7 Isomer A (faster eluting): 9.848 min; 17-7 Isomer B (slower eluting): 10.214 min).

Compound 17-7 Isomer A, which is either (S)-5-chloro-2-fluoro-4-((octahydroindolizin-8a-yl)methylamino)-N-(thiazol-2-yl)benzenesulfonamide or (R)-5-chloro-2-fluoro-4-((octahydroindolizin-8a-yl)methylamino)-N-(thiazol-2-yl)benzenesulfonamide, was evaluated by proton NMR: $^1$H NMR (400 MHz, $CD_3OD$) δ 7.74 (d, J=7.2 Hz, 1H), 7.10 (d, J=4.8 Hz, 1H), 6.80 (d, J=12.4 Hz, 1H), 6.73 (d, J=4.4 Hz, 1H), 3.65~3.76 (m, 2H), 3.54~3.58 (m, 2H), 3.42~3.48 (m, 1H), 3.21~3.26 (m, 1H), 2.17~2.20 (m, 1H), 1.99~2.06 (m, 3H), 1.83~1.99 (m, 3H), 1.72~1.75 (m, 3H). HRMS m/z (M+H) 445.0940 found, 445.0930 required.

Product 17-7 Isomer B, which is the enantiomer of 17-7 Isomer A, was evaluated by proton NMR: $^1$H NMR (400 MHz, $CD_3OD$) δ 7.74 (d, J=7.2 Hz, 1H), 7.10 (d, J=4.8 Hz, 1H), 6.80 (d, J=12.8 Hz, 1H), 6.73 (d, J=4.8 Hz, 1H), 3.65~3.76 (m, 2H), 3.54~3.58 (m, 2H), 3.42~3.48 (m, 1H), 3.21~3.25 (m, 1H), 2.17~2.23 (m, 1H), 2.01~2.08 (m, 3H), 1.83~1.99 (m, 3H), 1.72~1.75 (m, 3H). HRMS m/z (M+H) 445.0941 found, 445.0930 required.

TABLE 17

The following compound was prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

| Example | Structure | Name | Data |
|---|---|---|---|
| 17-9 | 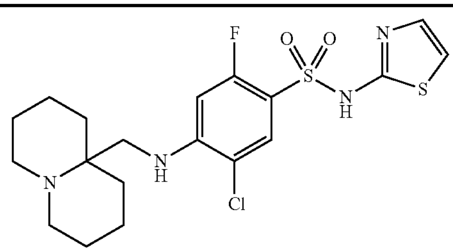 | 5-chloro-2-fluoro-4-(((octahydro-1H-quinolizin-9a-yl)methyl)amino)-N-(thiazol-2-yl)benzenesulfonamide | $^1$HNMR (400 MHz $CD_3OD$) δ 7.76 (d, J = 7.6 Hz, 1H), 7.10 (d, J = 4.4 Hz, 1H), 6.89 (d, J = 8.8 Hz, 1H), 6.72 (d, J = 4.4 Hz, 1H), 3.93 (s, 2H), 3.44~3.48 (m, 2H), 3.32~3.37 (m, 2H), 2.07~2.19 (m, 6H), 1.87~2.00 (m, 6H). HRMS m/z (M + H) 459.1098 found, 459.1086 required. |

Example 18

Preparation of 5-ethyl-2-fluoro-4-((((2R,7aS)-2-(4-methoxybenzyl)hexahydro-1H-pyrrolizin-7a-yl)methyl)amino)-N-(thiazol-2-yl)benzenesulfonamide and 5-ethyl-2-fluoro-4-((((2S,7a R)-2-(4-methoxybenzyl)hexahydro-1H-pyrrolizin-7a-yl)methyl)amino)-N-(thiazol-2-yl) (compounds 18-5 Isomer A and 18-5 Isomer B)

Scheme 18

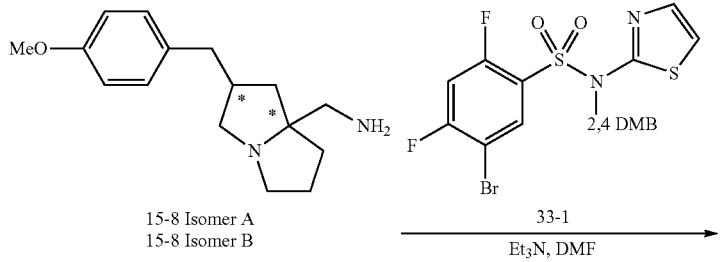

15-8 Isomer A
15-8 Isomer B 33-1

Et₃N, DMF

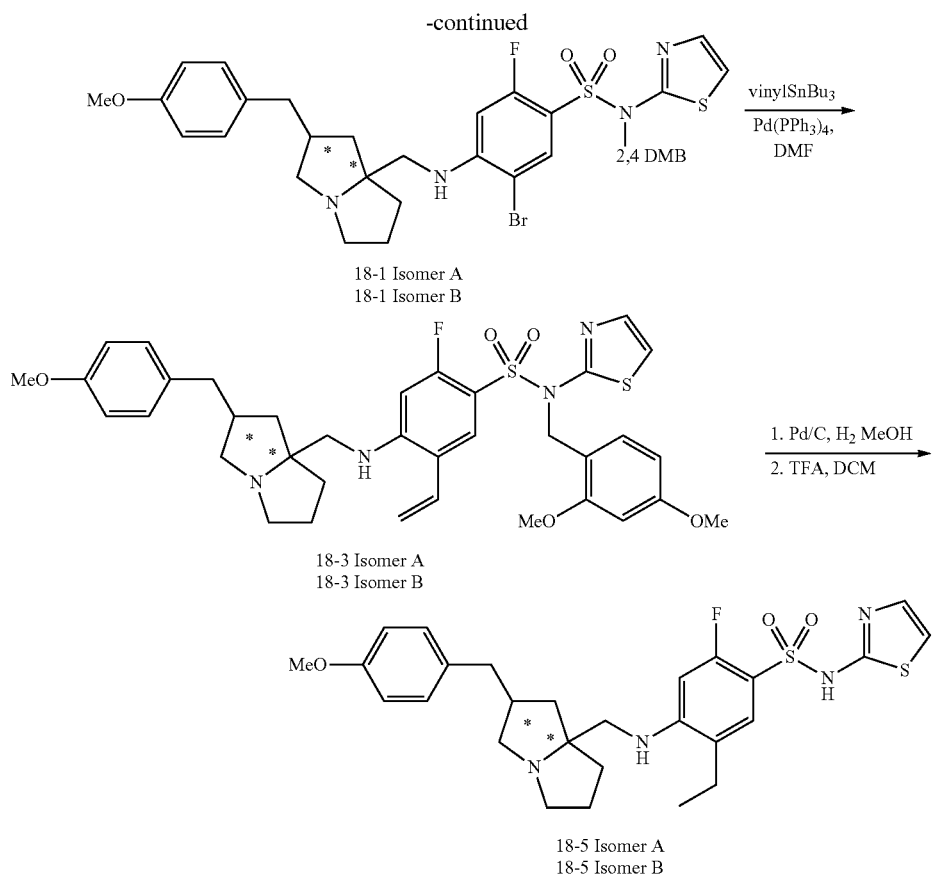

Preparation of 5-bromo-N-(2,4-dimethoxybenzyl)-2-fluoro-4-(((2R,7aS)-2-(4-methoxybenzyl)hexahydro-1H-pyrrolizin-7a-yl)methylamino)-N-(thiazol-2-yl)benzenesulfonamide and 5-bromo-N-(2,4-dimethoxybenzyl)-2-fluoro-4-(((2S,7aR)-2-(4-methoxybenzyl)hexahydro-1H-pyrrolizin-7a-yl)methylamino)-N-(thiazol-2-yl)benzenesulfonamide (18-1 Isomer A and 18-1 Isomer B)

A mixture of 15-8 Isomer A, as prepared in Example 15, (200 mg, 0.6 mmol), 33-1 (363 mg, 0.72 mmol) and Et$_3$N (303 mg, 3.0 mmol) in DMF was stirred at 50° C. under N$_2$ overnight. Then the mixture was diluted with water, extracted with EtOAc. The organic layer was washed with water, brine, dried over Na$_2$SO$_4$. The product, (18-1 Isomer A) was purified by prep-TLC (CH$_2$Cl$_2$: CH$_3$OH=30:1). MS m/z (M+H): 745.1

$^1$H NMR (400 MHz, CDCl$_3$) δ7.89(d,j =8.0Hz, 1H), 7.37 (d, J=8.0 Hz, 1H), 7.19 (d, J=8.0 Hz, 1H), 6.95~7.02 (m, 3H), 6.80 (d, J=8.0 Hz, 2H), 6.34 (s, 2H), 6.22 (d, J=8.0 Hz, 1H), 5.17 (s, 2H), 3.73~3.99 (m, 11H), 2.95~3.31 (m, 4H), 2.71~2.87 (m, 3H), 2.42~2.53 (m, 2H), 2.07~2.12 (m, 2H), 1.84~1.89 (m, 1H), 1.50~1.53 (m, 1H).

Compound 18-1 Isomer B was prepared from compound 15-8 Isomer B using the same procedure followed above for the preparation of compound 18-2 Isomer A from 15-8 Isomer A.

Preparation of N-(2,4-dimethoxybenzyl)-2-fluoro-4-(((2R,7aS)-2-(4-methoxybenzyl) hexahydro-1H-pyrrolizin-7a-yl)methylamino)-N-(thiazol-2-yl)-5 vinylbenzenesulfonamide and N-(2,4-dimethoxybenzyl)-2-fluoro-4-(((2S,7aR)-2-(4-methoxybenzyl) hexahydro-1H-pyrrolizin-7a-yl)methylamino)-N-(thiazol-2-yl)-5 vinylbenzenesulfonamide (compounds 18-3 Isomer A and 18-3 Isomer B)

To a solution of 18-1 Isomer A, prepared in the previous step, (75 mg, 0.1 mmol), vinylSnBu$_3$ (96 mg, 0.3 mmol) and LiCl (4 mg, 0.1 mmol) in dry DMF (2 mL) was added Pd(PPh$_3$)$_2$Cl$_2$. Then the mixture was stirred at 60° C. for 2 h under N$_2$. After the reaction completed, a solution of CsF$_2$ in water was added to the mixture. The mixture was extracted with EtOAc. The organic layer was washed with water, brine, dried over Na$_2$SO$_4$. The product 18-3 Isomer A was purified by prep-TLC on silic gel (CH$_2$Cl$_2$: CH$_3$OH=30: 1). MS m/z (M+H): 693.2

$^1$H NMR (400 MHz, CDCl$_3$) δ 7.75 (d, J=8.0 Hz, 1H), 7.35 (d, J=8.0 Hz, 1H), 7.20 (d, J=8.0 Hz, 1H), 6.93~6.98 (m, 4H), 6.81~6.92 (m, 2H), 6.79 (s, 2H), 6.16~6.35 (m, 1H), 5.57~5.61 (m, 1H), 5.44~5.47 (m, 1H), 5.19 (s, 2H), 3.48~3.99 (m, 10H), 2.95~3.27 (m, 5H), 2.42~2.72 (m, 4H), 1.90~2.13 (m, 3H), 1.24~1.69 (m, 2H).

This same procedure was followed to compound 18-3 Isomer B from 18-1 Isomer B.

Preparation of 5-ethyl-2-fluoro-4-(((2R,7aS)-2-(4-methoxybenzyl)hexahydro-1H-pyrrolizin-7a-yl)methylamino)-N-(thiazol-2-yl)benzenesulfonamide and 5-ethyl-2-fluoro-4-(((2S,7aR)-2-(4-methoxybenzyl)hexahydro-1H-pyrrolizin-7a-yl)methylamino)-N-(thiazol-2-yl)benzenesulfonamide (Compound 18-5 Isomer A and 18-5 Isomer B)

To a solution of 18-3 Isomer A, prepared in the previous step, (70 mg, 0.1 mmol) in MeOH was added Pd/C (20 mg, wt %: 10%). Then the mixture was stirred at room temperature under H$_2$ for 2 h. Pd/C was removed by filtering and the filtrate was concentrated by vacuo to afford reduced crude protected product used in the next step directly.

A mixture of the protected product prepared in the previous step and TFA (0.5 mL) in DCM (4 mL) was stirred at room temperature overnight. Then the mixture was concentrated by vacuo to give the crude deprotected product which was purified by prep-HPLC to give the final product 18-5 Isomer A, which is either 5-ethyl-2-fluoro-4-(((2R,7aS)-2-(4-methoxybenzyl)hexahydro-1H-pyrrolizin-7a-yl)methylamino)-N-(thiazol-2-yl)-benzenesulfonamide or 5-ethyl-2-fluoro-4-(((2S,7aR)-2-(4-methoxybenzyl)hexahydro-1H-pyrrolizin-7a-yl)methylamino)-N-(thiazol-2-yl)benzenesulfonamide.

The compound, 18-5 Isomer A, was characterized by proton NMR: $^1$H NMR (400 MHz, CD$_3$OD) δ 7.55 (d, J=8.0 Hz, 1H), 7.09 (d, J=8.0 Hz, 1H), 6.98 (d, J=8.0 Hz, 2H), 6.80 (d, J=8.0 Hz, 2H), 6.64~6.71 (m, 2H), 3.61~3.78 (m, 6H), 3.30~3.33 (m, 2H), 2.47~2.85 (m, 6H), 1.66~2.27 (m, 6H), 1.19~1.23 (m, 3H). HRMS m/z (M+H) 545.2055 found, 545.2051 required.

This same procedure was followed to prepare 18-5 Isomer B, the enantiomer of 18-5 Isomer A, from 18-3 Isomer B. The compound was characterized by proton NMR:

$^1$H NMR (400 MHz, CD$_3$OD) δ 7.55 (d, J=8.0 Hz, 1H), 7.09 (d, J=8.0 Hz, 1H), 6.99 (d, J=8.0 Hz, 2H), 6.80 (d, J=8.0 Hz, 2H), 6.64~6.71 (m, 2H), 3.61~3.75 (m, 6H), 3.30~3.35 (m, 2H), 2.50~2.85 (m, 6H), 1.67~2.28 (m, 6H), 1.20~1.24 (m, 3H). HRMS m/z (M+H) 545.2056 found, 545.2051 required.

TABLE 18

The following compounds were prepared using the methodology herein, but substituting the appropriately substituted reagent, as described in the Reaction Schemes and Examples. The requisite starting materials were commercially available, described in the literature, described in a previous Scheme herein or readily synthesized by one skilled in the art of organic synthesis without undue experimentation.

| Exp | Structure | Name | Data |
|---|---|---|---|
| 18-7 | 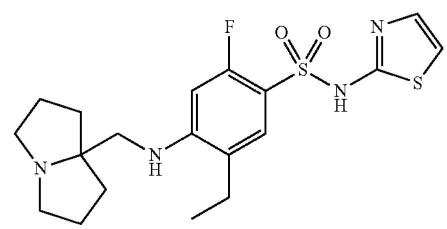 [SMILES: CCc1cc(S(=O)(=O)Nc2nccs2)c(F)cc1NCC12CCCN1CCC2] | 5-ethyl-2-fluoro-4-(((hexahydro-1H-pyrrolizin-7a-yl)-methyl)amino)-N-(thiazol-2-yl)-benzenesulfonamide | $^1$H NMR (400 MHz, CD$_3$OD) δ 7.68-7.59 (m, 1H), 7.58-7.47 (m, 1H), 7.09 (d, J = 4.4 Hz, 1H), 6.73-6.62 (m, 1H), 3.65-3.58 (m, 4H), 3.20 (s, 2H), 2.51 (t, J = 7.2 Hz, 2H), 2.15-2.02 (m, 8H), 1.22 (t, J = 7.4 Hz, 3H). HRMS m/z (M + H) 425.1483 found, 425.1476 required. |
| 18-8 | 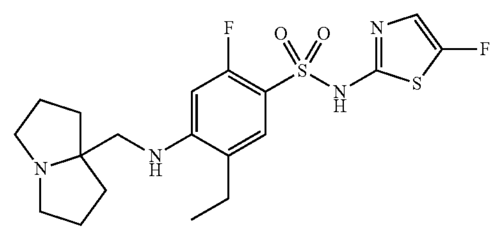 [SMILES: CCc1cc(S(=O)(=O)Nc2ncc(F)s2)c(F)cc1NCC12CCCN1CCC2] | 5-ethyl-2-fluoro-N-(5-fluorothiazol-2-yl)-4-(((hexahydro-1H-pyrrolizin-7a-yl)-methyl)amino)-benzenesulfonamide | $^1$H NMR (CD$_3$OD, 400 MHz) δ 7.55~7.49 (m, 1H), 7.01~6.94 (m, 1H), 6.75~6.67 (m, 1H), 3.65 (s, 2H), 3.63~3.53 (m, 2H), 3.29~3.21 (m, 2H), 2.60~2.50 (m, 2H), 2.23~1.99 (m, 8H), 1.25 (t, J = 7.2 Hz, 3H). HRMS m/z (M + H) 443.1387 found, 443.1382 required. |
| 18-9 Isomer A Enantiomer of 18-9 Isomer B | | (S or R)-4-(((2,2-dimethylhexahydro-1H-pyrrolizin-7a-yl)-methyl)-amino)-5-ethyl-2-fluoro-N-(thiazol-2-yl)-benzenesulfonamide | $^1$HNMR (400 MHz CD$_3$OD) δ 7.55 (d, J = 8.4 Hz, 1H), 7.09 (d, J = 4.8 Hz, 1H), 6.71 (d, J = 4.8 Hz, 1H), 6.66 (d, J = 13.6 Hz, 1H), 3.71 (s, 2H), 3.48 (d, J = 12.0 Hz, 1H), 3.37~3.48 (m, 2H), 3.05 (d, J = 11.6 Hz, 1H), 2.57~2.61 (m, 2H), 1.98~2.20 (m, 6H), 1.23~1.27 (m, 9H). HRMS m/z (M + H) 453.1796 found, 453.1789 required. |

TABLE 18-continued

The following compounds were prepared using the methodology herein, but substituting the appropriately substituted reagent, as described in the Reaction Schemes and Examples. The requisite starting materials were commercially available, described in the literature, described in a previous Scheme herein or readily synthesized by one skilled in the art of organic synthesis without undue experimentation.

| Exp | Structure | Name | Data |
|---|---|---|---|
| 19-9 Isomer B | 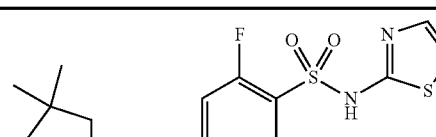<br>Enantiomer of 18-9 Isomer A | (R or S)-4-(((2,2-dimethylhexahydro-1H-pyrrolizin-7a-yl)methyl)-amino)-5-ethyl-2-fluoro-N-(thiazol-2-yl)-benzenesulfonamide | $^1$HNMR (400 MHz CD$_3$OD) δ 7.54 (d, J = 7.4 Hz, 1H), 7.07 (d, J = 4.4 Hz, 1H), 6.68 (d, J = 4.4 Hz, 1H), 6.65 (d, J = 13.2 Hz, 1H), 3.67~3.70 (m, 2H), 3.38~3.45 (m, 3H), 3.03~3.06 (m, 1H), 2.55~2.58 (m, 2H), 1.85~2.21 (m, 6H), 1.22~1.27 (m, 9H). HRMS m/z (M + H) 453.1796 found, 453.1789 required. |

The various compounds in Examples 1 through 18, and their corresponding Tables, exemplified above were assayed for activity and selectivity using the foregoing PatchXpress® technique. The results are reported in the following paragraph in a format expressing the identification of the compound with reference Example and compound (e.g. Ex 1-3 is Example 1, compound 3) followed by the observed potency in nM and the ratio of Na$_v$1.7 potency:Na$_v$ 1.5 potency as described here. Thus, Ex1-3: 1.7=10/ratio=735 identifies compound Example 1, compound 3 as having 10 nM potency for the Nav 1.7 sodium ion channel (as measured by PatchXpress®) and a ratio of 735 Na$_v$ 1.7:Na$_v$ 1.5 potency, determined by PatchXpress® measurement. The following results are reported:

Ex1-3: 1.7=10/ratio=735; Ex1-4: 1.7=166/ratio=181; Ex1-5: 1.7=370/ratio=81; Ex1-6: 1.7=86/ratio=349; Ex1-7: 1.7=8/ratio=4098; Ex1-8: 1.7=12/ratio=1458; Ex1-9: 1.7=142/ratio=170; Ex1-10: 1.7=221/ratio=94; Ex1-11: 1.7=35/ratio=469; Ex1-12: 1.7=5/ratio=412; Ex1-13: 1.7=43/ratio=1507; Ex1-14: 1.7=48/ratio=337; Ex1-15: 1.7=34/ratio=1149; Ex1-16: 1.7=62/ratio=484; Ex1-17: 1.7=5/ratio=670; Ex1-18: 1.7=129/ratio=462; Ex1-19: 1.7=44/ratio=512; Ex1-20: 1.7=14/ratio=765; Ex1-21: 1.7=30/ratio=1010; Ex2-2: 1.7=40/ratio=746; Ex2-3: 1.7=168/ratio=18; Ex2-4: 1.7=350/ratio=269; Ex3-3: 1.7=215/ratio=140; Ex3-4: 1.7=151/ratio=199; Ex3-5: 1.7=1000/ratio=100; Ex3-6; 1.7=58/ratio=617; Ex3-7; 1.7=320/ratio=94; Ex4-8; 1.7=27/ratio=1109; Ex4-9; 1.7=9/ratio=2512; Ex4-10; 1.7=10/ratio=2681; Ex4-11; 1.7=5/ratio=7180; Ex5-6; 1.7=245/ratio=122; Ex5-7; 1.7=525/ratio=57; Ex5-8; 1.7=52/ratio=407; Ex5-9; 1.7=1087/ratio=26; Ex6-6; 1.7=472/ratio=64; Ex6-7; 1.7=375/ratio=80; Ex6-8; 1.7=1300/ratio=19; Ex7-5; 1.7=320/ratio=94; Ex8-17-A; 1.7=16/ratio=1562; Ex8-17-B; 1.7=28/ratio=614; Ex8-19-A; 1.7=14/ratio=812; Ex8-19-B; 1.7=135/ratio=265; Ex8-21-A; 1.7=35/ratio=851; Ex8-21-B; 1.7=23/ratio=1290; Ex8-23-A; 1.7=172/ratio=175; Ex8-23-B; 1.7=31/ratio=981; Ex8-25; 1.7=32/ratio=947; Ex9-8-A; 1.7=57/ratio=134; Ex9-8-B; 1.7=35/ratio=781; Ex9-10-A; 1.7=148/ratio=137; Ex9-10-B; 1.7=58/ratio=122; Ex9-12-A; 1.7=89/ratio=338; Ex9-12-B; 1.7=80/ratio=300; Ex9-14-A; 1.7=144/ratio=208; Ex9-14-B; 1.7=176/ratio=171; Ex10-7-A; 1.7=10/ratio=3074; Ex10-7-B; 1.7=32/ratio=935; Ex10-9-A; 1.7=25/ratio=1210; Ex10-9-B; 1.7=108/ratio=277; Ex11-8-A; 1.7=35/ratio=305; Ex11-8-B; 1.7=6/ratio=2533; Ex11-10-A; 1.7=22/ratio=1376; Ex11-10-B; 1.7=40/ratio=755; Ex11-12-A; 1.7=22/ratio=1335; Ex11-12-B; 1.7=30/ratio=1017; Ex12-5; 1.7=41/ratio=288; Ex12-6; 1.7=95/ratio=180; Ex12-7; 1.7=26/ratio=163; Ex13-10-A; 1.7=126/ratio=113; Ex13-10-B; 1.7=16/ratio=406; Ex13-12-A; 1.7=22/ratio=756; Ex13-12-B; 1.7=7/ratio=3240; Ex14-10; 1.7=59/ratio=509; Ex14-11-A; 1.7=28/ratio=1062; Ex14-11-B; 1.7=10/ratio=3045; Ex15-10-A; 1.7=2/ratio=918; Ex15-10-B; 1.7=30/ratio=308; Ex15-12-A; 1.7=8/ratio=282; Ex15-12-B; 1.7=66/ratio=99; Ex16-12-A; 1.7=51/ratio=348; Ex16-12-B; 1.7=21/ratio=708; Ex17-7-A; 1.7=113/ratio=450; Ex17-7-B; 1.7=185/ratio=193; Ex17-9; 1.7=135/ratio=525; Ex18-5-A; 1.7=9/ratio=315; Ex18-5-B; 1.7=40/ratio=359; Ex18-7; 1.7=19/ratio=672; Ex18-8; 1.7=5/ratio=2595; Ex18-9-A; 1.7=55/ratio=548; Ex18-9-B; 1.7=16/ratio=1870.

PREP EXAMPLES

Synthesis of Aryl-Sulfonamide Cores

Useful in Preparing Compounds of the Invention

Example 19

5-chloro-N-(2,4-dimethoxybenzyl)-2,4-difluoro-N-(1,2,4-thiadiazol-5-yl) benzenesulfonamide (1-1)

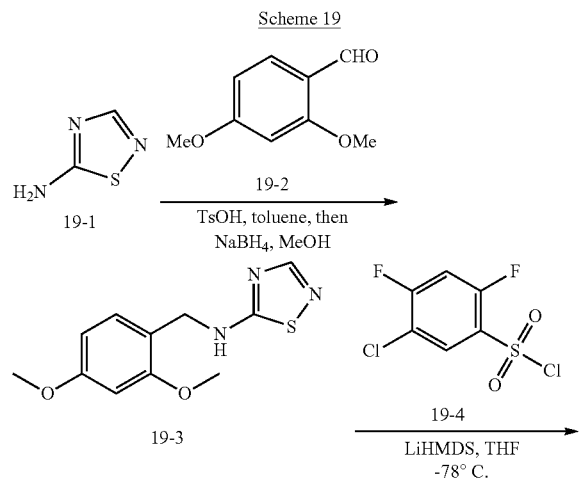

-continued

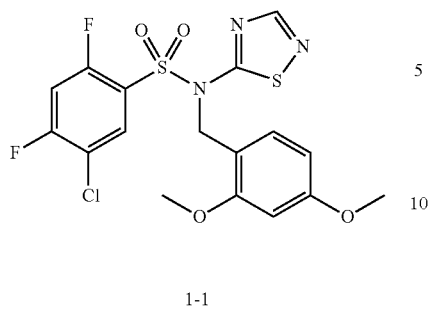

1-1

Preparation of N-(2,4-dimethoxybenzyl)-1,2,4-thiadiazol-5-amine (19-3)

Into a 20000-mL 4-necked round-bottom flask purged and maintained with an inert atmosphere of nitrogen was placed 19-1 (300 g, 2.97 mol), 19-2 (472 g, 2.84 mol, 1.05 equiv), p-TsOH (4.1 g, 23.81 mmol, 0.01 equiv), toluene (9 L). The resulting solution was heated to reflux overnight with a water-separator. The reaction mixture was cooled to room temperature and concentrated under vacuum. The residue was washed with methanol. The resulting yellow solid was used crude in the next reaction. Into a 10-L 4-necked round-bottom flask purged and maintained with an inert atmosphere of nitrogen was placed a solution of the crude yellow solid (550 g, 2.21 mol) in THF (5.5 L). This was followed by the addition of NaBH$_4$ (83 g, 2.25 mol) in several batches at 0° C. The resulting solution was stirred for 3 h at room temperature, then extracted with 3×1 L of ethyl acetate. The organic layers were combined, washed with 1×1000 mL of brine, dried over anhydrous magnesium sulfate and concentrated under vacuum. The residue was applied onto a silica gel column and eluted with dichloromethane/methanol (100:1) to give 19-3 as a white solid.

Preparation of 5-chloro-N-(2,4-dimethoxybenzyl)-2,4-difluoro-N-(1,2,4-thiadiazol-5-yl) benzenesulfonamide (1-1)

To a mixture of 19-3 (1.0 g, 4.0 mmol) in THF (20 mL) was added LiHMDS (5 mL, 5 mmol, 1M) at −78° C. under N$_2$. The mixture was warmed to room temperature and stirred for 1 h before cooled to −78° C. Then a solution of 19-4 (1.2 g, 4.8 mmol) in THF (4 mL) was added dropwise. The mixture was stirred at room temperature for additional 1 h, then quenched with saturated NH$_4$Cl. The mixture was extracted with EtOAc and the combined organic phases were dried with Na$_2$SO$_4$, filtered and concentrated. The residue was purified by column chromatography on silica gel (PE:EtOAc=6:1) to give 1-1. $^1$H NMR (400 MHz, CDCl$_3$) δ 8.22 (s, 1H), 7.73 (t, J=7.6 Hz, 1H), 7.19 (d, J=8.4 Hz, 1H), 6.87 (t, J=8.4 Hz, 1H), 6.35 (dd, J=2.4, 6.0 Hz, 1H), 6.15 (d, J=2.0 Hz, 1H), 5.36 (s, 2H), 3.74 (s, 3H), 3.66 (s, 3H). MS m/z (M+H): 462.0

Example 20

5-chloro-N-(2,4-dimethoxybenzyl)-2,4-difluoro-N-(thiazol-2-yl)benzene sulfonamide (20-4)

Scheme 20

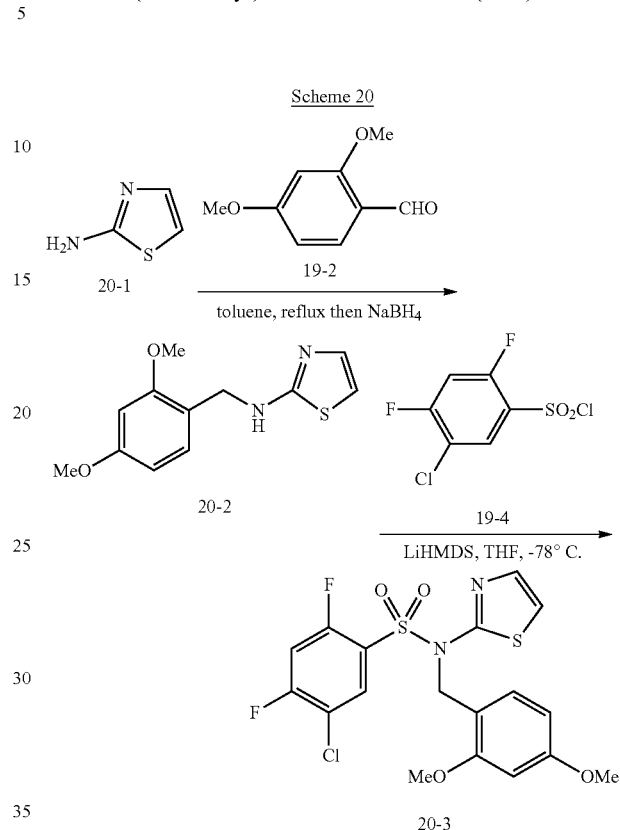

Preparation of N-(2,4-dimethoxybenzyl)thiazol-2-amine (10-3)

A mixture of 20-1 (100 g, 1 mol) and 19-2 (151 g, 0.91 mol) in 2 L of toluene was refluxed for 8 h with Dean-Stark apparatus to remove water. The mixture was cooled and the solvent was evaporated in vacuo. To the residue was added 3 L of MeOH and the resulting mixture was cooled to 0° C. NaBH$_4$ (151 g, 4 mol) was added carefully in portions. The mixture was then warmed to room temperature and stirred for 4 h. The mixture was quenched with water, then MeOH was evaporated in vacuo. The water layer was extracted with EtOAc and the combined organic layers were dried over Na$_2$SO$_4$, filtered and concentrated. The residue was purified by column chromatography on silica gel (PE:EtOAc=5:1 to 2:1) to give the product of 20-2. $^1$H NMR (400 MHz, CD$_3$OD) δ 7.16 (d, J=8.4 Hz, 1H), 6.97 (d, J=4.0 Hz, 1H), 6.50~6.52 (m, 2H), 6.44 (dd, J=8.0, 2.0 Hz, 1H), 4.35 (s, 2H), 3.81 (s, 3H), 3.76 (s, 3H).

Preparation of 5-chloro-N-(2,4-dimethoxybenzyl)-2,4-difluoro-N-(thiazol-2-yl)benzene sulfonamide (20-3)

Under an atmosphere of nitrogen, 20-2 (5 g, 20 mmol) was dissolved in THF (100 mL) and cooled to −78° C. LiHMDS (24 mL, 24 mmol) was added dropwise keeping the temperature below −60° C. After 30 minutes, the cooling bath was removed and the reaction was warmed to room temperature for a further 30 minutes then cooled back to −78° C. A solution of 19-4 (5.54 g, 22.4 mmol) in THF (10 mL) was added dropwise keeping the temperature below −60° C. and the reaction mixture was warmed to room temperature. Saturated aqueous ammonium chloride solution (50 mL) was added followed by water to dissolve the solid which had precipitated out. The aqueous layer was extracted with ethyl acetate (50 mL) and the organic extracts was dried over $Na_2SO_4$, filtered and concentrated. The residue was purified by column chromatography on silica gel (PE:EtOAc=10:1) to give the product of 20-3. $^1$H NMR (400 MHz, $CDCl_3$) δ 7.88~7.92 (m, 1H), 7.40 (d, J=4.0, 1H), 7.16~7.18 (m, 1H), 6.96~7.01 (m, 2H), 6.32~6.36 (m, 2H), 5.16 (s, 2H), 3.74 (s, 3H), 3.71 (s, 3H). MS m/z (M+H): 461.0

The following cores were made by analogy to Examples 19 and 20 using commercially available sulfonyl chlorides and heterocyclic amines or sulfonyl chlorides and amines in the published literature:

Example 21

5-chloro-N-(5-chlorothiazol-2-yl)-N-(2,4-dimethoxybenzyl)-2,4-difluoro benzenesulfonamide (21-1)

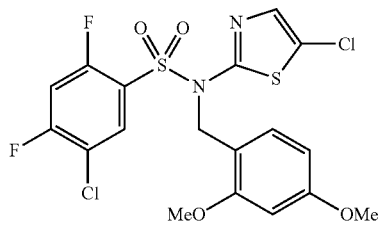

21-1

$^1$H NMR (400 MHz, $CDCl_3$) δ 7.88 (t, J=7.2 Hz, 1H), 7.24 (s, 1H), 7.18 (d, J=8.0 Hz, 1H), 7.00 (t, J=8.8 Hz, 1H), 6.37 (dd, J=8.4, 2.4 Hz, 1H), 6.32 (d, J=2.4 Hz, 1H), 5.12 (s, 2H), 3.77 (s, 3H), 3.73 (s, 3H). MS m/z (M+H): 495

Example 22

5-chloro-N-(2,4-dimethoxybenzyl)-2,4-difluoro-N-(5-methylthiazol-2-yl) benzenesulfonamide (22-1)

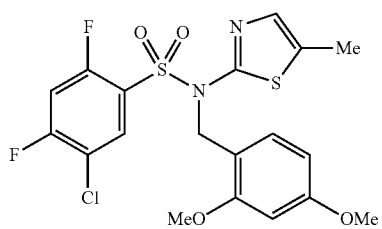

22-1

$^1$H NMR (400 MHz, DMSO-$d_6$) δ 7.92 (t, J=7.6 Hz, 1H), 7.82 (t, J=9.6 Hz, 1H), 7.20 (d, J=1.2 Hz, 1H), 6.05 (d, J=8.4 Hz, 1H), 6.40~4.44 (m, 2H), 4.95 (s, 2H), 3.71 (s, 3H), 3.67 (s, 3H), 2.24 (s, 3H). MS m/z (M+H): 475

Example 23

5-cyano-N-(2,4-dimethoxybenzyl)-2,4-difluoro-N-(thiazol-2-yl)benzene sulfonamide (23-1)

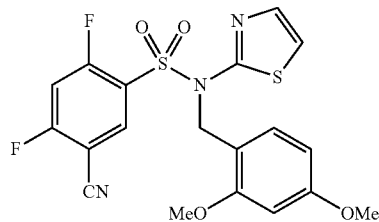

23-1

$^1$H NMR (400 MHz $CDCl_3$) δ 8.13 (t, J=7.2 Hz, 1H), 7.43 (d, J=3.6 Hz, 1H), 7.25 (s, 1H), 7.18 (d, J=8 Hz, 1H), 7.05~7.07 (m, 1H), 6.33~6.39 (m, 2H), 5.16 (s, 2H), 3.81 (s, 3H), 3.71 (s, 3H). MS m/z (M+H): 452

Example 24

N-(5-chlorothiazol-2-yl)-5-cyano-N-(2,4-dimethoxybenzyl)-2,4-difluoro benzenesulfonamide (24-1)

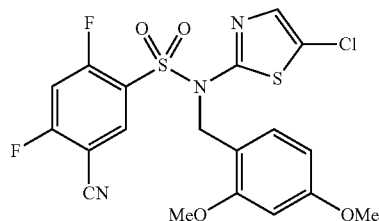

24-1

$^1$H NMR (400 MHz, $CDCl_3$) δ 8.05 (t, J=7.2 Hz, 1H), 7.24 (d, J=2.0 Hz, 1H), 7.15 (d, J=8 Hz, 1H), 7.05 (t, J=8.8 Hz, 1H), 6.37 (dd, J=8.4, 2.4 Hz, 1H), 6.29 (d, J=2.0 Hz, 1H), 5.09 (s, 2H), 3.77 (s, 3H), 3.69 (s, 3H). MS m/z (M+H): 486

Example 25

3-cyano-N-(2,4-dimethoxybenzyl)-4-fluoro-N-(thiazol-2-yl)benzene sulfonamide (25-1)

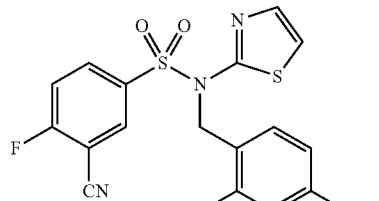

25-1

$^1$H NMR (400 MHz, $CDCl_3$) δ 8.04~8.08 (m, 1H), 7.98 (dd, J=5.6, 2.0 Hz, 1H), 7.45 (d, J=3.2 Hz, 1H), 7.25~7.27

(m, 1H), 7.08~7.15 (m, 2H), 6.35 (d, J=8.4 Hz, 1H), 6.31 (s, 1H), 5.01 (s, 2H), 3.76 (s, 3H), 3.62 (s, 3H). MS m/z (M+H): 434

Example 26

N-(2,4-dimethoxybenzyl)-2,4,5-trifluoro-N-(1,2,4-thiadiazol-5-yl) benzenesulfonamide (26-1)

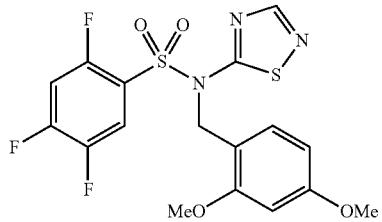

26-1

¹H NMR (300 MHz, d₆-DMSO) δ 8.47 (1H, s), 7.90-7.80 (2H, m), 7.10-7.08 (1H, d), 6.46-6.41 (1H, d), 6.35-6.34 (1H, d), 5.24 (2H, d, 3.75-3.17 (6H, d).

Example 27

3-cyano-N-(2,4-dimethoxybenzyl)-4-fluoro-N-(1,2,4-thiadiazol-5-yl)benzenesulfonamide (27-1)

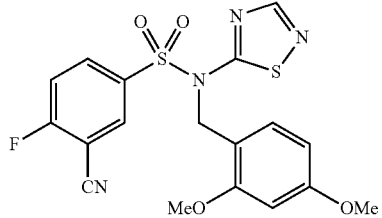

27-1

¹H NMR (400 MHz, d₆-DMSO) δ 8.44 (s, 1H), 8.35-8.33 (m, 1H), 8.28-8.24 (m, 1H), 7.72 (m, 1H), 7.03 (d, 1H), 6.46-6.42 (m, 2H), 5.23 (s, 2H), 3.74 (s, 3H), 3.65 (s, 3H).

Example 28

5-chloro-N-(2,4-dimethoxybenzyl)-2,4-difluoro-N-(5-fluorothiazol-2-yl)benzenesulfonamide (28-1)

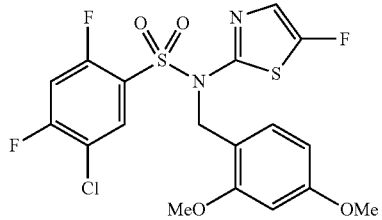

28-1

¹H NMR (400 MHz, CDCl₃) δ 7.87 (t, J=7.6 Hz, 1H), 7.16 (d, J=8.4 Hz, 1H), 7.01~7.06 (m, 2H), 6.38 (dd, J=8.4, 2.4 Hz, 1H), 6.33 (d, J=2.4 Hz, 1H), 5.04 (s, 2H), 3.77 (s, 3H), 3.72 (s, 3H). MS m/z (M+H): 479

Example 29

N-(5-bromothiazol-2-yl)-5-chloro-N-(2,4-dimethoxybenzyl)-2,4-difluorobenzenesulfonamide (29-1)

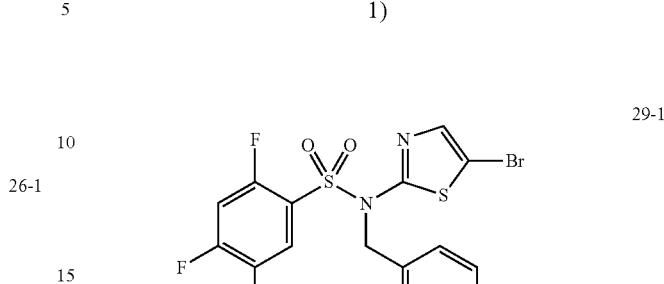

29-1

¹H NMR (400 MHz, CDCl₃) δ 7.88 (t, J=7.2 Hz, 1H), 7.33 (s, 1H), 7.17 (d, J=7.6 Hz, 1H), 7.00 (t, J=8.8 Hz, 1H), 6.37 (dd, J=8.8, 2.0 Hz, 1H), 6.32 (d, J=2.0 Hz, 1H), 5.14 (s, 2H), 3.77 (s, 3H), 3.73 (s, 3H). MS m/z (M+H): 539, 541

Example 30

3-chloro-N-(2,4-dimethoxybenzyl)-4-fluoro-N-(thiazol-2-yl)benzenesulfonamide (30-1)

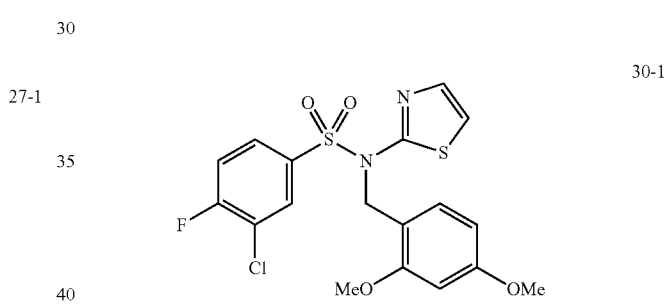

30-1

¹H NMR (400 MHz, CDCl₃) δ 7.74 (dd, J=6.8, 2.4 Hz, 1H), 7.62~7.66 (m, 1H), 7.35 (d, J=3.6 Hz, 1H), 7.12 (t, J=8.8 Hz, 1H), 7.05 (d, J=8.8 Hz, 1H), 6.97 (d, J=3.6 Hz, 1H), 6.26~6.28 (m, 2H), 4.96 (s, 2H), 3.67 (s, 3H), 3.60 (s, 3H). MS m/z (M+H): 443

Example 31

N-(2,4-dimethoxybenzyl)-2,4-difluoro-5-methyl-N-(thiazol-2-yl)benzenesulfonamide (31-1)

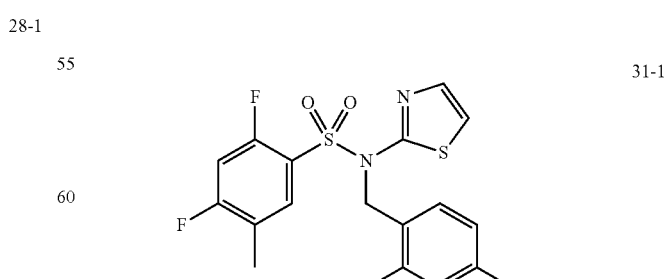

31-1

¹H NMR (400 MHz, CD₃OD) δ 7.70 (t, J=8.0 Hz, 1H), 7.43 (d, J=3.6 Hz, 1H), 7.27 (d, J=3.6 Hz, 1H), 7.14 (dd,

J=20.4, 10.0 Hz, 2H), 6.41 (d, J=6.4 Hz, 1H), 6.38 (d, J=1.6 Hz, 1H), 5.11 (s, 2H), 3.76 (s, 3H), 3.73 (s, 3H), 2.26 (s, 3H). MS m/z (M+H): 441

Example 32 ethyl 2-(5-chloro-N-(2,4-dimethoxybenzyl)-2,4-difluorophenylsulfonamido)thiazole-5-carboxylate (32-1)

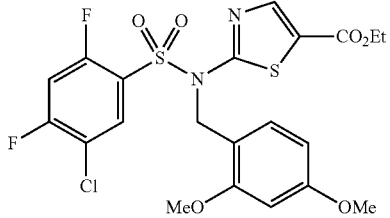

32-1

$^1$H NMR (400 MHz, CDCl$_3$) δ 7.88 (t, J=7.2 Hz, 1H), 7.32 (s, 1H), 7.17 (d, J=7.6 Hz, 1H), 7.01 (t, J=8.8 Hz, 1H), 6.37 (dd, J=8.8, 2.0 Hz, 1H), 6.32 (d, J=2.0 Hz, 1H), 5.14 (s, 2H), 4.31 (q, J=7.2 Hz, 2H), 3.77 (s, 3H), 3.73 (s, 3H). 1.33 (t, J=7.2 Hz, 3H). MS m/z (M+H): 533

Example 33

5-bromo-N-(2,4-dimethoxybenzyl)-2,4-difluoro-N-(thiazol-2-yl)benzenesulfonamide (33-1)

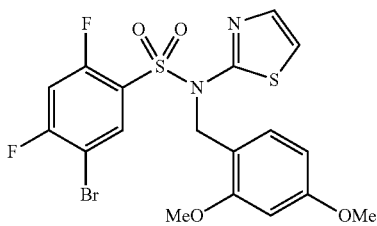

33-1

$^1$H NMR (400 MHz, CD$_3$OD) δ 8.06 (t, J=7.2 Hz, 1H), 7.43 (d, J=3.2 Hz, 1H), 7.20 (d, J=8.4 Hz, 1H), 7.03 (d, J=3.2 Hz, 1H), 6.97 (t, J=8.8 Hz, 1H), 6.38-6.34 (m, 2H), 5.18 (s, 2H), 3.77 (s, 3H), 3.73 (s, 3H). MS m/z (M+H): 505, 507

Example 34

2-chloro-N-(2,4-dimethoxybenzyl)-4,5-difluoro-N-(thiazol-2-yl)benzenesulfonamide (34-1)

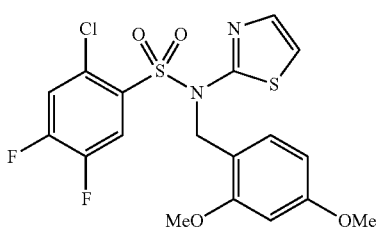

34-1

$^1$H NMR (400 MHz, CD$_3$OD) δ 7.99 (dd, J=10.0, 8.0 Hz, 1H), 7.66 (dd, J=9.6, 6.4 Hz, 1H), 7.44 (d, J=3.6 Hz, 1H), 7.26 (d, J=3.6 Hz, 1H), 7.15 (d, J=8.4 Hz, 1H), 6.41 (dd, J=8.8, 2.0 Hz, 2H), 5.18 (s, 1H), 3.76 (s, 3H), 3.74 (s, 3H). MS m/z (M+H): 461

Example 35

5-chloro-N-(2,4-dimethoxybenzyl)-2,4-difluoro-N-(4-methylthiazol-2-yl)benzenesulfonamide (35-1)

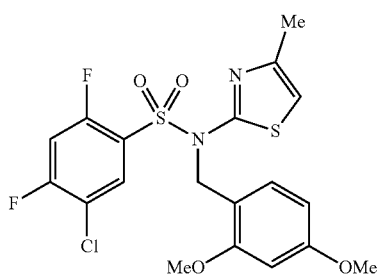

35-1

$^1$H NMR (400 MHz, CDCl$_3$) δ 7.94~7.96 (m, 1H), 7.21 (d, J=8.4 Hz, 1H), 7.00 (t, J=8.4 Hz, 1H), 6.56 (s, 1H), 6.34~6.40 (m, 2H), 5.15 (s, 2H), 3.76 (s, 3H), 3.73 (s, 3H), 2.26 (s, 3H). MS m/z (M+H): 475

Example 36

N-(2,4-dimethoxybenzyl)-4-fluoro-N-(thiazol-2-yl)-3-(trifluoromethyl)benzenesulfonamide (36-1)

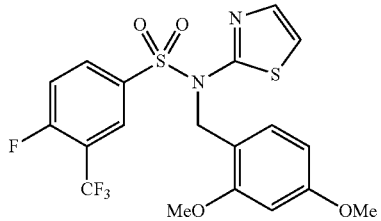

36-1

$^1$H NMR (CDCl$_3$, 400 MHz) δ8.05-8.03 (m, 2H), 7.47 (d, J=3.6 Hz, 1H), 7.29-7.27 (m, 1H), 7.13-7.09 (m, 2H), 6.36-6.33 (m, 2H), 5.04 (s, 2H), 3.77 (s, 3H), 3.67 (s, 3H). MS m/z (M+H): 477

Example 37

N-(2,4-dimethoxybenzyl)-4-fluoro-N-(5-fluorothiazol-2-yl)-3-(trifluoromethyl)benzenesulfonamide (37-1)

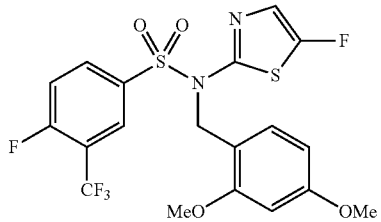

37-1

$^1$H NMR (400 MHz, CDCl$_3$) δ8.05 (d, J=5.6 Hz, 2H), 7.28~7.37 (m, 1H), 7.01~7.15 (m, 2H), 6.30~6.41 (m, 2H), 4.89 (s, 2H), 3.80 (s, 3H), 3.68 (s, 3H). MS m/z (M+H): 495

Example 38

3-chloro-N-(2,4-dimethoxybenzyl)-4-fluoro-N-(5-fluorothiazol-2-yl)benzenesulfonamide (38-1)

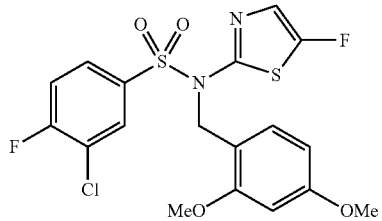

$^1$H NMR (400 MHz, CDCl$_3$) δ 7.84 (dd, J=6.8, 2.0 Hz, 1H), 7.71-7.07 (m, 1H), 7.23 (d, J=8.8 Hz, 1H), 7.12 (d, J=8.0 Hz, 1H), 7.03 (d, J=2.8 Hz, 1H), 6.39-6.36 (m, 2H), 4.89 (s, 2H), 3.78 (s, 3H), 3.70 (s, 3H). MS m/z (M+H): 461

Example 39

5-bromo-N-(2,4-dimethoxybenzyl)-2,4-difluoro-N-(5-fluorothiazol-2-yl)benzenesulfonamide (39-1)

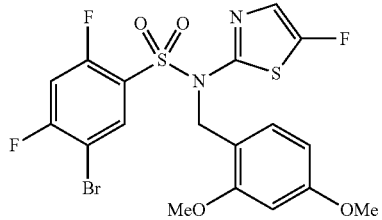

$^1$H NMR (400 MHz, CDCl$_3$) δ 8.01 (t, J=7.6 Hz, 1H), 7.16 (d, J=8.0 Hz, 1H), 7.03-6.98 (m, 2H), 6.38 (dd, J=8.4, 2.0 Hz, 1H), 6.33 (d, J=2.4 Hz, 1H), 5.04 (s, 2H), 3.78 (s, 3H), 3.72 (s, 3H). MS m/z (M+H): 523, 525

Example 40 tert-butyl (5-chloro-2,4-difluorophenyl)sulfonyl(thiazol-4-yl)carbamate (7-1)

Preparation of tert-butyl thiazol-4-ylcarbamate (40-2)

Scheme 40

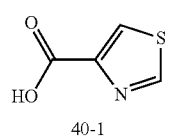

DPPA, t-BuOH
TEA
→

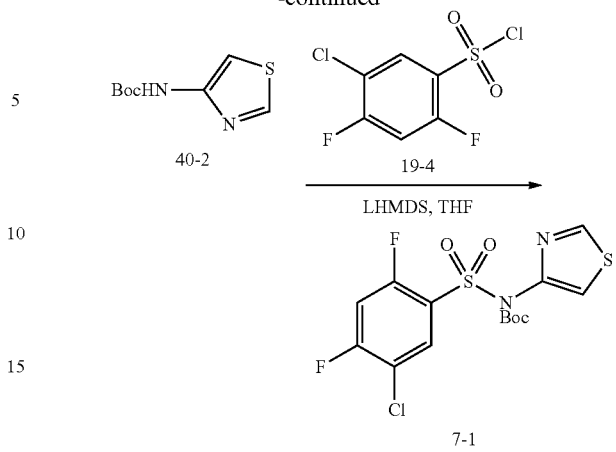

To a solution of 40-1 (8.9 g, 68 mmol), Et$_3$N (7.8 g, 76 mmol) in t-BuOH (100 mL) was added DPPA (21 g, 77 mmol), then the mixture was stirred for 8 h under N$_2$ at 100° C. After cooled to room temperature, the solvent was removed in vacuo. The residue was dissolved in CH$_2$Cl$_2$ and the organic layer was washed with water and brine, dried over Na$_2$SO$_4$. The crude product was purified by column chromatography on silica gel (PE:EtOAc=4:1) to give 40-2. $^1$H NMR (400 MHz CDCl$_3$) δ 8.87 (brs, 1H), 8.61~8.62 (m, 1H), 7.26~7.27 (m, 1H), 1.54 (s, 9H).

Preparation of tert-butyl (5-chloro-2,4-difluorophenyl)sulfonyl(thiazol-4-yl)carbamate (7-1)

To a solution of 40-2 (1.0 g, 4.9 mmol) in 20 mL of THF was added LiHMDS (5.8 mL, 5.8 mmol) at −78° C., and the mixture was stirred for 1 h under N$_2$ at room temperature. After being cooled back to −78° C., a solution of 19-4 (1.1 g, 4.5 mmol) in 2 mL of THF was added to the above solution. Then the mixture was warmed to room temperature and stirred for 1 h. The reaction was quenched with NH$_4$Cl and extracted with EtOAc. The organic layer was washed with water and brine, dried over MgSO$_4$, filtered and concentrated. The crude product was purified by column chromatography on silica gel (PE:EtOAc=8:1) to give 7-1. $^1$H NMR (400 MHz CDCl$_3$) δ 8.80 (d, J=2.0 Hz, 1H), 8.23 (t, J=7.6 Hz, 1H), 7.53 (d, J=2.0 Hz, 1H), 7.09 (t, J=8.4 Hz, 1H), 1.37 (s, 9H). MS m/z (M+H): 411

Example 41

5-chloro-2,4-difluoro-N-(6-fluoropyridin-2-yl)-N-(methoxymethyl)benzene sulfonamide (41-3)

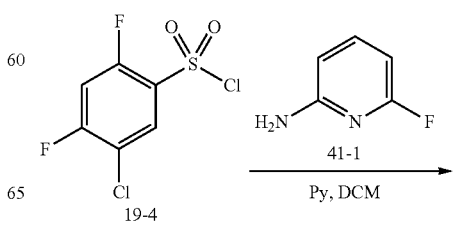

-continued

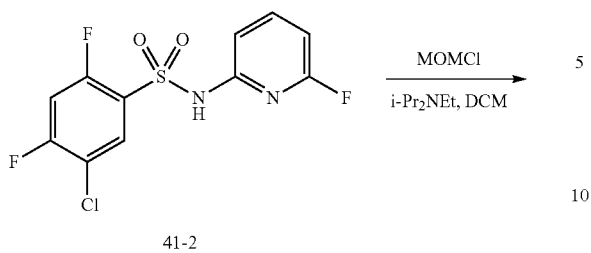

41-2

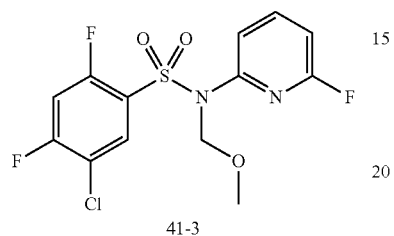

41-3

Preparation of 5-chloro-2,4-difluoro-N-(6-fluoropyridin-2-yl)benzenesulfonamide (41-2)

A mixture of 19-4 (1.3 g, 5.26 mmol), 41-1 (589 mg, 5.26 mmol), pyridine (2.1 g, 26.3 mmol) and DCM (20 mL) was stirred at room temperature under nitrogen overnight. H$_2$O (20 mL) was added into the mixture which was extracted with DCM. The combined organic layers were washed with brine, dried over Na$_2$SO$_4$, filtered and the filtrate was concentrated. The residue was purified by column chromatography on silica gel (PE:EtOAc=5:1) to give 41-2. $^1$H NMR (400 MHz CD$_3$OD) δ 8.16 (t, J=7.6 Hz, 1H), 7.75 (dd, J=16.0, 8.0 Hz, 1H), 7.34 (t, J=9.6 Hz, 1H), 6.89 (dd, J=8.0, 1.2 Hz, 1H), 6.60 (dd, J=8.0, 2.0 Hz, 1H).

Preparation of 5-chloro-2,4-difluoro-N-(6-fluoropyridin-2-yl)-N-(methoxymethyl) benzenesulfonamide (41-3)

To a mixture of 41-2 (1 g, 3.01 mmol) in DCM (20 mL) was added DIEA (1.16 g, 9.03 mmol) and MOMCl (602 mg, 7.4 mmol). The mixture was stirred at room temperature under nitrogen for 4 h. The mixture was poured into water and extracted with DCM. The combined organic layers were washed with brine, dried over Na$_2$SO$_4$, filtered and the filtrate was concentrated. The residue was purified by column chromatography on silica gel (PE:EtOAc=5:1) to give 41-3. $^1$H NMR (400 MHz CD$_3$OD) δ 8.06 (t, J=7.6 Hz, 1H), 7.91 (dd, J=16.0, 8.0 Hz, 1H), 7.35~7.41 (m, 2H), 6.85 (dd, J=8.4, 2.8 Hz, 1H), 5.35 (s, 2H), 3.42 (s, 3H). MS m/z (M+H): 367

The following cores were made by analogy to Examples 19 and 20 using commercially available sulfonyl chlorides and heterocyclic amines or sulfonyl chlorides and amines in the published literature:

Example 42

5-chloro-2,4-difluoro-N-(5-fluoropyridin-2-yl)-N-(methoxymethyl)benzene sulfonamide (42-1)

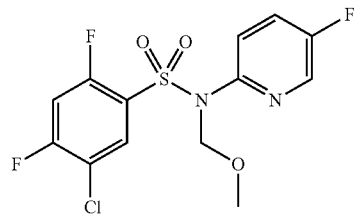

42-1

$^1$H NMR (400 MHz CD$_3$OD) δ 8.17 (d, J=3.2 Hz, 1H), 7.93 (t, J=7.2 Hz, 1H), 7.62~7.67 (m, 1H), 7.54 (dd, J=8.8, 3.6 Hz, 1H), 7.39 (t, J=9.2 Hz, 1H), 5.29 (s, 2H), 3.41 (s, 3H). MS m/z (M+H): 367

Example 43

5-chloro-2,4-difluoro-N-(methoxymethyl)-N-(pyrimidin-4-yl)benzene sulfonamide (3-1)

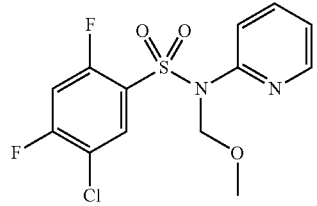

3-1

$^1$H NMR (400 MHz CDCl$_3$) δ 8.77 (s, 1H), 8.57 (d, J=8.0 Hz, 1H), 8.10~8.22 (m, 1H), 7.33~7.37 (m, 1H), 6.95~7.02 (m, 1H), 5.48 (s, 2H), 3.51 (s, 3H). MS m/z (M+H): 350

Example 44

5-chloro-2,4-difluoro-N-(methoxymethyl)-N-(pyridazin-3-yl)benzene sulfonamide (44-1)

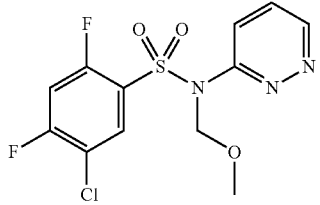

44-1

$^1$H NMR (400 MHz CDCl$_3$) δ 8.86 (d, J=4.8 Hz, 1H), 8.07~8.11 (m, 1H), 7.70 (dd, J=4.8 Hz, 1H), 7.20 (m, 1H), 6.97~7.02 (m, 1H), 5.10 (s, 2H), 3.29 (s, 3H). MS m/z (M+H): 350

Example 45

N-(5-chlorothiazol-2-yl)-3-cyano-4-fluoro-N-(methoxymethyl)benzene sulfonamide (45-1)

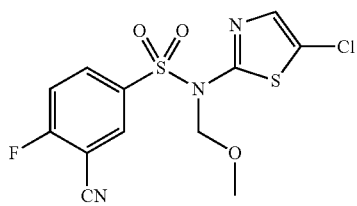

45-1

¹H NMR (400 MHz CDCl₃) δ 8.24~8.26 (m, 1H), 8.14~8.18 (m, 1H), 7.13 (t, J=8.4 Hz, 1H), 7.06 (s, 1H), 5.36 (s, 2H), 3.48 (s, 3H). MS m/z (M+H): 362

Example 46

2,4,5-trifluoro-N-(6-fluoropyridin-2-yl)benzenesulfonamide (46-2)

Scheme 46

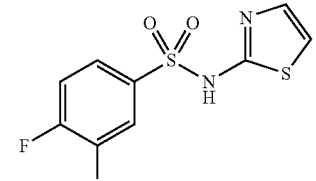

Preparation of 2,4,5-trifluoro-N-(6-fluoropyridin-2-yl)benzenesulfonamide (46-2)

A mixture of 46-1 (1.12 g, 10 mmol), 41-1 (2.3 g, 10 mmol), pyridine (4 g, 50 mmol) and DCM (30 mL) was stirred at room temperature under nitrogen overnight. H₂O (30 mL) was added into the mixture which was extracted with DCM. The combined organic layers were washed with brine, dried over Na₂SO₄, filtered and the filtrate was concentrated. The residue was purified by column chromatography on silica gel (PE:EtOAc=5:1) to give 46-2. ¹H NMR (400 MHz CD₃OD) δ 7.98 (dd, J=15.6, 8.8 Hz, 1H), 7.75 (dd, J=16.0, 8.0 Hz, 1H), 7.34~7.41 (m, 1H), 6.90 (t, J=1.2 Hz, 1H), 6.60 (dd, J=8, 2 Hz, 1H).

The following cores were made by analogy to Examples 19 and 20 using commercially available sulfonyl chlorides and heterocyclic amines or sulfonyl chlorides and amines in the published literature:

Example 47

3-cyano-4-fluoro-N-(6-fluoropyridin-2-yl)benzenesulfonamide (47-1)

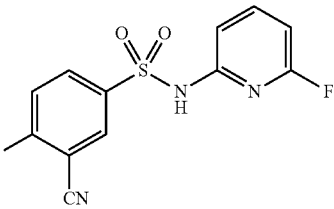

47-1

¹H NMR (400 MHz CD₃OD) δ 8.42 (dd, J=5.6, 2 Hz, 1H), 8.30~8.34 (m, 1H), 7.75 (dd, J=16, 8 Hz, 1H), 7.54 (t, J=8.8 Hz, 1H), 6.92 (t, J=1.2 Hz, 1H), 6.61 (dd, J=8, 2 Hz, 1H). MS m/z (M+H): 296

Example 48

3-cyano-4-fluoro-N-(1,3-thiazol-2-yl)benzenesulfonamide (2-1)

¹H NMR (300 MHz d₆-DMSO) δ 8.26 (t, 1H), 8.12 (m, 1H), 7.64 (m, 1H), 7.27 (d, 1H), 6.86 (d, 1H). MS m/z (M+H): 284

Example 49

N-(2,4-dimethoxybenzyl)-2,4,5-trifluoro-N-(1,3,4-thiadiazol-2-yl)-benzenesulfonamide (49-3)

Scheme 49

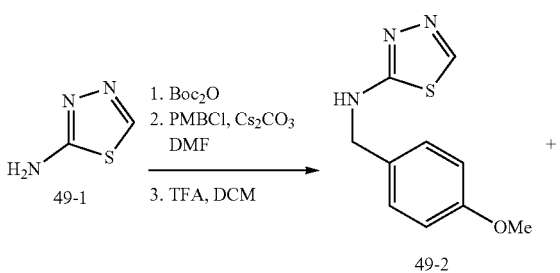

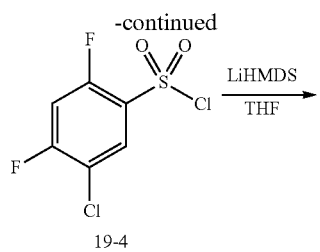

19-4

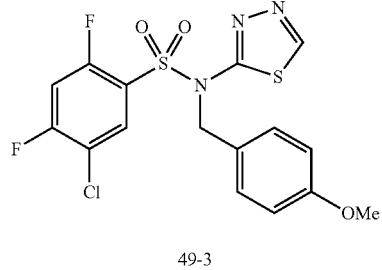

49-3

Preparation of N-(2,4-dimethoxybenzyl)-1,3,4-thiadiazol-2-amine (37-2)

To a solution of 49-1 (96 g, 949 mmol) in MeOH (949 mL) was added Boc$_2$O (207 g, 949 mmol). The mixture was warmed to 50° C. for 18 h. After 18 h, an additional 50 g of Boc$_2$O was added and the mixture was heated at 50° C. for 4 h. The mixture was concentrated and water and dichloromethane were added to provide the product which precipitated as a solid (122 g, 64%). To a solution of the resulting product (100 g, 497 mmol) in DMF (994 mL) was added cesium carbonate (194 g, 596 mmol) and PMBCl (86 g, 547 mmol) at ambient temperature. The mixture was stirred for 3 h and then partitioned between water and methyl-tert-butylether. The aqueous was extracted with methyl-tert-butylether, and the organic phase was dried over sodium sulfate, filtered, and concentrated. The crude product was used in the following reaction. To a solution of the crude product (160 g, 497 mmol) in dichloromethane (994 mL) was added TFA (283 g, 2.485 mol) at ambient temperature. The reaction was stirred for 4 h and the mixture was partitioned between saturated sodium bicarbonate (carefully) and EtOAc. The aqueous phase was extracted with EtOAc. The combined organic phase was dried over sodium sulfate, filtered, and concentrated. The crude product was slurried in methyl-tert-butylether and the precipitate was filtered to afford 49-2 as a solid (65 g, 59% over 2 steps).

$^1$H NMR (500 MHz d$_6$-DMSO) δ 8.62 (s, 1H), 8.20-8.16 (m, 1H), 7.28-7.22 (m, 2H), 6.90-6.84 (m, 2H), 4.42-4.37 (m, 2H), 3.74 (s, 3H).

Preparation of N-(2,4-dimethoxybenzyl)-2,4,5-trifluoro-N-(1,3,4-thiadiazol-2-yl) benzenesulfonamide (49-3)

To a solution of 49-2 (5 g, 22.6 mmol) in THF (37.5 mL) was added LHMDS (1.0 M in THF, 27.1 mL, 27.1 mmol) at −78° C. The mixture was stirred at −78° C. for 30 minutes. A solution of 19-4 (6.7 g, 27.1 mmol) in THF (12.5 mL) was added slowly to the mixture being careful to keep the temperature at −78° C. After 1 h, the reaction was allowed to warm to ambient temperature overnight. The product was partially crystallized from the reaction mixture via addition of a dilute solution of sodium bicarbonate. The resulting solids were filtered, washed with water, and dried under nitrogen. The damp solids were resuspended in dichloromethane, dried over sodium sulfate, filtered and concentrated to afford 49-3 as a white solid (8.74 g, 90%). $^1$H NMR (500 MHz d$_6$-DMSO) δ 8.82 (s, 1H), 7.86-7.80 (m, 1H), 7.41-7.35 (m, 2H), 7.00-6.92 (m, 1H), 6.78-6.72 (m, 2H), 5.28 (s, 2H) 3.76 (s, 3H).

Example 50

5-chloro-N-(2,4-dimethoxybenzyl)-2,4-difluoro-N-(5-fluoro-4-methylthiazol-2-yl)benzenesulfonamide (50-6)

Scheme 50

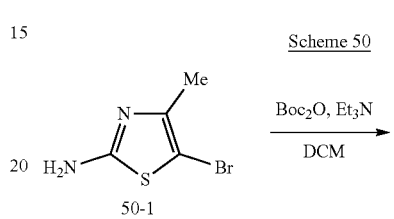

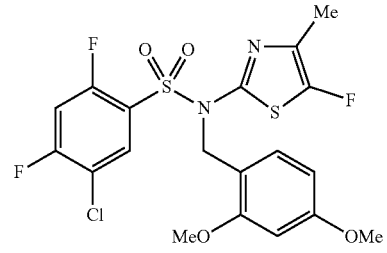

50-6

Preparation of tert-butyl (5-bromo-4-methylthiazol-2-yl)carbamate (50-2)

A mixture of 50-1 (17.4 g, 90 mmol), Boc$_2$O (25.7 g, 118 mmol) and Et$_3$N (27.3 g, 270 mmol) in 200 mL of DCM was stirred at room temperature overnight. The mixture was washed with water and brine, dried with Na$_2$SO$_4$, filtered and concentrated to give 50-2 (23.2 g, 88%) as a light yellow crystal.

Preparation of tert-butyl (5-fluoro-4-methylthiazol-2-yl)carbamate (50-3)

To a mixture of 50-2 (11.7 g, 40 mmol) in THF (150 mL) at −78° C. was added dropwise a solution of n-BuLi (2.5 M in hexane, 32 mL, 80 mmol). After 1 h, a solution of NFSI (18.9 g, 60 mmol) in 30 mL of THF was added. The mixture was stirred at −78° C. for 2 h. The same reaction was carried out for another batch on the same scale. Then the mixture was quenched with saturated NH$_4$Cl solution and extracted with EtOAc. The combined organic phases were dried with Na$_2$SO$_4$ and concentrated. The residue was purified by column chromatography on silica gel (PE:EtOAc=10:1) to give 50-3 as a white solid. MS m/z (M+H): 232.1

Preparation of 5-fluoro-4-methylthiazol-2-amine (50-4)

A mixture of 50-3 (928 mg, 4 mmol) in DCM/TFA (6 mL/2 mL) was stirred at room temperature overnight. The mixture was concentrated and partitioned between DCM and saturated NaHCO$_3$. The combined organic phases were dried with Na$_2$SO$_4$ and concentrated to give 50-4 (520 mg, 100%). MS m/z (M+H): 132

Preparation of N-(2,4-dimethoxybenzyl)-5-fluoro-4-methylthiazol-2-amine (50-5)

To a mixture of 50-4 (500 mg, 3.79 mmol) and 19-2 (630 mg, 3.79 mmol) in dry DCM (10 mL) at room temperature was added (iPrO)$_3$TiCl (9.5 mL, 9.5 mmol, 1M) dropwise. After 1 h, NaBH(OAc)$_3$ (1.61 g, 7.58 mmol) was added to the mixture in portions. The mixture was stirred at room temperature for 2 h. The reaction was quenched with saturated aqueous NaHCO$_3$ and adjusted to pH=9 with aqueous NaOH, then extracted with DCM. The organic layers were concentrated and the crude product was purified by column chromatography on silica gel (PE: EtOAc=5:1 to 4:1) to give 50-5. MS m/z (M+H): 282.1

Preparation of 5-chloro-N-(2,4-dimethoxybenzyl)-2,4-difluoro-N-(5-fluoro-4-methylthiazol-2-yl)-benzenesulfonamide (50-6)

To a solution of 50-5 (200 mg, 0.71 mmol) and 19-4 (261 mg, 1.06 mmol) in dry THF (15 mL) was added LiHMDS (0.85 mL, 0.85 mmol) dropwise slowly at −78° C. The mixture was stirred at −78° C. for 1 h and warmed to room temperature for 45 min. Then the mixture was quenched with saturated aqueous NH$_4$Cl and water, extracted with EtOAc. The organic layers were dried over Na$_2$SO$_4$, filtered and concentrated. The crude product was purified by prep-TLC (PE:EtOAc=5:1) to give 50-6 as a white solid. $^1$H NMR (400 MHz, CDCl$_3$) δ 7.90 (t, J=7.6 Hz, 1H), 7.18 (d, J=8.4 Hz, 1H), 7.00 (t, J=7.6 Hz, 1H), 6.34~6.40 (m, 2H), 5.15 (s, 2H), 3.76 (s, 3H), 3.73 (s, 3H), 2.26 (d, J=1.6 Hz, 3H). MS m/z (M+H): 492.0

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment. While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of Formula A-a, or a pharmaceutically acceptable salt thereof:

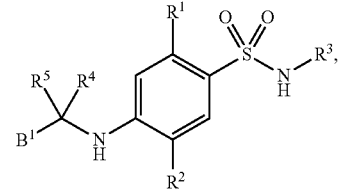

Formula A-a wherein:
$R^1$ and $R^2$ are independently: (a) hydrogen; (b) halogen; (c) —CN; or (d) an alkyl moiety which is —C$_{1-10}$-linear-alkyl, —C$_{3-10}$-branched-alkyl, or —C$_{3-10}$-cycloalkyl, which alkyl moiety is optionally substituted with one or more halogen atoms;

$R^3$ is:
(i) a moiety of Formula S1 or S2:

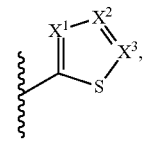

Formula S1

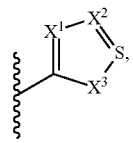

Formula S2 wherein: one or two of $X^1$ to $X^3$ is [=N-] and the others are [=CR$^6$—], where $R^6$ is:
A. —H;
B. an alkyl moiety which is —C$_{1-6}$-linear alkyl or —C$_{3-6}$-branched alkyl, which alkyl moiety is optionally substituted with one or more moieties which are independently for each occurrence: (a) halogen; or (b) —$C_{3-6}$-cycloalkyl, which is optionally substituted;

C. $C_{1-6}$-linear alkyl-C(O)—O—, $C_{3-6}$-branched alkyl-C(O)—O— or $C_{3-6}$-cycloalkyl-C(O)—O—;

D. —$C_{3-6}$-cycloalkyl optionally substituted with —F or $C_{1-6}$-linear alkyl; or E. halogen; or (ii) a moiety of Formula S4:

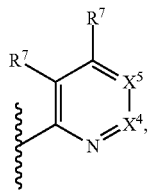

Formula S4 wherein $X^4$ and $X^5$ are independently [=N-] or [=CR$^7$—], wherein $R^7$ is independently for each occurrence —H or —F, and wherein no more than two $R^7$ are selected to be —F;

$R^4$ and $R^5$ are independently for each occurrence: (a) hydrogen; or (b) a cyclic-, branched-, or linear-alkyl moiety comprising up to 6 carbon atoms, which alkyl moiety is optionally substituted with one or more moieties which are, independently: (i) —F; (ii) perfluoro-$C_{1-4}$-linear-alkyl; (iii) $C_{3-6}$-cycloalkyl; (iv) —N(R$^{S4a}$)$_2$, wherein R$^{S4a}$ is independently for each occurrence, —H or lower-alkyl; or (v) an alkoxy moiety which is —$C_{1-6}$-linear-alkoxy, —$C_{3-6}$-branched-alkoxy or —$C_{3-6}$-cycloalkoxy; and $B^1$ is a moiety of the formula:

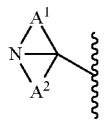

wherein, $A^1$ and $A^2$ are, independently, (—CR$^8$R$^9$—)$_n$, wherein:

n is independently for each occurrence 2, 3, 4 or 5; and
$R^8$ and $R^9$ are independently for each occurrence:
  (a) hydrogen;
  (b) halogen;
  (c) an alkyl moiety which is —$C_{1-6}$-linear-alkyl, —$C_{3-6}$-branched-alkyl, or —$C_{3-6}$-cycloalkyl, which alkyl moiety is optionally substituted with one or more moieties which are, independently:
    (i) halogen;
    (ii) —OH;
    (iii) an alkoxy moiety which is —$C_{1-6}$-linear-alkoxy, —$C_{3-6}$-branched-alkoxy, or —$C_{3-6}$-cyclic-alkoxy;
    (iv) —N(R$^{A4a}$)$_2$, wherein R$^{A4a}$ is independently for each occurrence, —H or an alkyl moiety which is $C_{1-6}$-linear-alkyl, $C_{3-6}$-branched-alkyl, or $C_{3-6}$-cycloalkyl;
    (v) -heterocycloalkyl, where said heterocycloalkyl comprises from 2 to 6 carbon atoms and one or two nitrogen atoms in the ring;
    (vi) —$C_{6-10}$-aryl which is optionally substituted on any ring carbon atom thereof with one or more moieties which are independently: halogen; an alkoxy moiety which is —$C_{1-6}$-linear-alkoxy, —$C_{3-6}$-branched-alkoxy, or —$C_{3-6}$-cyclic-alkoxy; or an alkyl moiety which is —$C_{1-6}$-linear-alkyl, $C_{3-6}$-branched-alkyl, or —$C_{3-6}$-cycloalkyl; or
    (vii) —$C_{6-10}$-heteroaryl, as defined herein, which is optionally substituted on any ring carbon atom thereof with one or more moieties which are independently: halogen; an alkoxy moiety which is —$C_{1-6}$-linear-alkoxy, —$C_{3-6}$-branched-alkoxy, or —$C_{3-6}$-cyclic-alkoxy; or an alkyl moiety which is —$C_{1-6}$-linear-alkyl, $C_{3-6}$-branched-alkyl, or $C_{3-6}$-cycloalkyl;
  (d) an alkoxy moiety which is —$C_{1-6}$-linear-alkoxy, —$C_{3-6}$-branched-alkoxy, or —$C_{3-6}$-cyclic-alkoxy;
  (e) —N(R$^{A5a}$)$_2$, wherein R$^{A5a}$ is independently for each occurrence: —H; or an alkyl moiety which is —$C_{1-6}$-linear-alkyl, $C_{3-6}$-branched-alkyl, or $C_{3-6}$-cycloalkyl;
  (f) —$C_{2-6}$-heterocycloalkyl, wherein said heterocycloalkyl comprises from 2 to 6 carbon atoms and one or two nitrogen atoms in the ring;
  (g) aryl, optionally substituted with one or more moieties which are, independently: (i) halogen; (ii) an alkoxy moiety which is —$C_{1-6}$-linear-alkoxy, —$C_{3-6}$-branched-alkoxy or —$C_{3-6}$-cyclic-alkoxy; or (iii) an alkyl moiety which is —$C_{1-6}$-linear-alkyl, $C_{3-6}$-branched-alkyl, or $C_{3-6}$-cycloalkyl;
  (h) heteroaryl, optionally substituted with one more moieties which are, independently: (i) halogen; (ii) an alkoxy moiety which is —$C_{1-6}$-linear-alkoxy, —$C_{3-6}$-branched-alkoxy or —$C_{3-6}$-cyclic-alkoxy; or (iii) an alkyl moiety which is —$C_{1-6}$-linear-alkyl, $C_{3-6}$-branched-alkyl, or $C_{3-6}$-cycloalkyl; or $R^8$ and $R^9$ on one carbon together form:
  (a) a dioxalane moiety;
  (b) an arylspirocycloalkyl moiety having a $C_{3-6}$-cycloalkyl portion that, together with the substrate carbon to which it is bonded forms a spirocycloalkyl structure wherein two carbons of the spirocycloalkyl ring portion is fused to an aryl moiety;
  (c) a heteroarylspirocycloalkyl moiety having a $C_{3-6}$-cycloalkyl portion that, together with the substrate carbon to which it is bonded forms a spirocycloalkyl structure wherein two carbon atoms of the cycloalkyl ring portion of the moiety are fused to a heteroaryl moiety; or
  (d) —$C_{3-6}$-spirocycloalkyl moiety.

2. A compound of claim 1, or a pharmaceutically acceptable salt thereof, wherein:

$R^4$ and $R^5$ are independently: —H; or a cyclic-, branched- or linear-alkyl moiety of up to 6 carbon atoms; and $R^1$ and $R^2$ are independently: —H; —F; —Cl; —Br; —CN; a cyclic-, branched, or linear-alkyl moiety comprising up to 6 carbon atoms; or —CF$_3$.

3. A compound of claim 2, or a pharmaceutically acceptable salt thereof, wherein:

$R^1$ is: —H; —F; —Cl; —Br; —CN; or —CH$_3$;

$R^2$ is: —H; —F; —Cl; —Br; —CN; CH$_3$; —CH$_2$CH$_3$; or —CF$_3$; and $R^4$ and $R^5$ are independently: (i) —H; or (ii) —CH$_3$.

4. A compound of claim 2, or a pharmaceutically acceptable salt thereof, wherein, in the structure of Formula A-a, the moiety of Formula $B^1$ has the structure of Formula $B^{1a}$:

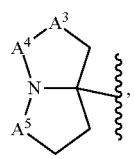

Formula $B^{1a}$ wherein:
$A^3$ is —$(CR^{10}R^{11})_p$, wherein:
  p is 1 or 2; and
  $R^{10}$ and $R^{11}$ are independently for each occurrence:
    (a) hydrogen;
    (b) halogen;
    (c) an alkyl moiety which is —$C_{1-6}$-linear-alkyl, —$C_{3-6}$-branched-alkyl, or —$C_{3-6}$-cycloalkyl, which moiety is optionally substituted with one or more substituents which are independently: (i) halogen; (ii) aryl, which is optionally substituted with lower alkoxy; or (iii) —OH; or
    (d) aryl, optionally substituted with an alkoxy moiety which is $C_{1-4}$-linear-alkoxy or $C_{3-4}$-branched-alkoxy; or
  $R^{10}$ and $R^{11}$ together form: (i) a dioxalane moiety or (ii) a $C_{3-6}$-spirocycloalkyl moiety;
$A^4$ is —$(CR^{12}R^{13})$, wherein $R^{12}$ and $R^{13}$ are independently: (a) hydrogen; (b) a cyclic-, branched-, or liner-alkyl moiety comprising up to 6 carbon atoms, which moiety is optionally substituted with one or more substituents which are, independently: (i) halogen; or (ii) —OH; or (c) aryl, which is optionally substituted with one or more substituents which are, independently: (i) lower-alkyl; or (ii) lower-alkoxy; and
$A^5$ is —$(CR^{14}R^{15})_m$, wherein: m is 1 or 2, and $R^{14}$ and $R^{15}$ are independently for each occurrence: (a) hydrogen; or (b)) an alkyl moiety which is —$C_{1-6}$-linear-alkyl, —$C_{3-6}$-branched-alkyl, or —$C_{3-6}$-cycloalkyl, which alkyl moiety is optionally substituted with one or more substituents which are, independently: (i) —OH or halogen.

5. A compound of claim 4, or a pharmaceutically acceptable salt thereof, wherein:
$A^3$, $A^4$ and $A^5$ are each [—$CH_2$—]; and
in the structure of Formula A-a:
  $R^1$ is independently: —H; —F; —Cl; —Br; —CN; or $CH_3$;
  $R^2$ is independently: —H; —F; —Cl; —Br; —CN; —$CF_3$, —$CH_3$; or —$CH_2CH_3$.

6. A compound of claim 4, or a pharmaceutically acceptable salt thereof, wherein:
A is [—$CR^{10a2}R^{11a2}$—], wherein:
  [—$R^{10a2}$] and [—$R^{11a2}$] are independently for each occurrence:
    (a) hydrogen;
    (b) halogen;
    (c) an alkyl moiety which is —$C_{1-6}$-linear-alkyl, —$C_{3-6}$-branched-alkyl, or —$C_{3-6}$-cycloalkyl, which alkyl moiety is optionally substituted with one or more: (i) halogen; (ii) an aryl moiety optionally substituted with $C_{1-4}$-linear-alkoxy or $C_{3-4}$-branched-alkoxy; or (iii) —OH; or
    (d) an aryl moiety optionally substituted with $C_{1-4}$-linear-alkoxy or $C_{3-4}$-branched-alkoxy; or
  $R^{10a2}$ and $R^{11a2}$ together form:
    (a) a dioxalane moiety; or
    (b) a $C_{3-6}$-spirocycloalkyl moiety;
$A^4$ and $A^5$ are each [—$CH_2$—]; and
in the moiety of Formula A-a:
  $R^1$ is independently: —H; or —F; and
  $R^2$ is independently: (i) —H; (ii) —Cl; (iii) —CN; or (iv) an alkyl moiety which is —$C_{1-6}$-linear-alkyl, —$C_{3-6}$-branched-alkyl, or —$C_{3-6}$-cycloalkyl, which alkyl moiety is optionally substituted with one or more —F.

7. A compound of claim 4, or a pharmaceutically acceptable salt thereof, wherein:
$A^4$ is [—$CR^{12a3}R^{13a3}$—], wherein:
  $R^{12a3}$ and $R^{13a3}$ are independently for each occurrence:
    (a) hydrogen; or
    (b) an alkyl moiety which is —$C_{1-6}$-linear-alkyl, —$C_{3-6}$-branched-alkyl, or —$C_{3-6}$-cycloalkyl, which alkyl moiety is optionally substituted with one or more: (i) halogen; (ii) —OH;
$A^3$ and $A^5$ are each [—$CH_2$—].

8. A compound of claim 4, or a pharmaceutically acceptable salt thereof, wherein:
$A^3$ is independently [—$CH_2$-] or [—$CH_2$—$CH_2$—];
$A^4$ is [—$CH_2$—];
$A^5$ is [—$CH_2$—$CH_2$—];
$R^1$ is independently: —H; —F; —Cl; —Br; —CN; or —$CH_3$; and
$R^2$ is, independently: —H; —F; —Cl; —Br; —CN; $CH_3$; —$CH_2CH_3$; or —$CF_3$.

9. A compound of any claim 2, or a pharmaceutically acceptable salt thereof, wherein the moiety [—$R^3$] in the structure of Formula A-a is a moiety of Formula $R^{3a}$:

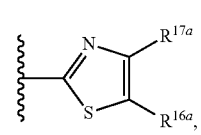

Formula $R^{3a}$ wherein: —$R^{16a}$ and —$R^{17a}$ are independently:
(a) —H;
(b) A branched- or linear-alkyl moiety comprising up to 6 carbon atoms which is optionally substituted with one or more halogen moieties;
(c) —$CF_3$;
(d) an ester moiety which is $C_{1-6}$-linear-alkyl-C(O)—O—, $C_{3-6}$-branched-alkyl-C(O)—O—, or $C_{3-6}$-cyclo-alkyl-C(O)—O—;
(e) —$C_{3-5}$-cycloalkyl which is optionally substituted with: (i) —F; or (ii) branched- or linear-alkyl moiety comprising up to 6 carbon atoms;
(f) —CN;
(g) a heteroaryl moiety;
(h) an aryl moiety; or
(i) halogen.

10. A compound of claim 9, or a pharmaceutically acceptable salt thereof wherein:
(a) —$R^{16a}$ is —H, —Cl, —$CH_3$, —F, —Br or —C(O)—$CH_2$—$CH_3$; and
(b) —$R^{17a}$ is —H, —Cl, or $CH_3$.

11. A compound of claim or a pharmaceutically acceptable salt thereof, wherein [—R³] is a moiety of Formula R³ᵇ:

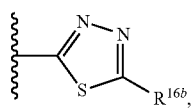

Formula R³ᵇ wherein: —R¹⁶ᵇ is:
(i) —H;
(ii) —CF₃;
(iii) a lower-alkyl comprising up to 6 carbon atoms and is optionally substituted with one or more substituents which are independently:
  (a) halogen;
  (b) —C₃₋₅-cycloalkyl optionally substituted with, independently for each occurrence: (1) —F; or (2) lower alkyl; or
  (c) a heteroaryl substituent; or
(iv) heteroaryl.

12. A compound of claim 4, or a pharmaceutically acceptable salt thereof, wherein [—R³] is a moiety of Formula R³ᶜ:

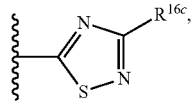

Formula R³ᶜ wherein: —R¹⁶ᶜ is:
(i) —H;
(ii) —CF₃;
(iii) a cyclic- or branched-, or linear-alkyl moiety comprising up to 6 carbon atoms which is optionally substituted with one or more substitutents which are independently for each occurrence:
  (a) halogen;
  (b) an ester of the formula: (1) C₁₋₆-linear-; (2) C₃₋₆-branched-; or (3) C₃₋₆-cyclic-alkyl-C(O)—O—; or
  (c) —C₃₋₅-cycloalkyl optionally substituted with, independently for each occurrence: (1) —F; or (2) lower alkyl.

13. A compound of claim 4, or a pharmaceutically acceptable salt thereof, wherein [—R³] is a moiety of Formula R³ᵉ:

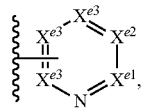

Formula R³ᵉ wherein:
one of Xᵉ¹ or Xᵉ² is [=CRᵉ⁴—], and the other is independently [=N-] or [=CRᵉ⁴—], wherein Rᵉ⁴ is, independently for each occurrence: (a) —H; (b) halogen; or (c) C₁₋₆-linear alkyl or —C₃₋₆-branched alkyl; and
Xᵉ³ is [=CRᵉ⁵—], wherein, one of Rᵉ⁵ is a bond to the substrate and the other two are, independently for each occurrence: (i) —H; (ii) lower alkyl.

14. A compound of claim 13, or a pharmaceutically acceptable salt thereof, wherein [—R³] is a moiety of Formula R³ᵉᵃ:

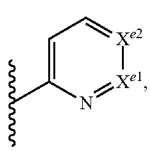

Formula R³ᵉ wherein:
one of Xᵉ¹ and Xᵉ² is [—CRᵉ⁴=], and the other is independently [—N=] or [—CRᵉ⁴=], wherein Rᵉ⁴ independently for each occurrence: (a) —H; (b) halogen; or (c) lower alkyl.

15. A compound of claim 4, or a pharmaceutically acceptable salt thereof, wherein R³ is:

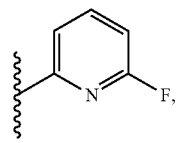

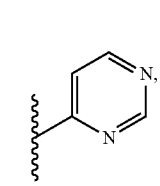 [SMILES: *c1ccncn1]

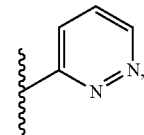 [SMILES: *c1cccnn1]

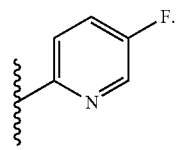

16. A compound of claim 1, or a pharmaceutically acceptable salt thereof, which is:
5-chloro-2-fluoro-4-[(tetrahydro-1H-pyrrolizin-7a(5H)-ylmethyl)amino]-N-(1,2,4-thiadiazol-5-yl)benzenesulfonamide;
2,5-difluoro-4-[(tetrahydro-1H-pyrrolizin-7a(5H)-ylmethyl)amino]-N-(1,2,4-thiadiazol-5-yl)benzenesulfonamide;
5-chloro-2-fluoro-4-[(tetrahydro-1H-pyrrolizin-7a(5H)-ylmethyl)amino]-N-(1,3,4-thiadiazol-2-yl)benzenesulfonamide;
3-cyano-4-[(tetrahydro-1H-pyrrolizin-7a(5H)-ylmethyl)amino]-N-(1,2,4-thiadiazol-5-yl)benzenesulfonamide;

5-chloro-2-fluoro-4-[(tetrahydro-1H-pyrrolizin-7a(5H)-ylmethyl)amino]-N-(1,3-thiazol-2-yl)benzenesulfonamide;
5-chloro-N-(5-chloro-1,3-thiazol-2-yl)-2-fluoro-4-[(tetrahydro-1H-pyrrolizin-7a(5H)-ylmethyl)amino]benzenesulfonamide;
5-chloro-2-fluoro-N-(5-methyl-1,3-thiazol-2-yl)-4-[(tetrahydro-1H-pyrrolizin-7a(5H)-ylmethyl)amino]benzenesulfonamide;
5-cyano-2-fluoro-4-[(tetrahydro-1H-pyrrolizin-7a(5H)-ylmethyl)amino]-N-(1,3-thiazol-2-yl)benzenesulfonamide;
N-(5-chloro-1,3-thiazol-2-yl)-5-cyano-2-fluoro-4-[(tetrahydro-1H-pyrrolizin-7a(5H)-ylmethyl)amino]benzenesulfonamide;
5-chloro-2-fluoro-N-(5-fluorothiazol-2-yl)-4-(((hexahydro-1H-pyrrolizin-7a-yl)methyl)amino)benzenesulfonamide;
N-(5-bromothiazol-2-yl)-5-chloro-2-fluoro-4-(((hexahydro-1H-pyrrolizin-7a-yl)methyl)amino)benzenesulfonamide;
3-chloro-4-(((hexahydro-1H-pyrrolizin-7a-yl)methyl)amino)-N-(thiazol-2-yl)benzenesulfonamide;
2-fluoro-4-(((hexahydro-1H-pyrrolizin-7a-yl)methyl)amino)-5-methyl-N-(thiazol-2-yl)benzenesulfonamide;
ethyl 2-(5-chloro-2-fluoro-4-(((hexahydro-1H-pyrrolizin-7a-yl)methyl)amino)phenylsulfonamido)thiazole-5-carboxylate;
5-bromo-2-fluoro-4-(((hexahydro-1H-pyrrolizin-7a-yl)methyl)amino)-N-(thiazol-2-yl)benzenesulfonamide;
2-chloro-5-fluoro-4-(((hexahydro-1H-pyrrolizin-7a-yl)methyl)amino)-N-(thiazol-2-yl)benzenesulfonamide;
5-chloro-2-fluoro-4-(((hexahydro-1H-pyrrolizin-7a-yl)methyl)amino)-N-(4-methylthiazol-2-yl)benzenesulfonamide;
4-(((hexahydro-1H-pyrrolizin-7a-yl)methyl)amino)-N-(thiazol-2-yl)-3-(trifluoromethyl)benzenesulfonamide;
5-chloro-2-fluoro-N-(5-fluoro-4-methylthiazol-2-yl)-4-(((hexahydro-1H-pyrrolizin-7a-yl)methyl)amino)benzenesulfonamide;
3-cyano-4-[(tetrahydro-1H-pyrrolizin-7a(5H)-ylmethyl)amino]-N-(1,3-thiazol-2-yl)benzenesulfonamide;
3-cyano-N-(6-fluoropyridin-2-yl)-4-[(tetrahydro-1H-pyrrolizin-7a(5H)-ylmethyl)amino]benzenesulfonamide;
2,5-difluoro-N-(6-fluoropyridin-2-yl)-4-[(tetrahydro-1H-pyrrolizin-7a(5H)-ylmethyl)amino]benzenesulfonamide;
5-chloro-2-fluoro-N-(pyrimidin-4-yl)-4-[(tetrahydro-1H-pyrrolizin-7a (5H)-ylmethyl)amino]benzenesulfonamide;
N-(5-chloro-1,3-thiazol-2-yl)-3-cyano-4-[(tetrahydro-1H-pyrrolizin-7a(5H)-ylmethyl)amino]benzenesulfonamide;
5-chloro-2-fluoro-N-(pyridazin-3-yl)-4-[(tetrahydro-1H-pyrrolizin-7a(5H)-ylmethyl)amino]benzenesulfonamide;
5-chloro-2-fluoro-N-(6-fluoropyridin-2-yl)-4-[(tetrahydro-1H-pyrrolizin-7a(5H)-ylmethyl)amino]benzenesulfonamide;
5-chloro-2-fluoro-N-(5-fluoropyridin-2-yl)-4-[(tetrahydro-1H-pyrrolizin-7a(5H)-ylmethyl)amino]benzenesulfonamide;
3-cyano-4-{[(2-methyltetrahydro-1H-pyrrolizin-7a(5Hyl)methyl]amino}-N-(1,3-thiazol-2-yl)benzenesulfonamide;
3-cyano-4-{[(2-methyltetrahydro-1H-pyrrolizin-7a(5H)-yl)methyl]amino}-N-(1,3-thiazol-2-yl)benzenesulfonamide;
3-cyano-4-{[((2S,7aR)-2-methyltetrahydro-1H-pyrrolizin-7a(5H)-yl)methyl]amino}-N-(1,3-thiazol-2-yl)benzenesulfonamide;
3-cyano-4-{[((2R,7aS)-2-methyltetrahydro-1H-pyrrolizin-7a(5H)-yl)methyl]amino}-N-(1,3-thiazol-2-yl)benzenesulfonamide;
5-chloro-2-fluoro-4-{[(2-methyltetrahydro-1H-pyrrolizin-7a(5H)-yl)methyl]amino}-N-(1,3-thiazol-2-yl)-benzenesulfonamide;
5-chloro-2-fluoro-4-{[((2S,7a R)-2-methyltetrahydro-1H-pyrrolizin-7a(5H)-yl)methyl]amino}-N-(1,3-thiazol-2-yl)-benzenesulfonamide;
5-chloro-2-fluoro-4-{[((2R,7aS)-2-methyltetrahydro-1H-pyrrolizin-7a(5H)-yl)methyl]amino}-N-(1,3-thiazol-2-yl)-benzenesulfonamide;
5-chloro-N-(5-chlorothiazol-2-yl)-2-fluoro-4-(((2-methylhexahydro-1H-pyrrolizin-7a-yl)methyl)amino)benzene-sulfonamide;
5-chloro-N-(5-chlorothiazol-2-yl)-2-fluoro-4-((((2S,7a R)-2-methylhexahydro-1H-pyrrolizin-7a-yl)methyl)amino)benzene-sulfonamide;
5-chloro-N-(5-chlorothiazol-2-yl)-2-fluoro-4-((((2R,7aS)-2-methylhexahydro-1H-pyrrolizin-7a-yl)methyl)amino)benzene-sulfonamide;
3-chloro-4-(((2-methylhexahydro-1H-pyrrolizin-7a-yl)methyl)amino)-N-(thiazol-2-yl)benzenesulfonamide;
3-chloro-4-((((2S,7a R)-2-methylhexahydro-1H-pyrrolizin-7a-yl)methyl)amino)-N-(thiazol-2-yl)benzenesulfonamide;
3-chloro-4-((((2R,7aS)-2-methylhexahydro-1H-pyrrolizin-7a-yl)methyl)amino)-N-(thiazol-2-yl)benzenesulfonamide;
3-cyano-4-{[1-(tetrahydro-1H-pyrrolizin-7a(5H)-yl)ethyl]amino}-N-(1,3-thiazol-2-yl)benzenesulfonamide;
(S)-3-cyano-4-{[1-(tetrahydro-1H-pyrrolizin-7a(5H)-yl)ethyl]amino}-N-(1,3-thiazol-2-yl)benzenesulfonamide;
(R)-3-cyano-4-{[1-(tetrahydro-1H-pyrrolizin-7a(5H)-yl)ethyl]amino}-N-(1,3-thiazol-2-yl)benzenesulfonamide;
5-chloro-2-fluoro-4-{[1-(tetrahydro-1H-pyrrolizin-7a(5H)-yl)ethyl]amino}-N-(1,3-thiazol-2-yl)benzenesulfonamide;
(S)-5-chloro-2-fluoro-4-{[(1R)-1-(tetrahydro-1H-pyrrolizin-7a(5H)-yl)ethyl]amino}-N-(1,3-thiazol-2-yl)benzenesulfonamide;
(R)-5-chloro-2-fluoro-4-{[(1S)-1-(tetrahydro-1H-pyrrolizin-7a(5H)-yl)ethyl]amino}-N-(1,3-thiazol-2-yl)benzenesulfonamide;
3-cyano-4-{[(2,2-difluorotetrahydro-1H-pyrrolizin-7a(5H)-yl)methyl]amino}-N-(1,3-thiazol-2-yl)benzenesulfonamide;
(S)-3-cyano-4-{[(2,2-difluorotetrahydro-1H-pyrrolizin-7a(5H)-yl)methyl]amino}-N-(1,3-thiazol-2-yl)benzenesulfonamide;
(R)-3-cyano-4-{[(2,2-difluorotetrahydro-1H-pyrrolizin-7a(5H)-yl)methyl]amino}-N-(1,3-thiazol-2-yl)benzenesulfonamide
5-chloro-4-{[(2,2-difluorotetrahydro-1H-pyrrolizin-7a(5H)-yl)methyl]amino}-2-fluoro-N-(1,3-thiazol-2-yl)benzenesulfonamide;

(R)-5-chloro-4-{[(2,2-difluorotetrahydro-1H-pyrrolizin-7a(5H)-yl)methyl]amino}-2-fluoro-N-(1,3-thiazol-2-yl)benzenesulfonamide;

(S)-5-chloro-4-{[(2,2-difluorotetrahydro-1H-pyrrolizin-7a(5H)-yl)methyl]amino}-2-fluoro-N-(1,3-thiazol-2-yl)benzenesulfonamide;

5-chloro-N-(5-chloro-1,3-thiazol-2-yl)-4-{[(2,2-difluorotetrahydro-1H-pyrrolizin-7a(5H)-yl)methyl]amino}-2-fluorobenzenesulfonamide;

(R)-5-chloro-N-(5-chloro-1,3-thiazol-2-yl)-4-{[(2,2-difluorotetrahydro-1H-pyrrolizin-7a(5H)-yl)methyl]amino}-2-fluorobenzenesulfonamide;

(S)-5-chloro-N-(5-chloro-1,3-thiazol-2-yl)-4-{[(2,2-difluorotetrahydro-1H-pyrrolizin-7a(5H)-yl)methyl]amino}-2-fluorobenzenesulfonamide;

5-chloro-2-fluoro-4-[(tetrahydro-1H-pyrrolizin-7a(5H)-ylmethyl)amino]-N-(1,3-thiazol-4-yl)benzenesulfonamide;

5-chloro-4-(((2,2-dimethylhexahydro-1H-pyrrolizin-7a-yl)methyl)amino)-2-fluoro-N-(thiazol-2-yl)benzenesulfonamide;

(R)-5-chloro-4-(((2,2-dimethylhexahydro-1H-pyrrolizin-7a-yl)methyl)amino)-2-fluoro-N-(thiazol-2-yl)benzenesulfonamide;

(S)-5-chloro-4-(((2,2-dimethylhexahydro-1H-pyrrolizin-7a-yl)methyl)amino)-2-fluoro-N-(thiazol-2-yl)benzenesulfonamide;

5-chloro-N-(5-chlorothiazol-2-yl)-4-(((2,2-dimethylhexahydro-1H-pyrrolizin-7a-yl)methyl)amino)-2-fluorobenzenesulfonamide;

(R)-5-chloro-N-(5-chlorothiazol-2-yl)-4-(((2,2-dimethylhexahydro-1H-pyrrolizin-7a-yl)methyl)amino)-2-fluorobenzenesulfonamide;

(S)-5-chloro-N-(5-chlorothiazol-2-yl)-4-(((2,2-dimethylhexahydro-1H-pyrrolizin-7a-yl)methyl)amino)-2-fluorobenzenesulfonamide;

5-chloro-4-(((2,2-dimethylhexahydro-1H-pyrrolizin-7a-yl)methyl)amino)-2-fluoro-N-(5-fluorothiazol-2-yl)benzenesulfonamide;

(S)-5-chloro-4-(((2,2-dimethylhexahydro-1H-pyrrolizin-7a-yl)methyl)amino)-2-fluoro-N-(5-fluorothiazol-2-yl)benzenesulfonamide;

(R)-5-chloro-4-(((2,2-dimethylhexahydro-1H-pyrrolizin-7a-yl)methyl)amino)-2-fluoro-N-(5-fluorothiazol-2-yl)benzenesulfonamide;

4-(((2,2-dimethylhexahydro-1H-pyrrolizin-7a-yl)methyl)amino)-N-(thiazol-2-yl)-3-(trifluoromethyl)benzenesulfonamide;

(S)-4-(((2,2-dimethylhexahydro-1H-pyrrolizin-7a-yl)methyl)amino)-N-(thiazol-2-yl)-3-(trifluoromethyl)benzenesulfonamide;

(R)-4-(((2,2-dimethylhexahydro-1H-pyrrolizin-7a-yl)methyl)amino)-N-(thiazol-2-yl)-3-(trifluoromethyl)benzenesulfonamide;

5-chloro-4-(((2,2-dimethylhexahydro-1H-pyrrolizin-7a-yl)methyl)amino)-2-fluoro-N-(4-methylthiazol-2-yl)benzenesulfonamide;

(S)-5-chloro-4-(((2,2-dimethylhexahydro-1H-pyrrolizin-7a-yl)methyl)amino)-2-fluoro-N-(4-methylthiazol-2-yl)benzenesulfonamide;

(R)-5-chloro-4-(((2,2-dimethylhexahydro-1H-pyrrolizin-7a-yl)methyl)amino)-2-fluoro-N-(4-methylthiazol-2-yl)benzenesulfonamide;

5-chloro-2-fluoro-4-(((2-fluorohexahydro-1H-pyrrolizin-7a-yl)methyl)amino)-N-(thiazol-2-yl)benzenesulfonamide;

5-chloro-2-fluoro-4-(((((2R,7aS)-2-fluorohexahydro-1H-pyrrolizin-7a-yl)methyl)amino)-N-(thiazol-2-yl)benzenesulfonamide;

5-chloro-2-fluoro-4-(((((2S,7aR)-2-fluorohexahydro-1H-pyrrolizin-7a-yl)methyl)amino)-N-(thiazol-2-yl)benzenesulfonamide;

5-chloro-2-fluoro-4-(((2-fluorohexahydro-1H-pyrrolizin-7a-yl)methyl)amino)-N-(5-fluorothiazol-2-yl)benzenesulfonamide;

5-chloro-2-fluoro-4-(((((2R,7aS)-2-fluorohexahydro-1H-pyrrolizin-7a-yl)methyl)amino)-N-(5-fluorothiazol-2-yl)benzenesulfonamide;

5-chloro-2-fluoro-4-(((((2S,7a R)-2-fluorohexahydro-1H-pyrrolizin-7a-yl)methyl)amino)-N-(5-fluorothiazol-2-yl)benzenesulfonamide;

4-(((2-fluorohexahydro-1H-pyrrolizin-7a-yl)methyl)amino)-N-(5-fluorothiazol-2-yl)-3-(trifluoromethyl)benzenesulfonamide;

4-(((((2R,7aS)-2-fluorohexahydro-1H-pyrrolizin-7a-yl)methyl)amino)-N-(5-fluorothiazol-2-yl)-3-(trifluoromethyl)benzenesulfonamide;

4-(((((2S,7aR)-2-fluorohexahydro-1H-pyrrolizin-7a-yl)methyl)amino)-N-(5-fluorothiazol-2-yl)-3-(trifluoromethyl)benzenesulfonamide;

3-chloro-4-(((2-fluorohexahydro-1H-pyrrolizin-7a-yl)methyl)amino)-N-(5-fluorothiazol-2-yl)benzenesulfonamide;

3-chloro-4-(((((2R,7aS)-2-fluorohexahydro-1H-pyrrolizin-7a-yl)methyl)amino)-N-(5-fluorothiazol-2-yl)benzenesulfonamide 3-chloro-4-(((((2S,7aR)-2-fluorohexahydro-1H-pyrrolizin-7a-yl)methyl)amino)-N-(5-fluorothiazol-2-yl)benzenesulfonamide 5-chloro-2-fluoro-4-(((hexahydrospiro[[1,3]dioxolane-2,2'-pyrrolizin]-7a'-yl)methyl)amino)-N-(thiazol-2-yl)benzenesulfonamide;

(S)-5-chloro-2-fluoro-4-(((hexahydrospiro[[1,3]dioxolane-2,2'-pyrrolizin]-7a'-yl)methyl)amino)-N-(thiazol-2-yl)benzenesulfonamide;

(R)-5-chloro-2-fluoro-4-(((hexahydrospiro[[1,3]dioxolane-2,2'-pyrrolizin]-7a'-yl)methyl)amino)-N-(thiazol-2-yl)benzenesulfonamide;

5-chloro-N-(5-chlorothiazol-2-yl)-2-fluoro-4-(((hexahydrospiro[[1,3]dioxolane-2,2'-pyrrolizin]-7a'-yl)methyl)amino)benzenesulfonamide;

(S)-5-chloro-N-(5-chlorothiazol-2-yl)-2-fluoro-4-(((hexahydrospiro[[1,3]dioxolane-2,2'-pyrrolizin]-7a'-yl)methyl)amino)benzenesulfonamide;

(R)-5-chloro-N-(5-chlorothiazol-2-yl)-2-fluoro-4-(((hexahydrospiro[[1,3]dioxolane-2,2'-pyrrolizin]-7a'-yl)methyl)amino)benzenesulfonamide;

5-chloro-2-fluoro-4-(((3-methylhexahydro-1H-pyrrolizin-7a-yl)methyl)amino)-N-(thiazol-2-yl)benzenesulfonamide;

5-chloro-2-fluoro-4-(((((3S,7aS)-3-methylhexahydro-1H-pyrrolizin-7a-yl)methyl)amino)-N-(thiazol-2-yl)benzenesulfonamide;

5-chloro-2-fluoro-4-(((((3R,7a R)-3-methylhexahydro-1H-pyrrolizin-7a-yl)methyl)amino)-N-(thiazol-2-yl)benzenesulfonamide;

4-(((3-methylhexahydro-1H-pyrrolizin-7a-yl)methyl)amino)-N-(thiazol-2-yl)-3-(trifluoromethyl)benzenesulfonamide;

4-(((((3S,7aS)-3-methylhexahydro-1H-pyrrolizin-7a-yl)methyl)amino)-N-(thiazol-2-yl)-3-(trifluoromethyl)benzenesulfonamide;

4-((((3R,7aR)-3-methylhexahydro-1H-pyrrolizin-7a-yl)methyl)amino)-N-(thiazol-2-yl)-3-(trifluoromethyl)benzenesulfonamide;

3-chloro-N-(5-fluorothiazol-2-yl)-4-(((3-methylhexahydro-1H-pyrrolizin-7a-yl)methyl)amino)benzenesulfonamide;

3-chloro-N-(5-fluorothiazol-2-yl)-4-((((3S,7aS)-3-methylhexahydro-1H-pyrrolizin-7a-yl)methyl)amino)benzenesulfonamide;

3-chloro-N-(5-fluorothiazol-2-yl)-4-((((3R,7a R)-3-methylhexahydro-1H-pyrrolizin-7a-yl)methyl)amino)benzenesulfonamide;

2-bromo-5-chloro-4-(((hexahydro-1H-pyrrolizin-7a-yl)methyl)amino)-N-(thiazol-2-yl)benzenesulfonamide;

5-chloro-2-cyano-4-(((hexahydro-1H-pyrrolizin-7a-yl)methyl)amino)-N-(thiazol-2-yl)benzenesulfonamide;

5-chloro-4-(((hexahydro-1H-pyrrolizin-7a-yl)methyl)amino)-2-methyl-N-(thiazol-2-yl)benzenesulfonamide;

5-chloro-2-fluoro-4-(((hexahydrospiro[cyclopropane-1,2'-pyrrolizin]-7a'-yl)-methyl)amino)-N-(thiazol-2-yl)benzenesulfonamide;

(S)-5-chloro-2-fluoro-4-(((hexahydrospiro[cyclopropane-1,2'-pyrrolizin]-7a'-yl)-methyl)amino)-N-(thiazol-2-yl)benzenesulfonamide;

(R)-5-chloro-2-fluoro-4-(((hexahydrospiro[cyclopropane-1,2'-pyrrolizin]-7a'-yl)-methyl)amino)-N-(thiazol-2-yl)benzenesulfonamide;

N-(5-fluorothiazol-2-yl)-4-(((hexahydrospiro[cyclopropane-1,2'-pyrrolizin]-7a'-yl)methyl)amino)-3-(trifluoromethyl)benzenesulfonamide; (racemic)

(S)-N-(5-fluorothiazol-2-yl)-4-(((hexahydrospiro[cyclopropane-1,2'-pyrrolizin]-7a'-yl)methyl)amino)-3-(trifluoromethyl)benzenesulfonamide;

(R)-N-(5-fluorothiazol-2-yl)-4-(((hexahydrospiro[cyclopropane-1,2'-pyrrolizin]-7a'-yl)methyl)amino)-3-(trifluoromethyl)benzenesulfonamide;

5-chloro-2-fluoro-4-(((3-(fluoromethyl)hexahydro-1H-pyrrolizin-7a-yl)methyl)amino)-N-(thiazol-2-yl)benzenesulfonamide;

5-chloro-2-fluoro-4-((((3R,7aR)-3-(fluoromethyl)hexahydro-1H-pyrrolizin-7a-yl)methyl)amino)-N-(thiazol-2-yl)benzenesulfonamide;

5-chloro-2-fluoro-4-((((3S,7aS)-3-(fluoromethyl)hexahydro-1H-pyrrolizin-7a-yl)methyl)amino)-N-(thiazol-2-yl)benzenesulfonamide;

5-chloro-2-fluoro-4-(((-3-(hydroxymethyl)hexahydro-1H-pyrrolizin-7a-yl)methyl)amino)-N-(thiazol-2-yl)benzenesulfonamide;

5-chloro-2-fluoro-4-((((3S,7aS)-3-(hydroxymethyl)hexahydro-1H-pyrrolizin-7a-yl)methyl)amino)-N-(thiazol-2-yl)benzenesulfonamide;

5-chloro-2-fluoro-4-((((3R,7a R)-3-(hydroxymethyl)hexahydro-1H-pyrrolizin-7a-yl)methyl)amino)-N-(thiazol-2-yl)benzenesulfonamide;

5-chloro-2-fluoro-4-(((-2-(4-methoxybenzyl)hexahydro-1H-pyrrolizin-7a-yl)methyl)amino)-N-(thiazol-2-yl)benzenesulfonamide;

5-chloro-2-fluoro-4-((((2R,7aS)-2-(4-methoxybenzyl)hexahydro-1H-pyrrolizin-7a-yl)methyl)amino)-N-(thiazol-2-yl)benzenesulfonamide;

5-chloro-2-fluoro-4-((((2S,7a R)-2-(4-methoxybenzyl)hexahydro-1H-pyrrolizin-7a-yl)methyl)amino)-N-(thiazol-2-yl)benzenesulfonamide;

5-chloro-2-fluoro-N-(5-fluorothiazol-2-yl)-4-(((-2-(4-methoxybenzyl)hexahydro-1H-pyrrolizin-7a-yl)methyl)amino)benzenesulfonamide;

5-chloro-2-fluoro-N-(5-fluorothiazol-2-yl)-4-((((2R,7aS)-2-(4-methoxybenzyl)hexahydro-1H-pyrrolizin-7a-yl)methyl)amino)benzenesulfonamide;

5-chloro-2-fluoro-N-(5-fluorothiazol-2-yl)-4-((((2S,7a R)-2-(4-methoxybenzyl)hexahydro-1H-pyrrolizin-7a-yl)methyl)amino)benzenesulfonamide;

5-chloro-2-fluoro-4-(((-2-(4-methoxyphenyl)hexahydro-1H-pyrrolizin-7a-yl)methyl)amino)-N-(thiazol-2-yl)benzenesulfonamide;

5-chloro-2-fluoro-4-((((2S,7aS)-2-(4-methoxyphenyl)hexahydro-1H-pyrrolizin-7a-yl)methyl)amino)-N-(thiazol-2-yl)benzenesulfonamide;

5-chloro-2-fluoro-4-((((2R,7a R)-2-(4-methoxyphenyl)hexahydro-1H-pyrrolizin-7a-yl)methyl)amino)-N-(thiazol-2-yl)benzenesulfonamide;

5-chloro-2-fluoro-4-(((octahydroindolizin-8a-yl)methyl)amino)-N-(thiazol-2-yl)benzenesulfonamide;

(R)-5-chloro-2-fluoro-4-(((octahydroindolizin-8a-yl)methyl)amino)-N-(thiazol-2-yl)benzenesulfonamide;

(S)-5-chloro-2-fluoro-4-(((octahydroindolizin-8a-yl)methyl)amino)-N-(thiazol-2-yl)benzenesulfonamide;

5-chloro-2-fluoro-4-(((octahydro-1H-quinolizin-9a-yl)methyl)amino)-N-(thiazol-2-yl)benzenesulfonamide;

5-ethyl-2-fluoro-4-(((2-(4-methoxybenzyl)hexahydro-1H-pyrrolizin-7a-yl)methyl)amino)-N-(thiazol-2-yl)benzenesulfonamide;

5-ethyl-2-fluoro-4-((((2R,7aS)-2-(4-methoxybenzyl)hexahydro-1H-pyrrolizin-7a-yl)methyl)amino)-N-(thiazol-2-yl)benzenesulfonamide;

5-ethyl-2-fluoro-4-((((2S,7a R)-2-(4-methoxybenzyl)hexahydro-1H-pyrrolizin-7a-yl)methyl)amino)-N-(thiazol-2-yl)benzenesulfonamide;

5-ethyl-2-fluoro-4-(((hexahydro-1H-pyrrolizin-7a-yl)methyl)amino)-N-(thiazol-2-yl)benzenesulfonamide;

5-ethyl-2-fluoro-N-(5-fluorothiazol-2-yl)-4-(((hexahydro-1H-pyrrolizin-7a-yl)methyl)amino)benzenesulfonamide;

4-(((2,2-dimethylhexahydro-1H-pyrrolizin-7a-yl)methyl)amino)-5-ethyl-2-fluoro-N-(thiazol-2-yl)benzenesulfonamide;

(S)-4-(((2,2-dimethylhexahydro-1H-pyrrolizin-7a-yl)methyl)amino)-5-ethyl-2-fluoro-N-(thiazol-2-yl)benzenesulfonamide; or (R)-4-(((2,2-dimethylhexahydro-1H-pyrrolizin-7a-yl)methyl)amino)-5-ethyl-2-fluoro-N-(thiazol-2-yl)benzenesulfonamide.

17. A pharmaceutical composition comprising at least one compound of claim 1, or a pharmaceutically acceptable salt thereof, and at least one pharmaceutically acceptable excipient.

18. A dosage form comprising an amount of the composition of claim 17 that provides an amount of said compound of claim 1, or a pharmaceutically acceptable salt thereof, which is sufficient to provide a therapeutic response when administered to a patient in need of therapy for a neuropathic pain disorder.

19. A method of treating a neuropathic pain disorder comprising administering to a patient in need thereof a therapeutically effective amount of a pharmaceutical composition of claim 17.

* * * * *

UNITED STATES PATENT AND TRADEMARK OFFICE
CERTIFICATE OF CORRECTION

PATENT NO. : 9,586,968 B2
APPLICATION NO. : 15/038805
DATED : March 7, 2017
INVENTOR(S) : Dansu Li et al.

Page 1 of 1

It is certified that error appears in the above-identified patent and that said Letters Patent is hereby corrected as shown below:

On the Title Page

Please amend (71) Applicants to read as follows:
(71) Applicants: Merck Sharp & Dohme Corp.
Rahway, NJ (US)

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*